(12) United States Patent
Ikeura et al.

(10) Patent No.: US 7,622,487 B2
(45) Date of Patent: Nov. 24, 2009

(54) PIPERIDINE DERIVATIVE, PROCESS FOR PRODUCING THE SAME, AND USE

(75) Inventors: Yoshinori Ikeura, Kashiba (JP); Tadatoshi Hashimoto, Ibaraki (JP); Naoki Tarui, Nara (JP); Junya Shirai, Amagasaki (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 574 days.

(21) Appl. No.: 10/516,252

(22) PCT Filed: May 29, 2003

(86) PCT No.: PCT/JP03/06754

§ 371 (c)(1),
(2), (4) Date: Nov. 29, 2004

(87) PCT Pub. No.: WO03/101964

PCT Pub. Date: Dec. 11, 2003

(65) Prior Publication Data

US 2006/0167052 A1    Jul. 27, 2006

(30) Foreign Application Priority Data

May 31, 2002    (JP) ............................. 2002-159338
Jan. 27, 2003    (JP) ............................. 2003-017885

(51) Int. Cl.
*A61K 31/445*    (2006.01)
*C07D 403/12*    (2006.01)

(52) U.S. Cl. ..................................... 514/326; 546/210

(58) Field of Classification Search ............... 514/326; 546/210

See application file for complete search history.

(56) References Cited

U.S. PATENT DOCUMENTS

| 5,232,929 | A |   | 8/1993  | Desai et al.      |
|-----------|---|---|---------|-------------------|
| 6,143,759 | A | * | 11/2000 | Flockerzi ........... 514/292 |
| 6,436,952 | B1|   | 8/2002  | Flockerzi         |
| 2004/0097548 | A1 | | 5/2004 | Takahashi et al.  |

FOREIGN PATENT DOCUMENTS

| DE | 4217401      | 1/1993  |
| JP | A 05-155853  | 6/1993  |
| JP | A 06 157539  | 6/1994  |
| WO | WO 93/01170  | 1/1993  |
| WO | WO 93/09780  | 5/1993  |
| WO | 96/41802     | 12/1996 |
| WO | WO 99/47511  | 9/1999  |
| WO | 01/85728     | 11/2001 |
| WO | WO 02/26710  | 4/2002  |
| WO | WO 03/057668 A1 | 7/2003 |

OTHER PUBLICATIONS

Ikeura et al. "preparation of piperidin . . . " CA 144:331270 (2006).*
Nagaoka et al. "Preparation of piperidine . . . " CA 145:471540 (2006).*
Bennett "concise chemical dictionary" p. 19 (1976).*
Database Caplus (Online), Chemical Abstracts Service, T. K. MandaL et al., "Synthesis and fungicidal activity of substituted 4-aminopiperidines and 4-aminotetrahydropyridines", XP002419437, Database Accession No. 1991:535888.
Database Caplus (Online), Chemical Abstracts Service, M. Minafuji et al., "Preparation of piperidine-containing arylcarboxylic acid esters as stabilizers for polymers", XP002419438, Database Accession No. 1994:106774.
Database Caplus (Online), Chemical Abstracts Service, M. Minafuji et al., "Preparation of hindered 4-(alkylated 5-piperidinyloxycarbonyl)benzal dehyde spiroacetal derivative as photostabilizers for organic materials", XP002419439, Database Accession No. 1994:655780.
K. Weber et al., "Homo-Freidinger Lactams: Stereoselective Synthesis of 4-Aminopiperidin-2-one Derivatives from Aspartic Acid", Synlett, vol. 8, pp. 885-887, Aug. 1998.

(Continued)

*Primary Examiner*—Celia Chang
(74) *Attorney, Agent, or Firm*—Wenderoth, Lind & Ponack, L.L.P.

(57) ABSTRACT

The present invention provides a compound represented by the formula:

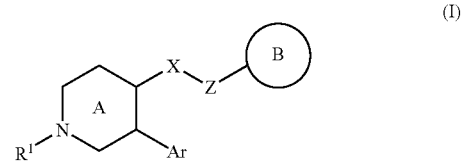

(I)

wherein Ar is an aryl group, an aralkyl group or an aromatic heterocyclic group, each of which may be substituted, $R^1$ is a hydrogen atom, an optionally substituted hydrocarbon group, an acyl group or an optionally substituted heterocyclic group, X is an oxygen atom or an optionally substituted imino group, Z is an optionally substituted methylene group, Ring A is an optionally further substituted piperidine ring, and Ring B is an optionally substituted aromatic ring, provided that when Z is a methylene group substituted with an oxo group, $R^1$ is not a methyl group, and when Z is a methylene group substituted with a methyl group, Ring B is a substituted aromatic ring, or a salt thereof, which is a novel piperidine derivative having excellent antagonistic action for a tachykinin receptor and useful as a medicament, particularly an agent for preventing and/or treating urinary frequency and/or urinary incontinence.

7 Claims, No Drawings

OTHER PUBLICATIONS

S. Knapp et al., "Synthesis of the Sialidase Inhibitor Siastatin B", Organic Letters, vol. 2, No. 25, pp. 4037-4040, 2000.

H. Sun et al., "A new asymmetric route to substituted piperidines: synthesis of N-alky1-3,4-dihydroxy-5-alkylpiperidines", Tetrahedron Letters, vol. 41, No .16, pp. 2801-2804, 2000.

S. M. McElvain et al.,"Piperidine Derivatives. XXXII. Reaction of 1-Acyl-4-piperidones with Organometallic Compounds", Journal of the American Chemical Society, vol. 82, pp. 3966-3970, 1960.

WEBER, K., et al., "Enantiopure 4- and 5-Aminopiperidine-2-ones: Regiocontrolled Synthesis and Conformational Characterization as Bioactive B-Turn Mimetics", *J. Org. Chem.*, (2000), vol. 65, No. 22, pp. 7406-7416.

Mandal, T.K., et al., "Synthesis and Fungicidic Activity of Substituted 4-Aminopiperidines and 4-Aminotetrahydropyridines", *Khimiko-Farmatsevticheskii Zhurnal*, (2000), vol. 25, No. 6, pp. 28-33.

Hallett, David J., et al., "Neighboring Group Participation of the Indole Nucleus: An Unusual DAST-Mediated Rearrangement Reaction", J. Org. Chem., (2000), pp. 4984-4993, vol. 65, No. 16.

* cited by examiner

PIPERIDINE DERIVATIVE, PROCESS FOR PRODUCING THE SAME, AND USE

This application is the National Phase filing of International Patent Application No. PCT/JP03/06754, filed May 29, 2003.

TECHNICAL FIELD

The present invention relates to a novel piperidine derivative having excellent antagonistic action for a tachykinin receptor, and a preparation method and use thereof.

BACKGROUND ART

Tachykinin is a generic term for a group of neuropeptides. Substance P (SP), neurokinin A and neurokinin B are known in mammals, and these peptides are known to bind to the corresponding receptors (neurokinin-1, neurokinin-2 and neurokinin-3) that exist in a living body and thereby to exhibit various biological activities.

Of such neuropeptides, SP has the longest history and has been studied in detail. In 1931, the existence of SP in the extract from equine intestines was confirmed, and in 1971, its structure was determined. SP is a peptide consisting of 11 amino acids.

SP is broadly distributed over the central and peripheral nervous systems, and has various physiological activities such as vasodilation, enhancement of vascular extravasation, contraction of smooth muscles, excitation of neurons, salivation, enhancement of diuresis, immunological enhancement and the like, in addition to the function as a transmitter substance for primary sensory neurons. In particular, it is known that SP released from the terminal of the spinal (dorsal) horn due to a pain impulse transmits the information of pain to secondary neurons, and that SP released from the peripheral terminal induces an inflammatory response in the receptor thereof. Thus, it is considered that SP is involved in various disorders (e.g., pain, headache, particularly migraine, Alzheimer's disease, multiple sclerosis, cardiovascular modulation, chronic inflammatory diseases such as chronic rheumatic arthritis, respiratory diseases including asthma or allergic rhinitis, intestinal inflammatory diseases including ulcerative colitis and Crohn's disease, ocular damage and ocular inflammatory diseases, proliferative vitreous retinopathy, irritable bowel syndrome, urinary frequency, psychosis, vomiting, etc.) [see a review article: Physiological Reviews, Vol. 73, pp. 229-308 (1993); Journal of Autonomic Pharmacology, Vol. 13, pp. 23-93 (1993)].

At present, the following compounds have been known as those having antagonistic action for SP receptors.

(1) In EP-A-436,334, disclosed are the compounds of a formula:

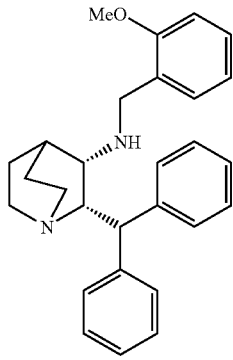

(2) in WO 92/17449, disclosed are the compounds of a formula:

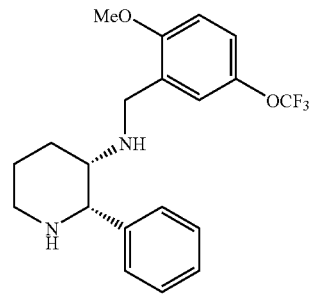

(3) in WO 95/16679, disclosed are the compounds of a formula:

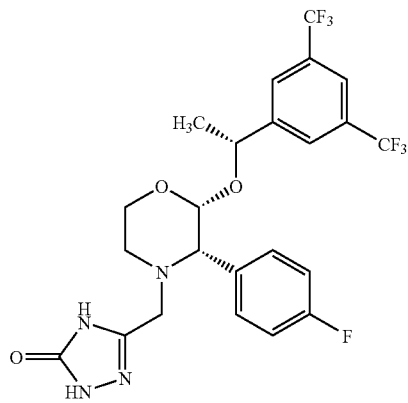

and (4) in JP-A-9-263585, disclosed are the heterocyclic compounds represented by a formula:

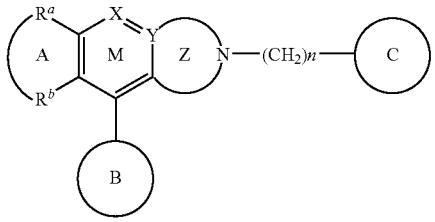

wherein Ring M is a heterocycle having —N=C<, —CO—N< or —CS—N< as a partial structure of

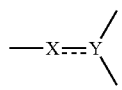

$R^a$ and $R^b$ are bonded to each other to form Ring A, or they are the same or different and represent a hydrogen atom or a substituent in Ring M; Ring A and Ring B are optionally substituted homocyclic or heterocyclic rings, respectively and at least one of them is an optionally substituted heterocyclic ring; Ring C is an optionally substituted homocyclic or heterocyclic ring; Ring Z is an optionally substituted nitrogen-containing heterocyclic ring; and n is an integer of 1 to 6, or salts thereof.

An object of the present invention is to provide a piperidine derivative having antagonistic action for a tachykinin receptor, etc. with a different chemical structure from the known compounds including the above-mentioned compounds, a method of preparing the compound, an agent for ameliorating abnormal micturition comprising the compound, and the like.

DISCLOSURE OF INVENTION

The present inventors have made extensive studies in consideration of the above-mentioned situation and, as a result, have found unexpectedly that piperidine derivatives represented by the formula (I) below or a salt thereof have excellent antagonistic action for a tachykinin receptor (particularly antagonistic action for a SP receptor) as based on their peculiar chemical structures and are sufficiently satisfactory as medicines. On the basis of these findings, the present inventors have completed the present invention.

Specifically, the present invention provides the following:

[1] a compound represented by the formula:

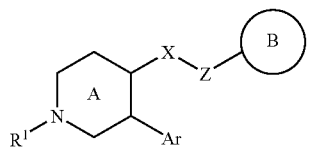

(I)

wherein Ar is an aryl group, an aralkyl group or an aromatic heterocyclic group, each of which may be substituted, $R^1$ is a hydrogen atom, an optionally substituted hydrocarbon group, an acyl group or an optionally substituted heterocyclic group, X is an oxygen atom or an optionally substituted imino group, Z is an optionally substituted methylene group, Ring A is a further optionally substituted piperidine ring, and Ring B is an optionally substituted aromatic ring, provided that when Z is a methylene group substituted with an oxo group, $R^1$ is not a methyl group, and when Z is a methylene group substituted with a methyl group, Ring B is a substituted aromatic ring, or a salt thereof;

[2] the compound as described in [1], wherein Ar is a phenyl group or a benzhydryl group, each of which may be substituted;

[3] the compound as described in [1], wherein $R^1$ is a hydrogen atom or an acyl group;

[4] the compound as described in [1], wherein Z is a methylene group optionally substituted with (i) an optionally substituted lower alkyl group or (ii) an oxo group, and Ring B is an optionally substituted benzene ring;

[5] the compound as described in [1], wherein Ar is a phenyl group, a benzhydryl group or a benzyl group, each of which optionally has 1 to 4 substituents selected from (A) a halogen atom, (B) a $C_{1-6}$ alkyl group, and (C) a heterocyclic group, $R^1$ is (1) a hydrogen atom, (2) a hydrocarbon group optionally having 1 to 3 substituents selected from (i) a $C_{1-6}$ alkoxy group, (ii) a $C_{1-6}$ alkoxy-carbonyl group, (iii) a carbamoyl group, (iv) a cyano group, (v) a $C_{1-6}$ alkylthio group, or (vi) a heterocyclic group optionally substituted with 1 or 2 oxo groups and optionally fused with a benzene ring, (3) an acyl group represented by the formula: —(C=O)—Ra, —(C=S)—Ra, —SO$_2$—Ra, —SO$_2$—NRa', —(C=O)NRaRa' or —(C=O)O—Ra wherein Ra is (A) a hydrogen atom or (B) (a) a hydrocarbon group or (b) a heterocyclic group, each of which may be substituted with 1 to 2 substituents selected from (i) a halogen atom, (ii) a $C_{1-6}$ alkyl group optionally substituted with a heterocyclic group, $C_{1-6}$ alkanoyl or $C_{6-14}$ aryl-carbonyl, (iii) a $C_{1-6}$ alkoxy group,
(iv) an amino group,
(v) a mono- or di-$C_{1-6}$ alkylamino group,
(vi) a $C_{1-6}$ alkanoylamino group,
(vii) a N—$C_{1-6}$ alkyl-N'—$C_{1-6}$ alkanoylamino group,
(viii) a $C_{1-6}$ alkoxy-carbonyl group,
(ix) a $C_{1-6}$ alkanoyl group optionally substituted with $C_{1-6}$ alkoxy, mono- or di-$C_{1-6}$ alkylamino, halogeno $C_{1-6}$ alkyl or a halogen atom,
(x) a $C_{6-14}$ aryl-carbonyl group,
(xi) a $C_{7-19}$ aralkyl-carbonyl group,
(xii) a $C_{3-6}$ cycloalkyl-carbonyl group,
(xiii) a heterocyclic-carbonyl group,
(xiv) a hydroxy group,
(xv) a $C_{7-19}$ aralkyloxy group,
(xvi) a $C_{3-6}$ cycloalkyloxy group,
(xvii) a $C_{1-6}$ alkoxy-$C_{1-6}$ alkoxy group,
(xviii) a carbamoyl group,
(xix) a mono- or di-$C_{1-6}$ alkylcarbamoyl group,
(xx) a $C_{1-6}$ alkylsulfonyl group,
(xxi) a mono- or di-$C_{1-6}$ alkylaminosulfonyl group,
(xxii) a formyl group,
(xxiii) a formylamino group,
(xxiv) an oxo group, and
(xxv) a heterocyclic group optionally having 1 or 2 substituents selected from $C_{1-6}$ alkanoyl and $C_{1-6}$ alkoxy-$C_{1-6}$ alkanoyl, and Ra' is a hydrogen atom or a $C_{1-6}$ alkyl group, or (4) a heterocyclic group optionally having 1 or 2 substituents selected from a $C_{1-6}$ alkyl group and an oxo group, X is O or NH, Z is a methylene group, and Ring B is a benzene ring optionally having 1 or 2 substituents selected from (i) a heterocyclic group optionally substituted with an optionally halogenated $C_{1-6}$ alkyl group or a $C_{1-6}$ alkylthio group, (ii) an optionally halogenated $C_{1-6}$ alkyl group, (iii) an optionally halogenated $C_{1-6}$ alkoxy group, (iv) a halogen atom, (v) nitro, (vi) a $C_{6-14}$ aryl group optionally substituted with optionally halogenated $C_{1-6}$ alkyl, (vii) an optionally halogenated $C_{1-6}$ alkylamino group, (viii) a cyano group, and (ix) a $C_{3-6}$ cycloalkyloxy, and optionally fused with a non-aromatic heterocyclic ring or a benzene ring;

[6] the compound as described in [1], wherein Ar is a phenyl group, $R^1$ is —(C=O)—Rb or —(C=O)NRbRb' (Rb is (1) a hydrocarbon group or (2) a heterocyclic group, each of which optionally has a substituent selected from (i) hydroxy, (ii) $C_{1-6}$ alkoxy, (iii) $C_{1-6}$ alkanoyl, (iv) $C_{1-6}$ alkylsulfonyl, (v) amino, (vi) mono- or di-$C_{1-6}$ alkylamino, (vii) $C_{1-6}$ alkanoylamino or (viii) a heterocyclic group optionally substituted with 1 or 2 oxo groups, and Rb' is a hydrogen atom or a $C_{1-6}$ alkyl group.), X is O or NH, Z is a methylene group, Ring B is a benzene ring optionally having 1 or 2 substituents selected from (i) a heterocyclic group optionally substituted with an optionally halogenated $C_{1-6}$ alkyl group, (ii) an optionally halogenated $C_{1-6}$ alkyl group and (iii) an optionally halogenated $C_{1-6}$ alkoxy group, and optionally fused with a non-aromatic heterocyclic ring;

[7]   cis-4-[[3,5-bis(trifluoromethyl)benzyl]oxy]-N-methyl-3-phenyl-1-piperidinecarboxamide, cis-1-[(1-acetyl-4-piperidinyl)carbonyl]-4-[[3,5-bis(trifluoromethyl)benzyl]oxy]-3-phenylpiperidine, cis-N-ethyl-4-[[2-methoxy-5-(trifluoromethoxy)benzyl]amino]-3-phenyl-1-piperidinecarboxamide, cis-N-methyl-3-phenyl-4-[[[5-[5-(trifluoromethyl)-1H-tetrazol-1-yl]-2,3-dihydro-1-benzofuran-7-yl]methyl]amino]-1-piperidinecarboxamide, cis-N-ethyl-3-phenyl-4-[[[5-[5-(trifluoromethyl)-1H-tetrazol-1-yl]-2,3-dihydro-1-benzofuran-7-yl]methyl]amino]-1-piperidinecarboxamide, cis-1-[(1-acetyl-4-piperidinyl)carbonyl]-3-phenyl-N-[[5-[5-(trifluoromethyl)-1H-tetrazol-1-yl]-2,3-dihydro-1-benzofuran-7-yl]methyl]-4-piperidineamine, cis-4-[[2-methoxy-5-[5-(trifluoromethyl)-1H-tetrazol-1-yl]benzyl]amino]-N-methyl-3-phenyl-1-piperidinecarboxamide, cis-N-ethyl-4-[[2-methoxy-5-[5-(trifluoromethyl)-1H-tetrazol-1-yl]benzyl]amino]-3-phenyl-1-piperidinecarboxamide, cis-1-(methoxyacetyl)-N-[2-methoxy-5-[5-(trifluoromethyl)-1H-tetrazol-1-yl]benzyl]-3-phenyl-4-piperidineamine, cis-1-[1-acetyl-4-piperidinyl)carbonyl]-N-[2-methoxy-5-[5-(trifluoromethyl)-1H-tetrazol-1-yl]benzyl]-3-phenyl-4-piperidineamine, cis-N-[2-[-4-[[2-methoxy-5-[5-(trifluoromethyl)-1H-tetrazol-1-yl]benzyl]amino]-3-phenyl-1-piperidinyl]-2-oxoethyl]acetamide, cis-N-[2-methoxy-5-[5-(trifluoromethyl)-1H-tetrazol-1-yl]benzyl]-1-[[1-(methylsulfonyl)-4-piperidinyl]carbonyl]-3-phenyl-4-piperidineamine, cis-N-[2-methoxy-5-[5-(trifluoromethyl)-1H-tetrazol-1-yl]benzyl]-3-phenyl-1-(1H-tetrazol-1-ylacetyl)-4-piperidineamine, cis-2-[4-[[2-methoxy-5-[5-(trifluoromethyl)-1H-tetrazol-1-yl]benzyl]amino ]-3-phenyl-1-piperidinyl]-2-oxoethanol, cis-N-[3-(4-[[2-methoxy-5-[5-(trifluoromethyl)-1H-tetrazol-1-yl]benzyl]amino]-3-phenyl-1-piperidinyl]-3-oxopropyl]acetamide, cis-1-acetyl-N-[2-methoxy-5-[5-(trifluoromethyl)-1H-tetrazol-1-yl]benzyl]-3-phenyl-4-piperidineamine, cis-N-[2-methoxy-5-[5-(trifluoromethyl)-1H-tetrazol-1-yl]benzyl]-1-[(methylsulfonyl)acetyl]-3-phenyl-4-piperidineamine, or cis-1-[2-[4-[[2-methoxy-5-[5-trifluoromethyl)-1H-tetrazol-1-yl]benzyl]amino]-3-phenyl-1-piperidinyl]-2-oxoethyl]-2,5-pyrrolidinedione, or a salt thereof;

[8] a prodrug of the compound as described in [1];

[9] a method of preparing the compound as described in [1], which comprises subjecting a compound represented by the formula:

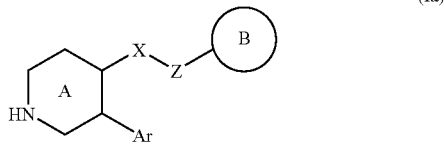

(Ia)

wherein each symbol has the same meanings as defined above, or a salt thereof to a reaction with a compound represented by the formula:

R$^{1a}$—OH wherein R$^{1a}$ is an optionally substituted hydrocarbon group, an acyl group or an optionally substituted heterocyclic group, a salt thereof or a reactive derivative thereof, and if desired, to deacylation or dealkylation;

[10] a compound represented by the formula:

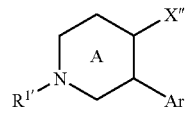

(II)

wherein R$^{1\prime\prime}$ is an acyl group or an optionally substituted heterocyclic group, X" is a hydroxy group or an amino group, and other symbols have the same meanings as defined above, provided that when X" is a hydroxy group, R$^{1\prime\prime}$ is neither an ethoxycarbonyl group nor a cyclopropylcarbonyl group, or a salt thereof;

[11] a method of preparing the compound as described in [1], which comprises subjecting a compound represented by the formula:

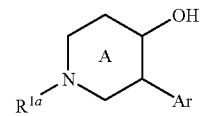

(IIa)

wherein each symbol has the same meanings as defined above, or a salt thereof to a reaction with a compound represented by the formula:

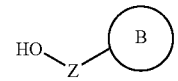

(III)

wherein each symbol has the same meanings as defined above, a salt thereof or a reactive derivative thereof, and if desired, to deacylation or dealkylation;

[12] a method of preparing the compound as described in [1], which comprises subjecting a compound represented by the formula:

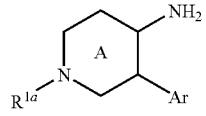

(IIb)

wherein each symbol has the same meanings as defined above, or a salt thereof to a reaction with a compound represented by the formula:

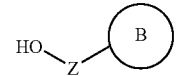

(III)

wherein each symbol has the same meanings as defined above, a salt thereof or a reactive derivative thereof, or subjecting Compound (IIb) to a reaction with a compound represented by the formula:

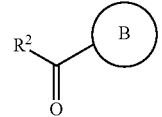

(IV)

wherein R$^2$ is a hydrogen atom or an optionally substituted hydrocarbon group, and Ring B has the same meaning as defined above, in the presence of a reducing agent, and if desired, to deacylation or dealkylation;

[13] a method of preparing optically active alcohol represented by the formula:

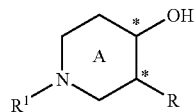

(IIc)

wherein R is an optionally substituted hydrocarbon group or an optionally substituted heterocyclic group, * is a chiral center, and other symbols have the same meanings as defined above. OH and R have a cis configuration relationship, or a salt thereof, which comprises subjecting a compound represented by the formula:

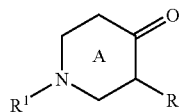

(V)

wherein each symbol has the same meanings as defined above, or a salt thereof to hydrogenation, in the presence of an optically active ruthenium-phosphine-amine complex and a base;

[14] a method of preparing optically active amine represented by the formula:

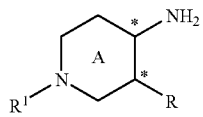

(IId)

wherein * is a chiral center and other symbols have the same meanings as defined above, $NH_2$ and R have a cis configuration relationship, or a salt thereof, which comprises subjecting a compound represented by the formula:

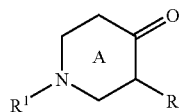

(V)

wherein each symbol has the same meanings as defined above, or a salt thereof, to condensation with an optically active compound represented by the formula:

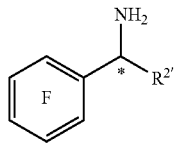

(VI)

wherein Ring F is an optionally substituted, optionally fused benzene ring and $R^{2'}$ is an optionally substituted hydrocarbon group, and other symbols have the same meanings as defined above, or a salt thereof, followed by hydrogenation and further hydrogenolysis;

[15] a medicament comprising the compound as described in [1] or a prodrug thereof;

[16] the medicament as described in [15], which is a tachykinin receptor antagonist;

[17] the medicament as described in [15], which is an agent for preventing and/or treating abnormality of lower urinary tract function, digestive organ diseases, inflammatory or allergic diseases, arthropathy and/or osteopathy, respiratory diseases, infection, cancer, central nerve diseases, circulatory diseases, pain, autoimmune diseases, hepatic diseases, pancreatic diseases, renal diseases, metabolic diseases, endocrine diseases, graft rejection, abnormality in characteristic of blood and/or blood components, gynecologic diseases, dermatic diseases, ophthalmic diseases, otolaryngological diseases, diseases due to environmental and/or occupational factors, ataxia or chronic fatigue syndrome;

[18] the medicament as described in [15], which is an agent for preventing and/or treating urinary frequency and/or urinary incontinence;

[19] a method of preventing and/or treating abnormality of lower urinary tract function, digestive organ diseases, inflammatory or allergic diseases, arthropathy and/or osteopathy, respiratory diseases, infection, cancer, central nerve diseases, circulatory diseases, pain, autoimmune diseases, hepatic diseases, pancreatic diseases, renal diseases, metabolic diseases, endocrine diseases, graft rejection, abnormality in characteristic of blood and/or blood components, gynecologic diseases, dermatic diseases, ophthalmic diseases, otolaryngological diseases, diseases due to environmental and/or occupational factors, ataxia or chronic fatigue syndrome, which comprises administering an effective amount of the compound as described in [1] or a prodrug thereof to a mammal; and

[20] use of the compound as described in [1] or a prodrug thereof for manufacturing an agent for preventing and/or treating abnormality of lower urinary tract function, digestive organ diseases, inflammatory or allergic diseases, arthropathy and/or osteopathy, respiratory diseases, infection, cancer, central nerve diseases, circulatory diseases, pain, autoimmune diseases, hepatic diseases, pancreatic diseases, renal diseases, metabolic diseases, endocrine diseases, graft rejection, abnormality in characteristic of blood and/or blood components, gynecologic diseases, dermatic diseases, ophthalmic diseases, otolaryngological diseases, diseases due to environmental and/or occupational factors, ataxia or chronic fatigue syndrome.

Ar is an aryl group, an aralkyl group or an aromatic heterocyclic group, each of which may be substituted.

The "aryl group" includes, for example, a $C_{6-14}$ aryl group such as phenyl, naphthyl, anthryl, phenanthryl, etc., preferably, phenyl.

The "aralkyl group" includes, for example, a $C_{7-19}$ aralkyl group such as benzyl, naphthylethyl, benzhydryl, trityl, etc., preferably, benzyl or benzhydryl.

The aromatic heterocyclic group includes, for example, a 5- or 6-membered aromatic heterocyclic group having 1 to 4 hetero atoms of one or two kinds selected from a nitrogen atom, an oxygen atom and a sulfur atom in addition to carbon atoms (e.g., furyl, thienyl, pyridyl, imidazolyl, thiazolyl, oxazolyl, thiadiazolyl, triazolyl, tetrazolyl, etc.) and the like.

The substituent in the "aryl group", the "aralkyl group" and the "aromatic heterocyclic group" includes, for example, 1 to 3 substituents selected from (1) a halogen atom (e.g., fluorine, chlorine, bromine, iodine, etc.), (2) $C_{1-3}$ alkylenedioxy (e.g., methylenedioxy, ethylenedioxy, etc.), (3) nitro, (4) cyano, (5) optionally halogenated $C_{1-6}$ alkyl, (6) optionally halogenated $C_{2-6}$ alkenyl, (7) optionally halogenated $C_{2-6}$ alkynyl, (8) optionally halogenated $C_{3-6}$ cycloalkyl, (9) $C_{6-14}$ aryl (e.g., phenyl, 1-naphthyl, 2-naphthyl, biphenylyl, 2-anthryl, etc.), (10) optionally halogenated $C_{1-6}$ alkoxy, (11) optionally halogenated $C_{1-6}$ alkylthio or mercapto, (12) hydroxy, (13) amino,

(14) mono-$C_{1-6}$ alkylamino (e.g., methylamino, ethylamino, etc.), (15) mono-$C_{6-14}$ arylamino (e.g., phenylamino, 1-naphthylamino, 2-napthylamino, etc.), (16) di-$C_{1-6}$ alkylamino (e.g., dimethylamino, diethylamino, etc.), (17) di-$C_{6-14}$ arylamino (e.g., diphenylamino, etc.), (18) acyl, (19) acylamino, (20) acyloxy, (21) optionally substituted 5- to 7-membered saturated cyclic amino, (22) a 5- to 10-membered aromatic heterocyclic group (e.g., 2- or 3-thienyl, 2-,3- or 4-pyridyl, 2-, 3-, 4-, 5- or 8-quinolyl, 1-, 3-, 4- or 5-isoquinolyl, 1-, 2- or 3-indolyl, 2-benzothiazolyl, 2-benzo[b]thienyl, benzo[b]furanyl, etc.), (23) sulfo, (24) $C_{6-14}$ aryloxy (e.g., phenyloxy, naphthyloxy, etc.) and the like.

The "optionally halogenated $C_{1-6}$ alkyl" includes, for example, $C_{1-6}$ alkyl (e.g., methyl, ethyl, propyl, isopropyl, butyl, isobutyl, sec-butyl, tert-butyl, pentyl, hexyl, etc.), optionally having 1 to 5, preferably 1 to 3 halogen atoms (e.g., fluorine, chlorine, bromine, iodine, etc.) and the like, specifically, methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, etc.

The "optionally halogenated $C_{2-6}$ alkenyl" includes, for example, $C_{2-6}$ alkenyl (e.g., vinyl, allyl, isopropenyl, butenyl, isobutenyl, sec-butenyl, etc.) optionally having 1 to 5, preferably 1 to 3 halogen atoms (e.g., fluorine, chlorine, bromine, iodine, etc.) and the like, specifically, vinyl, allyl, isopropenyl, butenyl, isobutenyl, sec-butenyl, 3,3,3-trifluoro-1-propenyl, 4,4,4-trifluoro-1-butenyl, etc.

The "optionally halogenated $C_{2-6}$ alkynyl" includes, for example, $C_{2-6}$ alkynyl (e.g., ethynyl, propargyl, butynyl, 1-hexynyl, etc.) optionally having 1 to 5, preferably 1 to 3 halogen atoms (e.g., fluorine, chlorine, bromine, iodine, etc.) and the like, specifically, ethynyl, propargyl, butynyl, 1-hexynyl, 3,3,3-trifluoro-1-propynyl, 4,4,4-trifluoro-1-butynyl, etc.

The "optionally halogenated $C_{3-6}$ cycloalkyl" includes, for example, $C_{3-6}$ cycloalkyl (e.g., cyclopropyl, cyclobutyl, cyclopentyl, cyclohexyl, etc.) optionally having 1 to 5, preferably 1 to 3 halogen atoms (e.g., fluorine, chlorine, bromine, iodine, etc.) and the like, specifically, cyclopropyl, cyclobutyl, cyclopentyl, cyclohexyl, 4,4-dichlorocyclohexyl, 2,2,3,3-tetrafluorocyclopentyl, 4-chlorocyclohexyl, etc.

The "optionally halogenated $C_{1-6}$ alkoxy" includes, for example, $C_{1-6}$ alkoxy (e.g., methoxy, ethoxy, propoxy, isopropoxy, butoxy, isobutoxy, sec-butoxy, pentyloxy, hexyloxy, etc.) optionally having 1 to 5, preferably 1 to 3 halogen atoms (e.g., fluorine, chlorine, bromine, iodine, etc.) and the like, specifically, methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, etc.

The "optionally halogenated $C_{1-6}$ alkylthio" includes, for example, $C_{1-6}$ alkylthio (e.g., methylthio, ethylthio, propylthio, isopropylthio, butylthio, sec-butylthio, tert-butylthio, etc.) optionally having 1 to 5, preferably 1 to 3 halogen atoms (e.g., fluorine, chlorine, bromine, iodine, etc.) and the like, specifically, methylthio, difluoromethylthio, trifluoromethylthio, ethylthio, propylthio, isopropylthio, butylthio, 4,4,4-trifluorobutylthio, pentylthio, hexylthio, etc.

The "acyl" includes, for example, —(C=O)—$R^3$, —(C=S)—$R^3$, —$SO_2$—$R^3$, —SO—$R^3$, —(P=O) (O$R^4$)(O$R^{4'}$) ($R^3$ is a hydrogen atom, an optionally substituted hydrocarbon group, an optionally substituted amino group, an optionally substituted hydroxy group or an optionally substituted heterocyclic group, and $R^4$ and $R^{4'}$ are the same or different and represents a hydrogen atom or an optionally substituted hydrocarbon group) and the like.

The "optionally substituted hydrocarbon group" represented by $R^3$, $R^4$ and $R^{4'}$ includes, for example, the same group as those referred to herein for the "optionally substituted hydrocarbon group" represented by $R^1$ which will be described below.

The "substituent" in the "optionally substituted amino group" represented by $R^3$ includes, for example, an optionally substituted hydrocarbon group, an optionally substituted hydroxy group, an acyl group and the like.

The "optionally substituted hydrocarbon group" as the "substituent" in the "optionally substituted amino group" represented by $R^3$ includes, for example, the same group as those referred to herein for the "optionally substituted hydrocarbon group" represented by $R^1$ which will be described below.

The "optionally substituted hydroxy group" as the "substituent" in the "optionally substituted amino group" represented by $R^3$ includes, for example, (i) a hydroxy group, (ii) a $C_{1-6}$ alkoxy group (e.g., a methoxy group, an ethoxy group, a propoxy group, an isopropoxy group, a butoxy group, a t-butoxy group, etc.), (iii) a $C_{6-14}$ aryloxy group (e.g., a phenyloxy group, a naphthyloxy group, etc.), (iv) a $C_{1-6}$ alkyl-carbonyloxy group (e.g., a formyloxy group, an acetoxy group, a propionyloxy group, etc.) and (v) a $C_{6-14}$ aryl-carbonyloxy group (e.g., a benzyloxy group, a naphthyl-carbonyloxy group, etc.) and the like, and preferably, a hydroxy group and a $C_{1-6}$ alkoxy group (e.g., a methoxy group, an ethoxy group, a propoxy group, an isopropoxy group, etc.).

The "acyl group" as the "substituent" in the "optionally substituted amino group" represented by $R^3$ includes, for example, —(C=O)—R", —(C=S)—R", —$SO_2$—R", —SO—R", —(C=O)NR"R"', —(C=O)O—R", —(C=S)O—R", —(C=S)NR"R"' (R" is a hydrogen atom or an optionally substituted hydrocarbon group, R"' is a hydrogen atom or lower alkyl group (e.g., a $C_{1-6}$ alkyl group such as methyl, ethyl, propyl, isopropyl, butyl, isobutyl, sec-butyl, tert-butyl, pentyl, hexyl, etc., and particularly preferably a $C_{1-3}$ alkyl group such as methyl, ethyl, propyl, isopropyl, etc.) and the like.

The "optionally substituted hydrocarbon group" represented by R" includes, for example, the same group as those referred to herein for the "optionally substituted hydrocarbon group" represented by $R^1$ which will be described below.

The "$C_{1-6}$ alkoxy group," the "$C_{6-14}$ aryloxy group," the "$C_{1-6}$ alkyl-carbonyloxy group" and the "$C_{6-14}$ aryl-carbonyloxy group" exemplified as "the optionally substituted hydroxy group" as the "substituent" in the "optionally substituted amino group" represented by $R^3$, may be optionally further substituted with the same group as those referred to herein for the "substituent" in the "optionally substituted hydrocarbon group" represented by $R^1$ which will be described below and the like, and such substituent is preferably a halogen atom (e.g., fluorine, chlorine, bromine, etc.) and the like.

The "optionally substituted amino group" represented by $R^3$ may form a cyclic amino group (e.g., a 5- to 9-membered cyclic amino group having 1 to 3 hetero atoms such as an oxygen atom, a sulfur atom, etc. in addition to a nitrogen atom (e.g., a pyrrolidino group, a piperidino group, a morpholino group, etc.) and the like.

The "optionally substituted hydroxy group" represented by $R^3$ includes, for example, the same group as those referred to herein for the "the optionally substituted hydroxy group" as the "substituent" in the "optionally substituted amino group" represented by $R^3$, and the like.

The "optionally substituted heterocyclic group" represented by $R^3$ includes, for example, the same group as those referred to herein for the "optionally substituted heterocyclic group" represented by $R^1$ which will be described below.

The "acylamino" as described above includes, for example, formylamino, $C_{1-6}$ alkyl-carbonylamino (e.g., acetylamino, etc.), $C_{6-14}$ aryl-carbonylamino (e.g., phenylcarbonylamino, naphthylcarbonylamino, etc.), $C_{1-6}$ alkoxy-carbonylamino (e.g., methoxycarbonylamino, ethoxycarbonylamino, propoxycarbonyl amino, butoxycarbonylamino, etc.), $C_{1-6}$ alkylsulfonylamino (e.g., methylsulfonylammo, ethylsulfonylamino, etc.), $C_{6-14}$ arylsulfonylamino (e.g., phenylsulfonylamino, 2-naphthylsulfonylamino, 1-naphthylsulfonylamino, etc.) and the like.

The "acyloxy" as described above includes, for example, $C_{1-6}$ alkyl-carbonyloxy (e.g., acetoxy, propionyloxy, etc.), $C_{6-14}$ aryl-carbonyloxy (e.g., benzoyloxy, naphthylcarbonyloxy, etc.), $C_{1-6}$ alkoxy-carbonyloxy (e.g., methoxycarbonyloxy, ethoxycarbonyloxy, propoxycarbonyloxy, butoxycarbonyloxy, etc.), mono-$C_{1-6}$ alkyl-carbamoyloxy (e.g., methylcarbamoyloxy, ethylcarbamoyloxy, etc.), di-$C_{1-6}$ alkyl-carbamoyloxy (e.g., dimethylcarbamoyloxy, diethylcarbamoyloxy, etc.), $C_{6-14}$ aryl-carbamoyloxy (e.g., phenylcarbamoyloxy, naphthylcarbamoyloxy, etc.), nicotinoyloxy, etc.

The "5- to 7-membered saturated cyclic amino" in the "optionally substituted 5- to 7-membered saturated cyclic amino" includes, for example, morpholino, thiomorpholino, piperazin-1-yl, piperidino, pyrrolidin-1-yl, etc. The "substituent" in the "optionally substituted 5- to 7-membered saturated cyclic amino" includes, for example, $C_{1-6}$ alkyl (e.g., methyl, ethyl, propyl, isopropyl, butyl, isobutyl, sec-butyl, tert-butyl, pentyl, hexyl, etc.), $C_{6-14}$ aryl (e.g., phenyl, 1-naphthyl, 2-naphthyl, biphenylyl, 2-anthryl, etc.), a 5- to 10-membered aromatic heterocyclic group (e.g., 2- or 3-thienyl, 2-, 3- or 4-pyridyl, 2-, 3-, 4-, 5- or 8-quinolyl, 1-, 3-, 4- or 5-isoquinolyl, 1-, 2- or 3-indolyl, 2-benzothiazolyl, 2-benzo[b]thienyl, benzo[b]furanyl, etc.) and the like. The number of the substituents is 1 to 3.

Ar is preferably a phenyl group, a benzhydryl group or a benzyl group, each of which may be substituted, and more preferably a phenyl group or a benzhydryl group, each of which may be substituted.

The "substituent" is preferably 1 to 4 (preferably 1 or 2) substituents selected from (A) a halogen atom (a chlorine atom, a fluorine atom, etc.), (B) a $C_{1-6}$ alkyl group, and (C) a heterocyclic group (a 5- or 6-membered aromatic heterocyclic group (pyridyl, etc.) having 1 to 4 hetero atoms of one or two kinds selected from a nitrogen atom, an oxygen atom and a sulfur atom in addition to carbon atoms and the like.

Ar is most preferably a phenyl group.

$R^1$ is a hydrogen atom, an optionally substituted hydrocarbon group, an acyl group or an optionally substituted heterocyclic group.

The "hydrocarbon group" in the "optionally substituted hydrocarbon group" represented by $R^1$ includes, for example, an aliphatic hydrocarbon group, a monocyclic saturated hydrocarbon group, an aromatic hydrocarbon group, etc., preferably having carbon number 1 to 16, and specifically, for example, an alkyl group, an alkenyl group, an alkynyl group, a cycloalkyl group, an aryl group, etc.

The "alkyl group" is preferably, for example, a lower alkyl group, etc., for example, a $C_{1-6}$ alkyl group such as methyl, ethyl, propyl, isopropyl, butyl, isobutyl, sec-butyl, tert-butyl, pentyl, hexyl, etc.

The "alkenyl group" is preferably, for example, a lower alkenyl group, etc., for example, a $C_{2-6}$ alkenyl group such as vinyl, 1-propenyl, allyl, isopropenyl, butenyl, isobutenyl, etc.

The "alkynyl group" is preferably, for example, a lower alkynyl group, etc., for example, a $C_{2-6}$ alkynyl group such as ethynyl, propargyl, 1-propynyl, etc.

The "cycloalkyl group" is preferably, for example, a lower cycloalkyl group, etc., for example, a $C_{3-6}$ cycloalkyl group such as cyclopropyl, cyclobutyl, cyclopentyl, cyclohexyl, etc.

The "aryl group" is preferably, for example, a $C_{6-14}$ aryl group such as phenyl, 1-naphthyl, 2-naphthyl, biphenylyl, 2-anthryl, etc., specifically, a phenyl group, etc.

The substituent that the "hydrocarbon group" in the "optionally substituted hydrocarbon group" represented by $R^1$ may have includes, for example, a halogen atom (e.g., fluorine, chlorine, bromine, iodine, etc.), a nitro group, a cyano group, a hydroxy group, an optionally halogenated lower alkyl group (e.g., an optionally halogenated $C_{1-6}$ alkyl group such as methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, isobutyl, sec-butyl, tert-butyl, 4,4,4-trifluorobutyl, pentyl, isopentyl, neopentyl, 5,5,5-trifluoropentyl, hexyl, 6,6,6-trifluorohexyl, etc.), a lower alkoxy group (e.g., a $C_{1-6}$ alkoxy group such as methoxy, ethoxy, propoxy, isopropoxy, butoxy, isobutoxy, pentyloxy and hexyloxy, etc.), an amino group, a mono-lower alkylamino group (e.g., a mono-$C_{1-6}$ alkylamino group such as methylamino and ethylamino, etc.), a di-lower alkylamino group (e.g., a di-$C_{1-6}$alkylamino group such as dimethylamino and diethylamino, etc.), a carboxyl group, a lower alkylcarbonyl group (e.g., a $C_{1-6}$ alkylcarbonyl group such as acetyl, propionyl, etc.), a lower alkoxycarbonyl group (e.g., a $C_{1-6}$ alkoxy-carbonyl group such as methoxycarbonyl, ethoxycarbonyl, propoxycarbonyl, butoxycarbonyl, etc.), a carbamoyl group, a thiocarbamoyl group, a mono-lower alkylcarbamoyl group (e.g., mono-$C_{1-6}$ alkyl-carbamoyl group such as methylcarbamoyl, ethylcarbamoyl, etc.), a di-lower alkylcarbamoyl group (e.g., a di-$C_{1-6}$ alkylcarbamoyl group such as dimethylcarbamoyl, diethylcarbamoyl, etc.), an arylcarbamoyl group (e.g., a $C_{6-10}$ arylcarbamoyl group such as phenylcarbamoyl, naphthylcarbamoyl, etc.), an aryl group (e.g., a $C_{6-10}$ aryl group such as phenyl, naphthyl, etc.), an aryloxy group (e.g., a $C_{6-10}$ aryloxy group such as phenyloxy and naphthyloxy, etc.), an optionally halogenated lower alkylcarbonylamino group (e.g., an optionally halogenated $C_{1-6}$ alkyl-carbonylamino group such as acetylamino and trifluoroacetylamino, etc.), an oxo group, a 5- or 6-membered heterocyclic group, etc. The "hydrocarbon group" in the "optionally substituted hydrocarbon group" may have 1 to 5, preferably 1 to 3 of the substituents at the substitutable positions of the hydrocarbon group. If the number of the substituents is 2 or more, the substituents may be the same or different.

The "5- or 6-membered heterocyclic group" represented as the "substituent" in the "optionally substituted hydrocarbon group" represented by $R^1$, includes, for example, a 5- or 6-membered aromatic heterocyclic group, a saturated or non-saturated 5- or 6-membered non-aromatic heterocyclic group, etc. having 1 to 4 hetero atoms of one or two kinds selected from a nitrogen atom, an oxygen atom and a sulfur atom in addition to carbon atoms.

The "5- or 6-membered aromatic heterocyclic group" includes, for example, furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2, 3-triazolyl, 1,2,4-triazolyl, tetrazolyl, pyridyl, pyridazinyl, pyrimidinyl, pyrazinyl, triazinyl and the like.

The above-mentioned "5- or 6-membered non-aromatic heterocyclic group" includes, for example, pyrrolidinyl, tetrahydrofuryl, tetrahydrothienyl, piperidyl, tetrahydropyranyl, morpholinyl, thiomorpholinyl, piperazinyl and the like.

Such non-aromatic heterocyclic group may be further fused with other aromatic and/or non-aromatic homocyclic ring or heterocyclic ring.

The "5- or 6-membered heterocyclic group" may have substituent such as an oxo group, etc.

The "acyl group" represented by $R^1$ includes, for example, the same group as those referred to herein above for the foregoing "acyl" as the substituent of the "aryl group", the "aralkyl group" and the "aromatic heterocyclic group" represented by Ar.

The "heterocyclic group" in the "optionally substituted heterocyclic group" represented by $R^1$ includes, for example, a 5- to 14-membered (preferably 5- to 10-membered) (monocyclic to tricyclic, preferably, monocyclic or dicyclic) heterocyclic group containing 1 to 4 (preferably 1 to 3) hetero atoms of one or two kinds selected from a nitrogen atom, an oxygen atom and a sulfur atom in addition to carbon atoms, etc. For example, it includes a 5-membered cyclic group containing 1 to 4 hetero atoms selected from an oxygen atom, a sulfur atom and a nitrogen atom in addition to carbon atoms, such as 2- or 3-thienyl, 2- or 3-furyl, 1-, 2- or 3-pyrrolyl, 1-, 2- or 3-pyrrolidinyl, 2-, 4- or 5-oxazolyl, 3-, 4- or 5-isoxazolyl, 2-, 4- or 5-thiazolyl, 3-, 4- or 5-isothiazolyl, 3-, 4- or 5-pyrazolyl, 2-, 3- or 4-pyrazolidinyl, 2-, 4- or 5-imidazolyl, 1,2,3-triazolyl, 1,2,4-triazolyl and 1H- or 2H-tetrazolyl, a 6-membered cyclic group containing 1 to 4 hetero atoms selected from an oxygen atom, a sulfur atom and a nitrogen atom in addition to carbon atoms, such as 2-, 3- or 4-pyridyl, 2-, 3- or 4-pyridyl N-oxide, 2-, 4- or 5-pyrimidinyl, 2-, 4- or 5-pyrimidinyl N-oxide, thiomorpholinyl, morpholinyl, piperidino, 2-, 3- or 4-piperidyl, thiopyranyl, 1,4-oxazinyl, 1,4-thiazinyl, 1,3-thiazinyl, piperazinyl, triazinyl, 3- or 4-pyridazinyl, pyrazinyl and 3- or 4-pyridazinyl N-oxide, a dicyclic or tricyclic fused cyclic group containing 1 to 4 hetero atoms selected from an oxygen atom, a sulfur atom and a nitrogen atom in addition to carbon atoms, such as indolyl, benzofuryl, benzothiazolyl, benzoxazolyl, benzimidazolyl, quinolyl, isoquinolyl, phthalazinyl, quinoxalinyl, quinoxalinyl, indolizinyl, quinolizinyl, 1,8-naphthyridinyl, dibenzofuranyl, carbazolyl, acridinyl, phenanthridinyl, chromanyl, phenothiazinyl and phenoxazinyl (preferably, a group formed by the fusion of the above-mentioned 5- or 6-membered ring to one or two 5- or 6-membered cyclic groups optionally having 1 to 4 hetero atoms selected from an oxygen atom, a sulfur atom and a nitrogen atom in addition to carbon atoms). Among these, a 5- to 7-membered (preferably 5- or 6-membered) heterocyclic group containing 1 to 3 hetero atoms selected from an oxygen atom, a sulfur atom and a nitrogen atom in addition to carbon atoms is preferred.

The substituent that the "heterocyclic group" in the "optionally substituted heterocyclic group" may have, includes, for example, a halogen atom (e.g., fluorine, chlorine, bromine, iodine, etc.), a lower alkyl group (e.g., a $C_{1-6}$ alkyl group such as methyl, ethyl, propyl, isopropyl, butyl, isobutyl, sec-butyl, tert-butyl, pentyl, hexyl, etc.), a cycloalkyl group (e.g., a $C_{3-6}$ cycloalkyl group such as cyclopropyl, cyclobutyl, cyclopentyl, cyclohexyl, etc.), a lower alkynyl group (e.g., a $C_{2-6}$ alkynyl group such as ethynyl, 1-propynyl, propargyl, etc.), a lower alkenyl group (e.g., a $C_{2-6}$ alkenyl group such as vinyl, allyl, isopropenyl, butenyl, isobutenyl, etc.), an aralkyl group (e.g., a $C_{7-11}$ aralkyl group such as benzyl, α-methylbenzyl, phenethyl, etc.), an aryl group (e.g., a $C_{6-10}$ aryl group such as phenyl, naphthyl, etc., preferably, a phenyl group, etc.), a lower alkoxy group (e.g., a $C_{1-6}$ alkoxy group such as methoxy, ethoxy, propoxy, isopropoxy, butoxy, isobutoxy, sec-butoxy, tert-butoxy, etc.), an aryloxy group (e.g., a $C_{6-10}$ aryloxy group such as phenoxy, etc.), a lower alkanoyl group (e.g., formyl; a $C_{1-6}$ alkyl-carbonyl group such as acetyl, propionyl, butyryl, isobutyryl, etc.), arylcarbonyl (e.g., a $C_{6-10}$ arylcarbonyl group such as a benzoyl group, a naphthoyl group, etc.), a lower alkanoyloxy group (e.g., formyloxy; a $C_{1-6}$ alkyl-carbonyloxy group such as acetyloxy, propionyloxy, butyryloxy, isobutyryloxy, etc.), an arylcarbonyloxy group (e.g., a $C_{6-10}$ aryl-carbonyloxy group such as benzoyloxy, naphthoyloxy, etc.), a carboxyl group, a lower alkoxycarbonyl group (e.g., a $C_{1-6}$ alkoxycarbonyl group such as methoxycarbonyl, ethoxycarbonyl, propoxycarbonyl, isopropoxycarbonyl, butoxycarbonyl, isobutoxycarbonyl, tert-butoxycarbonyl, etc.), aralkyloxycarbonyl (e.g., a $C_{7-11}$ aralkyloxycarbonyl group such as benzyloxycarbonyl, etc.), a carbamoyl group, a mono-, di- or tri-halogeno-lower alkyl group (e.g., a mono-, di- or tri-halogeno-$C_{1-4}$ alkyl group such as chloromethyl, dichloromethyl, trifluoromethyl, 2,2,2-trifluoroethyl, etc.), an oxo group, an amidino group, an imino group, an amino group, a mono-lower alkylamino group (e.g., a mono-$C_{1-4}$ alkylamino group such as methylamino, ethylamino, propylamino, isopropylamino, butylamino, etc.), a di-lower alkylamino group (e.g., a di-$C_{1-4}$ alkylamino group such as dimethylamino, diethylamino, dipropylamino, diisopropylamino, dibutylamino, methylethylamino, etc.), a 3- to 6-membered cyclic amino group which may contain 1 to 3 hetero atoms selected from an oxygen atom, a sulfur atom and a nitrogen atom in addition to carbon atoms and one nitrogen atom (e.g., a 3- to 6-membered cyclic amino group such as aziridinyl, azetidinyl, pyrrolidinyl, pyrrolinyl, pyrrolyl, imidazolyl, pyrazolyl, imidazolidinyl, piperidyl, morpholinyl, dihydropyridyl, pyridyl, N-methylpiperazinyl, N-ethylpiperazinyl, etc.), an alkylenedioxy group (e.g., a $C_{1-3}$ alkylenedioxy group such as methylenedioxy, ethylenedioxy, etc.), a hydroxy group, a nitro group, a cyano group, a mercapto group, a sulfo group, a sulfino group, a phosphono group, a sulfamoyl group, a monoalkylsulfamoyl group (e.g., a mono-$C_{1-6}$ alkylsulfamoyl group such as N-methylsulfamoyl, N-ethylsulfamoyl, N-propylsulfamoyl, N-isopropylsulfamoyl, N-butylsulfamoyl, etc.), a dialkylsulfamoyl group (e.g., a di-$C_{1-6}$ alkylsulfamoyl group such as N,N-dimethylsulfamoyl, N,N-diethylsulfamoyl, N,N-dipropylsulfamoyl, N,N-dibutylsulfamoyl, etc.), an alkylthio group (e.g., a $C_{1-6}$ alkylthio group such as methylthio, ethylthio, propylthio, isopropylthio, butylthio, sec-butylthio, tert-butylthio, etc.), an arylthio group (e.g., a $C_{6-10}$ arylthio group such as phenylthio, naphthylthio, etc.), a lower alkylsulfinyl group (e.g., a $C_{1-6}$ alkylsulfinyl group such as methylsulfinyl, ethylsulfinyl, propylsulfinyl, butylsulfinyl, etc.), an arylsulfinyl group (e.g., a $C_{6-10}$ arylsulfinyl group such as phenylsulfinyl, naphthylsulfinyl, etc.), a lower alkylsulfonyl group (e.g., a $C_{1-6}$ alkylsulfonyl group such as methylsulfonyl, ethylsulfonyl, propylsulfonyl, butylsulfonyl, etc.), an arylsulfonyl group (e.g., a $C_{6-10}$ arylsulfonyl group such as phenylsulfonyl, naphthylsulfonyl, etc.) and the like.

The "heterocyclic group" in the "optionally substituted heterocyclic group" may have 1 to 5, preferably 1 to 3 of the above-mentioned substituents at the substitutable positions of the heterocyclic group. If the number of the substituents is 2 or more, the substituents may be the same or different.

$R^1$ is preferably (1) a hydrogen atom,
(2) a hydrocarbon group (a $C_{1-6}$ alkyl group, $C_{7-19}$ aralkyl group (a benzyl group, etc.) or a $C_{6-14}$ aryl group (a phenyl group, etc.) optionally having 1 to 3 substituents selected from (i) a $C_{1-6}$ alkoxy group, (ii) a $C_{1-6}$ alkoxy-carbonyl group, (iii) a carbamoyl group, (iv) a cyano group, (v) a $C_{1-6}$ alkylthio group, or (vi) a heterocyclic group optionally substituted with 1 or 2 oxo groups and optionally fused with a benzene ring (e.g., a 5- or 6-membered aromatic heterocyclic group containing 1 to 4 hetero atoms of one or two kinds selected from a nitrogen atom, an oxygen atom and a sulfur atom in addition to carbon atoms, such as triazolyl, etc., optionally substituted with 1 or 2 oxo groups, and further optionally fused with a benzene ring, (3) an acyl group represented by the formula: —(C=O)—Ra, —(C=S)—Ra, —SO$_2$—Ra, —SO$_2$—NRaRa', —(C=O)NRaRa' or —(C=O)O—Ra wherein Ra is (A) a hydrogen atom or (B) (a) a hydrocarbon group (a $C_{1-6}$ alkyl group, a $C_{2-6}$ alkenyl group, a $C_{2-6}$ alkynyl group, $C_{3-6}$ cycloalkyl, a $C_{7-19}$ aralkyl group (benzyl, 2-phenylethyl, etc.) or a $C_{6-14}$ aryl group (a phenyl group optionally fused with a 5- or 6-membered aromatic heterocyclic ring, etc.), or (b) a heterocyclic group (e.g., a 5- or 6-membered aromatic or 4- to 6-membered non-aromatic heterocyclic group having 1 to 4 hetero atoms of one or two kinds selected from a nitrogen atom, an oxygen atom and a sulfur atom in addition to carbon atoms), each of which optionally has 1 to 2 substituents selected from (i) a halogen atom, (ii) a $C_{1-6}$ alkyl group optionally substituted with a heterocyclic group (e.g., a 5- or 6-membered aromatic or non-aromatic heterocyclic group having 1 to 4 hetero atoms of one or two kinds selected from a nitrogen atom, an oxygen atom and a sulfur atom in addition to carbon atoms), $C_{1-6}$ alkanoyl or $C_{6-14}$ aryl-carbonyl, (iii) a $C_{1-6}$ alkoxy group, (iv) an amino group, (v) a mono- or di-$C_{1-6}$ alkylamino group, (vi) a $C_{1-6}$ alkanoylamino group, (vii) a N—$C_{1-6}$ alkyl-N'—$C_{1-6}$ alkanoylamino group, (viii) a $C_{1-6}$ alkoxy-carbonyl group, (ix) a $C_{1-6}$ alkanoyl group optionally substituted with $C_{1-6}$ alkoxy, mono- or di-$C_{1-6}$ alkylamino, halogeno $C_{1-6}$ alkyl or a halogen atom, (x) a $C_{6-14}$ aryl-carbonyl group, (xi) a $C_{7-19}$ aralkyl-carbonyl group, (xii) a $C_{3-6}$ cycloalkyl-carbonyl group, (xiii) a heterocyclic-carbonyl group (e.g., a 5- or 6-membered aromatic or non-aromatic heterocyclic-carbonyl group having 1 to 4 hetero atoms of one or two kinds selected from a nitrogen atom, an oxygen atom and a sulfur atom in addition to carbon atoms), (xiv) a hydroxy group, (xv) a $C_{7-19}$ aralkyloxy group, (xvi) a $C_{3-6}$ cycloalkyloxy group, (xvii) a $C_{1-6}$ alkoxy-$C_{1-6}$ alkoxy group, (xviii) a carbamoyl group, (xix) a mono- or di-$C_{1-6}$ alkylcarbamoyl group, (xx) a $C_{1-6}$ alkylsulfonyl group, (xxi) a mono- or di-$C_{1-6}$ alkylaminosulfonyl group, (xxii) a formyl group, (xxiii) a formylamino group, (xxiv) an oxo group, and (xxv) a heterocyclic group (e.g., a 5- or 6-membered aromatic or non-aromatic heterocyclic group having 1 to 4 hetero atoms of one or two kinds selected from a nitrogen atom, an oxygen atom and a sulfur atom in addition to carbon atoms) optionally having 1 or 2 substituents selected from $C_{1-6}$ alkanoyl and $C_{1-6}$ alkoxy-$C_{1-6}$ alkanoyl, and Ra' is a hydrogen atom or a $C_{1-6}$ alkyl group, or (4) a heterocyclic group (e.g., a 5- or 6-membered aromatic heterocyclic group having 1 to 4 hetero atoms of one or two kinds selected from a nitrogen atom, an oxygen atom and a sulfur atom in addition to carbon atoms) optionally having 1 or 2 substituents selected from a $C_{1-6}$ alkyl group and an oxo group.

$R^1$ is preferably a hydrogen atom or an acyl group, most preferably, an acyl group represented by the formula: —(C=O)—Rb or —(C=O)NRbRb' [Rb is (1) a hydrocarbon group (e.g., a $C_{1-6}$ alkyl group, etc.) or (2) a heterocyclic group (e.g., a 5- or 6-membered non-aromatic heterocyclic group having 1 to 4 hetero atoms of one or two kinds selected from a nitrogen atom, an oxygen atom and a sulfur atom in addition to carbon atoms, such as piperidyl, etc.), each of which optionally has a substituent selected from (i) hydroxy, (ii) $C_{1-6}$ alkoxy, (iii) $C_{1-6}$ alkanoyl, (iv) $C_{1-6}$ alkylsulfonyl, (v) amino, (vi) mono- or di-$C_{1-6}$ alkylamino, (vii) $C_{1-6}$ alkanoylamino or (viii) a heterocyclic group optionally substituted with 1 or 2 oxo groups (e.g., a 5- or 6-membered aromatic or non-aromatic heterocyclic group containing 1 to 4 hetero atoms of one or two kinds selected from a nitrogen atom, an oxygen atom and a sulfur atom in addition to carbon atoms such as tetrazolyl, pyrrolidinyl, etc., and optionally substituted with 1 or 2 oxo groups), and Rb is a hydrogen atom or a $C_{1-6}$ alkyl group].

X is an oxygen atom or an optionally substituted imino group.

The "substituent" in the "optionally substituted an imino group" represented by X is preferably an optionally substituted hydrocarbon group or an acyl group.

The "optionally substituted hydrocarbon group" includes, for example, the same group as those referred to herein above for the foregoing "optionally substituted hydrocarbon group" represented by $R^1$.

The "acyl group" includes, for example, the same group as those referred to herein above for the foregoing "acyl" as the substituent of the "aryl group", the "aralkyl group" and the "aromatic heterocyclic group" represented by Ar.

X is preferably O or NH.

Z is an optionally substituted methylene group.

The "substituent" in the "optionally substituted methylene group" represented by Z includes, for example, 1 or 2 substituents selected from an optionally substituted hydrocarbon group and an acyl group, or an oxo group.

The "optionally substituted hydrocarbon group" includes, for example, the same group as those referred to herein above for the foregoing "optionally substituted hydrocarbon group" represented by $R^1$.

The "acyl group" includes, for example, the same group as those referred to herein above for the foregoing "acyl" as the substituent of the "aryl group", the "aralkyl group" and the "aromatic heterocyclic group" represented by Ar.

Z is preferably a methylene group optionally substituted with any one of (i) an optionally substituted lower alkyl group or (ii) an oxo group. In other words, in the formula (I), it is preferable that

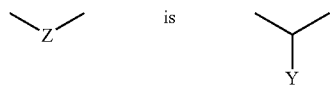

[Y is a hydrogen atom, an optionally substituted lower alkyl group or an oxo group].

The "lower alkyl group" of the "optionally substituted lower alkyl group" represented by Y includes, for example, a $C_{1-6}$ alkyl group such as methyl, ethyl, propyl, isopropyl, butyl, isobutyl, sec-butyl and tert-butyl, pentyl, hexyl, etc.

The "substituent" of the "optionally substituted lower alkyl group" represented by Y, includes, for example, the same group as those referred to herein above for the foregoing "substituent" in the "optionally substituted hydrocarbon group" represented by $R^1$.

Z is preferably a methylene group.

Ring A is an optionally further substituted piperidine ring. In other words, Ring A may further have 1 to 8 substituents in addition to X and Ar.

The "substituent" in the "optionally substituted piperidine ring" includes, for example, the same group as the substituent of the "aryl group", the "aralkyl group" and the "aromatic heterocyclic group" represented by Ar.

Ring A preferably has no substituent in addition to $R^1$, X and Ar.

Ring B is an optionally substituted aromatic ring.

The "aromatic ring" in the "optionally substituted aromatic ring" is preferably the foregoing "aromatic heterocyclic group" represented by Ar, a benzene ring or a fused ring thereof.

The "substituent" in the "optionally substituted aromatic ring" includes, for example, the same group as the substituent of the "aryl group", the "aralkyl group" and the "aromatic heterocyclic group" represented by Ar. The number of substituent is 1 to 5.

Ring B is preferably a benzene ring optionally having 1 or 2 substituents selected from (i) a heterocyclic group (a 5- or 6-membered aromatic heterocyclic group having 1 to 4 hetero atoms of one or two kinds selected from a nitrogen atom, an oxygen atom and a sulfur atom in addition to carbon atoms, etc.) optionally substituted with an optionally halogenated $C_{1-6}$ alkyl group or a $C_{1-6}$ alkylthio group, (ii) an optionally halogenated $C_{1-6}$ alkyl group, (iii) an optionally halogenated $C_{1-6}$ alkoxy group, (iv) a halogen atom (fluorine, chlorine, bromine, etc.), (v) nitro, (vi) a $C_{6-14}$ aryl group optionally substituted with optionally halogenated $C_{1-6}$ alkyl, (vii) an optionally halogenated $C_{1-6}$ alkylamino group, (viii) a cyano group, and (ix) a $C_{3-6}$ cycloalkyloxy, and optionally fused with a non-aromatic heterocyclic ring (a 5- or 6-membered non-aromatic heterocyclic group having 1 to 4 hetero atoms of one or two kinds selected from a nitrogen atom, an oxygen atom and a sulfur atom in addition to carbon atoms, such as furan, etc.) or a benzene ring.

Ring B is more preferably a benzene ring optionally having 1 or 2 substituents selected from (i) a heterocyclic group (e.g., a 5- or 6-membered aromatic heterocyclic group having 1 to 4 hetero atoms of one or two kinds selected from a nitrogen atom, an oxygen atom and a sulfur atom in addition to carbon atoms, such as tetrazolyl, etc.) optionally substituted with an optionally halogenated $C_{1-6}$ alkyl group (trifluoromethyl, etc.), (ii) an optionally halogenated $C_{1-6}$ alkyl group (trifluoromethyl, etc.) and (iii) an optionally halogenated $C_{1-6}$ alkoxy group (trifluoromethoxy, etc.), and optionally fused with a non-aromatic heterocyclic ring (a 5- or 6-membered non-aromatic heterocyclic group having 1 to 4 hetero atoms of one or two kinds selected from a nitrogen atom, an oxygen atom and a sulfur atom in addition to carbon atoms, such as furan, etc.).

Ring B is most preferably a benzene ring substituted with methoxy at 2-position, and with 5-(trifluoromethyl)-1H-tetrazol-1-yl at 5-position, respectively.

In Compound (I), when Z is a methylene group substituted with an oxo group, $R^1$ is not a methyl group, and when Z is a methylene group substituted with a methyl group, Ring B is a substituted aromatic ring.

Preferred is Compound (I) wherein

Ar is a phenyl group, a benzhydryl group or a benzyl group, each of which optionally has 1 to 4 (preferably 1 or 2) substituents selected from (A) a halogen atom (a chlorine atom, a fluorine atom, etc.), (B) a $C_{1-6}$ alkyl group, and (C) a heterocyclic group (e.g., a 5- or 6-membered aromatic heterocyclic group having 1 to 4 hetero atoms of one or two kinds selected from a nitrogen atom, an oxygen atom and a sulfur atom in addition to carbon atoms (pyridyl, etc.)), $R^1$ is (1) a hydrogen atom, (2) a hydrocarbon group (a $C_{1-6}$ alkyl group, a $C_{7-19}$ aralkyl group (a benzyl group, etc.) or a $C_{6-14}$ aryl group (a phenyl group, etc.) optionally having 1 to 3 substituents selected from (i) a $C_{1-6}$ alkoxy group, (ii) a $C_{1-6}$ alkoxy-carbonyl group, (iii) a carbamoyl group, (iv) a cyano group, (v) a $C_{1-6}$ alkylthio group, or (vi) a heterocyclic group optionally substituted with 1 or 2 oxo groups and optionally fused with a benzene ring (e.g., a 5- or 6-membered aromatic heterocyclic group containing 1 to 4 hetero atoms of one or two kinds selected from a nitrogen atom, an oxygen atom and a sulfur atom in addition to carbon atoms, optionally substituted with 1 or 2 oxo groups, and further optionally fused with a benzene ring, such as triazolyl, etc.), (3) an acyl group represented by the formula: —(C=O)—Ra, —(C=S)—Ra, —SO₂—Ra, —SO₂—NRaRa', —(C=O)NRaRa' or —(C=O)O—Ra wherein Ra is (A) a hydrogen atom or (B) (a) a hydrocarbon group (a $C_{1-6}$ alkyl group, a $C_{2-6}$ alkenyl group, a $C_{2-6}$ alkynyl group, $C_{3-6}$ cycloalkyl, a $C_{7-19}$ aralkyl group (benzyl, 2-phenylethyl, etc.) or a $C_{6-14}$ aryl group (a phenyl group optionally fused with 5- or 6-membered aromatic heterocyclic ring, etc., or (b) a heterocyclic group (e.g., a 5- or 6-membered aromatic or 4- to 6-membered non-aromatic heterocyclic group having 1 to 4 hetero atoms of one or two kinds selected from a nitrogen atom, an oxygen atom and a sulfur atom in addition to carbon atoms), each of which optionally has 1 to 2 substituents selected from (i) a halogen atom, (ii) a $C_{1-6}$ alkyl group optionally substituted with a heterocyclic group (e.g., a 5- or 6-membered aromatic or non-aromatic heterocyclic group having 1 to 4 hetero atoms of one or two kinds selected from a nitrogen atom, an oxygen atom and a sulfur atom in addition to carbon atoms), $C_{1-6}$ alkanoyl or $C_{6-14}$ aryl-carbonyl, (iii) a $C_{1-6}$ alkoxy group, (iv) an amino group, (v) a mono- or di-$C_{1-6}$ alkylamino group, (vi) a $C_{1-6}$ alkanoylamino group, (vii) a N—$C_{1-6}$ alkyl-N'-$C_{1-6}$ alkanoylamino group, (viii) a $C_{1-6}$ alkoxy-carbonyl group, (ix) a $C_{1-6}$ alkanoyl group optionally substituted with $C_{1-6}$ alkoxy, mono- or di-$C_{1-6}$ alkylamino, halogeno $C_{1-6}$ alkyl or a halogen atom, (x) a $C_{6-14}$ aryl-carbonyl group, (xi) a $C_{7-19}$ aralkyl-carbonyl group, (xii) a $C_{3-6}$ cycloalkyl-carbonyl group, (xiii) a heterocyclic-carbonyl group (e.g., a 5- or 6-membered aromatic or non-aromatic heterocyclic-carbonyl group having 1 to 4 hetero atoms of one or two kinds selected from a nitrogen atom, an oxygen atom and a sulfur atom in addition to carbon atoms), (xiv) a hydroxy group,
(xv) a $C_{7-19}$ aralkyloxy group,
(xvi) a $C_{3-6}$ cycloalkyloxy group,
(xvii) a $C_{1-6}$ alkoxy-$C_{1-6}$ alkoxy group,
(xviii) a carbamoyl group,
(xix) a mono- or di-$C_{1-6}$ alkylcarbamoyl group,
(xx) a $C_{1-6}$ alkylsulfonyl group,
(xxi) a mono- or di-$C_{1-6}$ alkylaminosulfonyl group,
(xxii) a formyl group,
(xxiii) a formylamino group,
(xxiv) an oxo group, and
(xxv) a heterocyclic group (e.g., a 5- or 6-membered aromatic or non-aromatic heterocyclic group having 1 to 4 hetero atoms of one or two kinds selected from a nitrogen atom, an oxygen atom and a sulfur atom in addition to carbon atoms) optionally having 1 or 2 substituents selected from $C_{1-6}$ alkanoyl and $C_{1-6}$ alkoxy-$C_{1-6}$ alkanoyl, and Ra' is a hydrogen atom or a $C_{1-6}$ alkyl group, or (4) a heterocyclic group (e.g., a 5- or 6-membered aromatic heterocyclic group having 1 to 4 hetero atoms of one or two kinds selected from a nitrogen atom, an oxygen atom and a sulfur atom in addition to carbon atoms) optionally having 1 or 2 substituents selected from a $C_{1-6}$ alkyl group and an oxo group, X is O or NH, Z is a methylene group, and Ring B is a benzene ring optionally having 1 or 2 substituents selected from (i) a heterocyclic group (a 5- or 6-membered aromatic heterocyclic group having 1 to 4 hetero atoms of one or two kinds selected from a nitrogen atom, an oxygen atom and a sulfur atom in addition to carbon atoms, etc.) optionally substituted with an optionally halogenated $C_{1-6}$ alkyl group or a $C_{1-6}$ alkylthio group, (ii) an optionally halogenated $C_{1-6}$ alkyl group, (iii) an optionally halogenated $C_{1-6}$ alkoxy group, (iv) a halogen atom (fluorine, chlorine, bromine, etc.), (v) nitro, (vi) a $C_{6-14}$ aryl group optionally substituted with optionally halogenated $C_{1-6}$ alkyl, (vii) an optionally halogenated $C_{1-6}$ alkylamino group, (viii) a cyano group, and (ix) a $C_{3-6}$ cycloalkyloxy, and optionally fused with a non-aromatic heterocyclic ring (a 5- or 6-membered non-aromatic heterocyclic group having 1 to 4 hetero atoms of one or two kinds selected from a nitrogen atom, an oxygen atom and a sulfur atom in addition to carbon atoms, such as furan, etc.) or a benzene ring.

More preferred is Compound (I) wherein

Ar is a phenyl group, $R^1$ is —(C=O)—Rb or —(C=O)NRbRb' (Rb is (1) a hydrocarbon group or (2) a heterocyclic group, each of which optionally has a substituent selected from (i) hydroxy, (ii) $C_{1-6}$ alkoxy, (iii) $C_{1-6}$ alkanoyl, (iv) $C_{1-6}$ alkylsulfonyl, (v) amino, (vi) mono- or di-$C_{1-6}$ alkylamino, (vii) $C_{1-6}$ alkanoylamino or (viii) a heterocyclic group optionally substituted with 1 or 2 oxo groups, and Rb' is a hydrogen atom or a $C_{1-6}$ alkyl group.), X is O or NH, Z is a methylene group, and Ring B is a benzene ring optionally having 1 or 2 substituents selected from (i) a heterocyclic group optionally substituted with an optionally halogenated $C_{1-6}$ alkyl group, (ii) an optionally halogenated $C_{1-6}$ alkyl group and (iii) an optionally halogenated $C_{1-6}$ alkoxy group, and optionally fused with a non-aromatic heterocyclic ring.

As Compound (I), preferred is the compound wherein when X is an oxygen atom, $R^1$ is an acyl group such as —(C=O)—$R^3$ [$R^3$ has the same meanings as defined above, but preferably a $C_{1-6}$ alkyl group or a 5- to 7-membered (preferably 5- or 6-membered) non-aromatic heterocyclic group containing 1 to 3 hetero atoms selected from an oxygen atom, a sulfur atom and a nitrogen atom in addition to carbon atoms (e.g., piperidyl and the like. The heterocyclic group may be substituted with $C_{1-6}$ alkyl-carbonyl group, etc.)], and Ring B is a benzene ring optionally having 1 or 2 substituents selected from a halogen atom and optionally halogenated $C_{1-6}$ alkyl.

Further, preferred is also the compound wherein when X is an imino group, $R^1$ is preferably an acyl group such as —(C=O)—$R^3$ or —(C=O)NR"R'" [R" and R'" have the same meanings as defined above, but R" is preferably a $C_{1-6}$ alkyl group optionally substituted with $C_{1-6}$ alkoxy, etc. or a 5- to 7-membered (preferably 5- or 6-membered) non-aromatic heterocyclic group containing 1 to 3 hetero atoms selected from an oxygen atom, a sulfur atom and a nitrogen atom in addition to carbon atoms (e.g., piperidyl, etc.) The heterocyclic group may be substituted with a $C_{1-6}$ alkylcarbonyl group, etc., and R'" is preferably a hydrogen atom or a $C_{1-6}$ alkyl group], and Ring B is preferably a benzene ring optionally having 1 or 2 substituents selected from a halogen atom, optionally halogenated $C_{1-6}$ alkyl, optionally halogenated $C_{1-6}$ alkoxy, or a 5- to 7-membered (preferably 5- or 6-membered) heterocyclic group containing 1 to 3 hetero atoms selected from an oxygen atom, a sulfur atom and a nitrogen atom in addition to carbon atoms (e.g., 1H- or 2H-tetrazolyl and the like. The heterocyclic group may have a substituent such as optionally halogenated $C_{1-6}$ alkyl, etc.), and optionally fused with a 5- or 6-membered ring containing 1 to 4 hetero atoms selected from an oxygen atom, a sulfur atom and a nitrogen atom in addition to carbon atoms (e.g., phenyl, benzofuranyl, etc).

A salt of Compound (I) includes, for example, a metal salt, an ammonium salt, a salt with an organic base, a salt with an inorganic acid, a salt with an organic acid, a salt with basic or acidic amino acid, etc. Suitable examples of the metal salt include an alkali metal salt such as a sodium salt, a potassium salt, etc.; an alkaline earth metal salt such as a calcium salt, a magnesium salt, a barium salt, etc.; an aluminum salt, etc. Suitable examples of the salts with an organic base include salts with trimethylamine, triethylamine, pyridine, picoline, 2,6-lutidine, ethanolamine, diethanolamine, triethanolamine, cyclohexylamine, dicyclohexylamine, N,N'-dibenzyl ethylenediamine, etc. Suitable examples of the salts with an inorganic acid include salts with hydrochloric acid, hydrobromic acid, nitric acid, sulfuric acid, phosphoric acid, etc. Suitable examples of the salts with an organic acid include salts with formic acid, acetic acid, trifluoroacetic acid, phthalic acid, fumaric acid, oxalic acid, tartaric acid, maleic acid, citric acid, succinimide, malic acid, methanesulfonic acid, benzenesulfonic acid, p-toluenesulfonic acid, etc. Suitable examples of the salts with basic amino acid include salts with arginine, lysine, ornithine, etc. Suitable examples of the salts with acidic amino acid include salts with asparaginic acid and glutamic acid, etc.

Among these, pharmaceutically acceptable salts are preferred. For example, if the compound has acidic functional group, preferred are inorganic salts such as an alkali metal salt (e.g., sodium salt, potassium salt, etc.), an alkaline earth metal salt (e.g., calcium salt, magnesium salt, barium salt, etc.), an ammonium salt, etc. If the compound has a basic functional group, preferred are salts with an inorganic acid such as hydrochloric acid, hydrobromic acid, nitric acid, sulfuric acid, phosphoric acid, etc., or salts with an organic acid such as acetic acid, phthalic acid, fumaric acid, oxalic acid, tartaric acid, maleic acid, citric acid, succinic acid, methanesulfonic acid, p-toluene sulfonic acid, etc.

The prodrug of Compound (I) or a salt thereof of the present invention means a compound which is converted to Compound (I) under the physiological condition in the living body by a reaction with an enzyme, a gastric acid, or the like, that is, by enzymatic oxidation, reduction, hydrolysis, etc.; by hydrolysis with gastric acid, etc.

The prodrug of Compound (I) of the present invention includes a compound wherein the amino group of Compound (I) is modified with acyl, alkyl or phosphoryl (e.g., a compound wherein the amino group of Compound (I), etc. is modified to eicosanyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl, tert-butyl, etc.), and the like; a compound wherein the hydroxy group of Compound (I) is modified with acyl, alkyl, phosphoric acid or boric acid (e.g., a compound wherein the hydroxy group of Compound (I) is modified with acetyl, palmitoyl, propanoyl, pivaloyl, succinyl, fumaryl, alanyl or dimethylaminomethylcarbonyl, etc.) and the like; a compound wherein a carboxyl group of Compound (I) is modified to ester or amide (e.g., a compound wherein a carboxyl group of Compound (I) is modified to ethylester, phenyl ester, carboxymethylester, dimethylaminomethylester, pivaloyloxymethylester, ethoxycarbonyloxyethylester, phthalidyl ester, (5-methyl-2-oxo-1, 3-dioxolen-4-yl)methylester, cyclohexyloxycarbonylethylester or methylamide, etc.) and the like; etc. These prodrugs can be produced by per se known methods from Compound (I), etc.

In addition, the prodrug of Compound (I) may be a compound, which is converted into Compound (I) under the physiological conditions, as described in "Pharmaceutical Research and Development", Vol. 7 (Drug Design), pp. 163-198 (1990), published by Hirokawa Publishing Co.

A solvate, for example, hydrate of the compound represented by the formula (I) and a salt thereof are all included in the scope of the present invention. The compound represented by the formula (I) may be labeled with an isotope (e.g. $^3$H $^{14}$C, $^{35}$S $^{125}$I etc.) and the like.

If Compound (I) according to the present invention has chiral center, isomers such as an enantiomer or a diastereomer may exist. Such isomers and a mixture thereof are all included in the scope of the present invention. In addition, there can be instances where the isomers by conformation are generated in cases, but such isomers or a mixture thereof are also included in Compound (I) or a salt thereof of the present invention. Compound (I) is preferably cis-isomer in view of activity.

A method of preparing Compound (I) or a salt thereof of the present invention will be explained in the following.

Compound (I) or a salt thereof of the present invention can be produced using Method A, Method B or Method C below.

[Method A]

Compound (I) or a salt-thereof of the present invention can be produced by subjecting a compound represented by the formula:

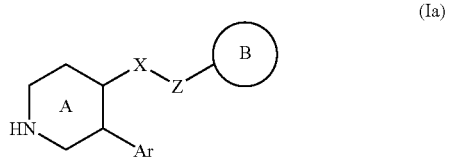

(Ia)

wherein each symbol has the same meanings as defined above, (hereinafter, referred to as Compound (Ia)) or a salt thereof, to a reaction with a compound represented by the formula $R^{1a}$—OH wherein $R^{1a}$ is an optionally substituted hydrocarbon group, an acyl group or an optionally substituted heterocyclic group, which is an alkylating agent or an acylating agent, a salt thereof or a reactive derivative thereof.

The "optionally substituted hydrocarbon group, the acyl group or the optionally substituted heterocyclic group" represented by $R^{1a}$ includes, for example, the same group as those referred to herein above for the foregoing group represented by $R^1$.

The reactive derivative of the compound represented by $R^{1a}$—OH or a salt thereof includes, for example, a compound represented by the formula:

$R^{1a}L$ wherein L is a leaving group, and $R^{1a}$ has the same meanings as defined above, (hereinafter, simply referred to as a reactive derivative) or a salt thereof.

The leaving group represented by L includes, for example, a hydroxy group, a halogen atom (e.g., a chlorine atom, a bromine atom, an iodine atom, etc.), a substituted sulfonyloxy group (e.g., a $C_{1-6}$ alkylsulfonyloxy group such as methanesulfonyloxy, ethanesulfonyloxy, etc.; a $C_{6-14}$ arylsulfonyloxy group such as benzenesulfonyloxy, p-toluenesulfonyloxy, etc.; and a $C_{7-16}$ aralkylsulfonyloxy group such as a benzylsulfonyloxy group, etc.), acyloxy (acetoxy, benzoyloxy, etc.), an oxy group substituted with a hetero ring or an aryl group (succinimide, benzotriazole, quinoline, 4-nitrophenyl, etc.), a hetero ring (imidazole, etc.) and the like.

The reaction using the above-mentioned reactive derivative as an alkylating agent can be carried out by subjecting the reactive derivative to a reaction, usually in a solvent in the presence of base. The solvent includes, for example, alcohols such as methanol, ethanol, propanol, etc., ethers such as dimethoxyethane, dioxane, tetrahydrofuran, etc., ketones such as acetone, etc., nitriles such as acetonitrile, etc., amides such as N,N-dimethylformamide, etc., sulfoxides such as dimethylsulfoxide, etc., water and the like, which may be used in a suitable mixture. The base includes, for example, an organic base such as trimethylamine, triethylamine, N-methylmorpholine, pyridine, picoline, N,N-dimethylaniline, etc., and an inorganic base such as potassium carbonate, sodium carbonate, potassium hydroxide, sodium hydroxide, etc. The amount of the base is, for example, in the order of about 1 to about 100 molar equivalents, preferably about 1 to about 10 molar equivalents, relative to 1 mole of the substrate.

The reactive derivative includes, for example, halides (e.g., chloride, bromide, iodide, etc.), sulfuric acid esters, or sulfonic acid esters (e.g., methanesulfonate, p-toluenesulfonate, benzenesulfonate, etc.) and the like, and particularly halides. The amount of the reactive derivative is, for example, in the order of 1 to 5 molar equivalents, preferably 1 to 3 molar equivalents, relative to 1 mole of the substrate.

If necessary, the reaction can be facilitated by adding an additive. Such additive includes, for example, iodides such as sodium iodide, potassium iodide, etc. and the amount is about 0.1 to 10 molar equivalents, preferably about 0.1 to 5 molar equivalents, relative to 1 mole of the substrate.

The reaction temperature is usually in the order of −10° C. to 200° C., preferably about 0° C. to 110° C., and the reaction time is usually in the order of 0.5 hour to 48 hours, preferably 0.5 hour to 16 hours.

In addition, if the leaving group L is a hydroxy group in the above-mentioned reactive derivative, the reaction can be also carried out by adding an organic phosphate compound in the presence of a base according to, for example, a method described in JP-A-1983-43979 and the like. The organic phosphate compound used herein includes, for example, alkyl o-phenylenephosphate such as methyl phenylenephosphate, ethyl o-phenylenephosphate (EPPA), etc., aryl o-phenylenephosphate such as phenyl o-phenylenephosphate, p-chlorophenyl o-phenylenephosphate, etc. and the like, and particularly EPPA. The base includes, for example, alkylamines such as trimethylamine, triethylamine, diisopropylethylamine, tri(n-butyl)amine, di(n-butyl)amine, diisobutylamine, dicyclohexylamine, etc., cyclic amines such as pyridine, 2,6-lutidine etc. and the like, and preferably, organic tertiary amines such as diisopropylethylamine, etc. The amounts of the above-mentioned reactive derivative, the base and the organic phosphate compound vary depending on the kinds of Compound (Ia), the above-mentioned reactive derivative, the base and the solvent to be used, and further other reaction conditions, but usually in the order of about 1 to about 10 molar equivalents, preferably about 1 to about 5 molar equivalents, respectively to 1 mole of Compound (Ia). The reaction is usually carried out in a solvent inert to the reaction. The solvent includes, for example, halogenated hydrocarbons such as dichloromethane, dichloroethane, chloroform, etc.; nitrites such as acetonitrile, etc.; esters such as ethyl acetate, etc.; ethers such as dimethoxyethane, tetrahydrofuran, dioxane, etc.; hydrocarbons such as benzene, toluene, etc.; amides such as dimethylformamide, hexamethylphosphoramide, etc.; non-protonic solvents including sulfoxides such as dimethylsulfoxide, etc., and a mixture thereof, and preferably, halogenated hydrocarbons such as dichloromethane, dichloroethane, etc.

The reaction temperature is for example, in the order of about −78° C. to about 200° C., preferably about −20° C. to about 150° C. The reaction time varies depending on the kinds of the Compound (Ia), the reactive derivative, the base and the solvent to be used, and further other reaction conditions, but for example, in the order of about 1 to about 72 hours, preferably about 1 to about 24 hours.

The reaction using the above-mentioned reactive derivative as an acylating agent depends on the kind of reactive derivative or substrate, but it is usually carried out in a solvent. If necessary, a convenient base may be added to facilitate the reaction. The solvent includes, for example, hydrocarbons such as benzene, toluene, etc., ethers such as ethyl ether, dioxane, tetrahydrofuran, etc., esters such as ethyl acetate, etc., halogenated hydrocarbons such as chloroform, dichloromethane, etc., esters such as ethyl acetate, etc., amides such as N,N-dimethylformamide, etc., aromatic amines such as pyridine, etc., water and the like, which may be used in a suitable-mixture. In addition, the base includes, for example, alkali metal hydroxides such as sodium hydroxide, potassium hydroxide, etc., hydrogen carbonates such as sodium hydrogen carbonate, potassium hydrogen carbonate, etc., carbonate such as sodium carbonate, potassium carbonate, etc., acetate such as sodium acetate, tertiary amines such as trimethylamine, triethylamine, N-methylmorpholine, etc., aromatic amines such as pyridine, picoline, N,N-dimethylaniline, etc. and the like. The amount of the base is, for example, in the order of about 1 to about 100 molar equivalents, preferably about 1 to about 10 molar equivalents, relative to 1 mole of the substrate.

The acylating agent includes, for example, carboxylic acid, sulfonic acid, phosphoric acid, carbonic acid or a reactive derivative thereof (e.g., acid halide, acid anhydride, mixed acid anhydride, active ester, etc.), isocyanic acid ester, isothiocyanic acid ester and the like.

The amount of such acylating agent is usually 1 to 10 molar equivalents, preferably 1 to 3 molar equivalents, relative to 1 mole of the substrate. The reaction temperature is usually in the order of −10° C. to 150° C., preferably about 0° C. to 100° C., and the reaction time is usually in the order of 15 minutes to 24 hours, preferably 30 minutes to 16 hours.

In addition, Compound (I) or a salt thereof can be also produced by reacting Compound (Ia) with aldehydes, and reducing the produced imine or iminium ion.

The reaction to produce imine or iminium ion is usually carried out in a solvent which has no adverse influence on the reaction. Such solvent includes, for example, aromatic hydrocarbons such as toluene, xylene, etc., aliphatic hydrocarbons such as heptane, hexane, etc., halogenated hydrocarbons such as chloroform, dichloromethane, etc., ethers such as diethyl ether, tetrahydrofuran, dioxane, etc., alcohols such as methanol, ethanol, 2-propanol, butanol, benzyl alcohol, etc., nitriles such as acetonitrile, etc., dimethylformamide, dimethylsulfoxide and the like. Such solvent may be used in a mixture at a suitable ratio. The aldehyde includes, for example, formalin, optionally substituted $C_{1-5}$alkyl-aldehyde (e.g., acetoaldehyde, etc.), optionally substituted aromatic aldehyde (e.g., benzaldehyde, etc.) and the like, and the amount is, for example, in the order of 1 to 100 molar equivalents, preferably 1 to 20 molar equivalents, relative to 1 mole of the substrate.

If necessary, the reaction can advantageously proceed by adding a catalyst. Such catalyst is preferably mineral acids (e.g., hydrochloric acid, hydrobromic acid, sulfuric acid, etc.), carboxylic acids (e.g., formic acid, acetic acid, propionic acid, trifluoroacetic acid, etc.), sulfonic acids (e.g., methanesulfonic acid, p-toluenesulfonic acid, etc.), Lewis acids (e.g., aluminum chloride, zinc chloride, zinc bromide, boron trifluoride, titanium chloride, etc.), acetates (sodium acetate, potassium acetate, etc.) and molecular sieves (molecular sieves 3A, 4A, 5A, etc.). The amount of the catalyst is, for example, in the order of about 0.01 to 50 molar equivalents, preferably about 0.1 to 10 molar equivalents, relative to 1 mole of Compound (Ia).

The reaction temperature is usually in the order of about 0° C. to 200° C., preferably about 20° C. to 150° C., and the reaction time is usually in the order of 0.5 hour to 48 hours, preferably 0.5 hour to 24 hours.

The reduction of imine or iminium ion can be carried out by per se known methods, for example, a method using metal hydride or a method by catalytic hydrogenation.

The metal hydride as the reducing agent includes, for example, sodium borohydride, lithium borohydride, zinc borohydride, sodium cyanoborohydride, sodium triacetoxyborohydride, lithium cyanoborohydride, aluminum dibutylhydride, aluminum hydride, lithium aluminum hydride, a borane complex (a borane-THF complex, catechol borane, etc.) and the like. The metal hydride includes preferably sodium borohydride, sodium cyanoborohydride, sodium triacetoxyborohydride, etc. The amount of the reducing agent is, for example, in the order of 1 to 50 molar equivalents, preferably 1 to 10 molar equivalents, relative-to 1 mole of the substrate. In addition, the reaction solvent includes, for example, aromatic hydrocarbons such as toluene, xylene, etc., aliphatic hydrocarbons such as heptane, hexane, etc., halogenated hydrocarbons such as chloroform, dichloromethane, etc., ethers such as diethyl ether, tetrahydrofuran, dioxane, etc., alcohols such as methanol, ethanol, 2-propanol, butanol, benzyl alcohol, etc., nitriles such as acetonitrile, etc., dimethylformamide, dimethylsulfoxide and the like. Such solvent may be used in a mixture at a suitable ratio. The reaction temperature is usually in the order of about −80° C.

to 80° C., preferably about −40° C. to 40° C., and the reaction time is usually in the order of 5 minutes to 48 hours, preferably 1 hour to 24 hours.

The catalytic hydrogenation can be carried out under hydrogen atmosphere and in the presence of a catalyst. The catalyst to be used is preferably palladium compounds such as palladium carbon, palladium hydroxide, palladium oxide, etc., nickel compounds such as Raney-nickel, etc., platinum compounds such as platinum oxide, platinum carbon, etc., rhodium compounds such as rhodium acetate, etc. and the like, and the amount is in the order of about 0.001 to 1 equivalent, preferably about 0.01 to 0.5 equivalent. The catalytic hydrogenation proceeds usually in a solvent inert to the reaction. Such solvent includes, for example, alcohols such as methanol, ethanol, propanol, butanol, etc.; hydrocarbons such as benzene, toluene, xylene, etc.; halogenated hydrocarbons such as dichloromethane, chloroform, etc.; ethers such as diethyl ether, dioxane, tetrahydrofuran, etc.; esters such as ethyl acetate, etc.; amides such as N,N-dimethylformamide, etc.; carboxylic acids such as acetic acid, etc.; water, or a mixture thereof. The hydrogen pressure under which the reaction proceeds is usually in the order of about 1 to 50 atm, preferably about 1 to 10 atm. The reaction temperature is usually in the order of about 0° C. to 150° C., preferably about 20° C. to 100° C., and the reaction time is usually in the order of 5 minutes to 72 hours, preferably 0.5 hour to 40 hours.

Compound (I) can be also produced directly from Compound (Ia) in the present process, while carrying out the reaction of producing and of reducing imine or iminium ion at the same time, without isolating the intermediate imine or iminium ion. In this case, pH of the reaction mixture is preferably from about 4 to about 5.

Compound (Ia) used as the starting compound in Method A can be produced by subjecting Compound (I) or a salt thereof obtained by Method B or Method C below to deacylation or dealkylation.

Such deacylation can be carried out according to a known method. For example, it is usually carried out in the presence of an acid or a base, if necessary, in a solvent which has no adverse influence on the reaction though it depends on the kinds of the substrate.

The acid is preferably mineral acids (e.g., hydrochloric acid, hydrobromic acid, sulfuric acid, etc.), carboxylic acids (e.g., acetic acid, trifluoroacetic acid, trichloroacetic acid, etc.), sulfonic acids (e.g., methanesulfonic acid, toluenesulfonic acid, etc.), Lewis acids (aluminum chloride, tin chloride, zinc bromide, etc.) and the like. If necessary, it may be used in a mixture of two or more. The amount of the acid varies depending on the kinds of the solvent and other reaction conditions, but it is usually about 0.1 molar equivalents or more, relative to 1 ole of Compound (I), and the acid can be used as solvent.

The base is preferably an inorganic base (alkali metal hydroxides such as sodium hydroxide, potassium hydroxide, etc., alkali metal hydrogen carbonates such as sodium hydrogen carbonate, potassium hydrogen carbonate, etc., alkali metal carbonates such as sodium carbonate, potassium carbonate, etc., alkoxides such as sodium methoxide, sodium ethoxide, etc. and the like), or an organic base (amines such as trimethylamine, triethylamine, diisopropylethylamine, etc., cyclic amines such as pyridine, 4-dimethylaminopyridine, etc.) and the like, and preferably, sodium hydroxide, potassium hydroxide, sodium ethoxide and the like.

The amount of the base varies depending on the kinds of the solvent and other reaction conditions, but is usually in the order of about 0.1 to about 10 molar equivalents, preferably about 0.1 to about 5 molar equivalents, relative 1.5 to 1 mole of Compound (I).

The solvent which has no adverse influence on the reaction includes, for example, alcohols such as methanol, ethanol, propanol, 2-propanol, butanol, isobutanol, tert-butanols; aromatic hydrocarbons such as benzene, toluene, xylene, etc.; aliphatic hydrocarbons such as hexane, heptane, etc.; halogenated hydrocarbons such as dichloromethane, chloroform, etc.; ethers such as diethyl ether, duisopropylether, tert-butylmethylether, tetrahydrofuran, dioxane, dimethoxyethane, etc.; nitriles such as acetonitrile, etc.; esters such as ethyl acetate, etc.; carboxylic acids such as acetic acid, etc.; amides such as dimethylformamide, dimethylacetamide, etc.; sulfoxides such as dimethylsulfoxide, etc.; water and the like. Such solvent may be used in a mixture of two or more at a suitable ratio.

The reaction temperature is for example, in the order of about −50° C. to about 200° C., preferably about 0° C. to about 100° C., and the reaction time varies depending on the kinds of Compound (I) or a salt thereof, the reaction temperature and the like, and it is for example, in the order of about 0.5 to 3.5 about 100 hours, preferably about 0.5 to about 24 hours.

Dealkylation can be carried out by a known method, for example, the method described in Theodora W. Greene, Peter G. M. Wuts, "Protective Groups in Organic Synthesis, 3$^{rd}$ Ed.," (1999) Wiley-Interscience, and the like, or an analogous method thereto. For example, the dealkylation can be carried out by treatment with an acid, a base, ultraviolet radiation, a transition metal catalyst and the like, or by oxidation, reduction or acylation, followed by hydrolysis, etc., or a combination thereof can be used.

[Method B]

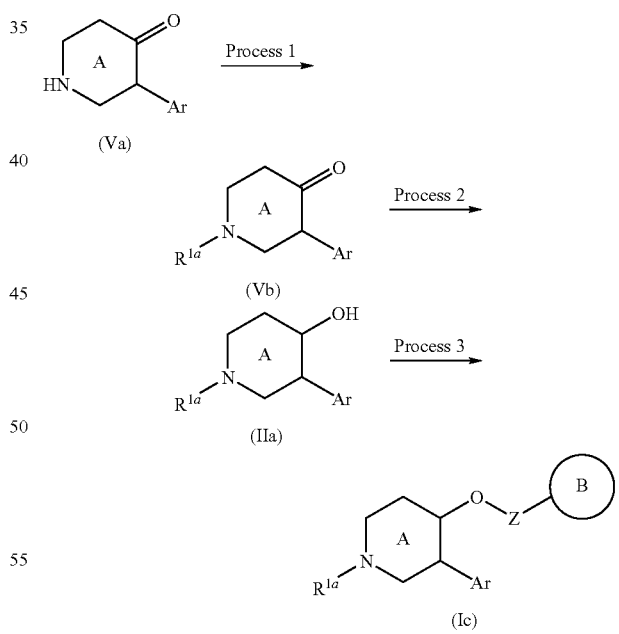

wherein each symbol has the same meanings as defined above.

Among Compounds (Va) or (Vb) or a salt thereof, the compound wherein Ar is an aryl group or an aromatic heterocyclic group, each of which may be substituted, Compound (Vc), can be produced according to Method D below or, per se known methods, for example, the method described in JP-A-1981-118062. Among Compounds (Va) or (Vb) or a salt thereof, the compound wherein Ar is a benzhydryl group, Compound (Vd), can be produced by Method E below. In addition, among Compounds (Va) or (Vb) or a salt thereof, the compound wherein Ar is a benzyl group, Compound (Ve), can be produced according to the known methods, for example, the method described in Bioorganic & Medicinal Chemistry Letters, Vol. 4, pp. 525-530 (1994).

(Process 1)

The present process can be carried out by the same method described in Method A, a process to produce Compound (Vb) by reacting Compound (Va) or a salt thereof, and a compound represented by the formula:

$$R^{1a}\text{—OH}$$

wherein $R^{1a}$ has the same meanings as defined above, a salt thereof or a reactive derivative thereof which is an alkylating agent or an acylating agent.

(Process 2)

The present process is a process of reducing Compound (Vb) to produce an alcohol compound (IIa).

The present reaction can be carried out according to the known methods, usually in a solvent inert to the reaction, with using various reducing agents.

The reducing agent to be used includes, for example, metal hydride such as sodium borohydride, lithium borohydride, zinc borohydride, sodium cyanoborohydride, sodium triacetoxyborohydride, lithium cyanoborohydride, L-Selectride (lithium-tri-sec-butylborohydride), K-Selectride (potassium-tri-sec-butylborohydride), diisobutylaluminum hydride, lithium aluminum hydride, etc., preferably L-Selectride (lithium-tri-sec-butylborohydride), K-Selectride (potassium-tri-sec-butylborohydride), etc. The amount of the reducing agent is, for example, in the order of 1 to 50 molar equivalents, preferably 1 to 2 molar equivalents, relative to 1 mole of the substrate.

The solvent which is inert to the reaction includes, for example, aromatic hydrocarbons such as toluene, xylene, etc., aliphatic hydrocarbons such as heptane, hexane, etc., halogenated hydrocarbons such as chloroform, dichloromethane, etc., ethers such as diethyl ether, tetrahydrofuran, dioxane, etc., alcohols such as methanol, ethanol, 2-propanol, butanol, benzyl alcohol, etc., dimethylformamide, dimethylsulfoxide and the like. Such solvent may be used alone or in a mixture. The reaction temperature is usually in the order of about –80° C. to 40° C., preferably about –50° C. to 25° C., and the reaction time is usually in the order of 5 minutes to 48 hours, preferably 1 hour to 24 hours.

(Process 3)

The present process is a process to produce Compound (Ic) by reacting an alcohol compound (IIa) with a compound represented by the formula:

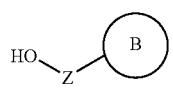

(III)

wherein each symbol has the same meanings as defined above, a salt thereof or a reactive derivative thereof which is an alkylating agent or an acylating agent.

The reactive derivative of the compound represented by Compound (III) or a salt thereof includes, for example, a compound represented by

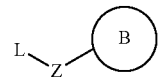

(IIIa)

wherein each symbol has the same meanings as defined above, (hereinafter, simply referred to as the reactive derivative) or a salt thereof.

The reaction using the above-mentioned reactive derivative as the alkylating agent, can be carried out by subjecting the reactive derivative to a reaction usually in a solvent in the presence of base. The solvent includes, for example, alcohols such as methanol, ethanol, propanol, etc., hydrocarbons such as benzene, toluene, xylene, etc., halogenated hydrocarbons such as dichloromethane, chloroform, etc., ethers such as dimethoxyethane, dioxane, tetrahydrofuran, etc., ketones such as acetone, etc., nitriles such as acetonitrile, etc., amides such as N,N-dimethylformamide, etc., sulfoxides such as dimethylsulfoxide, etc., water and the like, which may be used in a suitable mixture. The base includes, for example, organic amines (e.g., alkylamines such as trimethylamine, triethylamine, diisopropylethylamine, N-methylmorpholine, 1,8-diazabicyclo[5.4.0]undeca-7-ene, etc., aromatic amines such as pyridine, N,N-dimethylaniline, etc.), alkali metal salts (e.g., sodium hydrogen carbonate, potassium hydrogen carbonate, sodium carbonate, potassium carbonate, sodium hydroxide, potassium hydroxide, etc.), metal hydrides (e.g., potassium hydride, sodium hydride, etc.), alkali metal alkoxides (e.g., sodium methoxide, sodium ethoxide, sodium t-butoxide, potassium t-butoxide, etc.) and the like, and preferably, alkali metal salts such as sodium hydroxide, etc., metal hydride such as sodium hydride, etc. and the like.

The amount of the base is, for example, in the order of about 1 to about 100 molar equivalents, preferably about 1 to about 10 molar equivalents, relative to 1 mole of the substrate.

The reactive derivative includes, for example, halides (e.g., chloride, bromide, iodide, etc.), sulfuric acid esters, or sulfonic acid esters (e.g., methanesulfonate, p-toluenesulfonate, benzenesulfonate, etc.) and the like, and particularly halides. The amount of the reactive derivative is, for example, in the order of 1 to 10 molar equivalents, preferably 1 to 5 molar equivalents, relative to 1 mole of the substrate.

If necessary, the reaction can be facilitated by adding an additive. Such additive includes, for example, iodides such as sodium iodide, potassium iodide, etc., a phase transfer catalyst such as tetra-n-butylammonium hydrogen sulfate, benzyltriethylammonium chloride, etc., and the amount is in the order of about 0.1 to 10 molar equivalents, preferably about 0.1 to 5 molar equivalents, relative to 1 mole of the substrate.

The reaction temperature is usually in the order of –10° C. to 200° C., preferably about 0° C. to 110° C., and the reaction time is usually in the order of 0.5 hour to 48 hours, preferably 0.5 hour to 16 hours.

The reaction using the above-mentioned reactive derivative as the acylating agent, depends on the kinds of the reactive derivative or the substrate, but it can be usually carried out in a solvent. If necessary, a base may be added to facilitate the reaction. The solvent includes, for example, hydrocarbons such as benzene, toluene, etc., ethers such as ethyl ether, dioxane, tetrahydrofuran, etc., esters such as ethyl acetate, halogenated hydrocarbons such as chloroform, dichloromethane, etc., esters such as ethyl acetate, etc. amides such as N,N-dimethylformamide, etc., aromatic amines such as pyridine, etc., water and the like, which may be used in a suitable mixture. In addition, the base includes, for example, alkali metal hydroxides such as sodium hydroxide, potassium hydroxide, etc., hydrogen carbonates such as sodium hydrogen carbonate, potassium hydrogen carbonate, etc., carbonates such as sodium carbonate, potassium carbonate, etc., acetates such as sodium acetate, etc., tertiary amines such as trimethylamine, triethylamine, N-methylmorpholine, etc., aromatic amines such as pyridine, picoline, N,N-dimethylaniline, etc. and the like. The amount of the base is, for example, in the order of about 1 to about 100 molar equivalents, preferably about 1 to about 10 molar equivalents, relative to 1 mole of the substrate.

The acylating agent includes, for example, carboxylic acid or a reactive derivative thereof (e.g., acid halide, acid anhydride, mixed acid anhydride, active ester, etc.) and the like.

The amount of such acylating agent is usually 1 to 10 molar equivalents, preferably 1 to 3 molar equivalents, relative to 1 mole of the substrate. The reaction temperature is usually in the order of −10° C. to 150° C., preferably about 0° C. to 100° C., and the reaction time is usually in the order of 15 minutes to 24 hours, preferably 30 minutes to 16 hours.

etc., aliphatic hydrocarbons such as heptane, hexane, etc., halogenated hydrocarbons such as chloroform, dichloromethane, etc., ethers such as diethyl ether, tetrahydrofuran, dioxane, etc., alcohols such as methanol, ethanol, 2-propanol, butanol, benzyl alcohol, etc., nitriles such as acetonitrile, etc., dimethylformamide, dimethylsulfoxide and the like. Such solvent may be used in a mixture at a suitable ratio.

If necessary, the reaction can advantageously proceed by adding a catalyst. Such catalyst is preferably mineral acids (e.g., hydrochloric acid, hydrobromic acid, sulfuric acid, etc.), carboxylic acids (e.g., formic acid, acetic acid, propionic acid, trifluoroacetic acid, etc.), sulfonic acids (e.g., methanesulfonic acid, p-toluenesulfonic acid, etc.), Lewis acids (e.g., aluminum chloride, zinc chloride, zinc bromide, boron trifluoride, titanium chloride, etc.), acetate (e.g., sodium acetate, potassium acetate, etc.), and molecular sieves (e.g., molecular sieves 3A, 4A, 5A, etc). The amount of the catalyst is, for example, in the order of about 0.01 to 50 molar equivalents, preferably about 0.1 to 10 molar equivalents, relative to 1 mole of Compound (Vb).

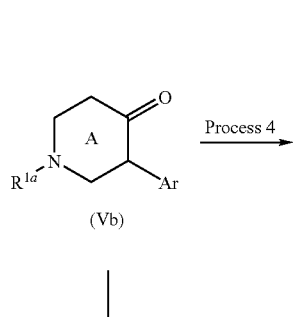

wherein $R^5$ is an optionally substituted hydrocarbon group or an optionally substituted heterocyclic group, and other symbols have the same meanings as defined above.

The "optionally substituted hydrocarbon group or the optionally substituted heterocyclic group" represented by $R^5$ includes, for example, the same group as those referred to herein above for the foregoing group represented by $R^1$.

Compound (Vb) which is used as the starting compound in the present method, can be produced by the method described in Process 1 of Method B, etc.

(Process 4)

The present process is a process of converting a ketone of Compound (Vb) to imine or oxime, followed by reducing it to thus convert it into an amine compound (IIb).

Conversion of Compound (Vb) into imine or oxime can be carried out by using a known method, for example, by using various amines in a solvent inert to the reaction.

The amines include, for example, ammonias such as aqueous ammonia, ammonium chloride, ammonium acetate, etc. hydroxyamines such as hydroxyamine, o-methylhydroxyamine, O-benzylhydroxyamine, etc., and may be used as a salt form such as hydrochloride, sulfate, etc. or as an aqueous solution thereof. The amount of the amines is, for example, in the order of about 1 to 50 molar equivalents, preferably about 1 to 10 molar equivalents, relative to 1 mole of Compound (Vb).

The solvent which is inert to the reaction includes, for example, aromatic hydrocarbons such as toluene, xylene, The reaction temperature is usually in the order of about 0° C. to 200° C., preferably about 20° C. to 150° C., and the reaction time is usually in the order of 0.5 hour to 48 hours, preferably 0.5 hour to 24 hours.

The conversion of imine or oxime into an amine compound (IIb) in a solvent inert to the reaction, can be carried out by various reductions. Such reduction can be carried out by per se known methods, for example, a method using metal hydride or a method by catalytic hydrogenation.

The metal hydride as the reducing agent includes, for example, sodium borohydride, lithium borohydride, zinc borohydride, sodium cyanoborohydride, sodium triacetoxyborohydride, lithium cyanoborohydride, aluminum dibutylhydride, aluminum hydride, lithium aluminum hydride, a borane complex (a borane-THF complex, catechol borane, etc.) and the like. The metal hydride includes preferably sodium borohydride, sodium cyanoborohydride, sodium triacetoxyborohydride, etc. The amount of the reducing agent is, for example, in the order of 1 to 50 molar equivalents, preferably 1 to 10 molar equivalents, relative-to 1 mole of the substrate. The reduction by the metal hydride is usually carried out in a solvent inert to the reaction. Such solvent includes, for example, aromatic hydrocarbons such as toluene, xylene, etc., aliphatic hydrocarbons such as heptane, hexane, etc., halogenated hydrocarbons such as chloroform, dichloromethane, etc., ethers such as diethyl ether, tetrahydrofuran, dioxane, etc., alcohols such as methanol, ethanol, 2-propanol, butanol, benzyl alcohol, etc., nitriles such as acetonitrile, etc., dimethylformamide, dimethylsulfoxide and the like. Such solvent may be used in a mixture at a suitable ratio. The reaction temperature is usually in the order of about −80° C. to 80° C., preferably about −40° C. to 40° C., and the reaction time is usually in the order of 5 minutes to 48 hours, preferably 1 hour to 24 hours.

The catalytic hydrogenation can be carried out under hydrogen atmosphere and in the presence of a catalyst. The catalyst to be used is preferably palladium compounds such as palladium carbon, palladium hydroxide, palladium oxide, etc., nickel compounds such as Raney-nickel, etc., platinum compounds such as platinum oxide, platinum carbons, etc., rhodium compounds such as rhodium acetate, etc. and the like, and the amount is in the order of about-0.001 to 1 equivalent, preferably about 0.01 to 0.5 equivalent. The catalytic hydrogenation is usually carried out in a solvent inert to the reaction. Such solvent includes, for example, alcohols such as methanol, ethanol, propanol, butanol, etc.; hydrocarbons such as benzene, toluene, xylene, etc.; halogenated hydrocarbons such as dichloromethane, chloroform, etc.; ethers such as diethyl ether, dioxane, tetrahydrofuran, etc.; esters such as ethyl acetate, etc.; amides such as N,N-dimethylformamide, etc.; carboxylic acids such as acetic acid, etc.; water, or a mixture thereof. The hydrogen pressure under which the reaction is carried out, is usually in the order of about 1 to 50 atm, preferably about 1 to 10 atm. The reaction temperature is usually in the order of about 0° C. to 150° C., preferably about 20° C. to 100° C., and the reaction time is usually in the order of 5 minutes to 72 hours, preferably 0.5 hour to 40 hours.

In the present process, Compound (IIb) can be also produced directly from Compound (Vb) while carrying out the reactions of producing and reducing the above-mentioned imine or oxime at the same time, without isolating imine or oxime which is an intermediate. In this case, pH of the reaction mixture is preferably from about 4 to about 5.

(Process 5)

The present process is a process of alkylating, acylating or reductively alkylating an amine compound (IIb) to thus convert it into Compound (Id).

The alkylation or acylation can be carried out by reacting an amine compound (IIb) with a compound represented by the formula:

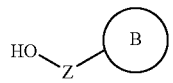

(III)

wherein each symbol has the same meanings as defined above, a salt thereof or a reactive derivative thereof which is an alkylating agent or an acylating agent, and can be carried out by the same method described in Process 3 of Method B.

The reductive alkylation can be carried out by per se known methods, for example, by reacting an amine compound (IIb) with a compound represented by the formula:

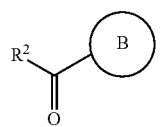

(IV)

wherein $R^2$ is a hydrogen atom or an optionally substituted hydrocarbon group, and Ring B has the same meaning as defined above, a salt thereof or a reactive derivative thereof, and reducing the produced imine or iminium ion.

The "optionally substituted hydrocarbon group" represented by $R^2$ includes, for example, the same group as those referred to herein above for the foregoing group represented by $R^1$.

The reaction to produce imine or iminium ion is usually carried out in a solvent which has no adverse influence on the reaction. Such solvent includes, for example, aromatic hydrocarbons such as toluene, xylene, etc., aliphatic hydrocarbons such as heptane, hexane, etc., halogenated hydrocarbons such as chloroform, dichloromethane, etc., ethers such as diethyl ether, tetrahydrofuran, dioxane, etc., alcohols such as methanol, ethanol, 2-propanol, butanol, benzyl alcohol, etc., nitriles such as acetonitrile, etc., dimethylformamide, dimethylsulfoxide and the like. Such solvent may be used in a mixture at a suitable ratio.

If necessary, the reaction can advantageously proceed by adding a catalyst. Such catalyst is preferably mineral acids (e.g., hydrochloric acid, hydrobromic acid, sulfuric acid, etc.), carboxylic acids (e.g., formic acid, acetic acid, propionic acid, trifluoroacetic acid, etc.), sulfonic acids (e.g., methanesulfonic acid, p-toluenesulfonic acid, etc.), Lewis acids (e.g., aluminum chloride, zinc chloride, zinc bromide, boron trifluoride, titanium chloride, etc.), acetates (e.g. sodium acetate, potassium acetate, etc.), molecular sieves (molecular sieves 3A, 4A, 5A, etc) and the like. The amount of the catalyst is, for example, in the order of about 0.01 to 50 molar equivalents, preferably about 0.1 to 10 molar equivalents, relative to 1 mole of Compound (IIb).

The reaction temperature is usually in the order of about 0° C. to 200° C., preferably about 20° C. to 150° C., and the reaction time is usually in the order of 0.5 hour to 48 hours, preferably 0.5 hour to 24 hours.

The reduction of imine or iminium ion can be carried out by per se known methods, for example, a method using metal hydride or a method by catalytic hydrogenation.

The metal hydride as the reducing agent includes, for example, sodium borohydride, lithium borohydride, zinc borohydride, sodium cyanoborohydride, sodium triacetoxyborohydride, lithium cyanoborohydride, aluminum dibutylhydride, aluminum hydride, lithium aluminum hydride, a borane complex (a borane-THF complex, catechol borane, etc.) and the like. The metal hydride includes preferably sodium borohydride, sodium cyanoborohydride, sodium triacetoxyborohydride, etc. The amount of the reducing agent is, for example, in the order of 1 to 50 molar equivalents, preferably 1 to 10 molar equivalents, relative to 1 mole of the substrate. In addition, the reaction solvent includes, for example, aromatic hydrocarbons such as toluene, xylene, etc., aliphatic hydrocarbons such as heptane, hexane, etc., halogenated hydrocarbons such as chloroform, dichloromethane, etc., ethers such as diethyl ether, tetrahydrofuran, dioxane, etc., alcohols such as methanol, ethanol, 2-propanol, butanol, benzyl alcohol, etc., nitriles such as acetonitrile, etc., dimethylformamide, dimethylsulfoxide and the like. Such solvent may be used in a mixture at a suitable ratio. The reaction temperature is usually in the order of about −80° C. to 80° C., preferably about −40° C. to 40° C., and the reaction time is usually in the order of 5 minutes to 48 hours, preferably 1 hour to 24 hours.

The catalytic hydrogenation can be carried out under hydrogen atmosphere and in the presence of a catalyst. The catalyst to be used is preferably palladium compounds such as palladium carbon, palladium hydroxide, palladium oxide, etc., nickel compounds such as Raney-nickel, etc., platinum compounds such as platinum oxide, platinum carbon, etc., rhodium compounds such as rhodium acetate, etc. and the like, and the amount is in the order of about 0.001 to 1 equivalent, preferably about 0.01 to 0.5 equivalent. The catalytic hydrogenation is usually carried out in a solvent inert to the reaction. Such solvent includes, for example, alcohols such as methanol, ethanol, propanol, butanol, etc.; hydrocarbons such as benzene, toluene, xylene, etc.; halogenated hydrocarbons such as dichloromethane, chloroform, etc.; ethers such as diethyl ether, dioxane, tetrahydrofuran, etc.; esters such as ethyl acetate, etc.; amides such as N,N-dimethylformamide, etc.; carboxylic acids such as acetic acid, etc.; water, or a mixture thereof. The hydrogen pressure under which the reaction is carried out, is usually in the order of about 1 to 50 atm, preferably about 1 to 10 atm. The reaction temperature is usually in the order of about 0° C. to 150° C., preferably about 20° C. to 100° C., and the reaction time is usually in the order of 5 minutes to 72 hours, preferably 0.5 hour to 40 hours.

In the present process, Compound (Id) can be also produced directly from Compound (IIb) while carrying out the reactions to produce imine or iminium ion and to reduce the products at the same time, without isolating imine or iminium ion which is an intermediate. In this case, pH of the reaction mixture is preferably from about 4 to about 5.

(Process 6)

The present reaction is a process of reductively aminating Compound (Vb) to thus convert it into Compound (Id). The present reaction can be carried out by the known methods, for example, by reacting Compound (Vb) with a compound represented by the formula:

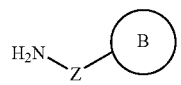

(VII)

wherein each symbol has the same meanings as defined above, a salt thereof or a reactive derivative thereof, and reducing the produced imine or iminium ion.

The reaction to produce imine or iminium ion and the reduction can be carried out by the same method described in the reductive amination of Process 5.

In the present process, Compound (Id) can be also produced directly from Compound (Vb) while carrying out the reaction to produce imine or iminium ion and to reduce the products at the same time, without isolating imine or iminium ion which is an intermediate. In this case, pH of the reaction mixture is preferably from about 4 to about 5.

Compound (I) obtained by the methods described in the above-mentioned Method A, Method B and Method C, can be further subjected to known reactions including condensation reactions such as various acylation, alkylation, or oxidation, reduction, etc. to prepare a further derivative. Such reactions can be carried out according to the known methods.

Among Compounds (Va) or (Vb) which is used as the starting compound in Method B the compound wherein Ar is an aryl group or an aromatic heterocyclic group, each of which may be substituted, Compound (Vc), can be produced, for example, by Method D below.

[Method D]

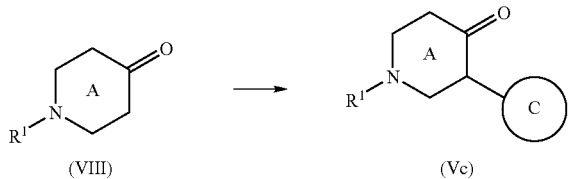

wherein Ring C is an aryl group or an aromatic heterocyclic group, each of which may be substituted, and other symbols have the same meanings as defined above.

The present reaction is a reaction of arylating ketone compound (VIII) to thus convert it into Compound (Vc). The present reaction can be carried out by the known methods, for example, by reacting Compound (VIII) with a compound represented by the formula:

(IX)

wherein $L^1$ is a leaving group, and Ring C has the same meaning as defined above, or a salt thereof in the presence of a base and a transition metal catalyst.

"The aryl group or the aromatic heterocyclic group, each of which may be substituted" represented by Ring C includes, for example, the same group as those referred to herein above for the foregoing group represented by Ar.

Compound (VIII) which is the starting compound is commercially available, or can be produced by known methods.

The leaving group represented by $L^1$ in Compound (IX) includes, for example, a halogen atom (e.g., a chlorine atom, a bromine atom, an iodine atom, etc.), a substituted sulfonyloxy group (e.g., an optionally substituted $C_{1-6}$ alkylsulfonyloxy group such as methanesulfonyloxy, ethanesulfonyloxy, trifluoromethanesulfonyloxy, etc.; a $C_{6-14}$ arylsulfonyloxy group such as benzenesulfonyloxy, p-toluenesulfonyloxy, etc.; a $C_{7-16}$ aralkylsulfonyloxy group such as benzylsulfonyloxy group, etc.), acyloxy (acetoxy, benzoyloxy, etc.) and the like, and preferably, a bromine atom, an iodine atom, a trifluoromethanesulfonyloxy group and the like.

The base to be used includes, for example, organic amines (e.g., alkylamines such as trimethylamine, triethylamine, diisopropylethylamine, N-methylmorpholine, 1,8-diazabicyclo[5.4.0]undeca-7-ene, etc., aromatic amines such as pyridine, N,N-dimethylaniline, etc.), alkali metal salts (e.g., sodium hydrogen carbonate, potassium hydrogen carbonate, sodium carbonate, potassium carbonate, cesium carbonate, sodium hydroxide, potassium hydroxide, etc.), metal hydrides (e.g., potassium hydride, sodium hydride, etc.), alkali metal alkoxides (e.g., sodium methoxide, sodium ethoxide, sodium t-butoxide, potassium t-butoxide, etc.), alkali disilazides (e.g., lithium disilazide, sodium disilazide, potassium disilazide, etc.) and the like, and preferably, alkali metal salts such as cesium carbonate, alkali metal alkoxides such as potassium t-butoxide, etc. and the like. The amount of Compound (IX) is, for example, in the order of about 1 to about 10 molar equivalents, preferably about 1 to about 5 molar equivalents, relative to 1 mole of the substrate. The amount of the base is, for example, in the order of about 1 to about 100 molar equivalents, preferably about 1 to about 10 molar equivalents, relative to 1 mole of the substrate.

The transition metal catalyst includes, for example, a palladium catalyst such as palladium acetate, palladium chloride, palladium tetrakistriphenylphosphine; a nickel catalyst such as nickel chloride, etc. and the like. If necessary, a ligand such as triphenylphosphine, tri-t-butylphosphine, etc. can be used.

The amount of the catalyst varies depending on the kinds of the catalyst, but it is usually in the order of about 0.0001 to about 1 molar equivalent, preferably about 0.01 to about 0.5 molar equivalents, relative to 1 mole of Compound (VIII). The amount of the ligand is usually in the order of about 0.0001 to about 4 molar equivalents, preferably about 0.01 to about 2 molar equivalents, relative to 1 mole of Compound (VIII).

The reaction condition (a solvent, temperature, time, etc.) varies depending on the kinds of Compound (VIII), Compound (IX), the base and the catalyst to be used. For example, the reaction is usually carried out in a solvent inert to the reaction. The solvent includes, for example, hydrocarbons such as benzene, toluene, xylene, etc.; halogenated hydrocarbons such as dichloromethane, chloroform, etc.; nitrites such as acetonitrile, etc.; ethers such as dimethoxyethane, tetrahydrofuran, etc.; alcohols such as methanol, ethanol, etc.; a non-protonic polar solvent such as dimethylformamide, dimethylsulfoxides, hexamethylphosphoramide, etc.; water, or a mixture thereof.

Among Compounds (Va) or (Vb) which is used as the starting compound in Method B, the compound wherein Ar is an optionally substituted benzhydryl group, Compound (Vd), can be produced, for example, by Method E below.

[Method E]

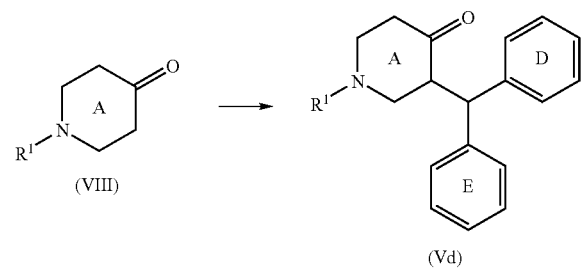

wherein Ring D and Ring E are an optionally substituted benzene ring, respectively and other symbols have the same meanings as defined above.

The "substituent" of the "an optionally substituted benzene ring, respectively" represented by Ring D and Ring E includes, for example, the same group as those referred to herein above for the foregoing "substituent" in "the aryl group, the aralkyl group or the aromatic heterocyclic group, each of which may be substituted" represented by Ar.

Compound (VIII), the starting compound, is commercially available, or can be produced by known methods.

The present reaction is a process of producing Compound (Vd) by reacting Compound (VIII) with Compound (X) represented by the formula:

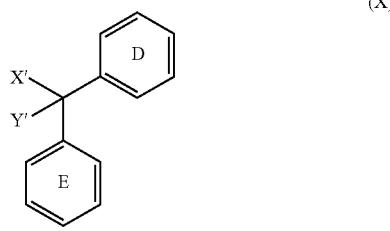

wherein X' and Y' are respectively a hydrogen atom, a hydroxy group or a halogen atom, and other symbols have the same meanings as defined above, provided that when X' is a hydrogen atom, Y' is a hydroxy group or a halogen atom, and when X' is a halogen atom, Y' is a halogen atom, or a salt thereof in the presence of trialkylsilyl triflate.

The trialkylsilyl triflate is not particularly limited, but preferably trimethylsilyltrifluoromethane sulfonate. The amount of the trialkylsilyl triflate is 1 to 10 molar equivalents, preferably 1 to 4 molar equivalents, relative to 1 mole of Compound (VIII) or a salt thereof.

If necessary, the reaction can advantageously proceed by adding an acid catalyst. The acid catalyst includes mineral acid, Lewis acid, etc., and is not particularly limited, but preferably, a zinc salt such as zinc chloride, zinc bromide, zinc iodide, etc., an aluminum salt such as aluminum chloride, etc., an iron salt such as iron chloride, etc., halogenated boron such as boron trifluoride, etc., and more preferably, a zinc salt such as zinc bromide, etc. The amount of the catalyst is 0.001 to 1 molar equivalents, preferably 0.1 to 1 molar equivalents, relative to 1 mole of Compound (VIII) or a salt thereof. When a benzhydrol derivative (when X' is a hydrogen atom and Y' is a hydroxy group in Compound (X)) is used as Compound (X), addition of a catalyst is not particularly needed, but a catalyst may be added depending on the case. The benzhydrol derivative used in the present process is a known one or, can be produced easily according to known methods [for example, Chem. Ber. 103, 2041-2051 (1970)] from the corresponding benzophenone derivative. The amount of Compound (X) is 1 to 5 molar equivalents, preferably 1 to 3 molar equivalents, relative to 1 mole of Compound (VIII) or a salt thereof. The reaction is usually carried out in a solvent inert to the reaction. The solvent includes, for example, halogenated hydrocarbons such as dichloromethane, dichloroethane, chloroform, etc.; nitrites such as acetonitrile, etc.; esters such as ethyl acetate, etc.; ethers such as dimethoxyethane, tetrahydrofuran, dioxane, etc.; hydrocarbons such as benzene, toluene, etc.; amides such as dimethylformamide, hexamethylphosphoramide, etc.; a non-protonic solvent including sulfoxides such as dimethylsulfoxides, etc., and preferably, halogenated hydrocarbons such as dichloromethane, dichloroethane, etc. The reaction temperature is usually from −78° C. to a boiling point of the solvent, particularly from −50° C. to room temperature. The reaction time varies depending on the kinds of Compound (VIII) or a salt thereof, the kinds of Compound (X), the reaction temperature and other reaction conditions, but it is usually 1 to 96 hours, preferably 1 to 16 hours.

An optically active form of Compound (I) or a salt thereof of the present invention can be produced by reacting an alcohol compound (IIc) or an amine compound (IId) obtained by Method F or Method G below, according to the method described in the above-mentioned Methods A to C.

[Method F]

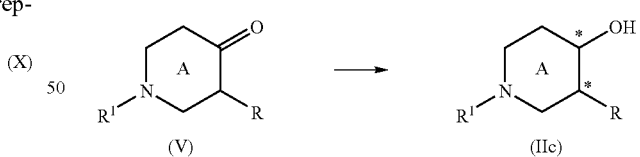

wherein R is an optionally substituted hydrocarbon group or an optionally substituted heterocyclic group, * is a chiral center, and other symbols have the same meanings as defined above. OH and R have a cis configuration relationship.

"The optionally substituted hydrocarbon group or the optionally substituted heterocyclic group" represented by R includes, for example, the same group as those-referred to herein above for the foregoing group represented by $R^1$.

The optically active alcohol compound (IIc) in which OH and R are in cis configuration can be obtained by hydrogenating a ketone compound (V) in the presence of an optically active ruthenium-phosphine-amine complex and a base in the present reaction.

Compound (V) used as a starting material in the present reaction can be produced by the above-mentioned Method D, Method E, or according to a known method.

The optically active ruthenium-phosphine-amine complex used in the present reaction can be produced by reacting phosphine or a salt thereof, amine or a salt thereof, and a ruthenium complex, according to the known methods, for example, the method described in J. Am. Chem. Soc., 120, 13529 (1998); Angew. Chem. Int. Ed., 37, 1703 (1998); JP-A-11-189600 and the like, or an analogous method thereto. Herein, at least one of phosphine or amine is preferably in optically active form. The time and sequence of adding phosphine, amine and a ruthenium complex to the reaction system in the present reaction are not particularly limited, and these may be added to the reaction system at the same time, or separately at timed intervals. Thus obtained optically active ruthenium-phosphine-amine complex is separated by known means, for example, concentration, solvent extraction, fractional distillation, crystallization, recrystallization, chromatography, etc., and is then used in the production method of the present invention, preferably after purification.

The phosphine to be used includes, for example, trimethylphosphine, triethylphosphine, tributylphosphine, triphenylphosphine, tricyclohexylphosphine, tri(p-tolyl)phosphine, diphenylmethylphosphine, dimethylphenylphosphine, bis(diphenylphosphino)methane, bis(diphenylphosphino)ethane, bis(diphenylphosphino)propane, bis(diphenylphosphino)butane, bis(dimethylphosphino)ethane, bis(dimethylphosphino)propane, 2,2'-bis-(diphenylphosphino)-1,1'-binaphthyl (hereinafter, briefly referred to as BINAP), a BINAP derivative having (a) substituent(s) such as an alkyl group, an aryl group, etc. on the naphthyl ring of BINAP (2,2'-bis-(diphenylphosphino)-6,6'-dimethyl-1,1'-binaphthyl), a BINAP derivative in which the naphthyl ring of BINAP is partially hydrogenated, such as H8 BINAP (2,2'-bis-(diphenylphosphino)-5,6,7,8,5',6',7',8'-octahydro-1,1'-binaphthyl), a BINAP derivative having 1 to 5 alkyl group substituents on one benzene ring on the phosphorus atom of BINAP, such as 2,2'-bis-(di-p-tolylphosphino)-1,1'-binaphthyl (Tol-BINAP), 2,2'-bis[bis(3,5-dimethylphenyl)phosphino]-1,1'-binaphthyl (Xyl-BINAP), 2,2'-bis (dicyclohexylphosphino)-6,6'-dimethyl-1,1'-biphenyl (BICHEP), 2,3-bis(diphenylphosphino)butane (CHIRAPHOS), 1-cyclohexyl-1,2-bis(diphenylphosphino)ethane (CYCPHOS), 1,2-bis[(o-methoxyphenyl)phenylphosphino] ethane (DIPAMP), 1,2-bis(diphenylphosphino)propane (PROPHOS), 2,4-bis(diphenylphosphino)pentane (SKEWPHOS), 1-[1',2-bis(diphenylphosphino)ferrocenyl]ethyldiamine (BPPFA), 1-substituted-3,4-bis-(diphenylphosphino)pyrrolidine (DEGPHOS), 2,3-O-isopropyliden-2,3-dihydroxy-1,4-bis(diphenylphosphino)butane (DIOP), (substituted-1,2-bis(phosphorano)benzene) (DuPHOS), 5,6-bis-diphenylphosphino)-2-norbornene (NORPHOS), N,N'-bis(diphenylphosphino)-N,N'-bis(1-phenylethyl)ethylenediamine (PNNP) and the like.

The phosphine is preferably optically active phosphine, more preferably, optically active phosphine such as BINAP, H8 BINAP, Tol-BINAP, Xyl-BINAP, BICHEP, CHIRAPHOS, CYCPHOS, DIPAMP, PROPHOS, SKEWPHOS, etc. and particularly BINAP, Xyl-BINAP and the like.

The amine to be used includes, for example, monoamines such as methylamine, ethylamine, propylamine, butylamine, pentylamine, hexylamine, cyclopentylamine, cyclohexylamine, benzylamine, dimethylamine, diethylamine, dipropylamine, dihexylamine, dicyclopentylamine, dicyclohexylamine, dibenzylamine, diphenylamine, phenylethylamine, piperidine, piperazine, phenylethylamine, naphthylethylamine, cyclohexylethylamine, cycloheptylethylamine, etc, diamines such as methylenediamine, ethylenediamine, 1,2-diaminopropane, 1,3-diaminopropane, 1,4-diaminobutane, 2,3-diaminobutane, 1,2-cyclopentanediamine, 1,2-cyclohexanediamine, N-methylethylenediamine, N,N'-dimethylethylenediamine, o-phenylenediamine, p-phenylenediamine, 1,2-diphenylethylenediamine (hereinafter, briefly referred to as DPEN), 1,2-cyclohexanediamine, 1,2-cycloheptanediamine, 2,3-dimethylbutanediamine, 1-methyl-2,2-diphenylethylenediamine, 1-isobutyl-2,2-diphenylethylenediamine, 1-isopropyl-2,2-diphenylethylenediamine, 1-methyl-2,2-bis(p-methoxyphenyl)ethylenediamine, 1-isobutyl-2,2-bis(p-methoxyphenyl)ethylenediamine, 1-isopropyl-2,2-bis(p-methoxyphenyl)ethylenediamine (hereinafter, briefly referred to as DAIPEN), 1-benzyl-2,2-bis(p-methoxyphenyl) ethylenediamine, 1-methyl-2,2-dinaphthylethylenediamine, 1-isobutyl-2,2-dinaphthylethylenediamine, 1-isopropyl-2,2-dinaphthylethylenediamine, a propanediamine derivative, a butanediamine derivative, a phenylenediamine derivative, a cyclohexanediamine derivative, etc. and the like.

The amine is preferably optically active amine, more preferably, optically active amine such as phenylethylamine, naphthylethylamine, cyclohexylethylamine, cycloheptylethylamine, 1,2-diphenylethylenediamine, 1,2-cyclohexandiamine, 1,2-cycloheptanediamine, 2,3-dimethylbutanediamine, 1-methyl-2,2-diphenylethylenediamine, 1-isobutyl-2,2-diphenylethylenediamine, 1-isopropyl-2,2-diphenylethylenediamine, 1-methyl-2,2-bis(p-methoxyphenyl)ethylenediamine, 1-isobutyl-2,2-bis(p-methoxyphenyl)ethylenediamine, 1-isopropyl-2,2-bis(p-methoxyphenyl)ethylenediamine, 1-benzyl-2,2-bis(p-methoxyphenyl)ethylenediamine, 1-methyl-2,2-dinaphthylethylenediamine, 1-isobutyl-2,2-dinaphthylethylenediamine, 1-isopropyl-2,2-dinaphthylethylenediamine, etc, and particularly 1,2-diphenylethylenediamine, 1-isopropyl-2,2-bis(p-methoxyphenyl)ethylenediamine and the like.

The ruthenium complex includes, for example, an inorganic ruthenium compound such as ruthenium chloride (III) hydrate, ruthenium bromide (III) hydrate, ruthenium iodide (III) hydrate, etc.; a ruthenium compound coordinated with diene such as [a polynuclear form of ruthenium(norbornadiene) dichloride], [a polynuclear form of ruthenium(cyclooctadiene) dichloride], bis(methylallyl)ruthenium(cyclooctadiene), etc.; a ruthenium complex coordinated with an aromatic compound such as [a dinuclear form of ruthenium (benzene) dichloride], [a dinuclear form of ruthenium(p-cymene) dichloride], [a dinuclear form of ruthenium(trimethylbenzene) dichloride], [a dinuclear form of ruthenium (hexamethylbenzene) dichloride], etc.; a ruthenium complex coordinated with phosphine such as dichlorotris(triphenylphosphine)ruthenium, etc. and the like.

The optically active ruthenium-phosphine-amine complex obtained by combination of the exemplified phosphine, amine and ruthenium complex can be used in the present reaction. For example, $RuCl_2$[(S)-BINAP] [(S,S)-DPEN],
$RuCl_2$[(R)-BINAP] [(R,R)-DPEN],
$RuCl_2$[(S)-xylBINAP] [(S)-DAIPEN],
$RuCl_2$[(R)-xylBINAP] [(R)-DAIPEN] and the like are particularly preferred.

The amount of the optically active ruthenium-phosphine-amine complex varies depending on the reaction vessel, the reaction type and the like, but it is for example, 0.0001 to 0.1 molar equivalents, preferably 0.0001 to 0.02 molar equivalents, relative to 1 mole of a ketone compound (V) which is the reaction substrate.

The base used in the present process includes, for example, alkali metal hydroxides such as potassium hydroxide, sodium hydroxide, cesium hydroxide, etc.; alkali metal alkoxides such as lithium methoxide, sodium methoxide, potassium methoxide, lithium ethoxide, sodium ethoxide, potassium ethoxide, lithium propoxide, sodium propoxide, potassium propoxide, lithium isopropoxide, sodium isopropoxide, potassium isopropoxide, potassium tert-butoxide, etc.; alkylthio alkali metals such as sodium thiomethoxide, etc. and the like. The alkali metal hydroxides and the alkali metal alkoxides are preferably sodium hydroxide, potassium hydroxide, potassium isopropoxide, potassium tert-butoxide and the like, and particularly potassium hydroxide and potassium tert-butoxide.

The amount of the base is, for example, 0.5 to 100 molar equivalents, preferably 2 to 40 molar equivalents, relative to 1 mole of the optically active ruthenium-phosphine-amine complex.

In the present process, hydrogenation of the compound represented by the ketone compound (V) or a salt thereof is usually carried out in a suitable solvent.

Such solvent is not particularly limited if it has no adverse influence on the reaction and solubilizes the starting compounds and the catalyst, and it includes, for example, aromatic hydrocarbons such as toluene, xylene, etc.; aliphatic hydrocarbons such as heptane, hexane, etc.; halogenated hydrocarbons such as methylene chloride, etc.; ethers such as diethyl ether, tetrahydrofuran, etc.; alcohols such as methanol, ethanol, 2-propanol, butanol, benzyl alcohol, etc.; nitriles such as acetonitrile, etc.;

dimethylformamide, dimethylsulfoxide and the like. Such solvent may be used in a mixture at a suitable ratio. The solvent is preferably alcohol, particularly 2-propanol.

The above-mentioned solvent is preferably used after drying and degassing.

The amount of the solvent is suitably determined by solubility of Compound (V) and the like. For example, if lo alcohol (preferably 2-propanol) is used as the solvent, the reaction can be carried out from in the nearly solventless state to in a solvent in an amount of 100 times by weight or more, preferably 2 to 50 times by weight as much as Compound (V).

The hydrogenation can be carried out in a batch mode or in a continuous mode. In addition, the hydrogenation is carried out in the presence of hydrogen, and the hydrogen pressure is, for example, 1 to 200 atm, preferably 1 to 10 atm.

The reaction temperature is preferably −30 to 100° C., further preferably 10 to 50° C., particularly preferably 20 to 50° C.

The reaction time is preferably 0.5 to 48 hours, further preferably 2 to 24 hours.

Thus obtained optically active alcohol compound (IIc) is subjected to the reactions described in the above-mentioned Methods A to C, to thus produce an optically active Compound (I) or a salt thereof.

[Method G]

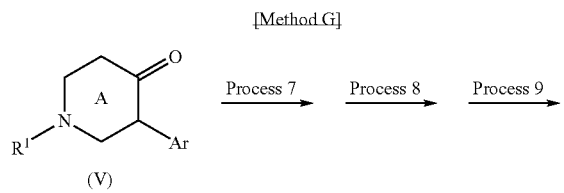

-continued

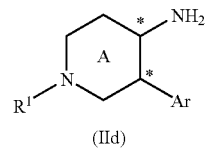

(IId)

wherein * is a chiral center, and other symbols have the same meanings as defined above. $NH_2$ and R have a cis configuration relationship.

In the present method, the ketone compound (V) is subjected to condensation with an optically active compound represented by the formula:

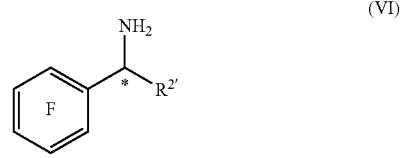

(VI)

wherein Ring F is an optionally substituted, optionally fused benzene ring, $R^{2'}$ is an optionally substituted hydrocarbon group, and other symbols have the same meanings as defined above, or a salt thereof, followed by hydrogenation and further hydrogenolysis, to give an optically active amine compound (IId) in which $NH_2$ and R are in cis configuration. Compound (V) used as the starting compound in the present method can be produced by the method described in the above-mentioned Method D and Method E, or according to a known method.

The "substituent" of the "optionally substituted, optionally fused benzene ring" represented by Ring F includes, for example, the same group as those referred to herein above for the foregoing "substituent" in the "optionally substituted aromatic ring" represented by Ring B. In addition, the benzene ring may be fused with the benzene ring or the "heterocyclic ring" represented by $R^1$.

The "optionally substituted hydrocarbon group" represented by $R^{2'}$ includes, for example, the same group as those referred to herein above for the foregoing group represented by $R^1$.

(Process 7)

The present process is a process of reacting Compound (V) with optically active amine (VI) to thus convert it into imine. The conversion of Compound (V) into imine can be carried out using the known methods, for example, by using optically active amine (VI), and if necessary, using a catalyst in a solvent inert to the reaction.

The optically active amine (VI) used in the present process is an optionally substituted, optically active 1-phenylethylamine derivative, for example, 1-phenylethylamine, 1-phenylpropylamine, 1-naphthylethylamine, 2-naphthylethylamine, 1-(4-tolyl)ethylamine and the like, and particularly preferably optically active 1-phenylethylamine. A desired isomer can be obtained selectively among the optically active forms represented by the formula (IId) by suitably selecting any optical isomer of (R)-configuration or (S)-configuration. The amount of the optically active amine (VI) is in the order of about 0.9 to about 10 molar equivalents, preferably about 1 to about 2 molar equivalents, relative to 1 mole of Compound (V).

The solvent used in the present process is not particularly limited if it has no adverse influence on the reaction and solubilizes the starting compounds, for example, aromatic hydrocarbons such as toluene, xylene, etc., aliphatic hydrocarbons such as heptane, hexane, etc., halogenated hydrocarbons such as chloroform, dichloromethane, etc., ethers such as diethyl ether, tetrahydrofuran, dioxane, etc., alcohols such as methanol, ethanol, 2-propanol, butanol, benzyl alcohol, etc., nitrites such as acetonitrile, etc., dimethylformamide, dimethylsulfoxide and the like. Such solvent may be used in a mixture at a suitable ratio. The solvent is preferably toluene. The amount of the solvent is suitably determined by solubility of Compounds (V) and (VI), etc. The reaction can be carried out from in the nearly solventless state, to in a solvent in an amount of 100 times by weight or more, preferably 5 to 30 times by weight as much as Compound (V).

If necessary, the reaction can advantageously proceed by adding a catalyst. Such catalyst includes, for example, mineral acids (e.g., hydrochloric acid, hydrobromic acid, sulfuric acid, etc.), carboxylic acids (e.g., formic acid, acetic acid, propionic acid, trifluoroacetic acid, etc.), sulfonic acids (e.g., methanesulfonic acid, p-toluenesulfonic acid, etc.), Lewis acids (e.g., aluminum chloride, zinc chloride, zinc bromide, boron trifluoride, titanium chloride, etc.), acetates (e.g. sodium acetate, potassium acetate, etc.) and molecular sieves (molecular sieves 3A, 4A, 5A, etc.), preferably Lewis acid, and particularly aluminum chloride. The amount of the catalyst is, for example, in the order of about 0.01 to 10 molar equivalents, preferably about 0.02 to 1 molar equivalents, relative to 1 mole of Compound (V).

The reaction temperature varies depending on the solvent to be used, and is in the order of usually about 30° C. to 200° C., preferably about 50° C. to 150° C., and the reaction time is usually in the order of 0.1 hour to 48 hours, preferably 0.1 hour to 24 hours.

The reaction can be facilitated in the present reaction by the known operation of azeotropic dehydration.

(Process 8)

The present process is a process of hydrogenating the imine obtained in Process 7 in a solvent inert to the reaction by various reductions. Such reduction can be carried out by the known methods, for example, a method using metal hydride or a method by catalytic hydrogenation.

The metal hydride as the reducing agent includes, for example, sodium borohydride, lithium borohydride, zinc borohydride, sodium cyanoborohydride, sodium triacetoxyborohydride, lithium cyanoborohydride, aluminum dibutylhydride, aluminum hydride, lithium aluminum hydride, a orane complex (a borane-THF complex, catechol borane, etc.) and the like, and preferably, sodium borohydride, sodium cyanoborohydride, sodium triacetoxyborohydride, etc. The amount of the reducing agent is, for example, in the order of 1 to 50 molar equivalents, preferably 1 to 10 molar equivalents, relative to 1 mole of the substrate. The solvent used herein is not particularly limited if has no adverse influence on the reaction and solubilizes the starting compounds, for example, aromatic hydrocarbons such as toluene, xylene, etc., aliphatic hydrocarbons such as heptane, hexane, etc., halogenated hydrocarbons such as chloroform, dichloromethane, etc., ethers such as diethyl ether, tetrahydrofuran, dioxane, etc., alcohols such as methanol, ethanol, 2-propanol, butanol, benzyl alcohol, etc., nitrites such as acetonitrile, etc., dimethylformamide, dimethylsulfoxide and the like. Such solvent may be used in a mixture at a suitable ratio. The amount of the solvent is from nearly zero, to 100 times by weight or more, preferably 5 to 30 times by weight as much as the substrate. The reaction temperature is usually in the order of about −80° C. to 200° C., preferably about −50° C. to 100° C., and the reaction time is usually in the order of 5 minutes to 72 hours, preferably 0.5 hour to 12 hours.

The catalytic hydrogenation can be carried out under hydrogen atmosphere and in the presence of a catalyst. The catalyst to be used includes, for example, palladium compounds such as palladium carbon, palladium hydroxide carbon, palladium oxide, etc., nickel compounds such as Raney-nickel, etc., platinum compounds such as platinum oxide, platinum carbon, etc., rhodium compounds such as rhodium acetate, etc. and the like, preferably, a heterogeneous supported nickel catalyst, and particularly Raney nickel. The amount is in the order of about 0.001 to 10 equivalents, preferably about 0.1 to 5 equivalents. The catalytic hydrogenation is usually carried out in a solvent inert to the reaction. Such solvent includes, for example, alcohols such as methanol, ethanol, propanol, butanol, benzylalcohol, etc.; aliphatic hydrocarbons such as heptane, hexane, etc.; aromatic hydrocarbons such as benzene, toluene, xylene, etc.; halogenated hydrocarbons such as dichloromethane, chloroform, etc.; ethers such as diethyl ether, dimethoxyethane, dioxane, tetrahydrofuran, etc.; esters such as ethyl acetate, etc.; amides such as N,N-dimethylformamide, etc.; carboxylic acids such as acetic acid, etc.; water, or a mixture thereof, preferably alcohols, and particularly ethanol. The amount of the solvent is from nearly zero, to preferably 100 times by weight, preferably 5 to 30 times by weight as much as the substrate. The hydrogenation can be carried out in a batch mode or in a continuous mode. The hydrogen pressure under which the reaction is carried out, is usually in the order of about 0.1 to 5 MPa, preferably about 0.1 to 1 MPa. The reaction temperature is usually in the order of about 0° C. to 150° C., preferably about 20° C. to 50° C., and the reaction time is usually in the order of 5 minutes to 120 hours.

(Process 9)

The present process is a process of hydrogenolysis of the compound obtained in Process 8 to obtain an optically active amine compound (IId) in which $NH_2$ and R are in cis configuration. Such hydrogenolysis can be carried out by the known methods, for example, a method by catalytic hydrogenation.

The catalytic hydrogenation can be carried out in the presence of a catalyst under hydrogen atmosphere. The catalyst to be used includes, for example, a heterogeneous catalyst in which transition metal is supported on a carrier. The heterogeneous catalyst includes, for example, palladium compounds such as palladium carbon, palladium hydroxide carbon, palladium oxide, etc., nickel compounds such as Raney-nickel, etc., platinum compounds such as platinum oxide, platinum carbon, etc., rhodium compounds such as rhodium acetate, etc. and the like. Such catalyst is preferably a heterogeneous, palladium-supported catalyst, particularly palladium carbon and palladium hydroxide carbon. The amount is in the order of about 0.0001 to 1 equivalent, preferably about 0.001 to 0.5 equivalent. The catalytic hydrogenation is usually carried out in a solvent inert to the reaction. Such solvent includes, for example, alcohols such as methanol, ethanol, propanol, butanol, benzyl alcohol, etc.; aliphatic hydrocarbons such as heptane, hexane, etc.; aromatic hydrocarbons such as benzene, toluene, xylene, etc.; halogenated hydrocarbons such as dichloromethane, chloroform, etc.; ethers such as diethyl ether, dimethoxyethane, dioxane, tetrahydrofuran, etc.; esters such as ethyl acetate, etc.; nitrites such as acetonitrile, etc.; amides such as N,N-dimethylformamide, etc.; carboxylic acids such as acetic acid, etc.; water, or a mixture thereof, preferably alcohols, and particularly ethanol. The amount of the solvent is from nearly zero, to 100 times by weight or more, preferably 5 to 30 times by weight part as much as the substrate. The hydrogenation can be carried out in a batch mode or in a continuous mode. The hydrogen pressure under which the reaction is carried out, is for example, usually in the order of about 0.1 to 5 MPa, preferably about 0.1 to 1 MPa. The reaction temperature is usually in the order of about 0° C. to 200° C., preferably about 20° C. to 60° C., and the reaction time is usually in the order of 5 minutes to 120 hours.

In the present method, Compound (IId) can be also produced directly from Compound (V) while carrying out the reaction to produce the above-mentioned imine and to reduce the products at the same time, without isolating the compound obtained in Process 7 or Process 8 which is an-intermediate.

Thus obtained optically active amine compound (IId) is subjected to the reactions described in Methods A to C to produce an optically active Compound (I) or a salt thereof.

Among the starting compounds of Compound (I), the compound represented by the formula:

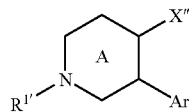

(II)

wherein $R^{1'}$ is an acyl group or an optionally substituted heterocyclic group, $X''$ is a hydroxy group or an amino group, and other symbols have the same meanings as defined above, provided that when $X''$ is a hydroxy group, $R^{1'}$ is neither an ethoxycarbonyl group nor a cyclopropylcarbonyl group, or a salt thereof, is a novel compound.

"The acyl group or the optionally substituted heterocyclic group" represented by $R^{1'}$ includes, for example, the same group as those referred to herein above for the foregoing group represented by $R^{1}$.

In each of the reactions for the synthesis of the objective compounds and the starting materials, when the starting compounds have an amino group, a carboxyl group or a hydroxy group as a substituent, such groups may be protected with the protecting groups which are generally used in peptide chemistry, etc. In such case, if necessary, such protecting groups can be removed to obtain the objective compounds after the reactions.

Such protecting group includes, for example, protecting groups described in "Protective Groups in Organic Synthesis, $3^{rd}$ Ed. (1999)", edited by Theodora W. Greene, Peter G. M. Wuts, published by Wiley-Interscience.

The protecting group for the amino group includes, for example, a formyl group, a $C_{1-6}$ alkyl-carbonyl group (e.g., an acetyl group, a propionyl group, etc.), a phenylcarbonyl group, a $C_{1-6}$ alkyl-oxycarbonyl group (e.g., a methoxycarbonyl group, an ethoxycarbonyl group, etc.), an aryloxycarbonyl group (e.g., a phenyloxycarbonyl group, etc.), a $C_{7-10}$ aralkyl-carbonyl group (e.g., a benzyloxycarbonyl group, etc.), a benzyl group, a benzhydryl group, a trityl group, a phthaloyl, etc., each of which may be substituted. Such substituent includes, for example, a halogen atom (e.g., a fluorine atom, a chlorine atom, a bromine atom, an iodine atom, etc.), a $C_{1-6}$ alkyl-carbonyl group (e.g., an acetyl group, a propionyl group, a butylcarbonyl group, etc.), a nitro group and the like. The number of substituent is in the order of 1 to 3.

A protecting group for the carboxyl group includes, for example, a $C_{1-6}$ alkyl group (e.g., a methyl group, an ethyl group, an n-propyl group, an i-propyl group, an n-butyl group, a tert-butyl group, etc.), a phenyl group, a trityl group, a silyl group and the like, each of which may be substituted. Such substituent includes, for example, a halogen atom (a fluorine atom, a chlorine atom, a bromine atom, an iodine atom), a formyl group, a $C_{1-6}$ alkyl-carbonyl group (e.g., an acetyl group, a propionyl group, a butylcarbonyl group, etc.), a nitro group and the like. The number of substituent is in the order of 1 to 3.

The protecting group for the hydroxy group includes, for example, a $C_{1-6}$ alkyl group (e.g., a methyl group, an ethyl group, an n-propyl group, an i-propyl group, an n-butyl group, a tert-butyl group, etc.), a phenyl group, a $C_{7-10}$ aralkyl group (e.g., a benzyl group, etc.), a formyl group, a $C_{1-6}$ alkyl-carbonyl group (e.g., an acetyl group, a propionyl group, etc.), an aryloxycarbonyl group (e.g., a phenyloxycarbonyl group, etc.), a $C_{7-10}$ aralkyloxy-carbonyl group (e.g., a benzyloxycarbonyl group, etc.), a pyranyl group, a furanyl group, a silyl group and the like, each of which may be substituted. Such substituent includes, for example, a halogen atom (a fluorine atom, a chlorine atom, a bromine atom, an iodine atom, etc.), a $C_{1-6}$ alkyl group, a phenyl group, a $C_{7-10}$ aralkyl group, a nitro group and the like. The number of substituent is in the order of 1 to 4.

Such protecting groups can be removed by a known deprotection method or the method described in "Protective Groups in Organic Synthesis, $3^{rd}$ Ed. (1999)", edited by Theodora W. Greene, Peter G. M. Wuts, published by Wiley-Interscience, or an analogous method thereto. For example, treatment with an acid, a base, reduction, ultraviolet radiation, hydrazine, phenylhydrazine, sodium N-methyldithiocarbamate, tetrabutylammonium fluoride, palladium acetate or the like, can be used.

When Compound (I) is obtained as a free compound in the above-mentioned method, a salt with for example, inorganic acids (e.g., hydrochloric acid, sulfuric acid, hydrobromic acid, etc.), organic acids (e.g., methanesulfonic acid, benzenesulfonic acid, toluenesulfonic acid, oxalic acid, fumaric acid, maleic acid, tartaric acid, etc.), inorganic bases (e.g., alkali metals such as sodium, potassium, etc., alkaline earth metals such as calcium, magnesium, etc., aluminum, ammonium, and the like), or organic bases (e.g., trimethylamine, triethylamine, pyridine, picoline, ethanolamine, diethanolamine, triethanolamine, dicyclohexylamine, N,N'-dibenzylethylenediamine, etc.) and the like can be produced in a routine manner. When Compound (I) is obtained in the form of a salt, the compound can be converted to a free compound or another salt in a routine manner.

In addition, when the starting compound forms a salt in each of the above-mentioned reactions, the compound may be used as a salt. Such salt includes, for example, those exemplified as a salt of Compound (I).

Compound (I) of the present invention thus produced by such method, can be isolated and purified by a typical separation means such as recrystallization, distillation, chromatography, etc.

When Compound (I) contains an optical isomer, a stereoisomer, a regioisomer or a rotamer, these are also encompassed in Compound (I), and can be obtained as a single product according to synthesis and separation methods known per se (for example, concentration, solvent extraction, column chromatography, recrystallization, etc.). For example, when Compound (I) has an optical isomer, an optical isomer resolved from this compound is also encompassed in Compound (I).

The optical isomer can be produced by a method known per se. To be specific, an optically active synthetic intermediate is used, or the final racemate product is subjected to optical resolution according to a conventional method to give an optical isomer.

The method of optical resolution may be a method known per se, such as a fractional recrystallization method, a chiral column method, a diastereomer method, etc.

1) Fractional Recrystallization Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine, etc.) is formed, which is separated by a fractional recrystallization method, and if desired, a free optical isomer is obtained by a neutralization step.

2) Chiral Column Method

A method wherein a racemate or a salt thereof is applied to a column for separation of an optical isomer (a chiral column) to allow separation. In the case of a liquid chromatography, for example, a mixture of the optical isomers is applied to a chiral column such as ENANTIO-OVM (manufactured by Tosoh Corporation), CHIRAL series (manufactured by Daicel Chemical Industries, Ltd.) and the like, and developed with water, various buffers (e.g., phosphate buffer) and organic solvents (e.g., ethanol, methanol, isopropanol, acetonitrile, trifluoroacetic acid, diethylamine, etc.) solely or in admixture to separate the optical isomer. In the case of a gas chromatography, for example, a chiral column such as CP-Chirasil-DeX CB (manufactured by GL Sciences Inc.) and the like is used to allow separation.

3) Diastereomer Method

A method wherein a racemic mixture is prepared into a diastereomeric mixture by chemical reaction with an optically active reagent, which is made into a single substance by a typical separation means (e.g., a fractional recrystallization method, a chromatography method, etc.) and the like, and is subjected to a chemical treatment such as hydrolysis and the like to separate an optically active reagent moiety, whereby an optical isomer is obtained. For example, when Compound (I) contains hydroxy, or primary or secondary amino in a molecule, the compound and an optically active organic acid (e.g., MTPA [α-methoxy-α-(trifluoromethyl)phenylacetic acid], (−)-menthoxyacetic acid, etc.) and the like are subjected to condensation reaction to give diastereomers in the ester form or in the amide form, respectively. When Compound (I) has a carboxylic acid group, this compound and an optically active amine or an alcohol reagent are subjected to condensation reaction to give diastereomers in the amide form or in the ester form, respectively. The separated diastereomer is converted to an optical isomer of the original compound by acid hydrolysis or base hydrolysis.

Compound (I) or a salt thereof may be in the form of a crystal.

The crystal of Compound (I) or a salt thereof (hereinafter, it may be referred to as crystal of the present invention) can be produced by crystallization of Compound (I) or a salt thereof by a crystallization method known per se.

Examples of the crystallization method include a method of crystallization from a solution, a method of crystallization from vapor, a method of crystallization from the melts and the like.

The "crystallization from a solution" is typically a method of shifting a non-saturated state to supersaturated state by varying factors involved in solubility of compounds (solvent composition, pH, temperature, ionic strength, redox state, etc.) or the amount of solvent. To be specific, for example, a concentration method, a cooling method, a reaction method (a diffusion method, an electrolysis method), a hydrothermal growth method, a flux method and the like can be mentioned. Examples of the solvent to be used include aromatic hydrocarbons (e.g., benzene, toluene, xylene, etc.), halogenated hydrocarbons (e.g., dichloromethane, chloroform, etc.), saturated hydrocarbons (e.g., hexane, heptane, cyclohexane, etc.), ethers (e.g., diethyl ether, diisopropyl ether, tetrahydrofuran, dioxane, etc.), nitriles (e.g., acetonitrile, etc.), ketones (e.g., acetone, etc.), sulfoxides (e.g., dimethylsulfoxide, etc.), acid amides (e.g., N,N-dimethylformamide, etc.), esters (e.g., ethyl acetate, etc.), alcohols (e.g., methanol, ethanol, isopropyl alcohol, etc.), water and the like. These solvents are used alone or in a combination of two or more at a suitable ratio (e.g., 1:1 to 1:100 (a volume ratio)).

The "crystallization from vapor" is, for example, a vaporization method (a sealed tube method, a gas stream method), a gas phase reaction method, a chemical transportation method and the like.

The "crystallization from the melt" is, for example, a normal freezing method (a Czockralski method, a temperature gradient method and a Bridgman method), a zone melting method (a zone leveling method and a floating zone method), a special growth method (a VLS method and a liquid phase epitaxy method) and the like.

Preferable examples of the crystallization method include a method of dissolving Compound (I) or a salt thereof in a suitable solvent (e.g., alcohols such as methanol, ethanol, etc. and the like) at a temperature of 20 to 120° C., and cooling the resulting solution to a temperature not higher than the temperature of dissolution (e.g., 0 to 50° C., preferably 0 to 20° C.) and the like.

The thus obtained crystals of the present invention can be isolated, for example, by filtration and the like.

In the present specification, the melting point means that measured using, for example, a micromelting point apparatus (Yanako, MP-500D) or a DSC (differential scanning calorimetry) device (SEIKO, EXSTAR6000) and the like.

In the present specification, the peak by a powder X-ray diffraction means that measured using, for example, RINT2100 (Rigaku Corporation), etc. with a Cu-Kα1 ray (tube voltage: 40 KV; tube current: 50 mA) as a ray source.

In general, the melting points and the peak by a powder X-ray diffraction vary depending on the measurement apparatuses, the measurement conditions and the like. The crystal in the present specification may show different values from the melting point described in the present specification or the peak by a powder X-ray diffraction vary depending on the measurement apparatuses, as long as they are within each of a general error range.

The crystal of the present invention is superior in physicochemical properties (e.g., melting point, solubility, stability, etc.) and biological properties (e.g., pharmacokinetics (absorption, distribution, metabolism, excretion), efficacy expression, etc.), and thus it is extremely useful as a medicament.

Compound (I) or a salt thereof or a prodrug of the present invention (hereinafter, it may be briefly referred to as the compound of the present invention) has excellent antagonistic action for a tachykinin receptor, particularly Substance P receptor antagonistic action, neurokinin A receptor antagonistic action, in addition to inhibitory action for the increased permeability of blood vessel of a trachea induced by capsaicin. The compound of the present invention has low toxicity and thus it is safe.

Accordingly, the compound of the present invention having excellent antagonistic action for Substance P receptors and neurokinin A receptors, etc. can be used as a safe medicine for preventing and treating the following diseases related to Substance P in mammals (e.g., mice, rats, hamsters, rabbits, cats, dogs, bovines, sheep, monkeys, humans, etc.).

(1) Abnormality of lower urinary tract functions [for example, abnormal micturition such as urinary frequency, urinary incontinence, etc.]

(2) Digestive organ diseases [for example, irritable bowel syndrome, ulcerative colitis, Crohn's disease, diseases caused by a spiral urease-positive gram-negative bacterium (e.g., Helicobacter pylori, etc.) (e.g., gastritis, gastric ulcer, etc.), gastric cancer, postgastrostomy disorder, dyspepsia, esophageal ulcer, pancreatitis, polyp of the colon, cholelithiasis, hemorrhoids, peptic ulcer, situational ileitis, vomiting, etc.]

(3) Inflammatory or allergic diseases [for example, allergic rhinitis, conjunctivitis, gastrointestinal allergy, pollinosis, anaphylaxis, dermatitis, herpes, psoriasis, bronchitis, expectoration, retinopathy, postoperative and posttraumatic inflammation, regression of puffiness, pharyngitis, cystitis, meningitidis, inflammatory ophthalmic diseases, etc.]

(4) Osteoarthropathy diseases [for example, rheumatoid arthritis (chronic rheumatoid arthritis), arthritis deformans, rheumatoid myelitis, osteoporosis, abnormal growth of cells, bone fracture, bone refracture, osteomalacia, osteopenia, osseous Behcet's disease, rigid myelitis, articular tissue destruction by gonarthrosis deformans and similar diseases thereto, etc.]

(5) Respiratory diseases [for example, cold syndrome, pneumonia, asthma, pulmonary hypertension, pulmonary thrombi/pulmonary obliteration, pulmonary sarcoidosis, pulmonary tuberculosis, interstitial pneumonia, silicosis, adult tachypnea syndrome, chronic obliterative pulmonary diseases, cough, etc.]

(6) Infectious diseases [HIV infectious diseases, virus infectious diseases due to cytomegalo virus, influenza virus, herpes virus and the like, rickettsia infectious diseases, bacterial infectious diseases, sexually-transmitted diseases, carinii pneumonia, helicobacter pylori infectious disease, systemic fungal infectious diseases, tuberculosis, invasive staphylococcal infectious diseases, acute viral encephalitis, acute bacterial meningitidis, AIDS encephalitis, septicemia, sepsis, sepsis gravis, septic shock, endotoxin shock, toxic shock syndromes, etc.]

(7) Cancers [for example, primary, metastatic or recurrent breast cancer, prostatic cancer, pancreatic cancer, gastric cancer, lung cancer, colorectal cancer (colon cancer, rectal cancer, anal cancer), esophagus cancer, duodenal cancer, head and neck cancer (tongue cancer, pharynx cancer, larynx cancer), brain tumor, neurinoma, non-small cell lung cancer, small cell lung cancer, hepatic cancer, renal cancer, colic cancer, uterine cancer (cancer of the uterine body, uterine cervical cancer), ovarian cancer, bladder cancer, skin cancer, hemangioma, malignant lymphoma, malignant melanoma, thyroid cancer, bone tumor, hemangioma, angiofibroma, retinosarcoma, penis cancer, pediatric solid cancer, Kaposi's sarcoma, Kaposi's sarcoma caused by AIDS, tumor of the maxillary sinus, fibrous histiocytoma, smooth muscle sarcoma, rhabdomyosarcoma, liposarcoma, fibroid tumors of the uterus, osteoblastoma, osteosarcoma, chondrosarcoma, carcinomatous mesothelial tumor, tumors such as leukemia, Hodgkin's disease, etc.]

(8) Central nerve diseases [for example, neurodegenerative diseases (e.g., Alzheimer's disease, Down's disease, Parkinson's disease, Creutzfeldt-Jakob's disease, amyotrophic lateral sclerosis (ALS), Huntington chorea, diabetic neuropathy, multiple sclerosis, etc.), mental diseases (e.g., schizophrenia, depression, mania, anxiety neurosis, obsessive-compulsive neurosis, panic disorder, epilepsy, alcohol dependence, anxiety symptom, anxious mental state, etc.), central and peripheral nerve disorders (e.g., head trauma, spinal cord injury, brain edema, disorders of sensory function, abnormality of sensory function, disorders of autonomic nervous function and abnormality of autonomic nervous function, whiplash injury, etc.), memory disorders (e.g., senile dementia, amnesia, cerebrovascular dementia, etc.), cerebrovascular disorders (e.g., disorders and aftereffect and/or complication from intracerebral hemorrhage, brain infarction, etc, asymptomatic cerebro-vascular accident, transient cerebral ischemic attack, hypertensive encephalopathia, blood-brain barrier disorder, etc.), recurrence and aftereffect of cerebro-vascular accident (neural symptoms, mental symptoms, subjective symptoms, disorders of daily living activities, etc.), post-cerebrovascular occlusion central hypofunction; disorder or abnormality of cerebral circulation and/or autoregulation of renal circulation]

(9) Circulatory diseases [for example, acute coronary artery syndromes (e.g., acute cardiac infarction, unstable angina, etc.), peripheral arterial obstruction, Raynaud's disease; Buerger disease; restenosis after coronary-artery intervention (percutaneous transluminal coronary angioplasty (PTCA), directional coronary atherectomy (DCA), stenting, etc.), restenosis after coronary-artery bypass operation, restenosis after intervention (angioplasty, atherectomy, stenting, etc.) or bypass operation in other peripheral artery, ischemic cardiac diseases (e.g., cardiac infarction, angina, etc.), myocarditis, intermittent claudication, lacunar infarction, arteriosclerosis (e.g., atherosclerosis, etc.), cardiac failure (acute cardiac failure, chronic cardiac failure accompanied by congestion), arrhythmia, progress of atherosclerotic plaque, thrombosis, hypertension, hypertensive tinnitus; hypotension, etc.]

(10) Pains [e.g., migraine, neuralgia, etc.]

(11) Autoimmune diseases [for example, collagen disease, systemic lupus erythematosus, scleroderma, polyarteritis, myasthenia gravis, multiple sclerosis, Sjogren's syndrome, Behcet's disease, etc.]

(12) Hepatic diseases [e.g., hepatitis (including chronic hepatitis), cirrhosis, interstitial hepatic diseases, etc.]

(13) Pancreatic diseases [e.g., pancreatitis (including chronic pancreatitis), etc.]

(14) Renal diseases [e.g., nephritis, glomerulonephritis, glomerulosclerosis, renal failure, thrombotic microangiopathy, dialysis complications, organ disorders including nephropathia by radiation, diabetic nephropathia, etc.]

(15) Metabolic diseases [e.g., diabetic diseases (insulin-dependent diabetes, diabetic complications, diabetic retinopathy, diabetic microangiopathy, diabetic neuropathy, etc.); glucose tolerance abnormality, obesity, prostatomegaly, sexual dysfunction, etc.]

(16) Endocrine diseases [e.g., Addison's disease, Cushing's syndrome, melanocytoma, primary aldosteronism, etc.]

(17) Other diseases (A) Transplant rejection [e.g., posttransplantational rejection, posttransplantational polycythemia, hypertension, organ disorder and/or vascular hypertrophy, graft-versus-host disease, etc.]

(B) Abnormality in characteristic of blood and/or blood components [e.g., enhancement in platelet aggregation, abnormality of erythrocyte deformability, enhancement in leukocyte adhesiveness, increase in blood viscosity, polycythemia, vascular peliosis, autoimmune hemolytic anemia, disseminated intravascular coagulation syndrome (DIC), multiple myelopathy, etc.]

(C) Gynecologic diseases [e.g., climacteric disorder, gestational toxicosis, endometriosis, hysteromyoma, ovarian disease, mammary disease, etc.]

(D) Dermatic diseases [e.g., keloid, angioma, psoriasis, pruritus, etc.]

(E) Ophthalmic diseases [e.g., glaucoma, ocular hypertension disease, etc.]

(F) Otolaryngological diseases [e.g., Menuel syndrome, tinnitus, gustation disorder, dizziness, disequilibrium, dysphagia, etc.]

(G) Diseases due to environmental and/or occupational factors (e.g., radiation disorder, disorders by ultraviolet ray-infrared ray-laser ray, altitude sickness, etc.)

(H) Ataxia (I) Chronic fatigue syndrome

Among the diseases as described above, particularly, the compounds of the present invention are useful as a tachykinin receptor antagonist and as an agent for ameliorating abnormality of lower urinary tract functions such as urinary frequency, urinary incontinence, etc., and even as an agent for treating such abnormality of lower urinary tract functions.

Pharmaceutical preparations comprising Compound of the present invention may be in any solid forms of powders, granules, tablets, capsules, suppositories, etc., and in any liquid forms of syrups, emulsions, injections, suspensions, etc.

The pharmaceutical preparations of the present invention can be produced by any conventional methods, for example, blending, kneading, granulation, tabletting, coating, sterilization, emulsification, etc., in accordance with the forms of the preparations to be produced. For the production of such pharmaceutical preparations, for example, each of the items in General Principles for pharmaceutical preparations in the Japanese Pharmacopeia, can be made reference to. In addition, the pharmaceutical preparations of the present invention may be formulated into a sustained release preparation containing active ingredients and biodegradable polymer compounds. The sustained release preparation can be produced according to the method described in JP-A-9-263545.

In the pharmaceutical preparations of the present invention, the content of the compound or a salt thereof in the present invention varies depending on the forms of the preparations, but is generally in the order of about 0.01 to 100% by weight, preferably about 0.1 to 50% by weight, more preferably 0.5 to 20% by weight, relative to the total weight of each preparation.

When the compound of the present invention is used in the above-mentioned pharmaceutical preparations, it may be used alone, or in admixture with a suitable, pharmaceutically acceptable carrier, for example, excipients (e.g., starch, lactose, sucrose, calcium carbonate, calcium phosphate, etc.), binders (e.g., starch, arabic gum, carboxymethyl cellulose, hydroxypropyl cellulose, crystalline cellulose, alginic acid, gelatin, polyvinyl pyrrolidone, etc.), lubricants (e.g., stearic acid, magnesium stearate, calcium stearate, talc, etc.), disintegrants (e.g., calcium carboxymethylcellulose, talc, etc.), diluents (e.g., water for injection, physiological saline, etc.) and if desired, with the additives (e.g., a stabilizer, a preservative, a colorant, a fragrance, a dissolution aid, an emulsifier, a buffer, an isotonic agent, etc.) and the like, by ordinary methods. It can be formulated into the solid preparations such as powders, fine granules, granules, tablets, capsules, etc., or into the liquid preparations such as injections, etc., and can be administered non-parenterally or parenterally.

The dose of the pharmaceutical preparation of the present invention varies depending on the kinds of the compound of the present invention or a pharmaceutically acceptable salts thereof, the administration route, the condition and the age of patients, etc. For example, the dose for oral administration of the pharmaceutical preparation to an adult patient suffering from abnormal urination is generally from about 0.005 to 50 mg/kg body/day, preferably from about 0.05 to 10 mg/kg body/day, more preferably from about 0.2 to 4 mg/kg body/day, in terms of the compound of the present invention, which may be administered once a day or in two or three divided portions a day.

The dose when the pharmaceutical composition of the present invention is a sustained release preparation varies depending on the kinds and the content of Compound (I) or a salt thereof, the formulation, the duration time of drug release, the animals to be administered (e.g., mammals such as humans, rats, mice, cats, dogs, rabbits, bovines, pigs, etc.), and the purpose of administration. For example, when it is applied by parenteral administration, preferably about 0.1 to about 100 mg of Compound (I) or a salt thereof is released from the preparation for 1 week.

The compound of the present invention can be used in a mixture or combination with other pharmaceutically active ingredients at a suitable ratio.

Combination of the compound of the present invention with other pharmaceutically active ingredients can give the following excellent effects:

(1) a dose can be reduced as compared with separate administration of the compound of the present invention or other pharmaceutically active ingredients. More specifically, when the compound of the present invention is combined with anticholinergic agents or NK-2 receptor antagonists, the dose can be reduced as compared with separate administration of anticholinergic agents or NK-2 receptor antagonists, and therefore, side effects such as dry mouth can be reduced;

(2) according to symptoms of patient (mild symptoms, severe symptoms, etc.), a drug to be combined with the compound of the present invention can be selected;

(3) by choosing other pharmaceutically active ingredients which have different mechanism of action from that of the compound of the present invention, the therapeutic period can be designed longer;

(4) by choosing other pharmaceutically active ingredients which have different mechanism of action from that of the compound of the present invention, continuation of therapeutic effects can be obtained; and (5) by combining the compound of the present invention and other pharmaceutically active ingredients, excellent effects such as synergic effects can be obtained.

A drug which is mixed or combined with the compound of the present invention (hereinafter, briefly referred to as combination drugs) includes the following:

(1) Agent For Treating Diabetes

Insulin preparations (e.g., animal insulin preparations extracted from the bovine or swine pancreas; human insulin preparations synthesized by a genetic engineering technique using Escherichia coli or a yeast; insulin zinc; protamine zinc insulin; a fragment or a derivative of insulin (e.g., INS-1, etc.), agents for potentiating insulin sensitivity (e.g., pioglitazone hydrochloride, troglitazone, rosiglitazone or its maleate, JTT-501, MCC-555, YM-440, GI-262570, KRP-297, FK-614, CS-011, etc.), α-glucosidase inhibitors (e.g., voglibose, acarbose, miglitol, emiglitate, etc.), biguanides (e.g., phenformin, metformin, buformin, etc.), sulfonylureas (e.g., tolbutamide, glibenclamide, gliclazide, chlorpropamide, tolazamide, acetohexamide, glyclopyramide, glimepiride, etc.) and other insulin secretagogues (e.g., repaglinide, senaglinide, mitiglinide or its calcium salt hydrate, GLP-1, nateglinide, etc.), dipeptidylpeptidase IV inhibitors (e.g., NVP-DPP-278, PT-100, P32/98, etc.), $β_3$ agonists (e.g., CL-316243, SR-58611-A, UL-TG307, AJ-9677, AZ40140, etc.), amylin agonists (e.g., pramlintide, etc.), phosphotyrosine phosphatase inhibitors (e.g., vanadic acid, etc.), gluconeogenesis inhibitors (e.g., glycogen phosphorylase inhibitors, glucose-6-phosphatase inhibitors, glucagon antagonists, etc.), SGLT (sodium-glucose cotransporter) inhibitors (e.g., T-1095, etc.) and the like.

(2) Agent For Treating Diabetic Complications

Aldose reductase inhibitors (e.g., tolrestat, epalrestat, zenarestat, zopolrestat, fidarestat (SNK-860), minalrestat (ARI-509), CT-112, etc.), neurotrophic factors (e.g., NGF, NT-3, etc.), AGE inhibitors (e.g., ALT-945, pimagedine, pyratoxathine, N-phenacylthiazolium bromide (ALT-766), EXO-226, etc.), active oxygen scavengers (e.g., thioctic acid, etc.), cerebral vasodilators (e.g., tiapuride, etc.) and the like.

(3) Antihyperlipidemic Agent

Statin compounds inhibiting cholesterol synthesis (e.g., pravastatin, simvastatin, lovastatin, atorvastatin, fluvastatin, cerivastatin or their salt (e.g., sodium salt salt, etc.) and the like), squalene synthase inhibitors or fibrate compounds having triglyceride lowering action (e.g., bezafibrate, clofibrate, simfibrate, clinofibrate, etc.) and the like.

(4) Hypotensive Agent

Angiotensin converting enzyme inhibitors (e.g., captopril, enalapril, delapril, etc.), angiotensin II antagonists (e.g., losartan, candesartan cilexetil, etc.), calcium antagonists (e.g., manidipine, nifedipine, amlodipine, efonidipine, nicardipine, etc.), clonidine, and the like.

(5) Antiobesity Agent

Antiobesity drugs acting on the central nervous system (e.g. dexfenfluramine, fenfluramine, phentermine, sibutramine, anfepramone, dexamphetamine, mazindol, phenylpropanolamine, clobenzorex, etc.), pancreatic lipase inhibitors (e.g. orlistat, etc.), $\beta_3$ agonists (e.g. CL-316243, SR-58611-A, UL-TG-307, AJ-9677, AZ40140, etc.), anorectic peptides (e.g. leptin, CNTF (Ciliary Neurotrophic Factor), etc.), cholecystokinin agonists (e.g. lintitript, FPL-15849, etc.).

(6) Diuretic Agent

Xanthine derivatives (e.g., theobromine sodium salicylate, theobromine calcium salicylate, etc.), thiazide preparations (e.g., ethiazide, cyclopenthiazide, trichlormethiazide, hydrochlorothiazide, hydroflumethiazide, benzylhydrochlorothiazide, penflutizide, polythiazide, methyclothiazide, etc.), antialdosterone preparations (e.g., spironolactone, triamterene, etc.), carbonic anhydrase inhibitors (e.g., acetazolamide, etc.), chlorobenzenesulfonamide preparations (e.g., chlorthalidone, mefruside, indapamide, etc.), azosemide, isosorbide, ethacrynic acid, piretanide, bumetanide, furosemide, etc.

(7) Chemotherapeutic Agent

Alkylating agents (e.g., cyclophosphamide, ifosamide, etc.), metabolic antagonists (e.g., methotrexate, 5-fluorouracil, etc.), antitumor antibiotics (e.g., mitomycin, adriamycin, etc.), plant-derived antitumor agents (e.g., vincristine, vindesine, taxol, etc.), cisplatin, carboplatin, etoposide, etc. Among these, 5-fluorouracil derivatives such as Furtulon and Neo-Furtulon are preferred.

(8) Immunotherapeutic Agent

Microorganism- or bacterium-derived components (e.g., muramyl dipeptide derivatives, Picibanil, etc.), immunopotentiator polysaccharides (e.g., lentinan, schizophyllan, krestin, etc.), genetically engineered cytokines (e.g., interferons, interleukins (IL), etc.), colony stimulating factors (e.g., granulocyte colony stimulating factor, erythropoietin, etc.) and the like. Among these, interleukins such as IL-1, IL-2, IL-12, etc. are preferred.

(9) Therapeutic Agent Recognized to Ameliorate Cachexia in Animal Models or Clinical Practice Progesterone derivatives (e.g., megestrol acetate) [Journal of Clinical Oncology, vol. 12, pp. 213-225, 1994], metoclopramide pharmaceuticals, tetrahydrocannabinol pharmaceuticals (the above references are applied to both), fat metabolism ameliorating agents (e.g., eicosapentanoic acid) [British Journal of Cancer, vol. 68, pp. 314-318, 1993], growth hormones, IGF-1, and antibodies to the cachexia-inducing factors such as TNF-$\alpha$, LIF, IL-6 and oncostatin M.

(10) Antiinflammatory Agent

Steroids (e.g., dexamethasone, etc.), sodium hyaluronate, cyclooxygenase inhibitors (e.g., indomethacin, ketoprofen, loxoprofen, meloxicam, ampiroxicam, celecoxib, rofecoxib, etc.) and the like.

(11) Miscellaneous glycosylation inhibitors (e.g., ALT-711, etc.), nerve regeneration promoting drugs (e.g., Y-128, VX853, prosaptide, etc.), drugs acting on the central nervous system (e.g., antidepressants such as desipramine, amitriptyline, imipramine, fluoxetine, paroxetine, doxepin, etc.), anticonvulsants (e.g., lamotrigine, carbamazepine), antiarrhythmic drugs (e.g., mexiletine), acetylcholine receptor ligands (e.g., ABT-594), endothelin receptor antagonists (e.g., ABT-627), monoamine uptake inhibitors (e.g., tramadol), indoleamine uptake inhibitors (e.g., fluoxetine, paroxetine), narcotic analgesics (e.g., morphine), GABA receptor agonists (e.g., gabapentin), GABA uptake inhibitors (e.g., tiagabine), $\alpha_2$ receptor agonists (e.g., clonidine), local analgesics (e.g., capsaicin), protein kinase C inhibitors (e.g., LY-333531), antianxiety drugs (e.g., benzodiazepines), phosphodiesterase inhibitors (e.g., sildenafil), dopamine receptor agonists (e.g., apomorphine), dopamine receptor antagonists (e.g., haloperidol), serotonin receptor agonists (e.g., tandospirone citrate, sumatryptan), serotonin receptor antagonists (e.g., cyproheptadine hydrochloride, ondansetron), serotonin uptake inhibitors (e.g., fluvoxamine maleate, fluoxetine, paroxetine), hypnotics (e.g., triazolam, zolpidem), anticholinergic agents, alreceptor blocking agents (e.g., tamsulosin), muscle relaxants (e.g., baclofen, etc.), potassium channel openers (e.g., nicorandil), calcium channel blocking agents (e.g., nifedipine), agents for preventing and/or treating Alzheimer's disease (e.g., donepezil, tivastigmine, galantamine), agents for treating Parkinson's disease (e.g., L-dopa), agents for preventing and/or treating multiple sclerosis (e.g., interferon $\beta$-1a), histamine $H_1$ receptor inhibitors (e.g., promethazine hydrochloride), proton pump inhibitors (e.g., lansoprazole, omeprazole), antithrombotic agents (e.g., aspirin, cilostazol), NK-2 receptor antagonists, agents of treating HIV infection (saquinavir, zidovudine, lamivudine, nevirapine), agents of treating chronic obstructive pulmonary diseases (salmeterol, thiotropium bromide, cilomilast), etc.

Anticholinergic agents include, for example, atropine, scopolamine, homatropine, tropicamide, cyclopentolate, butylscopolamine bromide, propantheline bromide, methylbenactyzium bromide, mepenzolate bromide, flavoxate, pirenzepine, ipratropium bromide, trihexyphenidyl, oxybutynin, propiverine, darifenacin, tolterodine, temiverine, trospium chloride or a salt thereof (e.g., atropine sulfate, scopolamine hydrobromide, homatropine hydrobromide, cyclopentolate hydrochloride, flavoxate hydrochloride, pirenzepine hydrochloride, trihexyphenidyl hydrochloride, oxybutynin chloride, tolterodine tartrate, etc.), preferably, oxybutynin, propiverine, darifenacin, tolterodine, temiverine, trospium chloride or a salt thereof (e.g., oxybutynin chloride, tolterodine tartrate, etc.). In addition, acetylcholinesterase inhibitors (e.g., distigmine, etc.) and the like can be used.

NK-2 receptor antagonists include, for example, a piperidine derivative such as GR159897, GR149861, SR48968 (saredutant), SR144190, YM35375, YM38336, ZD7944, L-743986, MDL105212A, ZD6021, MDL105172A, SCH205528, SCH62373, R-113281, etc., a perhydroisoindole derivative such as RPR-106145, etc., a quinoline derivative such as SB-414240, etc., a pyrrolopyrimidine derivative such as ZM-253270, etc., a pseudopeptide derivative such as MEN11420 (nepadutant), SCH217048, L-659877, PD-147714 (CAM-2291), MEN10376, S16474, etc., and others such as GR100679, DNK333, GR94800, UK-224671, MEN10376, MEN10627, or a salt thereof, and the like.

The pharmaceutical composition comprising a mixture or combination of the compound of the present invention and the combination drugs may be formulated into (1) a single formulation as a pharmaceutical composition containing the compound of the present invention and the combination drugs, or (2) a formulation comprising the compound of the present invention and the combination drugs which are separately formulated. Hereinafter, it is generally briefly referred to as the combination preparation of the present invention.

The combination preparation of the present invention can be formulated by mixing the compound of the present invention and active ingredients of the combination drugs separately or at the same time as itself or with pharmaceutically acceptable carriers in the same manner as in the method of producing the pharmaceutical preparation comprising the compound of the present invention.

A daily dose of the combination preparation of the present invention varies depending on severity of the symptoms, age, sex, weight and sensitivity of the subject to be administered, time and interval of administration, property, formulation and kinds of pharmaceutical preparation, kinds of active ingredients, etc., and is not particularly limited. The dose in terms of the compound of the present invention is not particularly limited if it causes no problems of side effects. In the case of oral administration, a daily dosage is usually in a range of about 0.005 to 100 mg, preferably about 0.05 to 50 mg, and more preferably about 0.2 to 30 mg, per 1 kg body weight of mammals, which may be administered once a day or in two or three divided portions a day.

The dose of the compound or the combination preparation of the present invention may be set within the range such that it causes no problems of side effects. The daily dose as the compound or the combination preparation of the present invention varies depending on severity of symptoms, age, sex, weight and sensitivity of the subject to be administered, time and interval of administration, property, formulation and kinds of pharmaceutical preparation, kinds of active ingredients, etc., and is not particularly limited. In the case of oral administration, a daily dosage in terms of active ingredients is usually in the order of about 0.001 to 2000 mg, preferably about 0.01 to 500 mg, and more preferably about 0.1 to 100 mg, per 1 kg body weight of mammals, which may be administered once a day or in two to four divided portions a day.

In administering the combination preparation of the present invention, the compound of the present invention and the combination drugs may be administered at the same time or, the combination drugs may be administered before administering the compound of the present invention, and vice versa. In case of staggered administration, the time interval varies depending on the active ingredients to be administered, a formulation and an administration route. For example, if the combination drugs are administered first, the compound of the present invention may be administered 1 minute to 3 days, preferably 10 minutes to 1 day, more preferably 15 minutes to 1 hour after administering the combination drugs. If the compound of the present invention is administered first, the combination drugs may be administered 1 minute to 1 day, preferably 10 minutes to 6 hours, more preferably 15 minutes to 1 hour after administering the compound of the present invention.

In a preferred administration method, about 0.001 to 200 mg/kg of the combination drugs formulated as an oral preparation is administered orally and then after about 15 minutes, about 0.005 to 100 mg/kg of the compound of the present invention formulated as an oral preparation is administered orally as a daily dose.

In the combination preparation of the present invention, the content of the compound of the present invention varies depending on the forms of the preparation, but usually in the order of 0.01 to 100 wt %, preferably 0.1 to 50 wt %, and further preferably 0.5 to 20 wt %, relative to the total preparation.

EXAMPLES

The present invention is further described in detail in with reference to Reference Examples, Examples, Preparative Examples and Experimental Example which are not intended to restrict the invention and may be modified without departing from the scope of the invention.

Elution in the column chromatography in the following Reference Examples and Examples was conducted under observation by TLC (thin layer chromatography), unless otherwise specifically indicated. In the TLC observation, $60F_{254}$, TLC plates, produced by Merck & Co., Inc. was used, and the solvent employed as an elution solvent in the column chromatography was used as an eluent. For the detection, a UV detector was used. As silica gel for the column chromatography, Silica Gel 60 (70 to 230 mesh) produced by Merck & Co., Inc. was used. "room temperature" referred herein means temperature generally from about 10° C. to 35° C. For drying extract, sodium sulfate or magnesium sulfate was used.

The meanings of the abbreviations as used in the following Examples and Reference Examples are as follows:

NMR: Nuclear Magnetic Resonance Spectrum
LC-MS: Liquid Chromatography-Mass Spectrometry
ESI: Electron Spray Ionization
DMF: Dimethylformamide, THF: Tetrahydrofuran, DMSO: Dimethylsulfoxide, IPE: diisopropyl ether, EPPA: ethyl o-phenylene phosphate, $NaBH(OAc)_3$: sodium triacetoxyborohydride, lo $HOBt.H_2O$: 1-hydroxybenzotriazole hydrate, WSC.HCl: 1-ethyl-3-(dimethylaminopropyl)carbodiimide hydrochloride, $Et_3N$: triethylamine, Hz: Hertz, J: coupling constant, m: multiplet, q: quartet, t: triplet, d: doublet, s: singlet, br: broad, like: approximation, M: Molecular ion peak, cis: cis, trans: trans, Rf: Retardation factor, N: normal concentration, M: molar concentration, MPa: Mega Pascal, wt %: percent by weight, Boc: tert-butyloxycarbonyl.

LC-MS in Examples and Reference Examples was measured under the following conditions.

LC-MS (Condition A)
Measurement Instrument: LC-MS system, Waters Corporation
  HPLC part: HP1100, Agilent Technologies, Inc.
  MS part: ZQ, Waters Corporation HPLC condition
  Column: CAPCELL PAK C18UG120, S-3 μm, 2.0×50 mm (Shiseido Co., Ltd.)
  Solvent: Solution A; 0.05% trifluoroacetic acid-containing water, Solution B; 0.04% trifluoroacetic acid-containing acetonitrile Gradient cycle: 0.00 minute (Solution A/Solution B=90/10), 4.00 minutes (Solution A/Solution B=5/95), 5.50 minutes (Solution A/Solution B=5/95), 5.51 minutes (Solution A/Solution B=90/10), 5.51 minutes (Solution A/Solution B=10/90), 8.00 minutes (Solution A/Solution B=90/10)

Injection amount: 2 μl, Flow rate: 0.5 ml/min, Detection method: UV 220 nm

MS condition

Ionization method: ESI

LC-MS (Condition B)

Measurement Instrument: LC-MS system, Waters Corporation

HPLC part: HP1100, Agilent Technologies, Inc.

MS part: ZMD, Micromass

HPLC condition

Column: CAPCELL PAK C18UG120, S-3 μm, 1.5×35 mm (Shiseido Co., Ltd.)

Solvent: Solution A; 0.05% trifluoroacetic acid-containing water, Solution B; 0.04% trifluoroacetic acid-containing acetonitrile Gradient cycle: 0.00 minute (Solution A/Solution B=90/10), 2.00 minutes (Solution A/Solution B=5/95), 2.75 minutes (Solution A/Solution B=5/95), 2.76 minutes (Solution A/Solution B=90/10), 3.60 minutes (Solution A/Solution B=90/10)

Injection amount: 2 μl, Flow rate: 0.5 ml/min, Detection method: UV 220 nm

MS condition

Ionization method: ESI

Purification by preparative HPLC in Examples and Reference Examples was carried out under the following conditions.

Instrument: High Throughput Purification System, Gilson Company, Inc.

Column: YMC CombiPrep ODS-AS-5 μm, 50×20 mm

Solvent: Solution A; 0.1% trifluoroacetic acid-containing water, Solution B; 0.1% trifluoroacetic acid-containing acetonitrile Gradient cycle: 0.00 minute (Solution A/Solution B=95/5), 1.00 minute (Solution A/Solution B=95/5), 5.20 minutes (Solution A/Solution B=5/95), 6.40 minutes (Solution A/Solution B=5/95), 6.50 minutes (Solution A/Solution B=95/5), 6.60 minutes (Solution A/Solution B=95/5)

Flow rate: 25 ml/min, Detection method: UV 220 nm

Reference Example 1 cis-4-[[3,5-Bis(trifluoromethyl)benzyl]oxy]-3-phenylpiperidine-1-carboxylic acid tert-butyl ester (Process 1)

To a solution of ethyl 3-[(3-ethoxy-3-oxopropyl)amino]-2-phenylpropanoate (1.0 g) and sodium carbonate (0.72 g) in acetonitrile (2 ml), benzyl bromide (0.64 g) was added, and the reaction mixture was stirred at 75° C. for 2 hours. The reaction mixture was poured into water, and then the product was extracted with ethyl acetate. The organic layer was washed with saturated brine, dried, and then the solvent was evaporated under reduced pressure to obtain ethyl 3-[benzyl(3-ethoxy-3-oxopropyl)amino]-2-phenylpropanoate as colorless oil (1.20 g).

$^1$H-NMR (CDCl$_3$): δ 1.22 (6H, t like, J=7.1 Hz), 2.35-2.48 (2H, m), 2.67-2.88 (3H, m), 3.27 (1H, dd, J=13.0, 9.8 Hz), 3.57 (1H, d, J=14.0 Hz), 3.72 (1H, d, J=14.0 Hz), 3.80 (1H, dd, J=9.8 Hz, 5.4 Hz), 4.02-4.24 (4H, m), 7.19-7.40 (10H, m).

(Process 2)

To a solution of sodium hydride (60% in oil, 0.27 g) in benzene (6.1 ml), a solution of the compound (1.30 g) obtained in Process 1 in ethanol (1.4 ml) was added, and the reaction mixture was stirred at 70° C. for 1 hour. The reaction mixture was cooled, and then concentrated hydrogen chloride (1.7 ml) was added thereto, and the mixture was concentrated under reduced pressure. To the obtained residue, acetic acid (4 ml) and concentrated hydrogen chloride (4 ml) were added, and the reaction mixture was stirred at 120° C. for 3 hours. The reaction mixture was concentrated under reduced pressure, and then into the obtained residue were water and ethyl acetate poured, the organic layer was washed with saturated brine, dried, and then the solvent was evaporated under reduced pressure. The obtained residue was isolated and purified by silica gel column chromatography (ethyl acetate:hexane=1:10) to obtain ethyl 1-benzyl-4-hydroxy-5-phenyl-1,2,5,6-tetrahydro-3-pyridine carboxylate as colorless oil (0.46 g).

$^1$H-NMR (CDCl$_3$): δ 1.30 (3H, t, J=7.1 Hz), 2.62 (1H, dd, J=11.6, 6.2 Hz), 2.88 (1H, dd, J=11.6, 5.2 Hz), 3.23-3.40 (2H, m), 3.63 (2H, s), 3.64-3.74 (1H, m), 4.23 (2H, q, J=7.1 Hz), 7.24-7.38 (10H, m).

(Process 3)

To a solution of the compound (15.0 g) obtained in Process 2 in acetic acid (90 ml), concentrated hydrogen chloride (90 ml) was added, and the reaction mixture was stirred at 120° C. for 12 hours. The reaction mixture was concentrated under reduced pressure, and then into the obtained residue was poured ethyl acetate, and made basic with an aqueous sodium hydroxide solution. The organic layer was washed with saturated brine, dried, and then the solvent was evaporated under reduced pressure to obtain 1-benzyl-3-phenyl-4-piperidinone as colorless oil (10.4 g).

$^1$H-NMR (CDCl$_3$): δ 2.47-2.85 (4H, m), 3.00-3.25 (2H, m), 3.67 (2H, s), 3.81 (1H, dd, J=10.0, 5.6 Hz), 7.19-7.40 (10H, m).

(Process 4)

A solution of the compound (2.00 g) obtained in Process 3, hydrochloric acid (0.2 ml) and palladium carbon (10 wt %, 0.30 g) in ethanol (30 ml) was stirred at 40° C. for 3 hours under hydrogen atmosphere of 0.5 MPa. The catalyst was removed by filtration, and then the reaction solution was concentrated under reduced pressure to obtain crude 3-phenyl-4-piperidone as pale yellow powder. The obtained product was used in the next process without further purification.

(Process 5)

To a solution of the compound (3.47 g) obtained in Process 4 and Et$_3$N (2.76 ml) in acetonitrile (50 ml), di-tert-butyl dicarbonate (6.55 g) was added, and the reaction mixture was stirred at room temperature for 14 hours. The reaction mixture was poured into water, and then the product was extracted with ethyl acetate. The organic layer was washed with an aqueous 10% citric acid solution and saturated brine, dried, and then the solvent was evaporated under reduced pressure. The obtained residue was isolated and purified by silica gel column chromatography (hexane:ethyl acetate=10:1) to obtain 4-oxo-3-phenylpiperidine-1-carboxylic acid tert-butyl ester as white powder (3.90 g, 71%). The obtained product was used in the next process without further purification.

(Process 6)

To a solution of the compound (9.70 g) obtained in Process 5 in THF (100 ml), a solution of 1 M L-selectride/THF (78 ml) was added at −78° C., and the reaction mixture was stirred at 0° C. for 1 hour. To the reaction mixture was added an aqueous saturated sodium hydrogen carbonate solution, and then the product was extracted with ethyl acetate. The organic layer was washed with an aqueous 10% citric acid solution and saturated brine, dried, and then the solvent was evaporated under reduced pressure. The obtained residue was isolated and purified by silica gel column chromatography (hexane:ethyl acetate=3:1) to obtain crude 4-hydroxy-3-phenylpiperidine-1-carboxylic acid tert-butyl ester (9.32 g, 95%) as colorless oil.

$^1$H-NMR (CDCl$_3$): δ 1.50 (9H, s), 2.57 (2H, t, J=6.1 Hz), 3.45-3.75 (3H, m), 4.10-4.40 (2H, m), 7.15-7.21 (2H, m), 7.28-7.41 (3H, m)

(Process 7)

To a solution of the compound (3.02 g) obtained in Process 6 in DMF (30 ml), sodium hydride (60% in oil, 0.87 g) was added, and then the reaction mixture was stirred at room temperature for 30 minutes. To the reaction solution, 3,5-bis (trifluoromethyl)benzyl bromide (5.00 g) was added at room temperature, and then the reaction solution was further stirred for 1 hour. The reaction solution was poured into water, and then the product was extracted with ethyl acetate. The organic layer was washed with an aqueous 10% citric acid solution and saturated brine, dried, and then the solvent was evaporated under reduced pressure. The obtained residue was isolated and purified by silica gel column chromatography (hexane:ethyl acetate=10:1) to obtain the title compound as colorless oil (4.07 g, 74%).

1H-NMR (CDCl$_3$): δ 1.46 (9H, s), 1.70-1.85 (1H, m), 2.00-2.10 (1H, m), 2.87-2.95 (1H, m), 3.08-3.20 (1H, m), 3.40-3.60 (1H, m), 3.84-3.90 (1H, br s), 3.90-4.20 (2H, m), 4.19 (1H, d, J=12.6 Hz), 4.57 (1H, d, J=12.6 Hz), 7.20-7.40 (5H, m), 7.53 (2H, s), 7.73 (1H, s)

Reference Example 2

4-[(2-Methoxybenzyl)amino]-3-phenylpiperidine-1-carboxylic acid tert-butyl ester (Process 1)

A mixed solution of the compound (8.82 g) obtained in Process 5 of Reference Example 1, hydroxyamine hydrochloride (6.67 g) and sodium acetate (7.88 g) in ethanol (50 ml) and water (20 ml) was stirred at 75° C. for 1 hour. The reaction mixture was poured into water, and then the product was extracted with ethyl acetate. The organic layer was washed with an aqueous saturated ammonium chloride solution and saturated brine, dried, and then the solvent was evaporated under reduced pressure to obtain 4-(hydroxyimino)-3-phenylpiperidine-1-carboxylic acid tert-butyl ester as a white paste-like material. The obtained product was used in the next process without further purification.

(Process 2)

A mixed solution of the compound obtained in Process 1 and Raney nickel (about 30 g) in THF (150 ml) and ethanol (150 ml) was stirred at 50° C. for 6 hours under hydrogen atmosphere of 5 atm. The catalyst was removed by filtration, and then the filtrate was concentrated under reduced pressure to obtain 4-amino-3-phenylpiperidine-1-carboxylic acid tert-butyl ester (8.79 g) as colorless solid matter. The obtained product was used in the next process without further purification.

(Process 3)

To a mixed solution of the compound (4.00 g) obtained in Process 2 and o-anisaldehyde (1.97 g) in acetic acid (0.15 ml) and dichloromethane (40 ml), NaBH(OAc)$_3$ (9.20 g) was added, and the reaction mixture was stirred at room temperature for 14 hours. The solvent was evaporated under reduced pressure, and then the residue was poured into a mixed solution of ethyl acetate and water. The organic layer was washed with an aqueous saturated sodium hydrogen carbonate solution and saturated brine, dried, and then the solvent was evaporated under reduced pressure. The obtained residue was isolated and purified by silica gel column chromatography (hexane:ethyl acetate=2:1) to obtain the cis-form of the title compound as colorless oil (3.41 g, 76%) and the trans-form of the title compound as colorless oil (0.96 g, 16%), respectively.

Cis-form: Rf=0.6 (hexane:ethyl acetate=1:2).
Trans-form: Rf=0.2 (hexane:ethyl acetate=1:2).

Reference Example 3 cis-3-Benzhydryl-4-[[3,5-bis(trifluoromethyl)benzyl] Oxy]piperidine-1-carboxylic acid tert-butyl ester (Process 1)

1-Acetyl-4-piperidinone (77 g) was dissolved in dichloromethane (300 ml), and trimethylsilyltrifluoromethanesulfonate (200 ml) and benzhydrol (92 g) were added thereto with stirring under ice-cooling. The mixture was allowed to stand at room temperature overnight, and then water (500 ml) and sodium acetate (50 g) were added thereto and the reaction mixture was vigorously stirred. The dichloromethane layer was preparatively separated, washed with an aqueous sodium bicarbonate solution, dried, and then the solvent was evaporated under reduced pressure. The residue was treated with ethyl ether to obtain 1-acetyl-3-benzhydryl-4-piperidinone as colorless crystals (132.6 g, 86%).

Melting point: 133-136° C. IR (KBr) 3060, 3025, 2900, 2860, 1715, 1640, 1490, 1450, 1420, 1250, 980, 745, 705, 695 cm$^{-1}$.

(Process 2)

To the compound (10.2 g) obtained in Process 1 were added water (200 ml) and concentrated hydrochloric acid (200 ml), and heated for 5 hours. The reaction mixture was further stirred at 80° C. overnight, and then filtered in a heated state and the filtrate was concentrated under reduced pressure. The residue (crystal) was suspended in ethanol and filtered to obtain 3-benzhydryl-4-piperidone hydrochloride as colorless crystals (8.00 g, 80%).

Melting point: 208-210° C.
IR (KBr) 2980, 2800, 2710, 1735, 1590, 1450, 1385, 1170, 755, 710, 700, 540 cm$^{-1}$.

(Process 3)

To a solution of the compound (7.55 g) obtained in Process 2 and Et$_3$N (6.97 ml) in DMF (350 ml), di-tert-butyl dicarbonate (6.00 g) was added, and the reaction mixture was stirred at room temperature for 5 hours. The reaction mixture was poured into water, and then the product was extracted with ethyl acetate. The organic layer was washed with an aqueous 10% citric acid solution and saturated brine, dried, and then the solvent was evaporated under reduced pressure. The residue was crystallized from diethyl ether to obtain 3-benzhydryl-4-oxopiperidine-1-carboxylic acid tert-butyl ester as white powder (8.86 g, 97%).

(Process 4)

To a solution of the compound (4.50 g) obtained in Process 3 in THF (80 ml), a solution of 1 M L-selectride/THF (18.5 ml) was added at −78° C., and the reaction solution was stirred at 0° C. for 3 hours. To the reaction solution was added an aqueous saturated sodium hydrogen carbonate solution, and then the product was extracted with ethyl acetate. The organic layer was washed with an aqueous 10% citric acid solution and saturated brine, dried, and then the solvent was evaporated under reduced pressure to obtain crude 3-benzhydryl-4-hydroxypiperidine-1-carboxylic acid tert-butyl ester (4.50 g, 99%) as colorless amorphous. The obtained product was used in the next process without further purification.

(Process 5)

To a solution of the compound (1.66 g) obtained in Process 4 in DMF (30 ml), sodium hydride (60% in oil, 0.90 g) was added, and then the reaction mixture was stirred at room temperature for 30 minutes. To the reaction solution, 3,5-bis (trifluoromethyl)benzyl bromide (6.89 g) and sodium iodide (3.37 g) were added at room temperature, and then the reaction solution was further stirred for 3 hours. The reaction solution was poured into water, and then the product was extracted with ethyl acetate. The organic layer was washed with an aqueous 10% citric acid solution and saturated brine, dried, and then the solvent was evaporated under reduced pressure to obtain yellow oil of the crude title compound. The obtained compound was used in the next process without purification.

MS (ESI+): 594 (M+H).

Reference Example 4 cis-3-Benzhydryl-4-[[3-fluoro-5-(trifluoromethyl) benzyl]oxy]piperidine-1-carboxylic acid tert-butyl ester To a solution of the compound (1.29 g) obtained in Process 4 of Reference Example 3 in DMF (30 ml), sodium hydride (60% in oil, 0.70 g) was added, and then the reaction solution was stirred at room temperature for 30 minutes. To the reaction solution, 3-fluoro-5-(trifluoromethyl)benzyl bromide (4.50 g) and sodium iodide (2.62 g) were added at room temperature, and then the reaction solution was further stirred for 3 hours. Then, the mixture was treated in the same manner as in Process 5 of Reference Example 3 to obtain yellow oil of the crude title compound. The obtained compound was used in the next process without purification.

MS (ESI+): 542 (M+H).

Reference Example 5 cis-3-Benzhydryl-4-[[3-(trifluoromethoxy)benzyl] oxy]piperidine-1-carboxylic acid tert-butyl ester To a solution of the compound (1.50 g), obtained in process 4 of Reference Example 3 in DMF (40 g), sodium hydride (60% in oil, 0.82 g) was added, and then the reaction mixture was stirred at room temperature for 30 minutes. To the reaction solution, 3-(trifluoromethoxy)benzyl bromide (5.20 g) and sodium iodide (3.06 g) were added at room temperature, and then the reaction mixture was further stirred for 3 hours. Then, the mixture was treated in the same manner as in Process 5 of Reference Example 3 to obtain yellow oil of the crude title compound. The obtained compound was used in the next process without purification.

MS (ESI+): 542 (M+H)

Reference Example 6 cis-3-Benzhydryl-4-[[4-(trifluoromethyl)benzyl]oxy] piperidine-1-carboxylic acid tert-butyl ester To a solution of the compound (1.50 g) obtained in Process 4 of Reference Example 3 in DMF (40 ml), sodium hydride (60% in oil, 0.82 g) was added, and then the reaction mixture was stirred at room temperature for 30 minutes. To the reaction solution, 4-(trifluoromethyl)benzyl bromide (4.88 g) and sodium iodide (3.06 g) were added at room temperature, and then the reaction mixture was further stirred for 3 hours. Then, the mixture was treated in the same manner as in Process 5 of Reference Example 3 to obtain yellow oil of the crude title compound. The obtained compound was used in the next process without purification.

MS (ESI+): 526 (M+H).

Reference Example 7

5-[(5-(Trifluoromethyl)-1H-tetrazol-1-yl]-2,3-dihydro-1-benzofuran-7-carbaldehyde (Process 1)

To a solution of 2,3-dihydro-1-benzofuran-5-amine (4.5 g) and $Et_3N$ (6.1 ml) in dichloromethane (40 ml), trifluoroacetic anhydride (6.2 ml) was added at 0° C., and the reaction mixture was stirred at room temperature for 2 hours. The reaction mixture was poured into water, and then the product was extracted with ethyl acetate. The organic layer was washed with an aqueous saturated ammonium chloride solution and saturated brine, dried, and then the solvent was evaporated under reduced pressure to obtain N-(2,3-dihydro-1-benzofuran-5-yl)-2,2,2-trifluoroacetamide (7.1 g) as pale orange crystals.

$^1$H-NMR (CDCl$_3$): δ 3.23 (2H, t, J=8.7 Hz), 4.60 (2H, t, J=8.7 Hz), 6.76 (1H, d, J=8.1 Hz), 7.12 (1H, dd, J=8.7, 2.4 Hz), 7.51 (1H, m), 7.65-7.80 (1H, br).

(Process 2)

To a solution of the compound (6.9 g) obtained in Process 1 in carbon tetrachloride (90 ml), triphenylphosphine (12.6 g) was added at room temperature, and the reaction mixture was stirred at 95° C. for 14 hours. The reaction mixture was concentrated under reduced pressure, and then the residue was dissolved in DMF (70 ml). The DMF solution was added dropwise to a solution of sodium azide (3.3 g) in DMF (50 ml) at 0° C., and the reaction mixture was stirred at room temperature for 1 hour. The reaction mixture was poured into water, and then the product was extracted with ethyl acetate. The organic layer was washed with an aqueous saturated sodium hydrogen carbonate solution and saturated brine, dried, and then the solvent was evaporated under reduced pressure. The obtained residue was isolated and purified by silica gel column chromatography (ethyl acetate:hexane=1: 2→1:2) to obtain the title compound (2.2 g) as white crystals.

$^1$H-NMR (CDCl$_3$): δ 3.33 (2H, t, J=9.0 Hz), 4.73 (2H, t, J=9.0 Hz), 6.92 (1H, dd, J=8.7, 0.6 Hz), 7.17-7.21 (1H, dd like), 7.24-7.28 (1H, m).

(Process 3)

To a solution of the compound (3.8 g) obtained in Process 2 in polyphosphoric acid (52 ml), hexamethylene tetramine (10.2 g) was added, and the reaction mixture was stirred at 100° C. for 48 hours. The reaction mixture was concentrated under reduced pressure, and then the residue was dissolved in ethyl acetate. The organic layer was washed with an aqueous saturated sodium hydrogen carbonate solution and brine, dried, and then the solvent was evaporated under reduced pressure. The obtained residue was treated with 4 N hydrochloric acid/ethyl acetate solution (1.0 ml) to obtain the title compound as colorless crystals (1.65 g, 47%).

$^1$H-NMR (CDCl$_3$): δ 3.41 (2H, t, J=8.7 Hz), 4.93 (2H, t, J=8.7 Hz), 7.46-7.47 (1H, m), 7.71-7.72 (1H, m), 10.24 (1H, s).

The compounds of the following Reference Examples were synthesized by reacting and treating in the same manner as in the method described in Reference Example 1 using ethyl phenylacetate derivatives.

TABLE 1

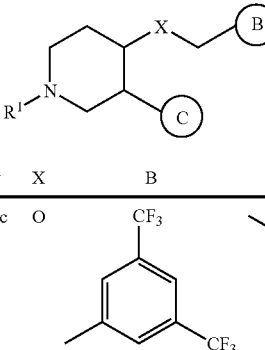

| Ref. Ex. No. | Stereochemistry | R¹ | X | B | C | MS (ESI) (M + H)⁺ |
|---|---|---|---|---|---|---|
| 8 | (±)-cis | Boc | O | 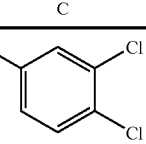 | 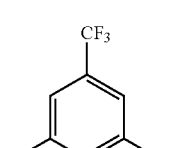 | 572 |
| 9 | (±)-cis | Boc | O | 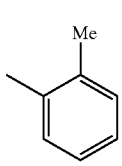 | 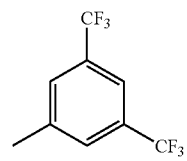 | 518 |
| 10 | (±)-cis | Boc | O | 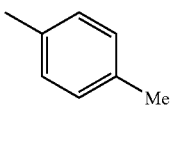 | 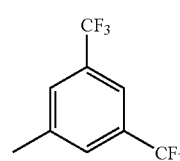 | 518 |
| 11 | (±)-cis | Boc | O | 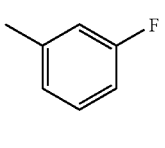 | | 522 |

Reference Example 12 cis-4-[[3,5-Bis(trifluoromethyl)benzyl]oxy]-3-(4-fluorophenyl)piperidine-1-carboxylic acid tert-butyl ester (Process 1)

(±)-BINAP (0.90 g), sodium tert-butoxide (5.02 g), tris(dibenzylideneacetone)dipalladium(0) (0.55 g) and toluene (200 ml) were mixed under nitrogen atmosphere, and 4-fluorobromobenzene (10.54 g), and then tert-butyl 4-oxo-1-piperidmecarboxylate (8.0 g) were added thereto. The mixture was stirred at room temperature for 5 minutes, and then at 60° C. for 7 hours (under nitrogen atmosphere). After cooling to room temperature, the reaction solution was washed with water and saturated brine, dried, and then the solvent was evaporated under reduced pressure. The obtained residue was isolated and purified by silica gel column chromatography (ethyl acetate:hexane=1:4) to obtain tert-butyl 3-(4-fluorophenyl)-4-oxo-1-piperidinecarboxylate (1.46 g) as colorless crystals.

¹H-NMR (CDCl₃): δ 1.50 (9H, s), 2.52-2.59 (2H, m), 3.44-3.51 (2H, m), 3.67-3.71 (1H, m), 4.18-4.21 (1H, m), 4.27 (1H, br.), 7.02-7.17 (4H, m).

(Process 2)

To a solution of the compound (1.20 g) obtained in Process 1 in THF (12 ml), a solution of 1 M K-selectride/THF (7 ml) was added at −78° C., and the reaction mixture was stirred at 0° C. for 1 hour. To the reaction solution, water was added, and the product was extracted with ethyl acetate. The obtained organic layer was washed with an aqueous saturated sodium hydrogen carbonate solution and saturated brine, dried, and then the solvent was evaporated under reduced pressure. The obtained residue was isolated and purified by silica gel column chromatography (haxane:ethyl acetate=2:1), and crystallized from hexane to obtain tert-butyl cis-3-(4-fluorophenyl)-4-hydroxy-1-piperidinecarboxylate (657 mg) as colorless crystals.

¹H-NMR (CDCl₃): δ 1.34 (1H, d, J=2.9 Hz), 1.47 (9H, s), 1.82-1.89 (2H, m), 2.86-2.89 (1H, m), 3.18-3.25 (1H, m), 3.45 (1H, br) 3.94 (2H, br), 4.08-4.09 (1H, m), 7.02-7.07 (2H, m), 7.20-7.24 (2H, m).

(Process 3)

To a solution of the compound (600 mg) obtained in Process 2 in DMF (12 ml), sodium hydride (60% in oil, 203 mg) was added, and then the reaction mixture was stirred at room temperature for 45 minutes. To the reaction solution, sodium iodide (914 mg) and 3,5-bis(trifluoromethyl)benzyl bromide (1.25 g) were added at room temperature, and then the reaction mixture was further stirred for 2.5 hours. To the reaction solution, water was added, and the product was extracted with ethyl acetate. The organic layer was washed with an aqueous 3% potassium hydrogensulfate solution and saturated brine, dried, and then the solvent was evaporated under reduced pressure. The obtained residue was isolated and purified by silica gel column chromatography (hexane:ethyl acetate=4:1) to obtain the title compound as colorless amorphous (920 mg).

MS (ESI+) : 522 (M+H).

The compounds of the following Reference Examples were synthesized by reacting and treating in the same manner as in the method described in Reference Example 12 using tert-butyl 4-oxo-1-piperidinecarboxylate and the respective corresponding halogenated compounds (4-fluoro-2-methyl-bromobenzene and 2-chloropyridine).

TABLE 2

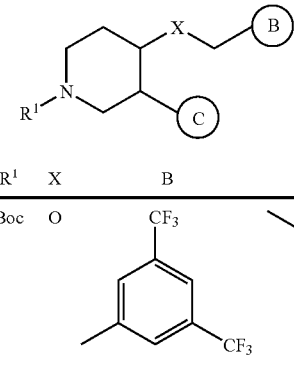

| Ref. Ex. No. | Stereochemistry | $R^1$ | X | B | C | MS (ESI) $(M + H)^+$ |
|---|---|---|---|---|---|---|
| 12 | (±)-cis | Boc | O | 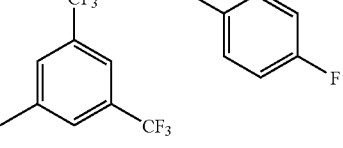 | 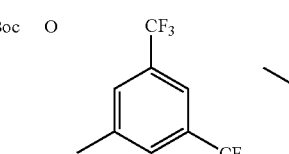 | 522 |
| 13 | (±)-cis | Boc | O | 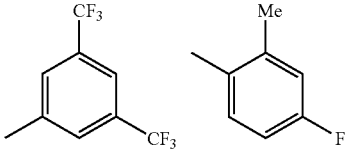 | 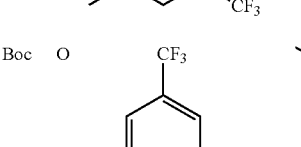 | 536 |
| 14 | (±)-cis | Boc | O | 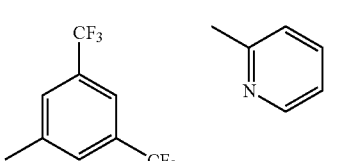 | 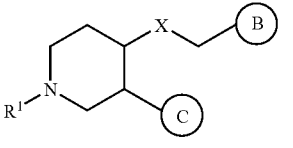 | 505 |

The compounds of the following Reference Examples were synthesized by reacting and treating in the same manner as in the method described in Process 7 of Reference Example 1 using the compound obtained in Process 6 of Reference Example 1 and the respective corresponding benzyl methanesulfonate derivatives or benzyl bromide derivatives.

TABLE 3

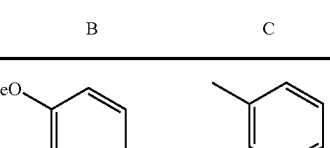

| Ref. Ex. No. | Stereochemistry | $R^1$ | X | B | C | MS (ESI) $(M + H)^+$ |
|---|---|---|---|---|---|---|
| 15 | (±)-cis | Boc | O | MeO, OCF₃ | phenyl | 482 |

TABLE 3-continued

| Ref. Ex. No. | Stereochemistry | R¹ | X | B | C | MS (ESI) (M + H)⁺ |
|---|---|---|---|---|---|---|
| 16 | (±)-cis | Boc | O | 3,5-dichlorophenyl | phenyl | 436 |
| 17 | (±)-cis | Boc | O | 3,5-dimethylphenyl | phenyl | 396 |
| 18 | (±)-cis | Boc | O | 2-fluoro-4-(trifluoromethyl)phenyl | phenyl | 454 |
| 19 | (±)-cis | Boc | O | 3-fluoro-5-(trifluoromethyl)phenyl | phenyl | 454 |
| 20 | (±)-cis | Boc | O | 3-bromo-5-(trifluoromethyl)phenyl | phenyl | 514, 516 |
| 21 | (±)-cis | Boc | O | 2,4-bis(trifluoromethyl)phenyl | phenyl | 504 |
| 22 | (±)-cis | Boc | O | 3-methyl-5-(trifluoromethyl)phenyl | phenyl | 450 |

Reference Example 23 cis-4-[[3-Nitro-5-(trifluoromethyl)benzyl]oxy]-3-phenylpiperidine (Process 1)

The compound (150 mg) obtained in Process 6 of Reference Example 1 and 3-nitro-5-(trifluoromethyl)benzyl methanesulfonate (178 mg) were dissolved in dichloromethane (10 ml), an aqueous 10% sodium hydroxide solution (10 ml), sodium iodide (325 mg) and tetra-n-butylammonium hydrogen sulfate (368 mg) were added thereto and the reaction mixture was stirred at 50° C. for 12 hours. To the reaction solution, water was added, and the reaction solution was extracted with dichloromethane. The obtained organic layer was dried, and then the solvent was evaporated under reduced pressure. The obtained residue was isolated and purified by silica gel column chromatography (haxane:ethyl acetate=4:1) to obtain the title compound as colorless amorphous.

MS (ESI+): 481 (M+H).

Reference Example 24

4-Nitrophenyl 4-acetyl-1-piperazinecarboxylate

A solution of 1-acetylpiperazine (1.30 g) and $Et_3N$ (1.23 g) in dichloromethane (10 ml) was added dropwise to a solution of 4-nitrophenyl chloroformate (2.05 g) in dichloromethane (20 ml) under ice-cooling. After stirring at 0° C. for 30 minutes and at room temperature for 1 hour, water was added to the reaction solution, and the reaction solution was extracted with dichloromethane. The organic layer was washed with an aqueous saturated sodium bicarbonate solution and saturated brine, dried, and then the solvent was evaporated under reduced pressure. The obtained residue was isolated and purified by silica gel column chromatography (ethyl acetate) to obtain the title compound (1.70 g) as colorless crystals.

$^1$H-NMR ($CDCl_3$): δ 2.16 (3H, s), 3.59-3.72 (8H, m), 7.31 (2H, d, J=9.0 Hz), 8.27 (2H, d, J=9.0 Hz).

The compounds of the following Reference Examples were synthesized by reacting and treating in the same manner as in the method described in Reference Example 24 using the respective corresponding amine derivatives.

TABLE 4

| Ref. Ex. No. | Structural formula | $^1$H-NMR($CDCl_3$): δ |
|---|---|---|
| 24 | AcN-piperazine-C(O)O-C6H4-NO2 | 2.16(3H, s), 3.59-3.72(8H, m), 7.31(2H, d, J=9.0Hz), 8.27(2H, d, J=9.0Hz) |
| 25 | $F_3C$-$CH_2$-NH-C(O)O-C6H4-NO2 | 3.88-3.99(2H, m), 5.46(1H, brs), 7.35(2H, d, J=9.0Hz), 8.27(2H, d, J=9.0Hz) |
| 26 | cyclopropyl-NH-C(O)O-C6H4-NO2 | 0.60-0.69(2H, m), 0.79-0.96(2H, m), 2.70-2.71(1H, m), 5.41(1H, brs), 7.29(2H, d, J=9.3Hz), 8.22(2H, d, J=9.3Hz) |
| 27 | BocN-piperidine-NH-C(O)O-C6H4-NO2 | 1.47(9H, s), 1.30-1.50(3H, m), 1.95-2.10(2H, m), 2.89(1H, t, J=12Hz), 3.68-3.77(1H, m), 4.07-4.20(2H, m), 7.32(2H, d, J=9.0Hz), 8.25(2H, d, J=9.0Hz) |

The compounds of the following Reference Examples were synthesized by reacting and treating in the same manner as in the method described in Process 3 of Reference Example 7 using the respective corresponding anisole derivatives or ethoxybenzene derivatives.

TABLE 5

| Ref. Ex. No. | Structural formula | $^1$H-NMR($CDCl_3$): δ |
|---|---|---|
| 28 | MeO, OHC-phenyl-oxadiazole-OMe | 2.78(3H, s), 4.04(3H, s), 7.17(1H, d, J=8.7Hz), 8.26(1H, dd, J=8.7, 2.7Hz), 8.39(1H, d, J=2.7Hz), 10.49(1H, s) |
| 29 | MeO, OHC-phenyl-oxadiazole-$CF_3$ | 4.07(3H, s), 7.21(1H, d, J=8.7Hz), 8.37(1H, dd, J=2.4Hz), 8.53(1H, d, J=2.4Hz), 10.51(1H, s) |

TABLE 5-continued

| Ref. Ex. No. | Structural formula | $^1$H-NMR(CDCl$_3$): δ |
|---|---|---|
| 30 | MeO-phenyl(Me)-thiazole(Me) | 2.50(3H, s), 3.99(3H, s), 6.86(1H, s), 7.07(1H, d, J=8.7Hz), 8.21(1H, dd, J=8.7, 2.4Hz), 8.31(1H, d, J=2.4Hz), 10.49(1H, s) |
| 31 | MeO-, OHC-phenyl-oxadiazole-Me | 2.61(3H, s), 4.03(3H, s), 7.14(1H, d, J=8.7Hz), 8.29(1H, dd, J=8.7, 2.1Hz), 8.41(1H, d, J=2.1Hz), 10.48(1H, s) |
| 32 | MeO-, OHC-phenyl-pyrazole-CF$_3$ | 4.02(3H, s), 6.81(1H, dd, J=1.8, 0.3Hz), 7.11(1H, d, J=8.7Hz), 7.66(1H, dd, J=8.7, 2.4Hz), 7.70(1H, m), 7.95(1H, d, J=2.4Hz), 10.49(1H, s) |
| 33 | MeO-, OHC-phenyl-triazole | 4.03(3H, s), 7.19(1H, d, J=9.2Hz), 7.86(1H, d, J=1.2Hz), 8.01(1H, d, J=1.2Hz), 8.04(1H, d, J=2.8Hz), 8.12(1H, dd, J=9.2, 2.8Hz), 10.51(1H, s) |
| 34 | EtO-, OHC-phenyl-tetrazole-CF$_3$ | 1.57(3H, t, J=7.1Hz), 4.29(2H, q, J=7.1Hz), 7.20(1H, d, J=9.0Hz), 7.63(1H, dd, J=9.0, 3.0Hz), 7.95(1H, d, J=3.0Hz), 10.51(1H, s) |

The compounds of the following Reference Examples were synthesized from the compound obtained in Process 2 of Reference Example 2 as a starting material by reacting and treating in the same manner as in the method described in Process 3 of Reference Example 2 using benzaldehyde derivatives obtained in Reference Example 7 or 28 to 34 or known benzaldehyde derivatives.

TABLE 6

| Ref. Ex. No. | Stereochemistry | R$^1$ | X | B | C | MS (ESI) (M + H)$^+$ |
|---|---|---|---|---|---|---|
| 35 | (±)-cis | Boc | NH | 3,5-bis(CF$_3$)phenyl | phenyl | 503 |

TABLE 6-continued
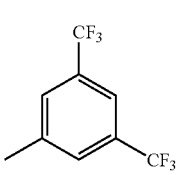
| Ref. Ex. No. | Stereochemistry | R¹ | X | B | C | MS (ESI) (M + H)⁺ |
|---|---|---|---|---|---|---|
| 36 | (±)-trans | Boc | NH | 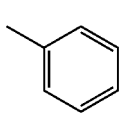 | 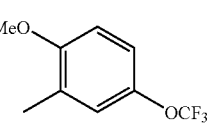 | 503 |
| 37 | (±)-cis | Boc | NH | 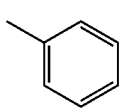 | 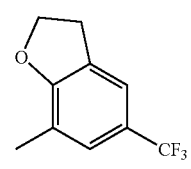 | 481 |
| 38 | (±)-cis | Boc | NH | 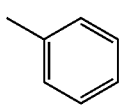 | 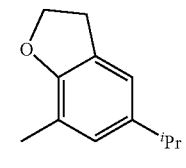 | 477 |
| 39 | (±)-cis | Boc | NH | 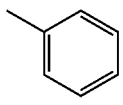 | 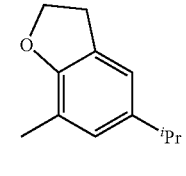 | 451 |
| 40 | (±)-trans | Boc | NH | 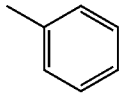 | 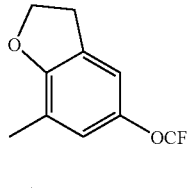 | 451 |
| 41 | (±)-cis | Boc | NH | 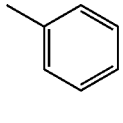 | 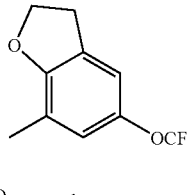 | 493 |
| 42 | (±)-trans | Boc | NH | 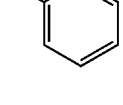 | 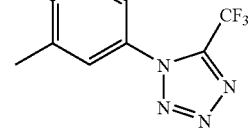 | 493 |
| 43 | (±)-cis | Boc | NH | 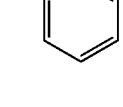 | | 533 |

TABLE 6-continued

| Ref. Ex. No. | Stereochemistry | R¹ | X | B | C | MS (ESI) (M + H)⁺ |
|---|---|---|---|---|---|---|
| 44 | (±)-trans | Boc | NH | MeO-phenyl(Me)-tetrazole-CF₃ | phenyl | 533 |
| 45 | (±)-cis | Boc | NH | MeO-phenyl(Me)-iPr | phenyl | 439 |
| 46 | (±)-trans | Boc | NH | MeO-phenyl(Me)-iPr | phenyl | 439 |
| 47 | (±)-cis | Boc | NH | MeO-phenyl(Me)-oxadiazole-CF₃ | phenyl | 533 |
| 48 | (±)-cis | Boc | NH | MeO-phenyl(Me)-thiazole-Me | phenyl | 494 |
| 49 | (±)-cis | Boc | NH | MeO-phenyl(Me)-pyrazole-CF₃ | phenyl | 531 |
| 50 | (±)-cis | Boc | NH | MeO-phenyl(Me)-triazole | phenyl | 464 |
| 51 | (±)-cis | Boc | NH | dihydrobenzofuran(Me)-tetrazole-CF₃ | phenyl | 545 |

TABLE 6-continued

| Ref. Ex. No. | Stereochemistry | R¹ | X | B | C | MS (ESI) (M + H)⁺ |
|---|---|---|---|---|---|---|
| 52 | (±)-trans | Boc | NH | 2,3-dihydrobenzofuran with methyl, linked to tetrazole bearing CF₃ | phenyl | 545 |
| 53 | (±)-cis | Boc | NH | EtO-/methyl-phenyl linked to tetrazole bearing CF₃ | phenyl | 547 |
| 54 | (±)-cis | Boc | NH | cyclopropyloxy-/methyl-phenyl linked to tetrazole bearing CF₃ | phenyl | 559 |

Reference Example 55 cis-3-Benzyl-4-[[3,5-bis(trifluoromethyl)benzyl]oxy]piperidine-1-carboxylic acid tert-butyl ester (Process 1)

To a solution of 4-oxopiperidine-1,3-dicarboxylic acid 1-tert-butyl 3-ethyl ester (6.0 g) in DMF (45 ml), sodium hydride (60% in oil, 0.85 g) was added, and then the reaction mixture was stirred at room temperature for 30 minutes. The reaction solution was cooled to 0° C., and then benzyl bromide (2.64 ml) was added thereto, and the reaction solution was stirred at room temperature for 1 hour. The reaction solution was diluted with ethyl acetate, and then sequentially washed with an aqueous 10% citric acid solution, water and saturated brine. The organic layer was dried, and then the solvent was evaporated under reduced pressure to obtain 3-benzyl-4-oxopiperidine-1,3-dicarboxylic acid 1-tert-butyl 3-ethyl ester as colorless crystals (7.19 g, 90%).

Melting point: 91-94° C.

¹H-NMR (CDCl₃): δ 1.15 (3H, t, J=7.2 Hz), 1.45 (9H, s), 2.3-2.5 (1H, m), 2.6-2.8 (1H, m), 2.95-3.25 (3H, m), 3.26 (1H, d, J=14 Hz), 4.07 (2H, q, J=7.2 Hz), 4.1-4.3 (1H, m), 4.5-4.7 (1H, m), 7.1-7.3 (5H, m).

(Process 2)

A mixture of the compound (6.0 g) obtained in Process 1, methanol (100 ml) and 6 N hydrochloric acid (250 ml) was stirred at 110° C. for 24 hours. To the reaction solution, concentrated hydrochloric acid (100 ml) was added, and the reaction mixture was further stirred at 110° C. for 24 hours. The solvent was evaporated under reduced pressure, and then an aqueous 4 N sodium hydroxide solution-ice was added to the residue to make it basic, and the mixture was extracted with dichloromethane. The extract was washed with saturated brine, dried, and then the solvent was evaporated under reduced pressure. The obtained residue was dissolved in THF (60 ml), cooled to 0° C., and then di-tert-butyl dicarbonate (5.0 ml) was added thereto, and the reaction mixture was stirred at room temperature for 1 hour.

The solvent was evaporated under reduced pressure, and then the obtained residue was isolated and purified by silica gel column chromatography (haxane:ethyl acetate=4:1) to obtain 3-benzyl-4-oxopiperidine-1-carboxylic acid tert-butyl ester as white crystals (4.20 g, 87%).

Melting point: 74-75° C.

¹H-NMR (CDCl₃): δ 1.42 (9H, s), 2.43-2.60 (3H, m), 2.70 (1H, m), 2.97 (1H, dd, J=13.2, 9.8 Hz), 3.14-3.41 (2H, m), 3.9-4.2 (2H, m), 7.15-7.35 (5H, m).

(Process 3)

To a solution of the compound (4.02 g) obtained in Process 2 in THF (60 ml), 1 M K-selectride/THF solution (20 ml) was added at −78° C., and the reaction mixture was stirred at room temperature for 1 hour. To the reaction mixture was added an aqueous saturated sodium hydrogen carbonate solution, and then the product was extracted with ethyl acetate. The extract was sequentially washed with an aqueous saturated sodium hydrogen carbonate solution, an aqueous 10% citric acid solution and saturated brine, dried, and then the solvent was evaporated under reduced pressure. The obtained residue was isolated and purified by silica gel column chromatography (haxane:ethyl acetate=3:1) to obtain cis-3-benzyl-4-hydroxypiperidine-1-carboxylic acid tert-butyl ester (4.07 g, quantitative) as colorless oil. The obtained product was used in the next process without further purification.

(Process 4)

To a solution of the compound (3.82 g) obtained in Process 3 in DMF (30 ml), sodium hydride (60% in oil, 0.84 g) was added, and then the reaction mixture was stirred at room temperature for 30 minutes. The reaction solution was cooled to 0° C., and then 3,5-bis(trifluoromethyl)benzyl bromide (6.03 g) was added thereto, and the obtained mixture was stirred at room temperature for 2 hours. The reaction solution was diluted with ethyl acetate, and then sequentially washed with water and saturated brine. The organic layer was dried, and then the solvent was evaporated under reduced pressure. The obtained residue was isolated and purified by silica gel column chromatography (hexane:ethyl acetate=5:1) to obtain the title compound as pale yellow oil (4.53 g, 67%).

$^1$H-NMR (CDCl$_3$): δ 1.40-1.70 (1H, m), 1.45 (9H, s), 1.85-2.10 (2H, m), 2.55-2.85 (2H, m), 3.00-3.80 (4H, m), 4.46 (1H, d, J=12.8 Hz), 4.69 (1H, d, J=12.8 Hz), 7.10-7.35 (5H, m), 7.83 (3H, s).

Reference Example 56

(+)-cis-tert-Butyl 4-amino-3-phenylpiperidine-1-carboxylate

A solution of the compound (60.6 g) obtained in Process 5 of Reference Example 1, (S)-1-phenylethylamine (40 g), aluminium chloride (1.5 g) in toluene (750 ml) was stirred at reflux temperature for 8 hours under argon air flow. The reaction solution was azeotropically dehydrated and reacted in Dean-Stark reflux tube with adding toluene (1000 ml). The reaction solution was concentrated under reduced pressure.

Raney nickel (110 g, water contained) was washed with ethanol, and then a solution thereof in ethanol (500 ml) was prepared. The previous residue was added thereto, and then the reaction mixture was stirred at 25° C. for 62 hours under hydrogen pressure of 0.5 MPa. Raney nickel was removed by decantation, and the supernatant was concentrated under reduced pressure. To the residue was added ethyl acetate, and then the precipitated crystal was filtered. The filtrate was concentrated under reduced pressure, and the residue was purified by silica gel column chromatography (haxane:ethyl acetate=3:1) to obtain yellow oil (77 g).

The obtained residue (77 g) was added to palladium carbon (5 wt %, 11.1 g) in ethanol (500 ml), and then, the reaction mixture was stirred at 45° C. for 13 hours under hydrogen pressure of 0.5 MPa. The palladium carbon was removed by filtration, and the filtrate was concentrated and dried. The residue was purified by silica gel column chromatography (hexane:ethyl acetate=2:1→only ethyl acetate→ethyl acetate:methanol=2:1) to obtain the title compound as colorless powder (52.2 g).

$^1$H-NMR (CDCl$_3$): δ 0.87 (1H, brs), 1.20 (1H, brs), 1.46 (9H, s), 1.61 (1H, m), 1.88 (1H, m), 2.93 (1H, m), 3.30-4.11 (5H, m), 7.00-7.52 (5H, m).

[α]$_D^{25}$+103° (c 1.0, CHCl$_3$).

Optical yield: 98.3% ee

High performance liquid chromatography condition

Column: CHIRALPAK AD-RH (Daicel Chemical Industries, Ltd.)

Solvent: phosphate buffer (20 mM disodium hydrogenphosphate)/acetonitrile (volume ratio: 60/40)

Flow rate: 0.6 ml/min

Detection: UV (220 nm)

Temperature: 30° C.

Retention time: 15 min (99.1%), 31 min (0.9%)

Reference Example 57

(−)-cis-tert-Butyl 4-amino-3-phenylpiperidine-1-carboxylate

Under argon air flow, the compound (2.07 g) obtained in Process 5 of Reference Example 1 and (R)-1-phenylethylamine (1.36 g) and aluminium chloride (0.05 g) were reacted and treated in the same manner as in the method described in Reference Example 56 to obtain the title compound as colorless powder (1.44 g).

Optical yield: 97.3% ee

Reference Example 58 cis-tert-Butyl 4-amino-3-phenylpiperidine-1-carboxylate

Under argon air flow, the compound (0.55 g) obtained in Process 5 of Reference Example 1, (R)-1-naphthylethylamine (0.41 g) and aluminium chloride (0.013 g) were reacted and treated in the same manner as in the method described in Reference Example 56 to obtain the title compound as colorless powder (0.31 g).

Optical yield: 96.9% ee.

Reference Example 59 cis-tert-Butyl 4-amino-3-phenylpiperidine-1-carboxylate

Under argon air flow, the compound (0.55 g) obtained in Process 5 of Reference Example 1, (R)-4-tolylethylamine (0.32 g) and aluminium chloride (0.013 g) were reacted and treated in the same manner as in the method described in Reference Example 56 to obtain the title compound as colorless powder (0.14 g).

Optical yield: 87.9% ee.

Example 1 cis-4-[[3,5-Bis(trifluoromethyl)benzyl]oxy]-3-phenylpiperidine hydrochloride

To the compound (4.00 g) obtained in Reference Example 1, trifluoroacetic acid (20 ml) was added at 0° C., and the reaction mixture was stirred at room temperature for 30 minutes. The reaction mixture was concentrated under reduced pressure, and then the residue was dissolved in ethyl acetate. The organic layer was washed with an aqueous saturated sodium hydrogen carbonate solution and brine, dried, and then the solvent was evaporated under reduced pressure. The obtained residue was treated with a 4 N hydrogen chloride/ethyl acetate solution (1.0 ml) to obtain the title compound as colorless crystals (1.65 g, 47%).

$^1$H-NMR (CDCl$_3$): δ 2.15-2.42 (2H, m), 3.20-3.72 (5H, m), 3.90 (1H, s), 4.13 (1H, d, J=12.3 Hz), 4, 52 (1H, d, J=12.3 Hz), 7.16-7.34 (5H, m), 7.45 (2H, s), 7.74 (1H, s), 9.60-10.00 (2H, br).

Example 2 cis-1-Acetyl-4-[[3,5-bis(trifluoromethyl)benzyl]oxy]-3-phenylpiperidine

To a solution of the compound (0.15 g) obtained in Example 1 in THF (5.0 ml), Et$_3$N (0.15 ml) was added, acetyl chloride (0.040 ml) was added at 0° C., and the reaction mixture was stirred at room temperature for 1 hour. The reaction mixture was poured into water, and then the product was extracted with ethyl acetate. The organic layer was washed with an aqueous 10% citric acid solution and saturated brine, dried, and then the solvent was evaporated under reduced pressure. The obtained residue was isolated and purified by silica gel column chromatography (ethyl acetate:hexane=1:1→1:0) to obtain the title compound as colorless oil (0.10 g, 66%).

HPLC analysis (Condition A): Purity 73% (Retention time: 3.77 minutes)

MS (ESI+): 446 (M+H)

Example 3 cis-1-Benzoyl-4-[[3,5-bis(trifluoromethyl)benzyl]oxy]-3-phenylpiperidine

The compound (0.15 g) obtained in Example 1 and benzoyl chloride (0.060 ml) were reacted and treated in the same manner as in the method described in Example 2 to obtain the title compound as colorless oil (0.16 g, 91%).

HPLC analysis (Condition A): Purity 91% (Retention time: 4.11 minutes)

MS (ESI+): 508 (M+H)

Example 4 cis-4-[[3,5-Bis(trifluoromethyl)benzyl]oxy]-1-methylsulfonyl-3-phenylpiperidine

The compound (0.15 g) obtained in Example 1 and methylsulfonyl chloride (0.040 ml) were reacted and treated in the same manner as in the method described in Example 2 to obtain the title compound as colorless oil (0.093 g, 57%).

$^1$H-NMR (CDCl$_3$): δ 1.86-2.26 (2H, m), 2.84 (3H, s), 2.98-3.18 (2H, m), 3.42 (1H, t, J=11.5 Hz), 3.66-3.94 (3H, m), 4.20 (1H, d, J=12.0 Hz), 4.57 (1H, d, J=12.0 Hz), 7.20-7.35 (5H, m), 7.52 (2H, s), 7.75 (1H, s).

Example 5 cis-4-[[3,5-Bis(trifluoromethyl)benzyl]oxy]-3-phenylpiperidine-1-carboxylic acid methyl ester The compound (0.15 g) obtained in Example 1 and methyl chloroformate (0.040 ml) were reacted and treated in the same manner as in the method described in Example 2 to obtain the title compound as colorless oil (0.11 g, 67%).

$^1$H-NMR (CDCl$_3$): δ 1.65-1.90 (1H, m), 2.00-2.15 (1H, m), 2.80-3.00 (1H, m), 3.21 (1H, t, J=12.0 Hz), 3.57 (1H, t, J=12.0 Hz), 3.71 (3H, s), 3.90 (1H, m), 4.15 (2H, m), 4.19 (1H, d, J=12.4 Hz), 4.58 (1H, d, J=12.4 Hz), 7.20-7.40 (5H, m), 7.53 (2H, s), 7.73 (1H, s)

Example 6 cis-4-[[3,5-Bis(trifluoromethyl)benzyl]oxy]-N-methyl-3-phenyl-1-piperidinecarboxamide To a solution of the compound (0.20 g) obtained in Example 1 and Et$_3$N (0.19 ml) in acetonitrile (5 ml), methyl isocyanate (0.050 ml) was added, and the reaction mixture was stirred at room temperature for 14 hours. The reaction mixture was poured into water, and then the product was extracted with ethyl acetate. The organic layer was washed with an aqueous 10% citric acid solution and saturated brine, dried, and then the solvent was evaporated under reduced pressure. The obtained residue was isolated and purified by silica gel column chromatography (ethyl acetate:methanol=20:1) to obtain the title compound as colorless oil (0.20 g, 95%).

$^1$H-NMR (CDCl$_3$): δ 1.75-1.87 (1H, m), 2.06 (1H, dq, J=14.1, 3.0 Hz), 2.82 (3H, d, J=4.8 Hz), 2.91-2.98 (1H, m), 3.21 (1H, dt, J=13.2, 3.0 Hz), 3.58-3.67 (1H, m), 3.76-3.82 (1H, m), 3.90-3.96 (2H, m), 4.20 (1H, d, J=12.6 Hz), 4.42-4.50 (1H, m), 4.58 (1H, d, J=12.6 Hz), 7.23-7.35 (5H, m), 7.53 (2H, s), 7.74 (1H, s).

Example 7

5-[[cis-4-[[3,5-Bis(trifluoromethyl)benzyl]oxy]-3-phenyl-1-piperidinyl]methyl]-2,4-dihydro-3H-1,2,4-triazol-3-one To a mixed solution of the compound (0.15 g) obtained in Example 1 and potassium carbonate (0.047 g) in DMF (2 ml) and water (0.02 ml), 5-(chloromethyl)-2,4-dihydro-3H-1,2,4-triazol-3-one (0.046 g) synthesized by the method described in the document (e.g., Tetrahedron Letters, Vol. 41, pages 8661-8664) was added at 0° C., and the reaction mixture was stirred at 0° C. for 3 hours. The reaction mixture was poured into water, and then the product was extracted with ethyl acetate. The organic layer was washed with saturated brine, dried, and then the solvent was evaporated under reduced pressure. The obtained residue was isolated and purified by silica gel column chromatography (ethyl acetate: methanol=20:1) to obtain the title compound as colorless crystals (0.050 g, 29%).

Melting point: 89-91° C. (recrystallized from ethyl acetate-IPE).

Example 8

[cis-4-[[3,5-Bis(trifluoromethyl)benzyl]oxy]-3-phenyl-1-piperidinyl]acetic acid ethyl ester The compound (0.21 g) obtained in Example 1 and ethyl bromoacetate (0.17 g) were reacted and treated in the same manner as in the method described in Example 7 to obtain the title compound as colorless oil (0.10 g, 42%).

$^1$H-NMR (CDCl$_3$): δ 1.27 (3H, t, J=7.2 Hz), 1.90-2.12 (2H, m), 2.58 (1H, dt, J=3.3, 12.0 Hz), 2.79-2.90 (2H, m), 2.97 (1H, t, J=1.7 Hz), 3.13-3.20 (1H, m), 3.29 (2H, s), 3.80 (1H, q, J=2.7 Hz), 4.19 (2H, q, J=7.0 Hz), 4.08-4.28 (1H, m), 4.55 (1H, d, J=12.3 Hz), 7.20-7.30 (5H, m), 7.54 (2H, s), 7.71 (1H, s).

Example 9

[cis-4-[[3,5-Bis(trifluoromethyl)benzyl]oxy]-3-phenyl-1-piperidinyl]acetamide

The compound (0.15 g) obtained in Example 1 and bromoacetamide (0.094 g) were reacted and treated in the same manner as in the method described in Example 7 to obtain the title compound as colorless crystals (0.083 g, 52%).

Melting point: 123-125° C. (recrystallized from diethyl ether-hexane).

Example 10

[cis-4-[[3,5-Bis(trifluoromethyl)benzyl]oxy]-3-phenyl-1-piperidinyl]acetonitrile The compound (0.15 g) obtained in Example 1 and bromoacetonitrile (0.082 g) were reacted and treated in the same manner as in the method described in Example 7 to obtain the title compound as colorless oil (0.13 g, 86%).

$^1$H-NMR (CDCl$_3$): δ 1.84-1.97 (1H, m), 2.13 (1H, dq, J=3.6, 14.4 Hz), 2.65-2.84 (3H, m), 3.04-3.20 (2H, m), 3.55 (1H, d, J=16.8 Hz), 3.62 (1H, d, J=16.8 Hz), 3.79 (1H, q like, J=3.0 Hz), 4.21 (1H, d, J=12.6 Hz), 4.56 (1H, d, J=12.6 Hz), 7.22-7.36 (5H, m), 7.52 (2H, s), 7.73 (1H, s).

Example 11 cis-4-[[3,5-Bis(trifluoromethyl)benzyl]oxy]-N,N-dimethyl-3-phenyl-1-piperidinecarboxamide The compound (0.15 g) obtained in Example 1 and N,N-dimethylcarbamic acid chloride (0.074 g) were reacted and treated in the same manner as in the method described in Example 6 to obtain the title compound as colorless oil (0.13 g, 80%).

$^1$H-NMR (CDCl$_3$): δ 1.82-1.95 (1H, m), 2.04 (1H, dq, J=3.0, 14.1 Hz), 2.80-2.90 (6H, m), 2.92-3.06 (1H, m), 3.15 (1H, dt, J=3.0, 13.2 Hz), 3.56-3.68 (3H, m), 3.90 (1H, q, J=3.0 Hz), 4.17 (1H, d, J=12.9 Hz), 4.57 (1H, d, J=12.9 Hz), 7.20-7.34 (5H, m), 7.52 (2H, s), 7.72 (1H, s).

Example 12 cis-4-[[3,5-Bis(trifluoromethyl)benzyl]oxy]-N,3-diphenyl-1-piperidinecarboxamide The compound (0.15 g) obtained in Example 1 and phenyl isocyanate (0.074 ml) were reacted and treated in the same maimer as in the method described in Example 6 to obtain the title compound as colorless oil (0.12 g, 67%).

$^1$H-NMR (CDCl$_3$): δ 1.80-2.00 (1H, m), 2.10-2.20 (1H, m), 2.99-3.05 (1H, m), 3.31 (1H, dt, J=2.7, 12.9 Hz), 3.75 (1H, t, J=12.0 Hz), 3.90-4.00 (2H, m), 4.02-4.12 (1H, m), 4.22 (1H, d, J=12.3 Hz), 4.60 (1H, d, J=12.3 Hz), 6.42 (1H, s), 7.00-7.10 (1H, m), 7.24-7.38 (9H, m), 7.54 (2H, s), 7.75 (1H, s).

Example 13 cis-4-[[3,5-Bis(trifluoromethyl)benzyl]oxy]-N-ethyl-3-phenyl-1-piperidinecarboxamide The compound (0.20 g) obtained in Example 1 and ethyl isocyanate (0.047 g) were reacted and treated in the same manner as in the method described in Example 6 to obtain the title compound as colorless oil (0.12 g, 74%).

$^1$H-NMR (CDCl$_3$): δ 1.13 (3H, t, J=7.1 Hz), 1.70-1.90 (1H, m), 2.00-2.15 (1H, m), 2.90-3.00 (1H, m), 3.12-3.36 (3H, m), 3.55-3.68 (1H, t like), 3.72-3.84 (1H, dd like), 3.86-4.00 (2H, m), 4.20 (1H, d, J=2.4 Hz), 4.38-4.46 (1H, m), 4.58 (1H, d, J=12.4 Hz), 7.22-7.40 (5H, m), 7.53 (2H, s), 7.73 (1H, s).

Example 14 cis-4-[[3,5-Bis(trifluoromethyl)benzyl]oxy]-1-(1H-imidazol-1-ylcarbonyl)-3-phenylpiperidine To a solution of the compound (0.15 g) obtained in Example 1 and Et$_3$N (0.048 ml) in THF (4 ml), N,N'-carbonyldiimidazole (0.071 g) was added, and the reaction mixture was stirred at room temperature for 14 hours. The reaction mixture was poured into water, and then the product was extracted with ethyl acetate. The organic layer was washed with an aqueous saturated ammonium chloride solution and saturated brine, dried, and then the solvent was evaporated under reduced pressure. The obtained residue was isolated and purified by silica gel column chromatography (ethyl acetate:hexane=4:1) to obtain the title compound as colorless crystals (0.12 g, 70%).

Melting point: 105-1070° C. (recrystallized from ethyl acetate-IPE).

Example 15 cis-N-Allyl-4-[[3,5-bis(trifluoromethyl)benzyl]oxy]-3-phenyl-1-piperidinecarboxamide (Process 1)

To a solution of the compound (0.17 g) obtained in Example 14 in acetonitrile (0.6 ml), methyl iodide (0.085 ml) was added, and the reaction mixture was stirred at room temperature for 14 hours. The reaction mixture was concentrated under reduced pressure to obtain 1-[[4-[[3,5-bistrifluoromethyl)benzyl]oxy]-3-phenylpiperidin-1-yl]carbonyl]-3-methyl-1H-imidazol-3-ium iodide as pale yellow amorphous. The obtained product was used in the next process without further purification.

(Process 2)

To a solution of the compound obtained in Process 1 in dichloromethane (1 ml), allylamine (0.040 ml) and Et$_3$N (0.048 ml) were added, and the reaction mixture was stirred at room temperature for 14 hours. The reaction mixture was poured into water, and then the product was extracted with ethyl acetate. The organic layer was washed with an aqueous 10% citric acid solution and saturated brine, dried, and then the solvent was evaporated under reduced pressure. The obtained residue was isolated and purified by silica gel column chromatography (ethyl acetate:hexane=4:1) to obtain the title compound as colorless oil (0.090 g, 54%).

$^1$H-NMR (CDCl$_3$): δ 1.75-1.87 (1H, m), 2.02-2.10 (1H, m), 2.91-2.97 (1H, m), 3.22 (1H, dt, J=2.7, 12.9 Hz), 3.65 (1H, d, J=12.3 Hz), 3.77-4.00 (5H, m), 4.19 (1H, d, J=12.6 Hz), 4.50-4.58 (1H, br), 4.57 (1H, d, J=12.6 Hz), 5.07-5.19 (2H, m), 5.81-5.94 (1H, m), 7.20-7.34 (5H, m), 7.52 (2H, s), 7.72 (1H, s).

Example 16 cis-4-[[3,5-Bis(trifluoromethyl)benzyl]oxy]-1-(2-methoxybenzyl)-3-phenylpiperidine To a solution of the compound (0.20 g) obtained in Example 1, 2-methoxybenzyl alcohol (0.075 g) and diisopropylethylamine (0.24 g) in dichloromethane (2 ml), EPPA (0.20 g) was added, and the reaction mixture was stirred at room temperature for 14 hours. The reaction mixture was poured into water, and then the product was extracted with ethyl acetate. The organic layer was washed with an aqueous saturated ammonium chloride solution and saturated brine, dried, and then the solvent was evaporated under reduced pressure. The obtained residue was isolated and purified by silica gel column chromatography (ethyl acetate:methanol=20:1) to obtain the title compound as colorless oil (0.15 g, 62%).

¹H-NMR (CDCl₃): δ 1.85-2.10 (2H, m), 2.45-2.60 (1H, m), 2.70-2.82 (1H, br), 2.88 (2H, d like, J=6.6 Hz), 3.08-3.20 (1H, br), 3.66 (2H, br s), 3.78 (1H, q, J=3.0 Hz), 3.82 (3H, s), 4.17 (1H, d, J=3.2 Hz), 4.54 (1H, d, J=3.2 Hz), 6.86 (1H, d, J=8.1 Hz), 6.91 (1H, dt, J=7.2, 0.9 Hz), 7.18-7.30 (6H, m), 7.38 (1H, d like, J=6.0 Hz), 7.52 (2H, s), 7.70 (1H, s).

Example 17 cis-4-[[3,5-Bis(trifluoromethyl)benzyl]oxy]-3-phenyl-1-piperidinecarboxamide

To a solution of the compound (0.20 g) obtained in Process 1 of Example 15 in THF (1 ml), 28% ammonia water (0.20 ml) was added, and the reaction solution was stirred at room temperature for 14 hours. The reaction solution was treated in the same manner as in the method described in Process 2 of Example 15 to obtain the title compound as colorless oil (0.075 g, 54%).
¹H-NMR (CDCl₃): δ 1.78-1.90 (1H, m), 2.05-2.14 (1H, m), 2.93-3.12 (1H, m), 3.24 (1H, dt, J=3.3, 13.2 Hz), 3.68 (1H, d, J=12.3 Hz), 3.78-3.85 (1H, m), 3.88-4.00 (2H, m), 4.20 (1H, d, J=12.6 Hz), 4.48 (2H, br s), 4.58 (1H, d, J=12.6 Hz), 7.20-7.34 (5H, m), 7.52 (2H, s), 7.73 (1H, s).

Example 18 cis-4-[[3,5-Bis(trifluoromethyl)benzyl]oxy]-3-phenyl-N-propyl-1-piperidinecarboxamide The compound (0.20 g) obtained in Process 1 of Example 15 and propylamine (0.056 g) were reacted and treated in the same manner as in the method described in Process 2 of Example 15 to obtain the title compound as colorless oil (0.099 g, 64%).
¹H-NMR (CDCl₃): δ 0.91 (3H, t, J=7.2 Hz), 1.51 (2H, m), 1.75-1.90 (1H, m), 2.02-2.10 (1H, m), 2.90-3.00 (1H, m), 3.14-3.26 (3H, m), 3.64 (1H, d, J=11.7 Hz), 3.72-3.80 (1H, m), 3.88-3.98 (2H, m), 4.20 (1H, d, J=12.3 Hz), 4.48 (1H, br s), 4.57 (1H, d, J=12.3 Hz), 7.21-7.34 (5H, m), 7.52 (2H, s), 7.72 (1H, s).

Example 19 cis-4-[[3,5-Bis(trifluoromethyl)benzyl]oxy]-1-(2,5-dimethoxybenzyl)-3-phenylpiperidine The compound (0.20 g) obtained in Example 1 and 2,5-dimethoxybenzyl alcohol (0.12 g) were reacted and treated in the same manner as in the method described in Example 16 to obtain the title compound as colorless oil (0.060 g, 23%).
¹H-NMR (CDCl₃): δ 1.80-2.12 (2H, m), 2.42-2.60 (1H, m), 2.70-2.82 (1H, m), 2.84-2.96 (2H, m), 3.06-3.20 (1H, m), 3.63 (2H, s), 3.76 (3H, s), 3.78 (3H, s), 3.74-3.84 (1H, m), 4.18 (1H, d, J=12.8 Hz), 4.55 (1H, d, J=14.8 Hz), 6.69-6.82 (2H, m), 7.02 (1H, d, J=3.0 Hz), 7.20-7.34 (5H, m), 7.53 (2H, s), 7.71 (1H, s).

Example 20 cis-4-[[3,5-Bis(trifluoromethyl)benzyl]oxy]-3-phenyl-N-(2-phenylethyl)-1-piperidinecarboxamide The compound (0.20 g) obtained in Process 1 of Example 15 and phenethylamine (0.11 g) were reacted and treated in the same manner as in the method described in Process 2 of Example 15 to obtain the title compound as colorless oil (0.12 g, 69%).

¹H-NMR (CDCl₃): δ 1.71-1.83 (1H, m), 2.00-2.10 (1H, m), 2.75-3.00 (3H, m), 3.18 (1H, dt, J=2.7, 12.9 Hz), 3.50 (2H, q, J=5.7 Hz), 3.60 (1H, d, J=12.0 Hz), 3.72 (1H, dd, J=13.2, 3.3 Hz), 3.80-3.92 (2H, m), 4.19 (1H, d, J=12.3 Hz), 4.47 (1H, t, J=2.6 Hz), 4.57 (1H, d, J=12.6 Hz), 7.17-7.35 (10H, m), 7.53 (2H, s), 7.73 (1H, s).

Example 21 cis-4-[[3,5-Bis(trifluoromethyl)benzyl]oxy]-3-phenyl-N-(2-propynyl)-1-piperidinecarboxamide The compound (0.20 g) obtained in Process 1 of Example 15 and propargylamine (0.052 g) were reacted and treated in the same manner as in the method described in Process 2 of Example 15 to obtain the title compound as colorless oil (0.11 g, 71%).
¹H-NMR (CDCl₃): δ 1.75-1.90 (1H, m), 2.00-2.13 (1H, m), 2.22 (1H, t, J=2.4 Hz), 2.90-3.00 (1H, m), 3.22 (1H, dt, J=3.3, 13.2 Hz), 3.66 (1H, d, J=12.3 Hz), 3.81 (1H, dd, J=13.2, 3.6 Hz), 3.88-4.00 (2H, m), 4.00-4.06 (2H, dd like), 4.20 (1H, d, J=12.3 Hz), 4.58 (1H, d, J=12.6 Hz), 4.63 (1H, t, J=5.1 Hz), 7.22-7.36 (5H, m), 7.53 (2H, s), 7.73 (1H, s).

Example 22 cis-4-[[3,5-Bis(trifluoromethyl)benzyl]oxy]-N-methoxy-N-methyl-3-phenyl-1-piperidinecarboxamide The compound (0.20 g) obtained in Process 1 of Example 15 and N,O-dimethyihydroxyamine hydrochloride (0.092 g) were reacted and treated in the same manner as in the method described in Process 2 of Example 15 to obtain the title compound as colorless oil (0.11 g, 70%).
¹H-NMR (CDCl₃): δ 1.79-1.91 (1H, m), 2.04-2.14 (1H, m), 2.96 (3H, s), 09-3.12 (1H, t like), 3.26 (1H, dt, J=2.4, 12.9 Hz), 3.57 (3H, s), 3.67 (1H, d, J=12.6 Hz), 3.90-3.94 (1H, m), 3.98-4.10 (2H, m), 4.19 (1H, d, J=12.3 Hz), 4.58 (1H, 12.3 Hz), 7.20-7.36 (5H, m), 7.53 (2H, s), 7.74 (1H, s).

Example 23 cis-N-(2-Methoxybenzyl)-3-phenylpiperidine-4-amine hydrochloride

To the compound (cis-form, 1.91 g) obtained in Process 3 of Reference Example 2, trifluoroacetic acid (20 ml) was added at 0° C., and the reaction mixture was stirred at room temperature for 10 minutes. The solvent was evaporated under reduced pressure, and then the residue was poured into a mixed solution of an aqueous 2 N sodium hydroxide solution and ethyl acetate. The organic layer was washed with an aqueous saturated sodium hydrogen carbonate solution and saturated brine, dried, and then the solvent was evaporated under reduced pressure. The obtained residue was treated with a 4 N hydrogen chloride/ethyl acetate solution (2.6 ml) to obtain the title compound as colorless crystals (1.20 g, 67%).
HPLC analysis (Condition A): Purity 80% (Retention time: 0.32 minutes)
MS (ESI+): 297 (M+H)

Example 24 trans-N-(2-Methoxybenzyl)-3-phenylpiperidine-4-amine

The compound (trans-form, 0.96 g) obtained in Process 3 of Reference Example 2 was reacted in the same manner as in the method described in Example 23. The solvent was evaporated under reduced pressure, and then the residue was poured into a mixed solution of an aqueous 2 N sodium hydroxide solution and ethyl acetate. The organic layer was washed with an aqueous saturated sodium hydrogen carbonate solution and saturated brine, dried, and then the solvent was evaporated under reduced pressure to obtain the title compound as colorless crystals (0.42 g, 58%).

HPLC analysis (Condition A): Purity 81% (Retention time: 0.31 minutes)

MS (ESI+): 297 (M+H)

Example 25 cis-3-Benzhydryl-4-[[3,5-bis(trifluoromethyl)benzyl]oxy]piperidine hydrochloride To the compound (2.65 g) obtained in Reference Example 3, a 4 N hydrogen chloride/ethyl acetate solution was added, the reaction mixture was stirred at room temperature for 30 minutes, and then the solvent was evaporated under reduced pressure. The residue was crystallized from diethyl ether and washed therewith to obtain the title compound as white powder (1.11 g, 47%).

$^1$H-NMR (CDCl$_3$): δ 1.80-1.88 (1H, t like), 2.20 (1H, d, J=14.4 Hz), 2.69 (1H, d, J=9.9 Hz), 2.82-3.17 (4H, m), 3.48 (1H, br s), 3.92 (1H, d, J=11.4 Hz), 4.08 (1H, d, J=12.3 Hz), 4.66 (1H, d, J=12.3 Hz), 7.13-7.40 (10H, m), 7.99 (2H, s), 8.04 (1H, s), 9.03 (2H, br).

Example 26 cis-3-Benzhydryl-4-[[3-fluoro-5-(trifluoromethyl)benzyl]oxy]piperidine hydrochloride To the compound (1.92 g) obtained in Reference Example 4, a 4 N hydrogen chloride/ethyl acetate solution was added, and the reaction mixture was stirred at room temperature for 30 minutes, and then the solvent was evaporated under reduced pressure. The residue was crystallized from diethyl ether and washed therewith to obtain the title compound as white powder (0.88 g, 52%).

$^1$H-NMR (CDCl$_3$): δ 1.77-1.86 (1H, t like), 2.17 (1H, d, J=14.4 Hz), 2.84-3.15 (4H, m), 3.42 (1H, br s), 3.97 (1H, d, J=11.4 Hz), 4.00 (1H, d, J=12.3 Hz), 4.56 (1H, d, J=12.3 Hz), 7.15-7.60 (13H, m), 9.06 (2H, br).

Example 27 cis-3-Benzhydryl-4-[[3-(trifluoromethoxy)benzyl]oxy]piperidine hydrochloride

To the compound (2.22 g) obtained in Reference Example 5, a 4 N hydrogen chloride/ethyl acetate solution was added, and the reaction mixture was stirred at room temperature for 30 minutes, and then the solvent was evaporated under reduced pressure. The residue was crystallized from IPE and washed therewith to obtain the title compound as white powder (1.31 g, 67%).

$^1$H-NMR (CDCl$_3$): δ 1.75-1.83 (1H, t like), 2.15 (1H, d, J=14.4 Hz), 2.62-3.15 (5H, m), 3.40 (1H, br s), 3.94 (1H, d, J=12.0 Hz), 3.96 (1H, d, J11.7 Hz), 4.50 (1H, d, J=11.7 Hz), 7.18-7.52 (14H, m), 9.03 (2H, br).

Example 28 cis-3-Benzhydryl-4-[[4-(trifluoromethyl)benzyl]oxy]piperine hydrochloride

To the compound (2.14 g) obtained in Reference Example 6, a 4 N hydrogen chloride/ethyl acetate solution was added, and the reaction mixture was stirred at room temperature for 30 minutes, and then the solvent was evaporated under reduced pressure. The residue was crystallized from IPE and washed therewith to obtain the title compound as white powder (1.20 g, 64%).

$^1$H-NMR (CDCl$_3$): δ 1.76-1.84 (1H, t like), 2.11-2.20 (1H, t like), 2.70-3.16 (5H, m), 3.40 (1H, br s), 3.98 (1H, d, J=11.7 Hz), 4.55 (1H, d, J=12.3 Hz), 7.16-7.33 (8H, m), 7.43 (2H, d, J=7.5 Hz), 7.55 (2H, d, J=7.8 Hz), 7.71 (2H, d, J=8.1 Hz), 9.08 (2H, br).

Example 29

2-[cis-3-Benzhydryl-4-[[3,5-bis(trifluoromethyl)benzyl]oxy]piperidin-1-yl]-2-oxoethanamine To a solution of the compound (31.8 mg) obtained in Example 25 in DMF (2.0 ml), Et$_3$N (8.4 μl) was added, Boc-glycine (21 mg) and WSC.HCl (23 mg) were added at room temperature and the reaction mixture was stirred at room temperature for 24 hours. The reaction mixture was poured into water, and then the product was extracted with ethyl acetate. The organic layer was washed with an aqueous 10% citric acid solution and saturated brine, and dried, and the solvent was evaporated under reduced pressure, and then the residue was purified by preparative HPLC. A 4 N hydrogen chloride/ethyl acetate solution was further added thereto, and the reaction mixture was stirred for 1 hour, and then the solvent was evaporated. The obtained residue was dissolved in ethyl acetate, washed with an aqueous saturated sodium hydrogen carbonate solution and brine, dried, and then the solvent was evaporated under reduced pressure to obtain the title compound.

Yield: 4.3 mg

HPLC analysis (Condition B): Purity 100% (Retention time: 2.05 minutes)

MS (ESI+): 551 (M+H)

Example 30 cis-3-Benzhydryl-4-[[3-fluoro-5-(trifluoromethyl)benzyl]oxy]-1-(methylsulfonyl)piperidine To a solution of the compound (28.8 mg) obtained in Example 26 in THF (2.0 ml), Et$_3$N (25.1 μl) was added, methylsulfonyl chloride (9.3 μl) was added at 0° C., and the reaction mixture was reacted at room temperature 24 hours. The reaction mixture was poured into water, and then the product was extracted with ethyl acetate. The organic layer was washed with an aqueous 10% citric acid solution and saturated brine, and dried, and the solvent was evaporated under reduced pressure, and then the residue was purified by preparative HPLC to obtain the title compound.

Yield: 18.7 mg

HPLC analysis (Condition B): Purity 98% (Retention time: 2.28 minutes)
MS (ESI+): 522 (M+H)

Example 31 cis-3-Benzhydryl-4-[[3,5-bis(trifluoromethyl)benzyl]oxy]-N-methyl-1-piperidinecarboxamide To a solution of the compound (31.8 mg) obtained in Example 25 and Et$_3$N (8.4 µl) in THF (3 ml), methyl isocyanate (6.8 mg) was added, and the reaction mixture was stirred at room temperature for 24 hours. The reaction mixture was poured into water, and then the product was extracted with ethyl acetate. The organic layer was washed with an aqueous 10% citric acid solution and saturated brine, and dried, and the solvent was evaporated under reduced pressure, and then the residue was purified by preparative HPLC to obtain the title compound.
Yield: 24.1 mg
HPLC analysis (Condition B): Purity 98% (Retention time: 2.28 minutes)
MS (ESI+): 551 (M+H)

Example 32 cis-2-[3-Benzhydryl-4-[[3,5-bis(trifluoromethyl)benzyl]oxy]-1-piperidinyl]-N,N-dimethyl-2-oxoethanamine To a solution of the compound (31.8 mg) obtained in Example 25 in DMF (2.0 ml), Et$_3$N (25.1 µl) was added, N,N-dimethylglycine hydrochloride (16.7 mg) and WSC.HCl (23 mg) were added thereto and the reaction mixture was stirred at room temperature for 24 hours. The reaction mixture was poured into water, and then the product was extracted with ethyl acetate. The organic layer was washed with an aqueous 10% citric acid solution and saturated brine, and dried, and the solvent was evaporated under reduced pressure, and then the residue was purified by preparative HPLC. The obtained compound was dissolved in ethyl acetate, washed with an aqueous saturated sodium hydrogen carbonate solution and brine, dried, and then the solvent was evaporated under reduced pressure to obtain the title compound.
Yield: 10.8 mg
HPLC analysis (Condition B): Purity 100% (Retention time: 1.92 minutes)
MS (ESI+): 579 (M+H)

Example 33 cis-1-Acetyl-3-benzhydryl-4-[[3,5-bis(trifluoromethyl)benzyl]oxy]piperidine

To a solution of the compound (31.8 mg) obtained in Example 25 in DMF (2.0 ml), Et$_3$N (8.4 µl) was added, acetic acid (6.9 µl) and WSC.HCl (23 mg) were added thereto and the reaction mixture was stirred at room temperature for 24 hours. The reaction mixture was poured into water, and then the product was extracted with ethyl acetate. The organic layer was washed with an aqueous 10% citric acid solution and saturated brine, and dried, and the solvent was evaporated under reduced pressure, and then the residue was purified by preparative HPLC to obtain the title compound.
Yield: 23.7 mg
HPLC analysis (Condition B): Purity 100% (Retention time: 2.32 minutes)
MS (ESI+): 536 (M+H)

Example 34 cis-3-Benzhydryl-4-[[3,5-bis(trifluoromethyl)benzyl]oxy]-1-(methoxyacetyl)piperidine The compound (31.8 mg) obtained in Example 25 and methoxyacetic acid (9.2 µl) were reacted and treated in the same manner as in the method described in Example 33 to obtain the title compound.
Yield: 18.6 mg
HPLC analysis (Condition B): Purity 100% (Retention time: 2.33 minutes)
MS (ESI+): 566 (M+H)

Example 35 cis-3-Benzhydryl-4-[[3,5-bis(trifluoromethyl)benzyl]oxy]-1-(methylsulfonyl)piperidine The compound (31.8 mg) obtained in Example 25 and methylsulfonyl chloride (9.3 µl) were reacted and treated in the same manner as in the method described in Example 30 to obtain the title compound.
Yield: 25.8 mg
HPLC analysis (Condition B): Purity 99% (Retention time: 2.34 minutes)
MS (ESI+): 572 (M+H)

Example 36 cis-3-Benzhydryl-4-[[3,5-bis(trifluoromethyl)benzyl]oxy]-1-(2-pyridinylacetyl)piperidine The compound (31.8 mg) obtained in Example 25 and 2-pyridineacetic acid hydrochloride (20.8 mg) were reacted and treated in the same manner as in the method described in Example.32 to obtain the title compound.
Yield: 5.5 mg
HPLC analysis (Condition B): Purity 100% (Retention time: 1.97 minutes)
MS (ESI+): 613 (M+H)

Example 37 cis-3-Benzhydryl-4-[[3,5-bis(trifluoromethyl)benzyl]oxy]-1-(1H-imidazol-4-ylacetyl)piperidine The compound (31.8 mg) obtained in Example 25 and 4-imidazoleacetic acid hydrochloride (19.5 mg) were reacted and treated in the same manner as in the method described in Example 32 to obtain the title compound.
Yield: 2.6 mg
HPLC analysis (Condition B): Purity 98% (Retention time: 2.06 minutes)
MS (ESI+): 602 (M+H)

Example 38 cis-3-Benzhydryl-4-[[3,5-bis(trifluoromethyl)benzyl]
oxy]-1-propionylpiperidine

The compound (31.8 mg) obtained in Example 25 and propionic acid (9.0 μl) were reacted and treated in the same manner as in the method described in Example 33 to obtain the title compound.
Yield: 16.7 mg
HPLC analysis (Condition B): Purity 98% (Retention time: 2.39 minutes)
MS (ESI+): 550 (M+H)

Example 39 cis-3-Benzhydryl-4-[[3-fluoro-5-(trifluoromethyl)
benzyl]oxy]-N-methyl-1-piperidinecarboxamide The compound obtained in Example 26 (28.8 mg) and methyl isocyanate (6.8 mg) were reacted and treated in the same manner as in the method described in Example 31 to obtain the title compound.
Yield: 21.3 mg
HPLC analysis (Condition B): Purity 100% (Retention time: 2.20 minutes)
MS (ESI+): 501 (M+H)

Example 40 cis-3-Benzhydryl-4-[[3-fluoro-5-(trifluoromethyl)
benzyl]oxy]-1-propionylpiperidine The compound (28.8 mg) obtained in Example 26 and propionic acid (9.0 μl) were reacted and treated in the same manner as in the method described in Example 33 to obtain the title compound.
Yield: 16.7 mg
HPLC analysis (Condition B): Purity 97% (Retention time: 2.32 minutes)
MS (ESI+): 500 (M+H)

Example 41 cis-1-Acetyl-3-benzhydryl-4-[[3-fluoro-5-(trifluoromethyl)benzyl]oxy]piperidine

The compound (28.8 mg) obtained in Example 26 and acetic acid (6.9 μl) were reacted and treated in the same manner as in the method described in Example 33 to obtain the title compound.
Yield: 13.7 mg
HPLC analysis (Condition B): Purity 99% (Retention time: 2.25 minutes)
MS (ESI+): 486 (M+H)

Example 42 cis-3-Benzhydryl-4-[[3-fluoro-5-(trifluoromethyl)
benzyl]oxy]-1-(methoxyacetyl)piperidine The compound (28.8 mg) obtained in Example 26 and methoxyacetic acid (9.2 μl) were reacted and treated in the same manner as in the method described in Example 33 to obtain the title compound.
Yield: 16.8 mg
HPLC analysis (Condition B): Purity 100% (Retention time: 2.25 minutes)
MS (ESI+): 516 (M+H)

Example 43 cis-3-Benzhydryl-4-[[3-fluoro-5-(trifluoromethyl)
benzyl]oxy]-1-(1H-imidazol-4-ylacetyl)piperidine The compound (28.8 mg) obtained in Example 26 and 4-imidazoleacetic acid hydrochloride (19.5 mg) were reacted and treated in the same manner as in the method described in Example 32 to obtain the title compound.
Yield: 3.1 mg
HPLC analysis (Condition B): Purity 100% (Retention time: 2.00 minutes)
MS (ESI+): 552 (M+H)

Example 44 cis-3-Benzhydryl-1-(1,3-benzodioxol-5-ylcarbonyl)-
4-[[3,5-bis(trifluoromethyl)benzyl]oxy]piperidine The compound (31.8 mg) obtained in Example 25 and piperonylic acid (19.9 mg) were reacted and treated in the same manner as in the method described in Example 33 to obtain the title compound.
Yield: 22.1 mg
HPLC analysis (Condition B): Purity 95% (Retention time: 2.39 minutes)
MS (ESI+): 642 (M+H)

Example 45 cis-2-[3-Benzhydryl-4-[[3-fluoro-5-(trifluoromethyl)
benzyl]oxy]-1-pipendinyl]-N,N-dimethyl-2-oxoethanamine The compound (28.8 mg) obtained in Example 26 and N,N-dimethylglycine hydrochloride (16.7 mg) were reacted and treated in the same manner as in the method described in Example 32 to obtain the title compound.
Yield: 13.6 mg
HPLC analysis (Condition B): Purity 100% (Retention time: 1.85 minutes)
MS (ESI+): 529 (M+H)

Example 46 cis-2-[3-Benzhydryl-4-[[3-fluoro-5-(trifluoromethyl)
benzyl]oxy]-1-piperidinyl]-2-oxoethanamine The compound (28.8 mg) obtained in Example 26 and Boc-glycine (21.0 mg) were reacted and treated in the same manner as in the method described in Example 29 to obtain the title compound.
Yield: 17.8 mg
HPLC analysis (Condition B): Purity 100% (Retention time: 1.97 minutes)
MS (ESI+): 501 (M+H)

Example 47 cis-3-Benzhydryl-1-(methoxyacetyl)-4-[[3-(trifluoromethoxy)benzyl]oxy])piperidine The compound (27.7 mg) obtained in Example 27 and methoxyacetic acid (9.2 μl) were reacted and treated in the same manner as in the method described in Example 33 to obtain the title compound.
Yield: 16.5 mg
HPLC analysis (Condition B): Purity 99% (Retention time: 2.25 minutes)
MS (ESI+): 514 (M+H)

Example 48 cis1-Acetyl-3-benzhydryl-4-[[3-(trifluoromethoxy)benzyl]oxy]piperidine

The compound (27.7 mg) obtained in Example 27 and acetic acid (6.9 μl) were reacted and treated in the same manner as in the method described in Example 33 to obtain the title compound.
Yield: 19.4 mg
HPLC analysis (Condition B): Purity 100% (Retention time: 2.25 minutes)
MS (ESI+): 484 (M+H)

Example 49 cis-3-Benzhydryl-1-propionyl-4-[[3-(trifluoromethoxy)benzyl]oxy]piperidine

The compound (27.7 mg) obtained in Example 27 and propionic acid (9.0 μl) were reacted and treated in the same manner as in the method described in Example 33 to obtain the title compound.
Yield: 15.3 mg
HPLC analysis (Condition B): Purity 96% (Retention time: 2.31 minutes)
MS (ESI+): 498 (M+H)

Example 50 cis-3-Benzhydryl-4-[[3-fluoro-5-(trifluoromethyl)benzyl]oxy]-1-(2-pyridinylacetyl)piperidine The compound (28.8 mg) obtained in Example 26 and 2-pyridineacetic acid hydrochloride (20.8 mg) were reacted and treated in the same manner as in the method described in Example 32 to obtain the title compound.
Yield: 7.4 mg
HPLC analysis (Condition B): Purity 98% (Retention time: 1.90 minutes)
MS (ESI+): 563 (M+H)

Example 51 cis-2-[3-Benzhydryl-4-[[3-(trifluoromethoxy)benzyl]oxy]-1-piperidinyl]-2-oxoethanamine The compound (27.7 mg) obtained in Example 27 and Boc-glycine (21.0 mg) were reacted and treated in the same manner as in the method described in Example 29 to obtain the title compound.
Yield: 11.7 mg
HPLC analysis (Condition B): Purity 96% (Retention time: 1.97 minutes)
MS (ESI+): 499 (M+H)

Example 52 cis-3-Benzhydryl-1-(1,3-benzodioxol-5-ylcarbonyl)-4-[[3-fluoro-5-(trifluoromethyl)benzyl]oxy]piperidine The compound (28.8 mg) obtained in Example 26 and piperonylic acid (19.9 mg) were reacted and treated in the same manner as in the method described in Example 33 to obtain the title compound.
Yield: 15.6 mg
HPLC analysis (Condition B): Purity 100% (Retention time: 2.33 minutes)
MS (ESI+): 592 (M+H)

Example 53 cis-3-Benzhydryl-1-(methylsulfonyl)-4-[[4-(trifluoromethyl)benzyl]oxy]piperidine The compound (28.7 mg) obtained in Example 28 and methylsulfonyl chloride (9.3 μl) were reacted and treated in the same manner as in the method described in Example 30 to obtain the title compound.
Yield: 22.8 mg
HPLC analysis (Condition B): Purity 100% (Retention time: 2.26 minutes)
MS (ESI+): 504 (M+H)

Example 54 cis-3-Benzhydryl-1-benzyl-4-[[3,5-bis(trifluoromethyl)benzyl]Oxy]piperidine

To a solution of the compound (31.8 mg) obtained in Example 25, diisopropylethylamine (40.5 μl) and benzyl alcohol (12.4 μl) in dichloromethane (2.0 ml), EPPA (17.3 μl) was added, and the reaction mixture was stirred at room temperature for 24 hours. The reaction mixture was poured into water, and then the product was extracted with ethyl acetate. The organic layer was washed with an aqueous 10% citric acid solution and saturated brine, and dried, and the solvent was evaporated under reduced pressure, and then the residue was purified by preparative HPLC to obtain the title compound.
Yield: 4.4 mg
HPLC analysis (Condition B): Purity 99% (Retention time: 1.99 minutes)
MS (ESI+): 584 (M+H)

Example 55 cis-2-[3-Benzhydryl-4-[[4-(trifluoromethyl)benzyl]oxy]piperidinyl]-2-oxoethanamine The compound (28.7 mg) obtained in Example 28 and Boc-glycine (21.0 mg) were reacted and treated in the same manner as in the method described in Example 29 to obtain the title compound.
Yield: 11.1 mg
HPLC analysis (Condition B): Purity 91% (Retention time: 1.96 minutes)
MS (ESI+): 483 (M+H)

Example 56 cis-1-Acetyl-3-benzhydryl-4-[[4-(trifluoromethyl)benzyl]oxy]piperidine

The compound (28.7 mg) obtained in Example 28 and acetic acid (6.9 μl) were reacted and treated in the same manner as m the method described in Example 33 to obtain the title compound.
Yield: 12.6 mg
HPLC analysis (Condition B): Purity 100% (Retention time: 2.24 minutes)
MS (ESI+): 468 (M+H)

Example 57 cis-3-Benzhydryl-1-benzyl-4-[[3-fluoro-5-(trifluoromethyl)benzyl]oxy]piperidine

The compound (28.8 mg) obtained in Example 26 and benzyl alcohol (12.4 μl) were reacted and treated in the same manner as in the method described in Example 54 to obtain the title compound.
Yield: 4.3 mg
HPLC analysis (Condition B): Purity 98% (Retention time: 1.93 minutes)
MS (ESI+): 534 (M+H)

Example 58 cis-3-Benzhydryl-N-methyl-4-[[4-(trifluoromethyl)benzyl]oxy]-1-piperidinecarboxamide The compound (28.7 mg) obtained in Example 28 and methyl isocyanate (6.8 mg) were reacted and treated in the same manner as in the method described in Example 31 to obtain the title compound.
Yield: 23.5 mg
HPLC analysis (Condition B): Purity 100% (Retention time: 2.19 minutes)
MS (ESI+): 483 (M+H)

Example 59 cis-3-Benzhydryl-1-(2-pyridinylacetyl)-4-[[4-(trifluoromethyl)benzyl]oxy]piperidine The compound (28.7 mg) obtained in Example 28 and 2-pyridineacetic acid hydrochloride (20.8 mg) were reacted and treated in the same manner as in the method described in Example 32 to obtain the title compound.
Yield: 5.0 mg
HPLC analysis (Condition B): Purity 100% (Retention time: 1.89 minutes)
MS (ESI+): 545 (M+H)

Example 60 cis-3-Benzhydryl-1-propionyl-4-[[4-(trifluoromethyl)benzyl]oxy]piperidine

The compound (28.7 mg) obtained in Example 28 and propionic acid (9.0 μl) were reacted and treated in the same manner as in the method described in Example 33 to obtain the title compound.
Yield: 14.8 mg
HPLC analysis (Condition B): Purity 99% (Retention time: 2.30 minutes)
MS (ESI+): 482 (M+H)

Example 61 cis-2-[3-Benzhydryl-4-[[4-(trifluoromethyl)benzyl]oxy]piperidinyl]-N,N-dimethyl-2-oxoethanamine The compound (28.7 mg) obtained in Example 28 and N,N-dimethylglycine hydrochloride (16.7 mg) were reacted and treated in the same manner as in the method described in Example 32 to obtain the title compound.
Yield: 6.5 mg
HPLC analysis (Condition B): Purity 98% (Retention time: 1.84 minutes)
MS (ESI+): 511 (M+H)

Example 62 cis-3-Benzhydryl-1-(methoxyacetyl)-4-[[4-(trifluoromethyl)benzyl]oxy]piperidine

The compound (28.7 mg) obtained in Example 28 and methoxyacetic acid (9.2 μl) were reacted and treated in the same manner as in the method described in Example 33 to obtain the title compound.
Yield: 13.0 mg
HPLC analysis (Condition B): Purity 99% (Retention time: 2.23 minutes)
MS (ESI+): 498 (M+H)

Example 63 cis-3-Benzhydryl-1-(1H-imidazol-4-ylacetyl)-4-[[4-(trifluoromethyl)benzyl]oxy]piperidine The compound (28.7 mg) obtained in Example 28 and 4-imidazoleacetic acid hydrochloride (19.5 mg) were reacted and treated in the same manner as in the method described in Example 32 to obtain the title compound.
Yield: 1.8 mg
HPLC analysis (Condition B): Purity 100% (Retention time: 1.98 minutes)
MS (ESI+): 534 (M+H)

Example 64 cis-3-Benzhydryl-1-[3,5-bis(trifluoromethyl)benzoyl]-4-[[3,5-bis(trifluoromethyl)benzyl]oxy]piperidine The compound (31.8 mg) obtained in Example 25 and 3,5-bis(trifluoromethyl)benzoic acid (31.0 mg) were reacted and treated in the same manner as in the method described in Example 33 to obtain the title compound.
Yield: 9.8 mg
HPLC analysis (Condition B): Purity 95% (Retention time: 2.57 minutes)
MS (ESI+): 734 (M+H)

Example 65 cis-3-Benzhydryl-1-[3,5-bis(trifluoromethyl)benzoyl]-4-[[3-fluoro-5-(trifluoromethyl)benzyl]oxy]piperidine The compound (28.8 mg) obtained in Example 26 and 3,5-bis(trifluoromethyl)benzoic acid (31.0 mg) were reacted and treated in the same manner as in the method described in Example 33 to obtain the title compound.
Yield: 10.9 mg
HPLC analysis (Condition B): Purity 100% (Retention time: 2.50 minutes)
MS (ESI+): 684 (M+H)

Example 66 cis-3-Benzhydryl-1-[3,5-bis(trifluoromethyl)benzoyl]-4-[[4-(trifluoromethyl)benzyl]oxy]piperidine The compound (28.7 mg) obtained in Example 28 and 3,5-bis(trifluoromethyl)benzoic acid (31.0 mg) were reacted and treated in the same manner as in the method described in Example 33 to obtain the title compound.
Yield: 12.4 mg
HPLC analysis (Condition B): Purity 100% (Retention time: 2.49 minutes)
MS (ESI+): 666 (M+H)

Example 67 cis-3-Benzhydryl-1-(1,3-benzodioxol-5-ylcarbonyl)-4-[[4-(trifluoromethyl)benzyl]oxy]piperidine The compound (28.7 mg) obtained in Example 28 and piperonylic acid (19.9 mg) were reacted and treated in the same manner as in the method described in Example 33 to obtain the title compound.
Yield: 12.8 mg
HPLC analysis (Condition B): Purity 100% (Retention time: 2.31 minutes)
MS (ESI+): 574 (M+H)

Example 68 cis-3-Benzhydryl-1-[3,5-bis(trifluoromethyl)benzoyl]-4-[[3-(trifluoromethoxy)benzyl]oxy]piperidine The compound (27.7 mg) obtained in Example 27 and 3,5-bis(trifluoromethyl)benzoic acid (31.0 mg) were reacted and treated in the same manner as in the method described in Example 33 to obtain the title compound.
Yield: 18.2 mg
HPLC analysis (Condition B): Purity 99% (Retention time: 2.52 minutes)
MS (ESI+): 682 (M+H)

Example 69 cis-1-[(1-Acetyl-4-piperidinyl)carbonyl]-4-[[3,5-bis(trifluoromethyl)benzyl]oxy]-3-phenylpiperidine (Process 1)
To a solution of the compound (0.53 g) obtained in Example 1 in DMF (10 ml), Et$_3$N (0.17 ml) was added, Boc-isonipecotinic acid (0.41 g), WSC.HCl (0.46 g) and HOBt.H$_2$O (0.37 g) were added thereto and the reaction mixture was stirred at room temperature for 24 hours. The reaction mixture was poured into water, and then the product was extracted with ethyl acetate. The organic layer was washed with an aqueous saturated sodium hydrogen carbonate solution and saturated brine, dried, and then the solvent was evaporated under reduced pressure. The obtained residue was isolated and purified by silica gel column chromatography (ethyl acetate:hexane=1:3→1:1) to obtain cis-4-[[[3,5-bis(trifluoromethyl)benzyl]oxy]-3-phenyl-1-piperidinyl]carbonyl]-1-piperidinecarboxylic acid tert-butyl ester as colorless amorphous (0.71 g).

(Process 2)
The compound (0.65 g) obtained in Process 1 and trifluoroacetic acid (8 ml) were reacted and treated in the same manner as in the method described in Example 1 to obtain cis-4-[[3,5-bis(trifluoromethyl)benzyl]oxy]-3-phenyl-1-(4-piperidinylcarbonyl)piperidine hydrochloride as white powder (0.54 g).

(Process 3)
To a solution of the compound (0.27 g) obtained in Process 2 in pyridine (2 ml), N,N-dimethylaminopyridine (0.030 g) and acetic anhydride (0.10 g) were added, and the reaction mixture was stirred at room temperature for 4 hours. The reaction mixture was poured into water, and then the product was extracted with ethyl acetate. The organic layer was washed with an aqueous saturated sodium hydrogen carbonate solution and saturated brine, dried, and then the solvent was evaporated under reduced pressure. The obtained residue was purified by preparative HPLC to obtain the title compound as colorless amorphous (0.21 g).
$^1$H-NMR (CDCl$_3$): δ 1.60-1.96 (6H, m), 2.00-2.20 (4H, m), 2.58-3.18 (4H, m), 3.28-3.58 (1H, m), 3.76-3.96 (3H, m), 4.19 (1H, dd, J=12.0, 3.0 Hz), 4.51-4.69 (3H, m), 7.21-7.38 (5H, m), 7.52 (2H, s), 7.73 (1H, s).

Example 70

(+)-(3R,4S)-1-[(1-Acetyl-4-piperidinyl)carbonyl]-4-[[3,5-bis(trifluoromethyl)benzyl]oxy]-3-phenylpiperidine (Process 1)
A mixture of the compound (1.51 g) obtained in Process 5 of Reference Example 1, [RuCl$_2$[(R)-BINAP][(R,R)-DPEN]] catalyst (0.0055 g), a 1 M solution (5.5 ml) of potassium tert-butoxide in tert-butyl alcohol, 2-propanol (20 ml) and toluene (5 ml) was stirred at 30° C. for 2.5 hours under hydrogen atmosphere of 0.7 MPa, after the inner atmosphere was sufficiently replaced with the argon gas. To the reaction mixture, 1 N hydrogen chloride (5 ml) was added, and then the mixture was concentrated and dried under reduced pressure. The residue was dispersed in water and ethyl acetate, the organic layer was separated and washed with saturated brine, dried, and then the solvent was evaporated under reduced pressure. The obtained residue was purified by preparative HPLC to obtain (3R,4S)-4-hydroxy-3-phenyl-1-piperidinecarboxylic acid tert-butyl ester as colorless amorphous (1.08 g).

(Process 2)
To a solution of the compound (0.70 g) obtained in Process 1 in DMF (7 ml), sodium hydride (60% in oil, 0.25 g) was added, and then the reaction mixture was stirred at room temperature for 30 minutes. To the reaction solution, sodium iodide (1.14 g) and 3,5-bis(trifluoromethyl)benzyl bromide (1.55 g) were added at room temperature, and then the reaction solution was further stirred for 1 hour. The reaction solution was poured into water, and then the product was extracted with ethyl acetate. The organic layer was washed with an aqueous 10% citric acid solution and saturated brine, dried, and then the solvent was evaporated under reduced pressure. The obtained residue was isolated and purified by silica gel column chromatography (hexane:ethyl acetate=4:1) to obtain (3R,4S)-4-[[3,5-bis(trifluoromethyl)benzyl]oxy]-3-phenylpiperidine-1-carboxylic acid tert-butyl ester as colorless amorphous. The obtained product was used in the next process without further purification.

(Process 3)

To a solution of the compound obtained in Process 2 in methanol (15 ml), a 4 N hydrogen chloride/ethyl acetate solution (1.5 ml) was added, and the reaction solution was stirred at 70° C. for 30 minutes. The reaction solution was concentrated and dried under reduced pressure to obtain (3R, 4S)-4-[[3,5-bis(trifluoromethyl)benzyl]oxy]-3-phenylpiperidine hydrochloride (0.99 g) as white powder. The obtained product was used in the next process without further purification.

(Process 4)

The compound (0.50 g) obtained in Process 3 and 1-acetylpiperidine-4-carboxylic acid (0.29 g) were reacted and treated in the same manner as in the method described in Process 1 of Example 69 to obtain the title compound as colorless amorphous (0.51 g).

$^1$H-NMR (CDCl$_3$): δ 1.60-1.96 (6H, m), 2.00-2.20 (4H, m), 2.58-3.18 (4H, m), 3.28-3.58 (1H, m), 3.76-3.96 (3H, m), 4.19 (1H, dd, J=12.0, 3.0 Hz), 4.51-4.69 (3H, m), 7.21-7.38 (5H, m), 7.52 (2H, s), 7.73 (1H, 6).

$[α]_D^{25}$+103.9° (c 1.0, MeOH).

Example 71 cis-4-[[2-Methoxy-5-[5-(trifluoromethyl)-1H-tetrazol-1-yl]benzyl]amino]-N-methyl-3-phenyl-1-piperidinecarboxamide hydrochloride (Process 1)

The compound (1.50 g) obtained in Process 2 of Reference Example 2, 2-methoxy-5-(5-(trifluoromethyl)-1H-tetrazol-1-yl)benzaldehyde (1.33 g) synthesized by the method described in the document (e.g., J. Labelled Cpd. Radiopharm., Vol. 43, pages 29-45), NaBH(OAc)$_3$ (3.5 g), acetic acid (0.050 ml) and dichloromethane (20 ml) were reacted and treated in the same manner as in the method described in Process 3 of Reference Example 2 to obtain cis-4-[[2-methoxy-5-[5-(trifluoromethyl)-1H-tetrazol-1-yl]benzyl]amino]-3-phenyl-1-piperidinecarboxylic acid tert-butyl ester as colorless amorphous (1.85 g).

(Process 2)

The compound (1.85 g) obtained in Process 1 was reacted and treated in the same manner as in the method described in Process 3 of Example 70 to obtain cis-N-[2-methoxy-5-[5-(trifluoromethyl)-1H-tetrazol-1-yl]benzyl]-3-phenyl-4-piperidineamine hydrochloride (1.83 g) as white powder.

(Process 3)

The compound (0.30 g) obtained in Process 2, methyl isocyanate (0.042 ml) and Et$_3$N (0.17 ml) were reacted and treated in the same manner as in the method described in Example 6 to obtain colorless amorphous.

$^1$H-NMR (CDCl$_3$): δ 1.65-1.80 (1H, m), 1.83-1.95 (1H, m), 2.80 (3H, d, J==4.8 Hz), 2.94-3.06 (2H, m), 3.35-3.48 (1H, m), 3.55-3.70 (6H, m), 3.76-3.84 (2H, m), 4.45-4.50 (1H, m), 6.75 (1H, d, J=8.7 Hz), 7.02 (1H, d, 2.7 Hz), 7.08-7.28 (6H, m).

The obtained product was treated with 4 N hydrogen chloride/ethyl acetate (0.13 ml), and recrystallized from ethyl acetate-IPE to obtain the title compound (0.23 g) as white powder.

Melting point: 198-200° C.

Example 72

(+)-cis-4-[[2-Methoxy-5-[5-(trifluoromethyl)-1H-tetrazol-1-yl]benzyl]amino]-N-methyl-3-phenyl-1-piperidinecarboxamide hydrochloride The compound (0.36 g) obtained in Process 3 of Example 71 was optically resolved with chiral HPLC, and the fractions were concentrated under reduced pressure. The obtained residue was treated with 4 N hydrogen chloride/ethyl acetate (0.070 ml), and recrystallized from ethyl acetate-IPE to obtain the title compound (0.14 g) as white powder.

Chiral HPLC condition
Column: CHIRALPAK AD 50 mm ID×500 mm L
Solvent: hexane/ethanol=87/13
Flow rate: 70 ml/min
Temperature: 35° C.
Detection method: UV 220 nm
$[α]_D^{25}$+1.6° (c 1.0, MeOH).

Example 73

(−)-cis-4-[[2-Methoxy-5-[5-(trifluoromethyl)-1H-tetrazol-1-yl]benzyl]amino]-N-methyl-3-phenyl-1-piperidinecarboxamide hydrochloride The compound (0.36 g) obtained in Process 3 of Example 71 was treated in the same manner as in the method described in Example 72 to obtain the title compound (0.13 g) as white powder.

$[α]_D^{25}$−2.2° (c 1.0, MeOH).

Example 74 cis-N-Ethyl-4-[[2-methoxy-5-[5-(trifluoromethyl)-1H-tetrazol-1-yl]benzyl]amino]-3-phenyl-1-piperidinecarboxamide hydrochloride The compound (0.89 g) obtained in Process 2 of Example 71, ethyl isocyanate (0.14 ml) and Et$_3$N (0.49 ml) were reacted and treated in the same manner as in the method described in Example 6 to obtain colorless amorphous.

$^1$H-NMR (CDCl$_3$): δ 1.12 (3H, t, J=7.2 Hz), 1.65-1.80 (1H, m), 1.85-1.95 (1H, m), 2.95-3.06 (2H, m), 3.22-3.32 (2H, m), 3.36-3.46 (1H, m), 3.55-3.70 (6H, m), 3.76-3.84 (2H, m), 4.36-4.44 (1H, m), 6.84 (1H, d, J=8.7 Hz), 7.04 (1H, d, J=2.7 Hz), 7.12-7.30 (6H, m).

The obtained product was treated with 4 N hydrogen chloride/ethyl acetate (0.42 ml), and recrystallized from ethyl acetate-IPE to obtain the title compound (0.86 g) as white powder.

Melting point: 143-145° C.

Example 75

(+)-cis-N-Ethyl-4-[[2-methoxy-5-[5-(trifluoromethyl)-1H-tetrazol-1-yl]benzyl]amino]-3-phenyl-1-piperidinecarboxamide hydrochloride The compound (0.80 g) obtained in Example 74 was optically resolved with chiral HPLC, and the fractions were concentrated under reduced pressure. The obtained residue was treated with 4 N hydrogen chloride/ethyl acetate (0.14 ml), and recrystallized from ethyl acetate-IPE to obtain the title compound (0.25 g) as white powder.
Chiral HPLC condition
Column: CHIRALPAK AD 50 mm ID×500 mm L
Solvent: hexane/ethanol=87/13
Flow rate: 70 ml/min
Temperature: 35° C.
Detection method: UV 220 nm
$[\alpha]_D^{25}+4.1°$ (c 1.0, MeOH).

Example 76

(−)-cis-N-Ethyl-4-[[2-methoxy-5-[5-(trifluoromethyl)-1H-tetrazol-1-yl]benzyl]amino]-3-phenyl-1-piperidinecarboxamide hydrochloride The compound (0.80 g) obtained in Example 74 was treated in the same manner as in the method described in Example 75 to obtain the title compound (0.25 g) as white powder.
$[\alpha]_D^{25}-3.9°$ (c 1.0, MeOH).

Example 77 cis-1-(Methoxyacetyl)-N-[2-methoxy-5-[5-(trifluoromethyl)-1H-tetrazol-1-yl]benzyl]-3-phenyl-4-piperidineamine hydrochloride The compound (0.30 g) obtained in Process 2 of Example 71, methoxyacetic acid (0.048 g), WSC.HCl (0.17 g), HOBt.H$_2$O (0.14 g), Et$_3$N (0.17 ml) and DMF (5.0 ml) were reacted and treated in the same manner as in the method described in Example 69 to obtain colorless amorphous.
$^1$H-NMR (CDCl$_3$): δ 1.60-1.80 (1H, m), 1.90-2.05 (1H, m), 2.94-3.06 (2H, m), 3.20-3.90 (11H, m), 4.00-4.60 (3H, m), 6.84 (1H, dd, J=8.7, 5.7 Hz), 7.01 (1H, d, J=2.4 Hz), 7.04-7.14 (2H, m), 7.15-7.30 (4H, m).
The obtained product was treated with 4 N hydrogen chloride/ethyl acetate (0.15 ml), and recrystallized from ethyl acetate-IPE to obtain the title compound (0.28 g) as white powder.
Melting point: 126-128° C.

Example 78

(+)-cis-1-(Methoxyacetyl)-N-[2-methoxy-5-[5-(trifluoromethyl)-1H-tetrazol-1-yl]benzyl]-3-phenyl-4-piperidineamine hydrochloride The compound (0.43 g) obtained in Example 77 was optically resolved with chiral HPLC, and the fractions were concentrated under reduced pressure. The obtained residue was treated with 4 N hydrogen chloride/ethyl acetate (0.10 ml), and recrystallized from ethyl acetate-IP to obtain the title compound (0.22 g) as white powder.
Chiral HPLC condition
Column: CHIRALPAK AD 50 mm ID×500 mm L
Solvent: hexane/ethanol=1/1
Flow rate: 60 ml/mm
Temperature: 35° C.
Detection method: UV 220 nm
$[\alpha]_D^{25}+6.1°$ (c 1.0, MeOH).

Example 79

(−)-cis-1-(Methoxyacetyl)-N-[2-methoxy-5-[5-(trifluoromethyl)-1H-tetrazol-1-yl]benzyl]-3-phenyl-4-piperidineamine hydrochloride The compound (0.43 g) obtained in Example 77 was treated in the same manner as in the method described in Example 78 to obtain the title compound (0.21 g) as white powder.
$[\alpha]_D^{25}-6.3°$ (c 1.0, MeOH).

Example 80 cis-1-[(1-Acetyl-4-piperidinyl)carbonyl]-N-[2-methoxy-5-[5-(trifluoromethyl)-1H-tetrazol-1-yl]benzyl]-3-phenyl-4-piperidmeamine hydrochloride The compound (0.30 g) obtained in Process 2 of Example 71, 1-acetylpiperidine-4-carboxylic acid (0.092 g), WSC.HCl (0.17 g), HOBt.H$_2$O (0.14 g), Et$_3$N (0.17 ml) and DMF (5.0 ml) were reacted and treated in the same manner as in the method described in Example 69 to obtain colorless amorphous.
$^1$H-NMR (CDCl$_3$): δ 1.50-2.00 (4H, m), 2.05-2.15 (3H, m), 2.50-4.00 (16H, m), 4.20-4.68 (2H, m), 6.80-6.87 (1H, m), 6.97-7.08 (2H, m), 7.10-7.32 (5H, m).
The obtained product was treated with 4 N hydrogen chloride/ethyl acetate (0.14 ml), and recrystallized from ethyl acetate-IPE to obtain the title compound (0.29 g) as white powder.
Meltingpoint: 150-152° C.

Example 81

(−)-cis-1-[(1-Acetyl-4-piperidinyl)carbonyl]-N-[2-methoxy-5-[5-(trifluoroinethyl)-1H-tetrazol-1-yl]benzyl]-3-phenyl-4-piperidineamine hydrochloride The compound (0.54 g) obtained in Example 80 was optically resolved with chiral HPLC, and the fractions were concentrated under reduced pressure to obtain colorless amorphous.
Chiral HPLC condition
Column: CHIRALPAK AD 50 mm ID×500 mm L
Solvent: hexane/ethanol=50/50 (0 minute)→0/100 (100 minutes)
Flow rate: 80 ml/min
Temperature: 30° C.
Detection method: UV 220 nm
$[\alpha]_D^{25}+55.8°$ (c 1.0, MeOH).
Meltingpoint: 129-131° C.
$^1$H-NMR (CDCl$_3$): δ 1.50-2.00 (4H, m), 2.05-2.15 (3H, m), 2.50-4.00 (16H, m), 4.20-4.68 (2H, m), 6.80-6.87 (1H, m), 6.97-7.08 (2H, m), 7.10-7.32 (5H, m).
The obtained product was treated with 4 N hydrogen chloride/ethyl acetate (0.11 ml), and recrystallized from ethyl acetate-IPE to obtain the title compound (0.25 g) as white powder.
$[\alpha]_D^{25}-9.2°$ (c 1.0, MeOH).

Example 82

(+)-cis-1-[(1-Acetyl-4-piperidinyl)carbonyl]-N-[2-methoxy-5-[5-(trifluoromethyl)-1H-tetrazol-1-yl]benzyl]-3-phenyl-4-piperidineamine hydrochloride The compound (0.54 g) obtained in Example 80 was treated in the same manner as in the method described in Example 81 to obtain the title compound (0.26 g) as white powder.
[α]$_D^{25}$+8.6° (c 1.0, MeOH).

Example 83 cis-N-Ethyl-3-phenyl-4-[[[5-[5-(trifluoromethyl)-1H-tetrazol-1-yl]-2,3-dihydro-1-benzofuran-7-yl]methyl]amino]-1-piperidinecarboxamide (Process 1)

The compound (1.25 g) obtained in Process 2 of Reference Example 2, the compound (1.35 g) obtained in Process 3 of Reference Example 7, NaBH(OAc)$_3$ (3.1 g), acetic acid (0.050 ml) and dichloromethane (20 ml) were reacted and treated in the same manner as in the method described in Process 3 of Reference Example 2 to obtain cis-3-phenyl-4-[[[5-[5-(trifluoromethyl)-1H-tetrazol-1-yl]-2,3-dihydro-1-benzofuran-7-yl]methyl]amino]-1-piperidinecarboxylic acid tert-butyl ester (1.95 g) as colorless amorphous.

(Process 2)

The compound (1.95 g) obtained in Process 1 was reacted and treated in the same manner as in the method described in Process 3 of Example 70 to obtain cis-3-phenyl-N-[[5-[5-(trifluoromethyl)-1H-tetrazol-1-yl]-2,3-dihydro-1-benzofuran-7-yl]methyl]-4-piperidineamine hydrochloride (2.00 g) as white powder.

(Process 3)

The compound (0.50 g) obtained in Process 2, ethyl isocyanate (0.076 ml), Et$_3$N (0.27 ml) and acetonitrile (10 ml) were reacted and treated in the same manner as in the method described in Example 6 to obtain colorless amorphous. The obtained product was recrystallized from ethyl acetate-IPE to obtain the title compound (0.42 g) as white powder.
$^1$H-NMR (CDCl$_3$): δ 1.12 (3H, t, J=7.2 Hz), 1.65-1.80 (1H, m), 1.84-1.94 (1H, m), 2.95-3.06 (2H, m), 3.18-3.33 (4H, m), 3.36-3.46 (1H, m), 3.55 (1H, d, J=14.7 Hz), 3.60-3.70 (2H, m), 3.75 (1H, d, J=14.7 Hz), 3.75-3.82 (1H, m), 4.38-4.60 (3H, m), 6.79 (1H, s like), 7.09 (1H, s like), 7.12-7.20 (3H, m), 7.22-7.25 (2H, m). Melting point: 157-159° C.

Example 84

(−)-cis-N-Ethyl-3-phenyl-4-[[[5-[5-(trifluoromethyl)-1H-tetrazol-1-yl]-2,3-dihydro-1-benzofuran-7-yl]methyl]amino]-1-piperidinecarboxamide hydrochloride The compound (0.42 g) obtained in Example 83 was optically resolved with chiral HPLC, and the fractions were concentrated under reduced pressure. The obtained residue was treated with 4 N hydrogen chloride/ethyl acetate (0.090 ml), and recrystallized from ethyl acetate-IPE to obtain the title compound (0.17 g) as white powder.
Chiral HPLC condition
Column: CHIRALPAK AD 50 mm ID×500 mm L
Solvent: hexane/ethanol=85/15
Flow rate: 60 ml/min
Temperature: 30° C.
Detection method: UV 254 nm
[α]$_D^{25}$−11.8° (c 1.0, MeOH).

Example 85

(+)-cis-N-Ethyl-3-phenyl-4-[[[5-[5-(trifluoromethyl)-1H-tetrazol-1-yl]-2,3-dihydro-1-benzofuran-7-yl]methyl]amino]-1-piperidinecarboxamide hydrochloride The compound (0.54 g) obtained in Example 83 was treated in the same manner as in the method described in Example 84 to obtain the title compound (0.19 g) as white powder.
[α]$_D^{25}$+10.4° (c 1.0, MeOH).

Example 86 cis-1-[(1-Acetyl-4-piperidinyl)carbonyl]-3-phenyl-N-[[5-[5-(trifluoromethyl)-1H-tetrazol-1-yl]-2,3-dihydro-1-benzofuran-7-yl]methyl]-4-piperidineamine hydrochloride The compound (0.30 g) obtained in Process 2 of Example 83, 1-acetylpiperidine-4-carboxylic acid (0.080 g), WSC.HCl (0.17 g), HOBt.H$_2$O (0.16 g), Et$_3$N (0.16 ml) and DMF (5.0 ml) were reacted and treated in the same manner as in the method described in Example 69 to obtain colorless amorphous.
$^1$H-NMR (CDCl$_3$): δ 1.40-2.10 (9H, m), 2.50-4.00 (12H, m), 4.20-4.65 (5H, m), 6.74-6.82 (1H, m), 7.04-7.32 (6H, m).
The obtained product was treated with 4 N hydrogen chloride/ethyl acetate (0.12 ml), and recrystallized from ethyl acetate-IPE to obtain the title compound (0.21 g) as white powder.
Melting point: 152-154° C.

Example 87

(+)-cis-1-[(1-Acetyl-4-piperidinyl)carbonyl]-3-phenyl-N-[[5-[5-(trifluoromethyl)-1H-tetrazol-1-yl]-2,3-dihydro-1-benzofuran-7-yl]methyl]-4-piperidineamine hydrochloride The compound (0.40 g) obtained in Example 86 was optically resolved with chiral HPLC, and the fractions were concentrated under reduced pressure. The obtained residue was treated with 4 N hydrogen chloride/ethyl acetate (0.074 ml), and recrystallized from ethyl acetate-IPE to obtain the title compound (0.18 g) as white powder.
Chiral HPLC condition
Column: CHIRALPAK OD 50 mm ID×500 mm L
Solvent: hexane/ethanol=70/30
Flow rate: 60 ml/min
Temperature: 30° C.
Detection method: UV 254 nm
[α]$_D^{25}$+14.9° (c 1.0, MeOH).

Example 88

(−)-cis-1-[(1-Acetyl-4-piperidinyl)carbonyl]-3-phenyl-N-[[5-[5-(trifluoromethyl)-1H-tetrazol-1-yl]-2,3-dihydro-1-benzofuran-7-yl]methyl]-4-piperidineamine hydrochloride The compound (0.40 g) obtained in Example 86 was treated in the same manner as in the method described in Example 87 to obtain the title compound (0.18 g) as white powder.
[α]$_D^{25}$−16.9° (c 1.0, MeOH).

The chemical structural formulae of the compounds obtained in the above-mentioned Examples are as follows.

TABLE 7
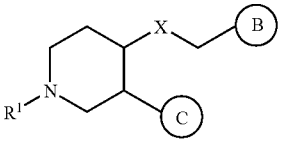
| Ex. No. | stereochemistry | R¹ | X | B | C |
|---|---|---|---|---|---|
| 1 | (±)-cis | H | O | 3,5-(CF₃)₂-C₆H₃ | C₆H₅ |
| 2 | (±)-cis | CH₃CO | O | 3,5-(CF₃)₂-C₆H₃ | C₆H₅ |
| 3 | (±)-cis | PhCO | O | 3,5-(CF₃)₂-C₆H₃ | C₆H₅ |
| 4 | (±)-cis | CH₃SO₂ | O | 3,5-(CF₃)₂-C₆H₃ | C₆H₅ |
| 5 | (±)-cis | CH₃OCO | O | 3,5-(CF₃)₂-C₆H₃ | C₆H₅ |
| 6 | (±)-cis | CH₃NHCO | O | 3,5-(CF₃)₂-C₆H₃ | C₆H₅ |
| 7 | (±)-cis | 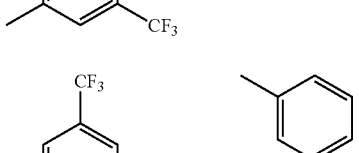 | O | 3,5-(CF₃)₂-C₆H₃ | C₆H₅ |
| 8 | (±)-cis | C₂H₅OCOCH₂ | O | 3,5-(CF₃)₂-C₆H₃ | C₆H₅ |

TABLE 7-continued

| Ex. No. | stereochemistry | R¹ | X | B | C |
|---|---|---|---|---|---|
| 9 | (±)-cis | H₂NCOCH₂ | O | 3,5-bis(CF₃)phenyl | phenyl |
| 10 | (±)-cis | NCCH₂ | O | 3,5-bis(CF₃)phenyl | phenyl |
| 11 | (±)-cis | (CH₃)₂NCO | O | 3,5-bis(CF₃)phenyl | phenyl |
| 12 | (±)-cis | PhNHCO | O | 3,5-bis(CF₃)phenyl | phenyl |
| 13 | (±)-cis | C₂H₅NHCO | O | 3,5-bis(CF₃)phenyl | phenyl |
| 14 | (±)-cis | imidazol-1-yl-C(O)- | O | 3,5-bis(CF₃)phenyl | phenyl |
| 15 | (±)-cis | allyl-NHC(O)- | O | 3,5-bis(CF₃)phenyl | phenyl |
| 16 | (±)-cis | 2-methoxyphenethyl | O | 3,5-bis(CF₃)phenyl | phenyl |

TABLE 7-continued
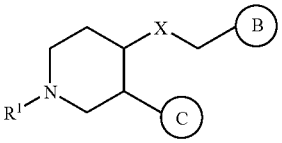
| Ex. No. | stereochemistry | R[1] | X | B | C |
| --- | --- | --- | --- | --- | --- |
| 17 | (±)-cis | H₂NCO | O | 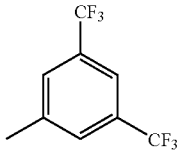 | 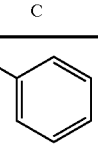 |
| 18 | (±)-cis | "PrNHCO | O | 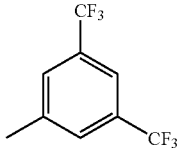 | 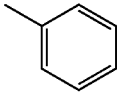 |
| 19 | (±)-cis | 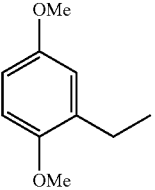 | O | 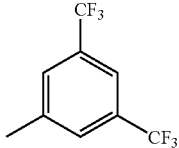 | 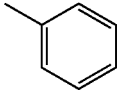 |
| 20 | (±)-cis | 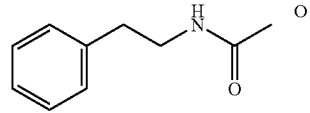 | O | 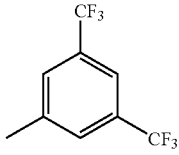 | 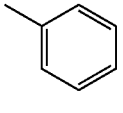 |
| 21 | (±)-cis | 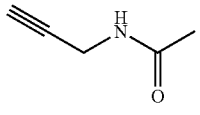 | O | 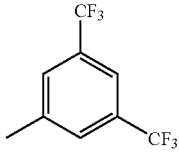 | 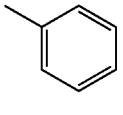 |
| 22 | (±)-cis | 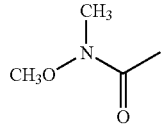 | O | 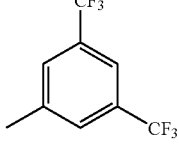 | 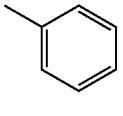 |
| 23 | (±)-cis | H | NH | 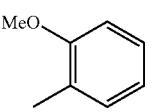 | 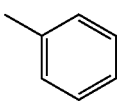 |
| 24 | (±)-trans | H | NH | 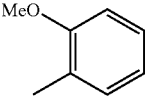 | 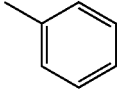 |

TABLE 7-continued

| Ex. No. | stereochemistry | R¹ | X | B | C |
|---|---|---|---|---|---|
| 69 | (−)-cis | AcN-piperidine-C(O)- | O | 3,5-bis(CF₃)phenyl | phenyl |
| 70 | (+)-cis | AcN-piperidine-C(O)- | O | 3,5-bis(CF₃)phenyl | phenyl |
| 71 | (±)-cis | CH₃NHCO | NH | 4-MeO-3-Me-phenyl-(5-CF₃-tetrazol-1-yl) | phenyl |
| 72 | (+)-cis | CH₃NHCO | NH | 4-MeO-3-Me-phenyl-(5-CF₃-tetrazol-1-yl) | phenyl |
| 73 | (−)-cis | CH₃NHCO | NH | 4-MeO-3-Me-phenyl-(5-CF₃-tetrazol-1-yl) | phenyl |
| 74 | (±)-cis | C₂H₅NHCO | NH | 4-MeO-3-Me-phenyl-(5-CF₃-tetrazol-1-yl) | phenyl |
| 75 | (+)-cis | C₂H₅NHCO | NH | 4-MeO-3-Me-phenyl-(5-CF₃-tetrazol-1-yl) | phenyl |
| 76 | (−)-cis | C₂H₅NHCO | NH | 4-MeO-3-Me-phenyl-(5-CF₃-tetrazol-1-yl) | phenyl |

TABLE 7-continued
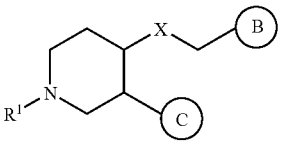
| Ex. No. | stereochemistry | R¹ | X | B | C |
| --- | --- | --- | --- | --- | --- |
| 77 | (±)-cis | CH₃OCH₂CO | NH |  | 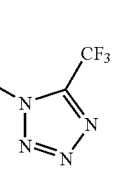 |
| 78 | (+)-cis | CH₃OCH₂CO | NH |  | 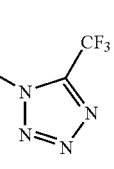 |
| 79 | (−)-cis | CH₃OCH₂CO | NH |  | 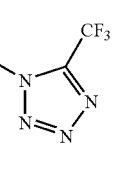 |
| 80 | (±)-cis | 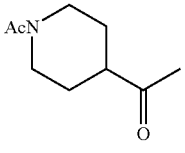 | NH |  | 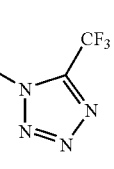 |
| 81 | (−)-cis | 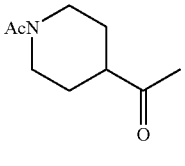 | NH |  | 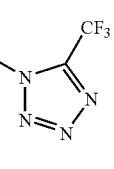 |
| 82 | (+)-cis | 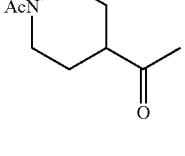 | NH |  | 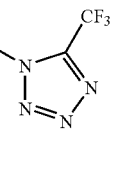 |
| 83 | (±)-cis | C₂H₅NHCO | NH | 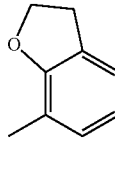 |  |

TABLE 7-continued
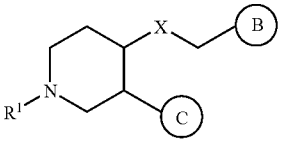
| Ex. No. | stereochemistry | R¹ | X | B | C |
|---|---|---|---|---|---|
| 84 | (−)-cis | C₂H₅NHCO | NH | 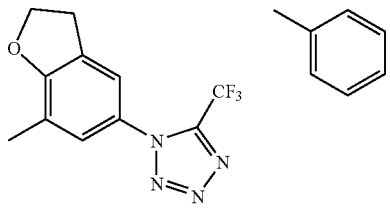 | 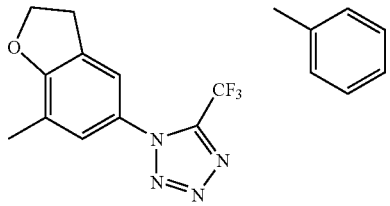 |
| 85 | (+)-cis | C₂H₅NHCO | NH | 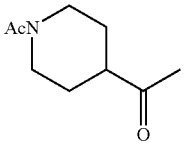 | 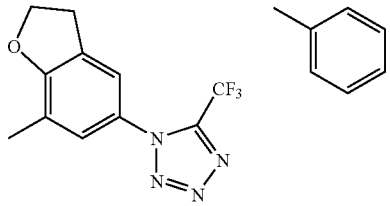 |
| 86 | (±)-cis | 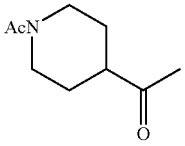 | NH | 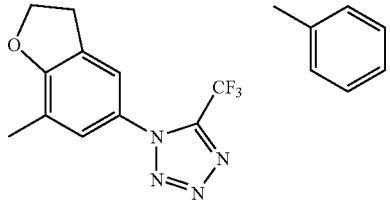 | 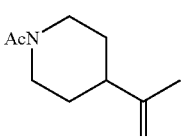 |
| 87 | (+)-cis | 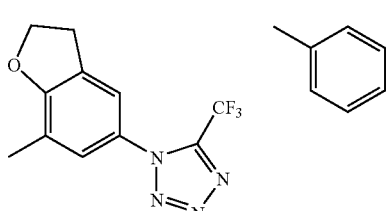 | NH | | |
| 88 | (−)-cis | | NH | | |

TABLE 8
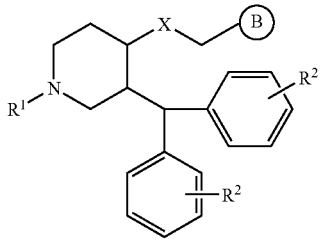
| Ex. No. | stereochemistry | R¹ | X | B | R² |
|---|---|---|---|---|---|
| 25 | (±)-cis | H | O | 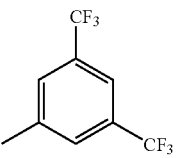 | H |
| 26 | (±)-cis | H | O | 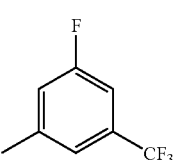 | H |
| 27 | (±)-cis | H | O | 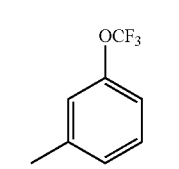 | H |
| 28 | (±)-cis | H | O | 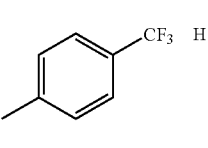 | H |
| 29 | (±)-cis | 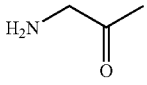 | O | 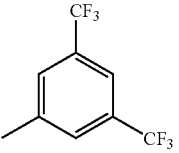 | H |
| 30 | (±)-cis | CH₃SO₂ | O |  | H |
| 31 | (±)-cis | CH₃NHCO | O | 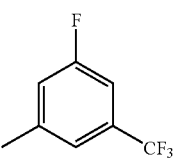 | H |
| 32 | (±)-cis |  | O | 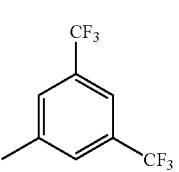 | H |

TABLE 8-continued
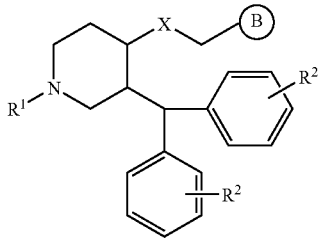
| Ex. No. | stereochemistry | R¹ | X | B | R² |
|---|---|---|---|---|---|
| 33 | (±)-cis | CH₃CO | O | 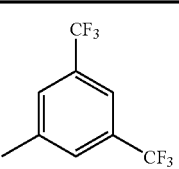 | H |
| 34 | (±)-cis | CH₃OCH₂CO | O | 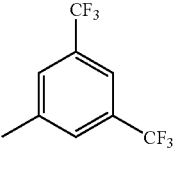 | H |
| 35 | (±)-cis | CH₃SO₂ | O | 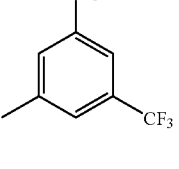 | H |
| 36 | (±)-cis | 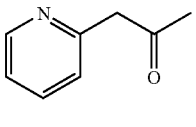 | O | 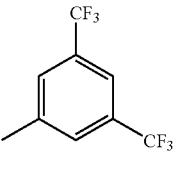 | H |
| 37 | (±)-cis | 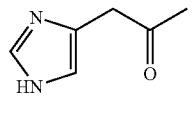 | O | 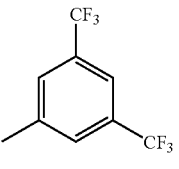 | H |
| 38 | (±)-cis | C₂H₅CO | O | 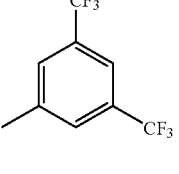 | H |
| 39 | (±)-cis | CH₃NHCO | O | 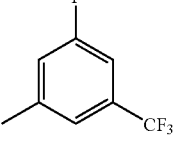 | H |

TABLE 8-continued
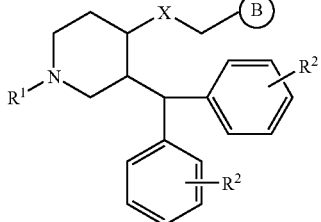
| Ex. No. | stereochemistry | R¹ | X | B | R² |
|---|---|---|---|---|---|
| 40 | (±)-cis | C₂H₅CO | O | 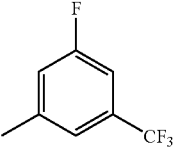 | H |
| 41 | (±)-cis | CH₃CO | O | 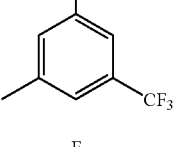 | H |
| 42 | (±)-cis | CH₃OCH₂CO | O | 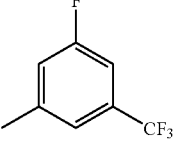 | H |
| 43 | (±)-cis | 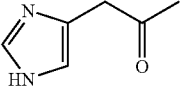 | O | 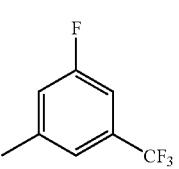 | H |
| 44 | (±)-cis | 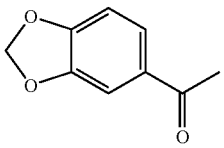 | O | 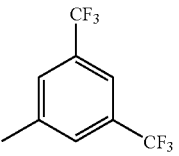 | H |
| 45 | (±)-cis | 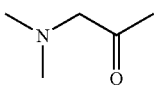 | O | 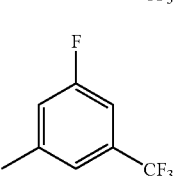 | H |
| 46 | (±)-cis | 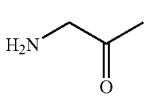 | O | 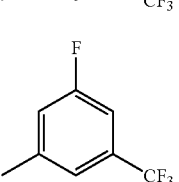 | H |
| 47 | (±)-cis | CH₃OCH₂CO | O | 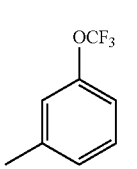 | H |

TABLE 8-continued
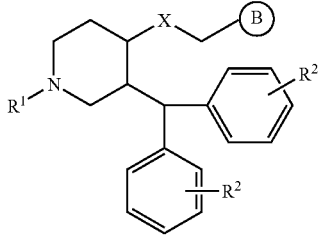
| Ex. No. | stereochemistry | R¹ | X | B | R² |
|---|---|---|---|---|---|
| 48 | (±)-cis | CH₃CO | O |  | H |
| 49 | (±)-cis | C₂H₅CO | O |  | H |
| 50 | (±)-cis | 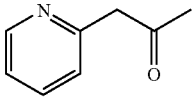 | O | 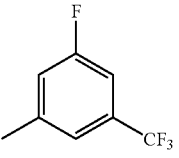 | H |
| 51 | (±)-cis | 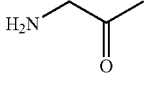 | O | 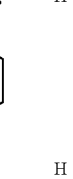 | H |
| 52 | (±)-cis | 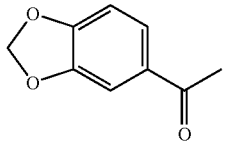 | O | 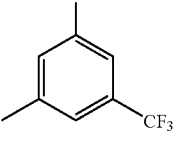 | H |
| 53 | (±)-cis | CH₃SO₂ | O | 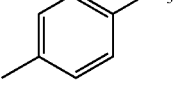 | H |
| 54 | (±)-cis | PhCH₂ | O | 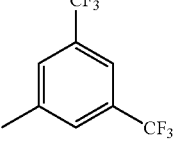 | H |
| 55 | (±)-cis | 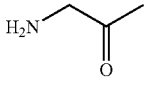 | O | 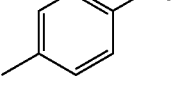 | H |

TABLE 8-continued
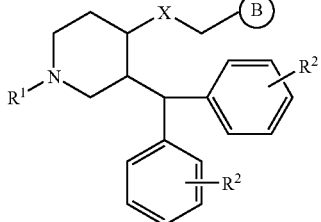
| Ex. No. | stereochemistry | R¹ | X | B | R² |
|---|---|---|---|---|---|
| 56 | (±)-cis | CH₃CO | O | 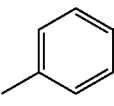 4-CF₃-phenyl | H |
| 57 | (±)-cis | PhCH₂ | O | 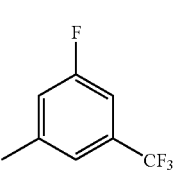 3-F,5-CF₃-phenyl | H |
| 58 | (±)-cis | CH₃NHCO | O | 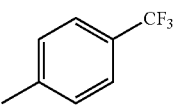 4-CF₃-phenyl | H |
| 59 | (±)-cis | 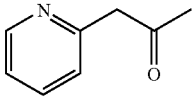 | O | 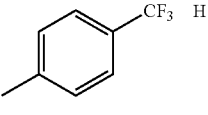 4-CF₃-phenyl | H |
| 60 | (±)-cis | C₂H₅CO | O | 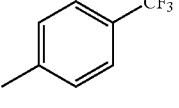 4-CF₃-phenyl | H |
| 61 | (±)-cis | 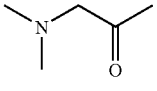 | O | 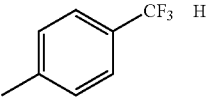 4-CF₃-phenyl | H |
| 62 | (±)-cis | CH₃OCH₂CO | O | 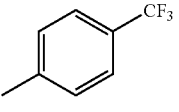 4-CF₃-phenyl | H |
| 63 | (±)-cis | 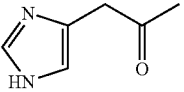 | O | 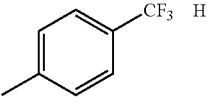 4-CF₃-phenyl | H |
| 64 | (±)-cis | 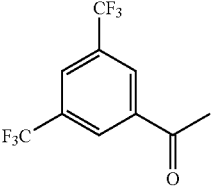 | O | 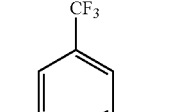 | H |

TABLE 8-continued

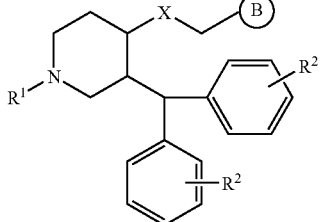

| Ex. No. | stereochemistry | R¹ | X | B | R² |
|---|---|---|---|---|---|
| 65 | (±)-cis |  | O | 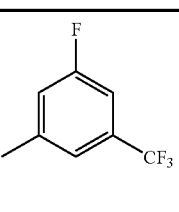 | H |
| 66 | (±)-cis |  | O | 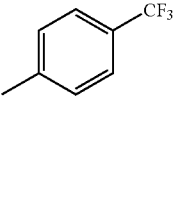 | H |
| 67 | (±)-cis |  | O | 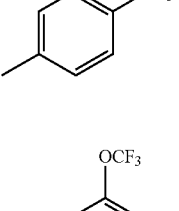 | H |
| 68 | (±)-cis |  | O | 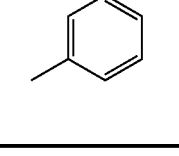 | H |

Example 89 cis-3-Benzhydryl-4-[[3,5-bis(trifluoromethyl)benzyl]oxy]-1-[3-(1-piperidinyl)propanoyl]piperidine trifluoroacetate The compound (28.7 mg) obtained in Example 25 and 1-piperidinepropionic acid (18.9 mg) were reacted and treated in the same manner as in the method described in Example 33 to obtain the title compound.

Yield: 36.1 mg

HPLC analysis (Condition B): Purity 97% (Retention time: 1.90 minutes)

MS (ESI+): 633 (M+H)

The compounds of the following Examples were synthesized from the compounds obtained in Examples 25, 152, 217, 245, 271, 295 and 320 as starting materials by reacting and treating in the same manner as in the method described in Example 89 using the respective corresponding carboxylic acid derivatives.

TABLE 9

| Ex. No. | Stereochemistry | R¹ | X | B | R² | MS (ESI) (M + H)⁺ |
|---|---|---|---|---|---|---|
| 89 | (±)-cis | piperidinyl-CH₂CH₂C(O)CH₃ | O | 3,5-bis(CF₃)phenyl | H | 633 |
| 90 | (±)-cis | 2-thienyl-CH₂C(O)CH₃ | O | 3,5-bis(CF₃)phenyl | H | 618 |
| 91 | (±)-cis | tetrazol-1-yl-CH₂C(O)CH₃ | O | 3,5-bis(CF₃)phenyl | H | 604 |
| 92 | (±)-cis | pyrazin-2-yl-C(O)CH₃ | O | 3,5-bis(CF₃)phenyl | H | 600 |
| 93 | (±)-cis | PhS-CH₂C(O)CH₃ | O | 3,5-bis(CF₃)phenyl | H | 644 |
| 94 | (±)-cis | 2-furyl-CH=CH-C(O)CH₃ | O | 3,5-bis(CF₃)phenyl | H | 614 |
| 95 | (±)-cis | 4-(H₂NSO₂)phenyl-C(O)CH₃ | O | 3,5-bis(CF₃)phenyl | H | 677 |

TABLE 9-continued
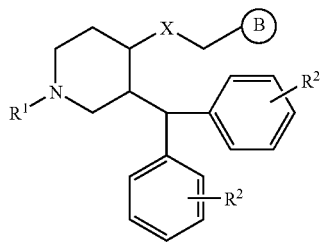
| Ex. No. | Stereochemistry | R¹ | X | B | R² | MS (ESI) (M + H)⁺ |
|---|---|---|---|---|---|---|
| 96 | (±)-cis | 3-acetylthiophene | O | 3,5-bis(CF₃)phenyl | H | 604 |
| 97 | (±)-cis | Et₂N-CH₂CH₂-C(O)CH₃ | O | 3,5-bis(CF₃)phenyl | H | 621 |
| 98 | (±)-cis | 1-methyl-3-acetylindole | O | 3,5-bis(CF₃)phenyl | H | 651 |
| 99 | (±)-cis | MeO₂C-CH₂CH₂-C(O)CH₃ | O | 3,5-bis(CF₃)phenyl | H | 608 |
| 100 | (±)-cis | AcHN-CH₂-C(O)CH₃ | O | 3,5-bis(CF₃)phenyl | H | 593 |
| 101 | (±)-cis | AcHN-CH₂CH₂-C(O)CH₃ | O | 3,5-bis(CF₃)phenyl | H | 621 |
| 102 | (±)-cis | MeO₂C-CH=CH-C(O)CH₃ | O | 3,5-bis(CF₃)phenyl | H | 606 |

TABLE 9-continued
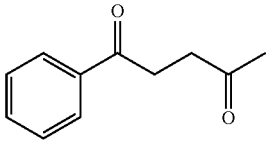
| Ex. No. | Stereochemistry | R¹ | X | B | R² | MS (ESI) (M + H)⁺ |
|---|---|---|---|---|---|---|
| 103 | (±)-cis | 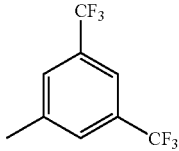 | O | 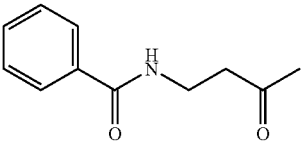 | H | 654 |
| 104 | (±)-cis | 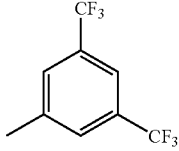 | O | 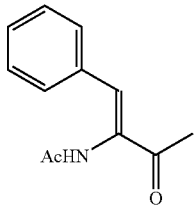 | H | 669 |
| 105 | (±)-cis | 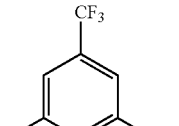 | O | 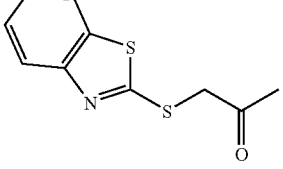 | H | 681 |
| 106 | (±)-cis | 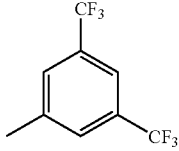 | O | 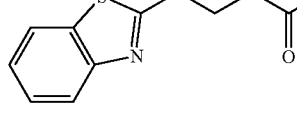 | H | 701 |
| 107 | (±)-cis | 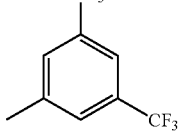 | O | 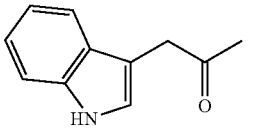 | H | 715 |
| 108 | (±)-cis | 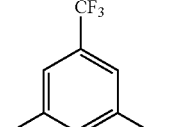 | O | 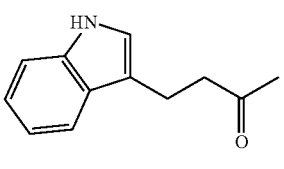 | H | 651 |
| 109 | (±)-cis | 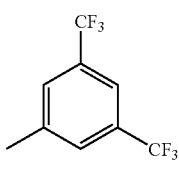 | O |  | H | 665 |

TABLE 9-continued
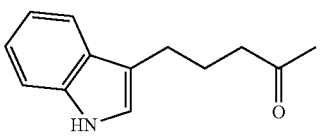
| Ex. No. | Stereochemistry | R¹ | X | B | R² | MS (ESI) (M + H)⁺ |
|---|---|---|---|---|---|---|
| 110 | (±)-cis | 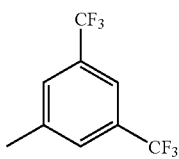 | O | 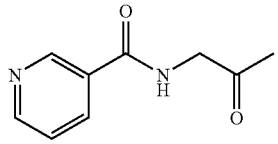 | H | 679 |
| 111 | (±)-cis | 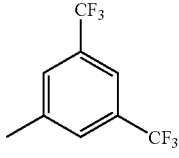 | O | 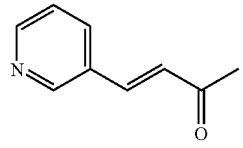 | H | 656 |
| 112 | (±)-cis | 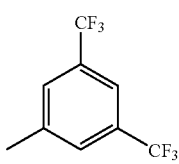 | O | 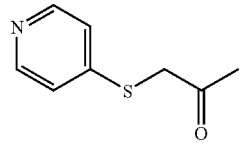 | H | 625 |
| 113 | (±)-cis | 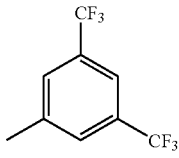 | O | 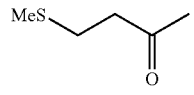 | H | 645 |
| 114 | (±)-cis | 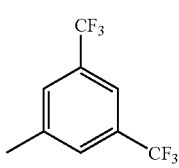 | O | 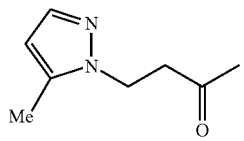 | H | 596 |
| 115 | (±)-cis | 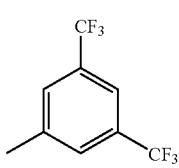 | O | 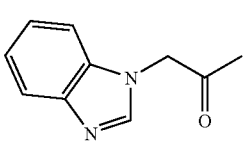 | H | 630 |
| 116 | (±)-cis | 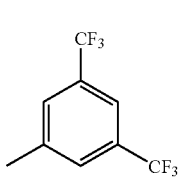 | O | | H | 652 |

TABLE 9-continued

| Ex. No. | Stereochemistry | R¹ | X | B | R² | MS (ESI) (M + H)⁺ |
|---|---|---|---|---|---|---|
| 117 | (±)-cis | 4-(pyrazol-1-yl)phenyl-C(=O)-CH₂- | O | 3,5-bis(CF₃)phenyl | H | 665 |
| 118 | (±)-cis | quinolin-4-yl-C(=O)-CH₂- | O | 3,5-bis(CF₃)phenyl | H | 649 |
| 119 | (±)-cis | (E)-1H-imidazol-4-yl-CH=CH-C(=O)-CH₂- | O | 3,5-bis(CF₃)phenyl | H | 614 |
| 153 | (±)-cis | piperidin-1-yl-CH₂-CH₂-C(=O)-CH₂- | O | 3,5-bis(CF₃)phenyl | 4-F | 669 |
| 154 | (±)-cis | thiophen-2-yl-CH₂-C(=O)-CH₂- | O | 3,5-bis(CF₃)phenyl | 4-F | 654 |
| 155 | (±)-cis | tetrazol-1-yl-CH₂-C(=O)-CH₂- | O | 3,5-bis(CF₃)phenyl | 4-F | 640 |
| 156 | (±)-cis | pyrazin-2-yl-C(=O)-CH₂- | O | 3,5-bis(CF₃)phenyl | 4-F | 636 |

TABLE 9-continued

| Ex. No. | Stereochemistry | R¹ | X | B | R² | MS (ESI) (M + H)⁺ |
|---|---|---|---|---|---|---|
| 157 | (±)-cis | phenylthio-acetone | O | 3,5-bis(CF₃)phenyl | 4-F | 680 |
| 158 | (±)-cis | 4-(2-furyl)-3-buten-2-one | O | 3,5-bis(CF₃)phenyl | 4-F | 650 |
| 159 | (±)-cis | 4-sulfamoyl-acetophenone | O | 3,5-bis(CF₃)phenyl | 4-F | 713 |
| 160 | (±)-cis | 3-acetylthiophene | O | 3,5-bis(CF₃)phenyl | 4-F | 640 |
| 161 | (±)-cis | Et₂N-CH₂CH₂-C(O)CH₃ | O | 3,5-bis(CF₃)phenyl | 4-F | 657 |
| 162 | (±)-cis | 3-acetyl-1-methylindole | O | 3,5-bis(CF₃)phenyl | 4-F | 687 |
| 163 | (±)-cis | NCCH₂CO | O | 3,5-bis(CF₃)phenyl | 4-F | 597 |

TABLE 9-continued

| Ex. No. | Stereochemistry | R¹ | X | B | R² | MS (ESI) (M + H)⁺ |
|---|---|---|---|---|---|---|
| 164 | (±)-cis | MeO₂C-CH₂CH₂-C(=O)- | O | 3,5-(CF₃)₂-phenyl | 4-F | 644 |
| 165 | (±)-cis | AcHN-CH₂-C(=O)- | O | 3,5-(CF₃)₂-phenyl | 4-F | 629 |
| 166 | (±)-cis | AcHN-CH₂CH₂-C(=O)- | O | 3,5-(CF₃)₂-phenyl | 4-F | 657 |
| 167 | (±)-cis | MeO₂C-CH=CH-C(=O)- | O | 3,5-(CF₃)₂-phenyl | 4-F | 642 |
| 168 | (±)-cis | Ph-C(=O)-CH₂CH₂-C(=O)- | O | 3,5-(CF₃)₂-phenyl | 4-F | 690 |
| 169 | (±)-cis | Ph-C(=O)NH-CH₂CH₂-C(=O)- | O | 3,5-(CF₃)₂-phenyl | 4-F | 705 |
| 170 | (±)-cis | Ph-CH=C(NHAc)-C(=O)- | O | 3,5-(CF₃)₂-phenyl | 4-F | 717 |

TABLE 9-continued

| Ex. No. | Stereochemistry | R¹ | X | B | R² | MS (ESI) (M + H)⁺ |
|---------|-----------------|----|---|---|----|-------------------|
| 171 | (±)-cis | benzothiazol-2-ylthio-CH₂-C(O)-CH₃ | O | 3,5-bis(CF₃)phenyl | 4-F | 737 |
| 172 | (±)-cis | benzothiazol-2-ylthio-CH₂CH₂-C(O)-CH₃ | O | 3,5-bis(CF₃)phenyl | 4-F | 751 |
| 173 | (±)-cis | (1H-indol-3-yl)-CH₂-C(O)-CH₃ | O | 3,5-bis(CF₃)phenyl | 4-F | 687 |
| 174 | (±)-cis | (1H-indol-3-yl)-CH₂CH₂-C(O)-CH₃ | O | 3,5-bis(CF₃)phenyl | 4-F | 701 |
| 175 | (±)-cis | pyridin-3-yl-C(O)-NH-CH₂-C(O)-CH₃ | O | 3,5-bis(CF₃)phenyl | 4-F | 692 |
| 176 | (±)-cis | pyridin-3-yl-CH=CH-C(O)-CH₃ | O | 3,5-bis(CF₃)phenyl | 4-F | 661 |
| 177 | (±)-cis | pyridin-4-ylthio-CH₂-C(O)-CH₃ | O | 3,5-bis(CF₃)phenyl | 4-F | 681 |

TABLE 9-continued

| Ex. No. | Stereochemistry | R¹ | X | B | R² | MS (ESI) (M + H)⁺ |
|---|---|---|---|---|---|---|
| 178 | (±)-cis | MeS-CH₂CH₂-C(O)- | O | 3,5-bis(CF₃)phenyl | 4-F | 632 |
| 179 | (±)-cis | 5-Me-pyrazol-1-yl-CH₂CH₂-C(O)- | O | 3,5-bis(CF₃)phenyl | 4-F | 666 |
| 180 | (±)-cis | benzimidazol-1-yl-CH₂-C(O)- | O | 3,5-bis(CF₃)phenyl | 4-F | 688 |
| 181 | (±)-cis | 4-(pyrazol-1-yl)phenyl-C(O)- | O | 3,5-bis(CF₃)phenyl | 4-F | 701 |
| 182 | (±)-cis | quinolin-4-yl-C(O)- | O | 3,5-bis(CF₃)phenyl | 4-F | 685 |
| 183 | (±)-cis | (E)-1H-imidazol-4-yl-CH=CH-C(O)- | O | 3,5-bis(CF₃)phenyl | 4-F | 650 |
| 218 | (±)-cis | piperidin-1-yl-CH₂CH₂-C(O)- | O | 3-F-5-CF₃-phenyl | 4-F | 619 |

TABLE 9-continued
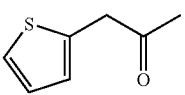
| Ex. No. | Stereochemistry | R¹ | X | B | R² | MS (ESI) (M + H)⁺ |
|---|---|---|---|---|---|---|
| 219 | (±)-cis | 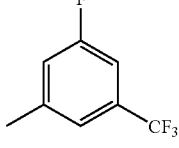 | O | 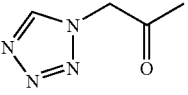 | 4-F | 604 |
| 220 | (±)-cis | 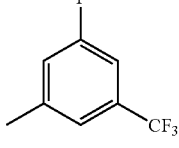 | O | 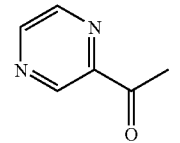 | 4-F | 590 |
| 221 | (±)-cis | 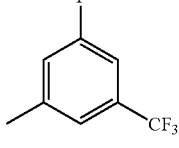 | O | 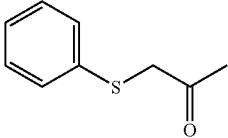 | 4-F | 586 |
| 222 | (±)-cis | 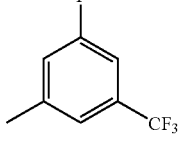 | O | 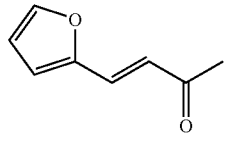 | 4-F | 630 |
| 223 | (±)-cis | 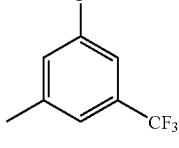 | O | 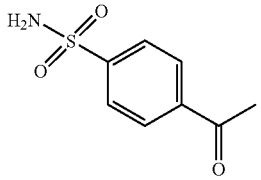 | 4-F | 600 |
| 224 | (±)-cis | 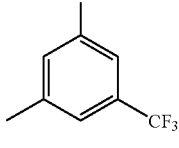 | O | 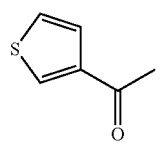 | 4-F | 663 |
| 225 | (±)-cis | 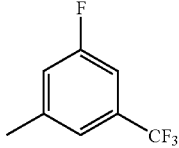 | O |  | 4-F | 590 |

TABLE 9-continued
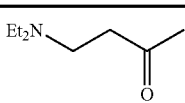
| Ex. No. | Stereochemistry | R¹ | X | B | R² | MS (ESI) (M + H)⁺ |
|---|---|---|---|---|---|---|
| 226 | (±)-cis | 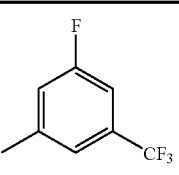 | O | 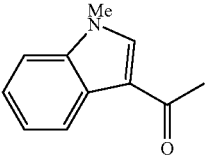 | 4-F | 607 |
| 227 | (±)-cis | 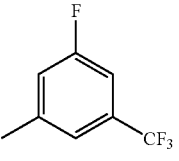 | O | 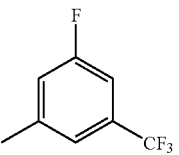 | 4-F | 637 |
| 228 | (±)-cis | NCCH₂CO | O | 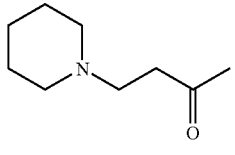 | 4-F | 547 |
| 246 | (±)-cis | 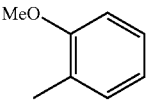 | NH | 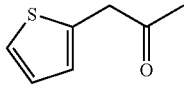 | H | 526 |
| 247 | (±)-cis | 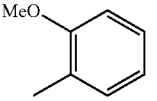 | NH | 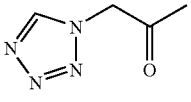 | H | 511 |
| 248 | (±)-cis | 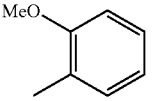 | NH | 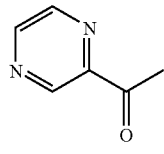 | H | 497 |
| 249 | (±)-cis | 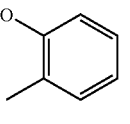 | NH | 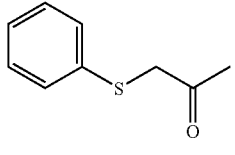 | H | 493 |
| 250 | (±)-cis | 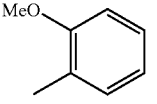 | NH | MeO-phenyl | H | 537 |

TABLE 9-continued

| Ex. No. | Stereochemistry | R¹ | X | B | R² | MS (ESI) (M + H)⁺ |
|---|---|---|---|---|---|---|
| 251 | (±)-cis | furan-CH=CH-C(O)- | NH | 2-MeO, 3-Me-phenyl | H | 507 |
| 252 | (±)-cis | 4-(H₂NSO₂)-phenyl-C(O)- | NH | 2-MeO, 3-Me-phenyl | H | 570 |
| 253 | (±)-cis | thiophen-3-yl-C(O)- | NH | 2-MeO, 3-Me-phenyl | H | 497 |
| 254 | (±)-cis | Et₂N-CH₂CH₂-C(O)- | NH | 2-MeO, 3-Me-phenyl | H | 514 |
| 255 | (±)-cis | 1-Me-indol-3-yl-C(O)- | NH | 2-MeO, 3-Me-phenyl | H | 544 |
| 272 | (±)-cis | Ac | NH | 3,5-(CF₃)₂, 4-Me-phenyl | H | 535 |
| 273 | (±)-cis | EtCO | NH | 3,5-(CF₃)₂, 4-Me-phenyl | H | 549 |
| 274 | (±)-cis | 3,5-(CF₃)₂-phenyl-C(O)- | NH | 3,5-(CF₃)₂, 4-Me-phenyl | H | 733 |

TABLE 9-continued

| Ex. No. | Stereochemistry | R¹ | X | B | R² | MS (ESI) (M + H)⁺ |
|---|---|---|---|---|---|---|
| 275 | (±)-cis | CH₃OCH₂CO | NH | 3,5-bis(CF₃)phenyl | H | 565 |
| 276 | (±)-cis | Me₂NCH₂C(O)- | NH | 3,5-bis(CF₃)phenyl | H | 578 |
| 277 | (±)-cis | 2-pyridyl-CH₂C(O)- | NH | 3,5-bis(CF₃)phenyl | H | 612 |
| 278 | (±)-cis | 1H-imidazol-4-yl-CH₂C(O)- | NH | 3,5-bis(CF₃)phenyl | H | 601 |
| 279 | (±)-cis | benzo[1,3]dioxol-5-yl-C(O)CH(CH₃)- | NH | 3,5-bis(CF₃)phenyl | H | 641 |
| 280 | (±)-cis | piperidin-1-yl-CH₂CH₂C(O)- | NH | 3,5-bis(CF₃)phenyl | H | 632 |
| 281 | (±)-cis | thiophen-2-yl-CH₂C(O)- | NH | 3,5-bis(CF₃)phenyl | H | 617 |

TABLE 9-continued

| Ex. No. | Stereochemistry | R¹ | X | B | R² | MS (ESI) (M + H)⁺ |
|---------|-----------------|----|----|---|----|--------------------|
| 282 | (±)-cis | tetrazolyl-CH₂-C(O)-CH₃ | NH | 3,5-bis(CF₃)phenyl | H | 603 |
| 283 | (±)-cis | pyrazinyl-C(O)-CH₃ | NH | 3,5-bis(CF₃)phenyl | H | 599 |
| 284 | (±)-cis | PhS-CH₂-C(O)-CH₃ | NH | 3,5-bis(CF₃)phenyl | H | 643 |
| 285 | (±)-cis | furyl-CH=CH-C(O)-CH₃ | NH | 3,5-bis(CF₃)phenyl | H | 613 |
| 286 | (±)-cis | H₂N-SO₂-C₆H₄-C(O)-CH₃ | NH | 3,5-bis(CF₃)phenyl | H | 676 |
| 287 | (±)-cis | thienyl-C(O)-CH₃ | NH | 3,5-bis(CF₃)phenyl | H | 603 |
| 288 | (±)-cis | Et₂N-CH₂-CH₂-C(O)-CH₃ | NH | 3,5-bis(CF₃)phenyl | H | 620 |

TABLE 9-continued

| Ex. No. | Stereochemistry | R¹ | X | B | R² | MS (ESI) (M + H)⁺ |
|---|---|---|---|---|---|---|
| 289 | (±)-cis | 1-methyl-indol-3-yl-CO | NH | 3,5-bis(CF₃)phenyl | H | 650 |
| 290 | (±)-cis | MeO₂C-CH₂CH₂-CO | NH | 3,5-bis(CF₃)phenyl | H | 607 |
| 296 | (±)-cis | Ac | NH | 4-OMe-3-Me-phenyl with OCF₃ | H | 513 |
| 297 | (±)-cis | EtCO | NH | 4-OMe-3-Me-phenyl with OCF₃ | H | 527 |
| 298 | (±)-cis | 3,5-bis(CF₃)phenyl-CO | NH | 4-OMe-3-Me-phenyl with OCF₃ | H | 711 |
| 299 | (±)-cis | CH₃OCH₂CO | NH | 4-OMe-3-Me-phenyl with OCF₃ | H | 543 |
| 300 | (±)-cis | Me₂N-CH₂-CO | NH | 4-OMe-3-Me-phenyl with OCF₃ | H | 556 |
| 301 | (±)-cis | pyridin-2-yl-CH₂-CO | NH | 4-OMe-3-Me-phenyl with OCF₃ | H | 590 |
| 302 | (±)-cis | 1H-imidazol-4-yl-CH₂-CO | NH | 4-OMe-3-Me-phenyl with OCF₃ | H | 579 |

TABLE 9-continued

| Ex. No. | Stereochemistry | R¹ | X | B | R² | MS (ESI) (M + H)⁺ |
|---|---|---|---|---|---|---|
| 303 | (±)-cis | benzo[1,3]dioxol-5-yl-C(O)CH₂- | NH | 4-MeO, 3-Me, (OCF₃) phenyl | H | 619 |
| 304 | (±)-cis | piperidin-1-yl-CH₂CH₂C(O)CH₂- | NH | 4-MeO, 3-Me, (OCF₃) phenyl | H | 610 |
| 305 | (±)-cis | thiophen-2-yl-CH₂C(O)CH₂- | NH | 4-MeO, 3-Me, (OCF₃) phenyl | H | 595 |
| 306 | (±)-cis | tetrazol-1-yl-CH₂C(O)CH₂- | NH | 4-MeO, 3-Me, (OCF₃) phenyl | H | 581 |
| 307 | (±)-cis | pyrazin-2-yl-C(O)CH₂- | NH | 4-MeO, 3-Me, (OCF₃) phenyl | H | 577 |
| 308 | (±)-cis | PhS-CH₂-C(O)CH₂- | NH | 4-MeO, 3-Me, (OCF₃) phenyl | H | 621 |
| 309 | (±)-cis | furan-2-yl-CH=CH-C(O)CH₂- | NH | 4-MeO, 3-Me, (OCF₃) phenyl | H | 591 |
| 310 | (±)-cis | 4-(H₂NSO₂)-phenyl-C(O)CH₂- | NH | 4-MeO, 3-Me, (OCF₃) phenyl | H | 654 |

TABLE 9-continued

| Ex. No. | Stereochemistry | R¹ | X | B | R² | MS (ESI) (M + H)⁺ |
| --- | --- | --- | --- | --- | --- | --- |
| 311 | (±)-cis | 2-thienyl-C(O)- | NH | 4-OCF₃-2-Me-MeO-phenyl | H | 581 |
| 312 | (±)-cis | Et₂N-CH₂CH₂-C(O)- | NH | 4-OCF₃-2-Me-MeO-phenyl | H | 598 |
| 313 | (±)-cis | (1-Me-indol-3-yl)-C(O)- | NH | 4-OCF₃-2-Me-MeO-phenyl | H | 628 |
| 314 | (±)-cis | MeO₂C-CH₂CH₂-C(O)- | NH | 4-OCF₃-2-Me-MeO-phenyl | H | 585 |
| 321 | (±)-cis | Ac | NH | 4-Br-2-Me-MeO-phenyl | H | 507, 509 |
| 322 | (±)-cis | EtCO | NH | 4-Br-2-Me-MeO-phenyl | H | 521, 523 |
| 323 | (±)-cis | 3,5-bis(CF₃)-phenyl-C(O)- | NH | 4-Br-2-Me-MeO-phenyl | H | 705, 707 |
| 324 | (±)-cis | CH₃OCH₂CO | NH | 4-Br-2-Me-MeO-phenyl | H | 537, 539 |
| 325 | (±)-cis | Me₂N-CH₂-C(O)- | NH | 4-Br-2-Me-MeO-phenyl | H | 550, 552 |

TABLE 9-continued
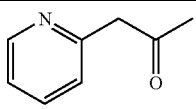
| Ex. No. | Stereochemistry | R¹ | X | B | R² | MS (ESI) (M + H)⁺ |
|---|---|---|---|---|---|---|
| 326 | (±)-cis | 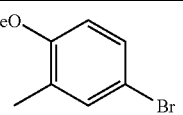 | NH | 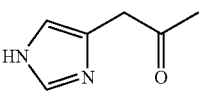 | H | 584, 586 |
| 327 | (±)-cis | 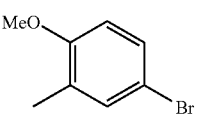 | NH | 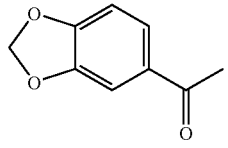 | H | 573, 575 |
| 328 | (±)-cis | 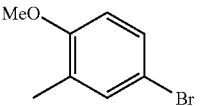 | NH | 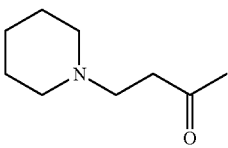 | H | 613, 615 |
| 329 | (±)-cis | 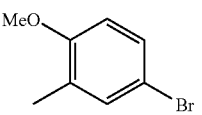 | NH | 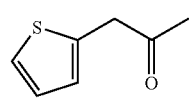 | H | 604, 606 |
| 330 | (±)-cis | 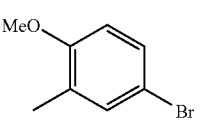 | NH | 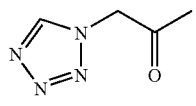 | H | 589, 591 |
| 331 | (±)-cis | 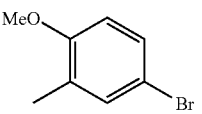 | NH | 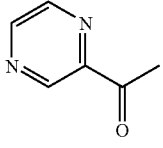 | H | 575, 577 |
| 332 | (±)-cis | 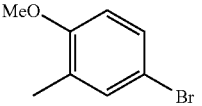 | NH | 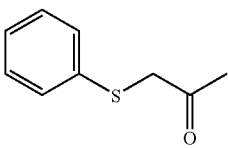 | H | 571, 573 |
| 333 | (±)-cis | 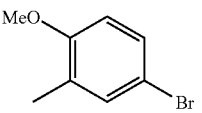 | NH |  | H | 615, 617 |

TABLE 9-continued

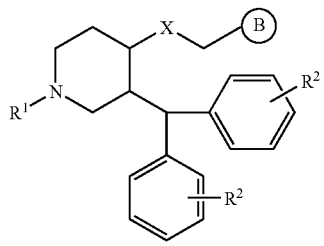

| Ex. No. | Stereochemistry | R¹ | X | B | R² | MS (ESI) (M + H)⁺ |
|---|---|---|---|---|---|---|
| 334 | (±)-cis | furan-CH=CH-C(=O)-CH₃ | NH | MeO-phenyl-Br (with Me) | H | 585, 587 |
| 335 | (±)-cis | H₂N-SO₂-phenyl-C(=O)-CH₃ | NH | MeO-phenyl-Br (with Me) | H | 648, 650 |
| 336 | (±)-cis | thiophene-C(=O)-CH₃ | NH | MeO-phenyl-Br (with Me) | H | 575, 577 |
| 337 | (±)-cis | Et₂N-CH₂-CH₂-C(=O)-CH₃ | NH | MeO-phenyl-Br (with Me) | H | 592, 594 |
| 338 | (±)-cis | MeO₂C-CH₂-CH₂-C(=O)-CH₃ | NH | MeO-phenyl-Br (with Me) | H | 579, 581 |

Example 120

2-[cis-3-Benzhydryl-4-[[3,5-bis(trifluoromethyl)benzyl]oxy]-1-piperidinyl]-2-oxoethylamine trifluoroacetate The compound (28.7 mg) obtained in Example 25 and Boc-glycine (21.0 mg) were reacted and treated in the same manner as in the method described in Example 29 to obtain the title compound.
Yield: 26.8 mg HPLC analysis (Condition B): Purity 99% (Retention time: 1.82 minutes)
MS (ESI+): 551 (M+H)

The compounds of the following Examples were synthesized from the compounds obtained in Examples 25, 152, 217, 245, 271, 295 and 320 as starting materials by reacting and treating in the same manner as in the method described in Example 120 using the respective corresponding amino acids protected with Boc group.

TABLE 10

[Structure: piperidine with N-R¹, 3-position bearing CH(Ph-R²)(Ph-R²), 4-position bearing X-CH₂-B]

| Ex. No. | Stereochemistry | R¹ | X | B | R² | MS (ESI) (M + H)⁺ |
|---|---|---|---|---|---|---|
| 120 | (±)-cis | H₂N-CH₂-C(=O)- | O | 3,5-bis(CF₃)phenyl | H | 551 |
| 121 | (±)-cis | H₂N-(CH₂)₃-C(=O)- | O | 3,5-bis(CF₃)phenyl | H | 579 |
| 184 | (±)-cis | H₂N-CH₂-C(=O)- | O | 3,5-bis(CF₃)phenyl | 4-F | 587 |
| 185 | (±)-cis | H₂N-(CH₂)₃-C(=O)- | O | 3,5-bis(CF₃)phenyl | 4-F | 615 |
| 229 | (±)-cis | H₂N-CH₂-C(=O)- | O | 3-F-5-CF₃-phenyl | 4-F | 537 |
| 230 | (±)-cis | H₂N-(CH₂)₃-C(=O)- | O | 3-F-5-CF₃-phenyl | 4-F | 565 |
| 256 | (±)-cis | H₂N-CH₂-C(=O)- | NH | 2-MeO-6-Me-phenyl | H | 444 |
| 257 | (±)-cis | H₂N-(CH₂)₃-C(=O)- | NH | 2-MeO-6-Me-phenyl | H | 472 |

TABLE 10-continued

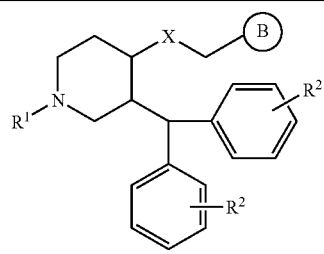

| Ex. No. | Stereochemistry | R¹ | X | B | R² | MS (ESI) (M + H)⁺ |
|---|---|---|---|---|---|---|
| 291 | (±)-cis | 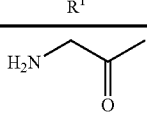 | NH | 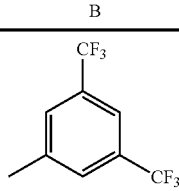 | H | 550 |
| 292 | (±)-cis | 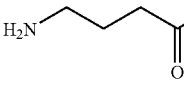 | NH | 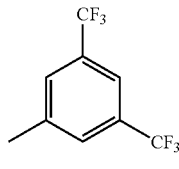 | H | 578 |
| 315 | (±)-cis | 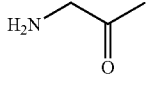 | NH | 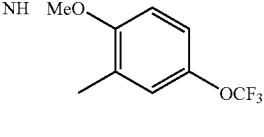 | H | 528 |
| 316 | (±)-cis | 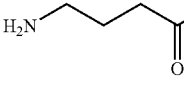 | NH | 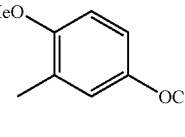 | H | 556 |
| 339 | (±)-cis | 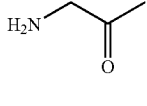 | NH | 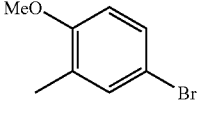 | H | 522, 524 |
| 340 | (±)-cis | 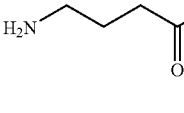 | NH | 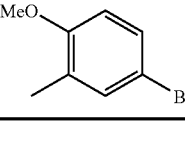 | H | 550, 552 |

Example 122 cis-3-Benzhydryl-1-(benzylsulfonyl)-4-[[3,5-bis(trifluoromethyl)benzyl]oxy]piperidine The compound (28.7 mg) obtained in Example 25 and α-toluenesulfonyl chloride (17.2 mg) were reacted and treated in the same manner as in the method described in Example 30 to obtain the title compound.

Yield: 19.0 mg

HPLC analysis (Condition B): Purity 98% (Retention time: 2.44 minutes)

MS (ESI+): 648 (M+H)

The compounds of the following Examples were synthesized from the compounds obtained in Examples 25, 152, 217 and 245 as starting materials by reacting and treating in the same manner as in the method described in Example 122 using the respective corresponding sulfonyl chloride derivatives.

TABLE 11

| Ex. No. | Stereochemistry | R¹ | X | B | R² | MS (ESI) (M + H)⁺ |
|---|---|---|---|---|---|---|
| 122 | (±)-cis | benzyl-SO₂-CH₂- (PhCH₂SO₂-) | O | 3,5-bis(CF₃)phenyl | H | 648 |
| 123 | (±)-cis | 4-(AcHN)-phenyl-SO₂- | O | 3,5-bis(CF₃)phenyl | H | 691 |
| 124 | (±)-cis | 4-(MeO)-phenyl-SO₂- | O | 3,5-bis(CF₃)phenyl | H | 664 |
| 125 | (±)-cis | 3,4-di(MeO)-phenyl-SO₂- | O | 3,5-bis(CF₃)phenyl | H | 694 |
| 126 | (±)-cis | 2-(AcHN)-4-Me-thiazol-5-yl-SO₂- | O | 3,5-bis(CF₃)phenyl | H | 712 |
| 127 | (±)-cis | EtSO₂ | O | 3,5-bis(CF₃)phenyl | H | 586 |
| 128 | (±)-cis | PhSO₂ | O | 3,5-bis(CF₃)phenyl | H | 634 |

TABLE 11-continued
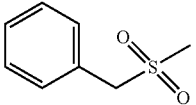
| Ex. No. | Stereochemistry | R¹ | X | B | R² | MS (ESI) (M + H)⁺ |
|---|---|---|---|---|---|---|
| 186 | (±)-cis | 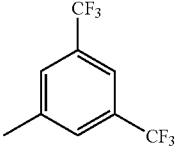 | O | 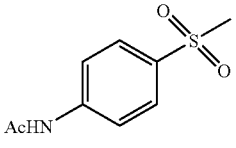 | 4-F | 684 |
| 187 | (±)-cis | 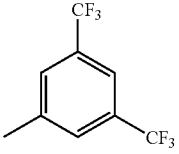 | O | 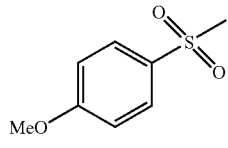 | 4-F | 727 |
| 188 | (±)-cis | 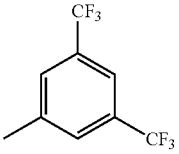 | O | 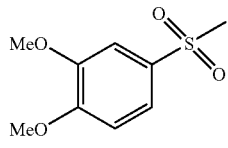 | 4-F | 700 |
| 189 | (±)-cis | 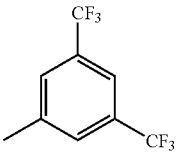 | O | 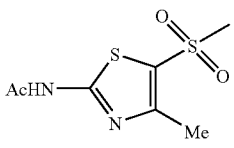 | 4-F | 730 |
| 190 | (±)-cis | 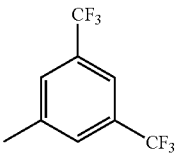 | O | 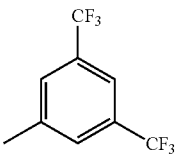 | 4-F | 748 |
| 191 | (±)-cis | EtSO$_2$ | O | 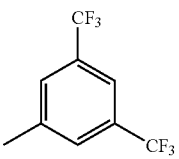 | 4-F | 622 |
| 192 | (±)-cis | PhSO$_2$ | O |  | 4-F | 670 |

TABLE 11-continued
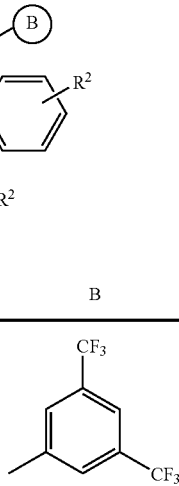
| Ex. No. | Stereochemistry | R[1] | X | B | R[2] | MS (ESI) (M + H)[+] |
|---|---|---|---|---|---|---|
| 193 | (±)-cis | MeSO$_2$ | O | 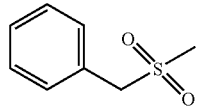 | 4-F | 608 |
| 231 | (±)-cis | 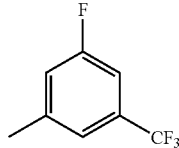 | O | 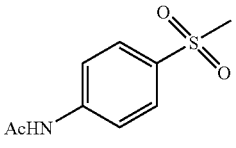 | 4-F | 634 |
| 232 | (±)-cis | 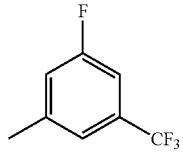 | O | 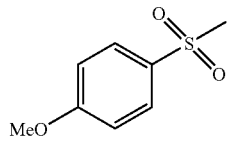 | 4-F | 677 |
| 233 | (±)-cis | 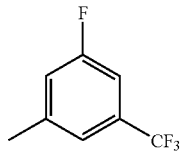 | O | 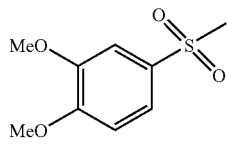 | 4-F | 650 |
| 234 | (±)-cis | 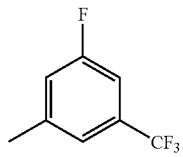 | O | 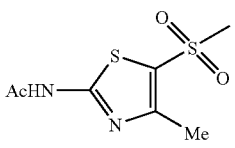 | 4-F | 680 |
| 235 | (±)-cis | 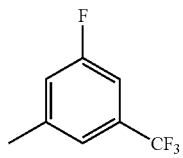 | O | 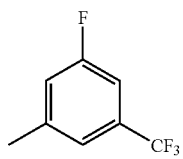 | 4-F | 698 |
| 236 | (±)-cis | EtSO$_2$ | O |  | 4-F | 572 |

TABLE 11-continued
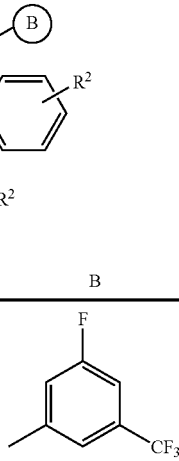
| Ex. No. | Stereochemistry | R¹ | X | B | R² | MS (ESI) (M + H)⁺ |
|---|---|---|---|---|---|---|
| 237 | (±)-cis | PhSO$_2$ | O | 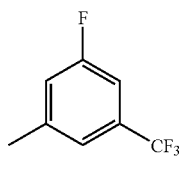 | 4-F | 620 |
| 238 | (±)-cis | MeSO$_2$ | O | 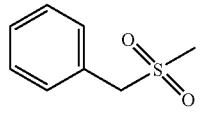 | 4-F | 558 |
| 258 | (±)-cis | 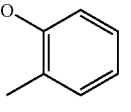 | NH | 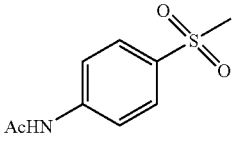 | H | 541 |
| 259 | (±)-cis | 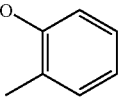 | NH | 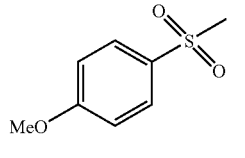 | H | 584 |
| 260 | (±)-cis | 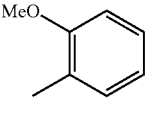 | NH | 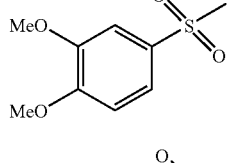 | H | 557 |
| 261 | (±)-cis | 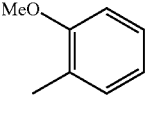 | NH | 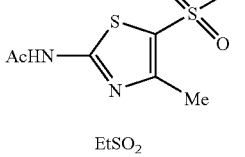 | H | 587 |
| 262 | (±)-cis | 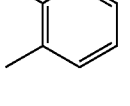 | NH | 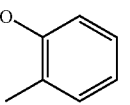 | H | 605 |
| 263 | (±)-cis | EtSO$_2$ | NH | 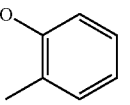 | H | 479 |
| 264 | (±)-cis | PhSO$_2$ | NH | 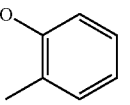 | H | 527 |

TABLE 11-continued

| Ex. No. | Stereochemistry | R¹ | X | B | R² | MS (ESI) (M + H)⁺ |
|---|---|---|---|---|---|---|
| 265 | (±)-cis | MeSO₂ | NH | 2-MeO-phenyl (with methyl) | H | 465 |

Example 129

Ethyl [[[cis-3-benzhydryl-4-[[3,5-bis(trifluoromethyl)benzyl]oxy]-1-piperidinyl]carbonyl]amino]acetate The compound (28.7 mg) obtained in Example 25 and ethyl isocyanoacetate (11.6 mg) were reacted and treated in the same manner as in the method described in Example 31 to obtain the title compound.

Yield: 30.1 mg
HPLC analysis (Condition B): Purity 95% (Retention time: 2.27 minutes)
MS (ESI+): 623 (M+H)

The compounds of the following Examples were synthesized from the compounds obtained in Examples 25, 152, 217, 245, 271, 295 and 320 as starting materials by reacting and treating in the same manner as in the method described in Example 129 using the respective corresponding isocyanate derivatives.

TABLE 12

| Ex. No. | Stereochemistry | R¹ | X | B | R² | MS (ESI) (M + H)⁺ |
|---|---|---|---|---|---|---|
| 129 | (±)-cis | EtO₂C-CH₂-NH-C(=O)- | O | 3,5-bis(CF₃)phenyl | H | 623 |
| 130 | (±)-cis | EtNHCO | O | 3,5-bis(CF₃)phenyl | H | 565 |
| 131 | (±)-cis | cyclohexyl-NH-C(=O)- | O | 3,5-bis(CF₃)phenyl | H | 619 |

TABLE 12-continued

| Ex. No. | Stereochemistry | R¹ | X | B | R² | MS (ESI) (M + H)⁺ |
|---|---|---|---|---|---|---|
| 132 | (±)-cis | PhCH₂NHCO- (benzyl acetamide) | O | 3,5-bis(CF₃)phenyl | H | 627 |
| 133 | (±)-cis | 4-Me₂N-C₆H₄-NHCO- | O | 3,5-bis(CF₃)phenyl | H | 656 |
| 134 | (±)-cis | ⁿPrNHCO | O | 3,5-bis(CF₃)phenyl | H | 579 |
| 135 | (±)-cis | ⁿBuNHCO | O | 3,5-bis(CF₃)phenyl | H | 593 |
| 136 | (±)-cis | morpholino-CH₂CH₂-NHC(=S)- | O | 3,5-bis(CF₃)phenyl | H | 666 |
| 137 | (±)-cis | 3-NC-C₆H₄-NHCO- | O | 3,5-bis(CF₃)phenyl | H | 638 |
| 194 | (±)-cis | EtO₂C-CH₂-NHCO- | O | 3,5-bis(CF₃)phenyl | 4-F | 659 |

TABLE 12-continued
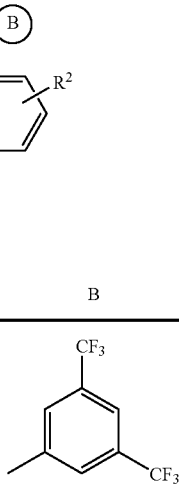
| Ex. No. | Stereochemistry | R¹ | X | B | R² | MS (ESI) (M + H)⁺ |
|---|---|---|---|---|---|---|
| 195 | (±)-cis | EtNHCO | O | 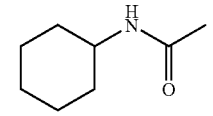 | 4-F | 601 |
| 196 | (±)-cis | 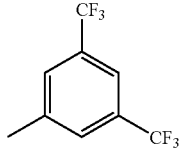 | O | 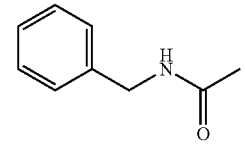 | 4-F | 655 |
| 197 | (±)-cis | 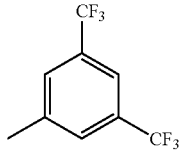 | O | 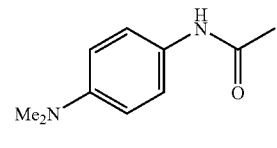 | 4-F | 663 |
| 198 | (±)-cis | 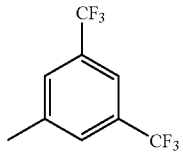 | O | 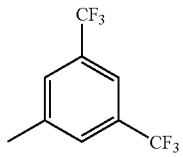 | 4-F | 692 |
| 199 | (±)-cis | ⁿPrNHCO | O | 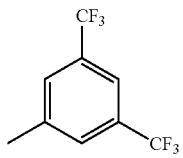 | 4-F | 615 |
| 200 | (±)-cis | ⁿBuNHCO | O | 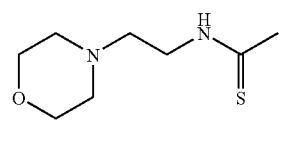 | 4-F | 629 |
| 201 | (±)-cis | 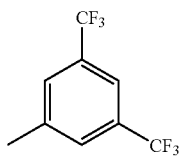 | O | | 4-F | 702 |

TABLE 12-continued
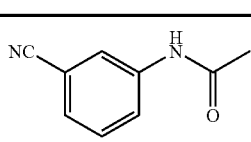
| Ex. No. | Stereochemistry | R¹ | X | B | R² | MS (ESI) (M + H)⁺ |
|---|---|---|---|---|---|---|
| 202 | (±)-cis | 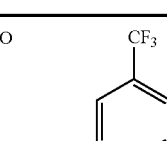 | O | 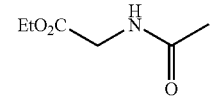 | 4-F | 674 |
| 239 | (±)-cis | 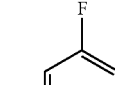 | O | 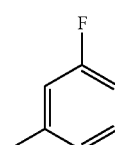 | 4-F | 609 |
| 240 | (±)-cis | EtNHCO | O | 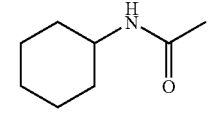 | 4-F | 551 |
| 241 | (±)-cis | 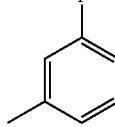 | O | 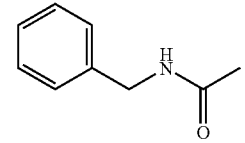 | 4-F | 605 |
| 242 | (±)-cis | 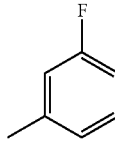 | O | 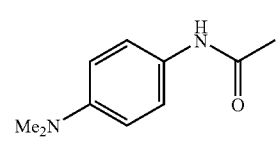 | 4-F | 613 |
| 243 | (±)-cis | 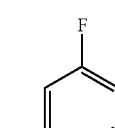 | O | 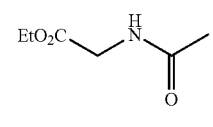 | 4-F | 642 |
| 266 | (±)-cis | 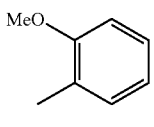 | NH | 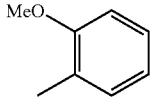 | H | 516 |
| 267 | (±)-cis | EtNHCO | NH | 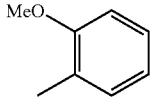 | H | 458 |

TABLE 12-continued
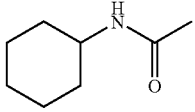
| Ex. No. | Stereochemistry | R¹ | X | B | R² | MS (ESI) (M + H)⁺ |
|---|---|---|---|---|---|---|
| 268 | (±)-cis | 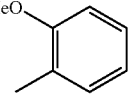 | NH | 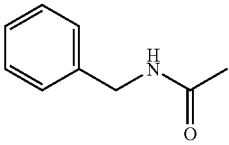 | H | 512 |
| 269 | (±)-cis | 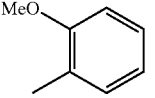 | NH | 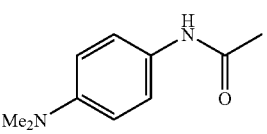 | H | 520 |
| 270 | (±)-cis | 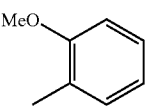 | NH | 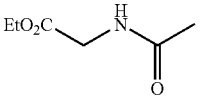 | H | 549 |
| 293 | (±)-cis | 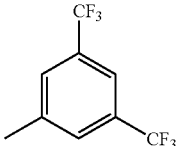 | NH | 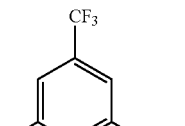 | H | 622 |
| 294 | (±)-cis | EtNHCO | NH | 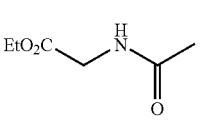 | H | 564 |
| 317 | (±)-cis | 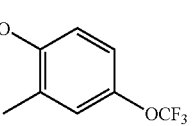 | NH | 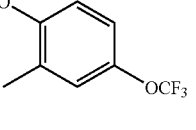 | H | 600 |
| 318 | (±)-cis | EtNHCO | NH | 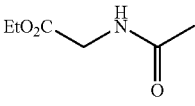 | H | 542 |
| 341 | (±)-cis | 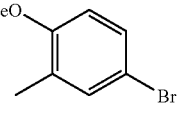 | NH | 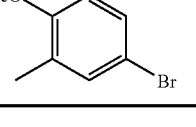 | H | 594, 596 |
| 342 | (±)-cis | EtNHCO | NH | 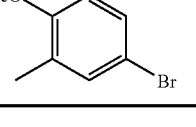 | H | 536, 538 |

Example 138 cis-3-Benzhydryl-4-[[3,5-bis(trifluoromethyl)benzyl]oxy]-1-propylpiperidine trifluoroacetate To a mixed solution of the compound (28.7 mg) obtained in Example 25 and propionaldehyde (5.2 mg) in dichloromethane (2 ml), NaBH(OAc)$_3$ (20.0 mg) was added, and the reaction mixture was stirred at room temperature for 14 hours. The solvent was evaporated under reduced pressure, and then the residue was poured into a mixed solution of ethyl acetate and water. The organic layer was washed with saturated brine, and dried, and the solvent was evaporated under reduced pressure, and then the residue was purified by preparative HPLC to obtain the title compound.

Yield: 22.9 mg

HPLC analysis (Condition B): Purity 99% (Retention time: 1.89 minutes)

MS (ESI+): 536 (M+H)

The compounds of the following Examples were synthesized from the compounds obtained in Examples 25 and 152 as starting materials by reacting and treating in the same manner as in the method described in Example 138 using the respective corresponding aldehyde derivatives.

TABLE 13

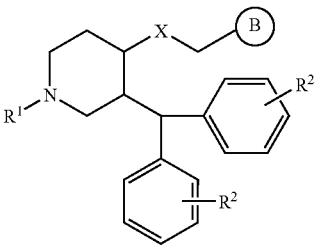

| Ex. No. | Stereochemistry | $R^1$ | X | B | $R^2$ | MS (ESI) (M + H)$^+$ |
|---|---|---|---|---|---|---|
| 138 | (±)-cis | $^n$Pr | O | 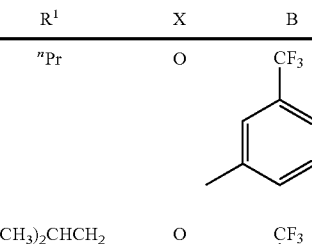 | H | 536 |
| 139 | (±)-cis | (CH$_3$)$_2$CHCH$_2$ | O | 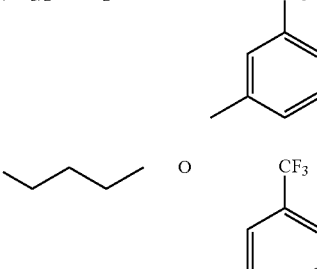 | H | 550 |
| 140 | (±)-cis | 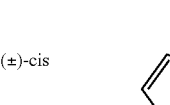 | O |  | H | 582 |
| 141 | (±)-cis | 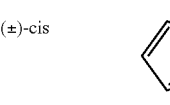 | O |  | H | 574 |
| 142 | (±)-cis |  | O |  | H | 590 |
| 143 | (±)-cis | (indolylethyl) | O | (3,5-bis-CF$_3$-phenyl) | H | 623 |

TABLE 13-continued
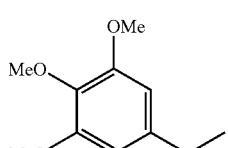
| Ex. No. | Stereochemistry | R¹ | X | B | R² | MS (ESI) (M + H)⁺ |
|---|---|---|---|---|---|---|
| 144 | (±)-cis | 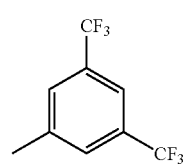 | O | 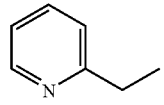 | H | 674 |
| 145 | (±)-cis | 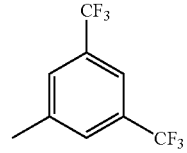 | O | 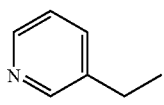 | H | 585 |
| 146 | (±)-cis | 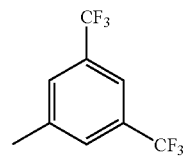 | O | 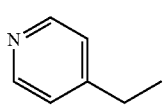 | H | 585 |
| 147 | (±)-cis | 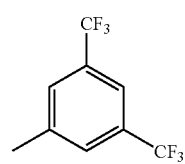 | O | 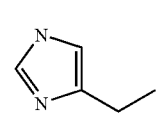 | H | 585 |
| 148 | (±)-cis | 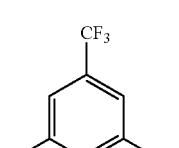 | O | 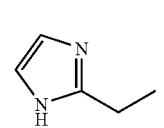 | H | 574 |
| 149 | (±)-cis | 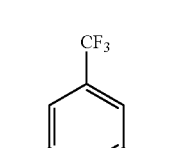 | O |  | H | 574 |

TABLE 13-continued

| Ex. No. | Stereochemistry | R¹ | X | B | R² | MS (ESI) (M + H)⁺ |
|---------|-----------------|-----|---|---|-----|-------------------|
| 203 | (±)-cis | ⁿPr | O | 3,5-(CF₃)₂-phenyl | 4-F | 572 |
| 204 | (±)-cis | (CH₃)₂CHCH₂ | O | 3,5-(CF₃)₂-phenyl | 4-F | 586 |
| 205 | (±)-cis | MeS(CH₂)₃ | O | 3,5-(CF₃)₂-phenyl | 4-F | 618 |
| 206 | (±)-cis | 2-furyl-CH₂CH₂ | O | 3,5-(CF₃)₂-phenyl | 4-F | 610 |
| 207 | (±)-cis | 2-thienyl-CH₂CH₂ | O | 3,5-(CF₃)₂-phenyl | 4-F | 626 |
| 208 | (±)-cis | 3-(1H-indolyl)-CH₂CH₂ | O | 3,5-(CF₃)₂-phenyl | 4-F | 659 |

TABLE 13-continued
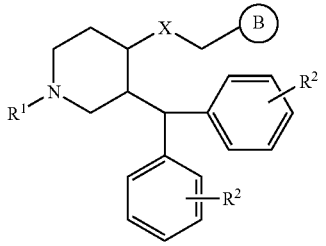
| Ex. No. | Stereochemistry | R¹ | X | B | R² | MS (ESI) (M + H)⁺ |
|---|---|---|---|---|---|---|
| 209 | (±)-cis | 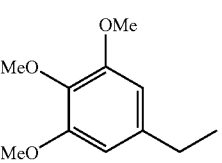 | O | 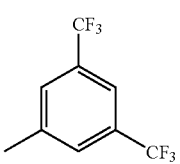 | 4-F | 710 |
| 210 | (±)-cis | 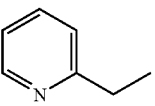 | O | 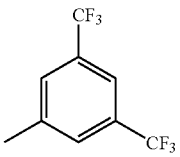 | 4-F | 621 |
| 211 | (±)-cis | 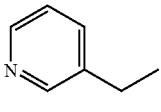 | O | 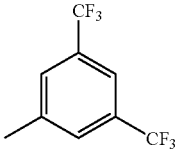 | 4-F | 621 |
| 212 | (±)-cis | 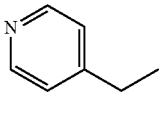 | O | 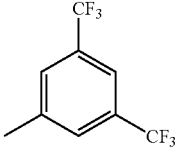 | 4-F | 621 |
| 213 | (±)-cis | 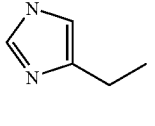 | O | 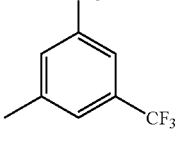 | 4-F | 610 |
| 214 | (±)-cis | 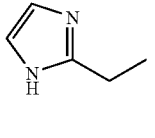 | O | 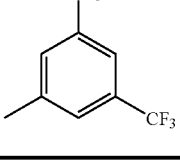 | 4-F | 610 |

Example 150

5-[[cis-3-Benzhydryl-4-[[3,5-bis(trifluoromethyl)benzyl]oxy]-1-piperidinyl]methyl]-1,2-dihydro-3H-1,2,4-triazol-3-one trifluoroacetate

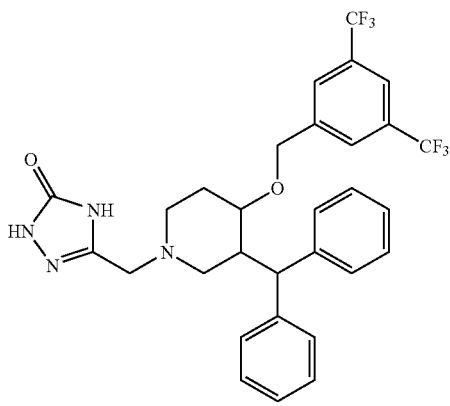

The compound (28.7 mg) obtained in Example 25 and 5-(chloromethyl)-2,4-dihydro-3H-1,2,4-triazol-3-one (12.0 mg) were reacted and treated in the same manner as in the method described in Example 7 to obtain the title compound.

Yield: 26.9 mg

HPLC analysis (Condition B): Purity 98% (Retention time: 1.76 minutes)

MS (ESI+): 591 (M+H)

Example 151

4-[cis-3-Benzhydryl-4-[[3,5-bis(trifluoromethyl)benzyl]oxy]-1-piperidinyl]-4-oxobutanoic acid

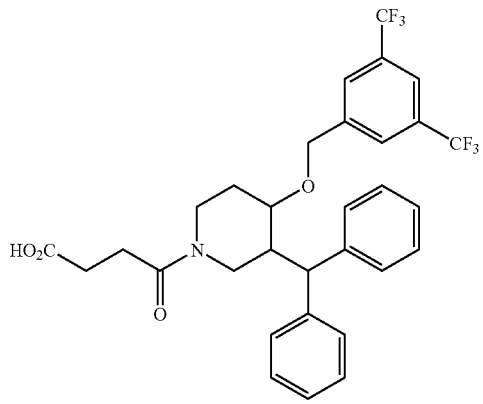

To a solution of the compound (36.4 mg) obtained in Example 99 in methanol (2.0 ml), a solution of an aqueous 1 N NaOH solution (0.9 ml) was added, and the reaction mixture was stirred at room temperature for 14 hours. The solvent was evaporated under reduced pressure, and then the residue was poured into ethyl acetate and a diluted aqueous hydrogen chloride solution. The organic layer was washed with saturated brine, and dried, and the solvent was evaporated under reduced pressure, and then the residue was purified by preparative HPLC to obtain the title compound.

Yield: 23.3 mg

HPLC analysis (Condition B): Purity 90% (Retention time: 2.27 minutes)

MS (ESI+): 594 (M+H)

The compounds of the following Examples were synthesized from the compound obtained in Process 4 of Reference Example 3 or a known 3-benzhydryl-4-oxopiperidine-1-carboxylic acid tert-butyl ester derivatives as a starting material by reacting and treating in the same manner as in the method described in Process 5 of Reference Example 3 and Example 25 using the respective corresponding benzyl halide derivatives.

TABLE 14

| Ex. No. | Stereo-chemistry | $R^1$ | X | B | $R^2$ | MS (ESI) $(M + H)^+$ |
|---|---|---|---|---|---|---|
| 152 | (±)-cis | H | O | 3,5-bis(CF$_3$)phenyl | 4-F | 530 |
| 217 | (±)-cis | H | O | 3-F-5-CF$_3$-phenyl | 4-F | 480 |
| 244 | (±)-cis | H | O | 3-OCF$_3$-5-methylphenyl | 4-F | 478 |

Example 215

5-[[cis-3-[Bis(4-fluorophenyl)methyl]-4-[[3,5-bis(trifluoromethyl)benzyl]oxy]-1-piperidinyl]methyl]-1,2-dihydro-3H-1,2,4-triazol-3-one trifluoroacetate

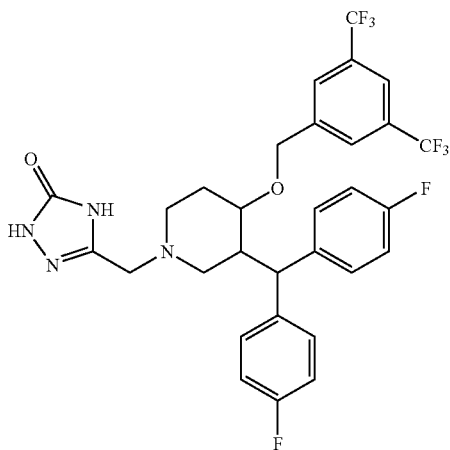

The compound (31.7 mg) obtained in Example 152 and 5-(chloromethyl)-2,4-dihydro-3H-1,2,4-triazol-3-one (12.0 mg) were reacted and treated in the same manner as in the method described in Example 7 to obtain the title compound.

Yield: 19.6 mg

HPLC analysis (Condition B): Purity 93% (Retention time: 1.76 minutes)

MS (ESI+): 627 (M+H)

Example 216

4-[cis-3-[Bis(4-fluorophenyl)methyl]-4-[[3,5-bis(trifluoromethyl)benzyl]oxy]-1-piperidinyl]-4-oxobutanoic acid

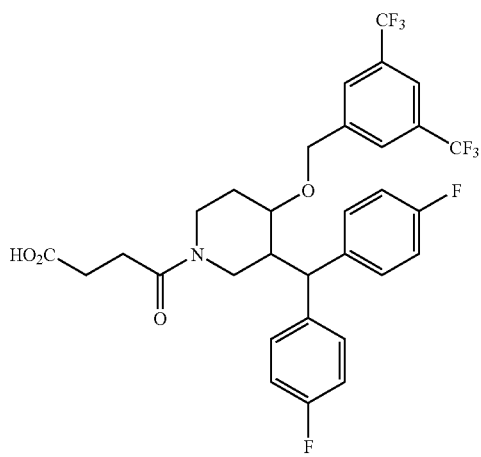

The compound (38.6 mg) obtained in Example 164 was reacted and treated in the same manner as in the method described in Example 151 to obtain the title compound.

Yield: 18.8 mg

HPLC analysis (Condition B): Purity 95% (Retention time: 2.27 minutes)

MS (ESI+): 630 (M+H)

Example 245

3-Benzhydryl-N-(2-methoxybenzyl)-4-piperidineamine hydrochloride (Process 1)

The compound obtained in Process 3 of Reference Example 3 was reacted and treated in the same manner as in the method described in Process 2 of Reference Example 2 to obtain 4-amino-3-benzhydryl-1-piperidinecarboxylic acid tert-butyl ester.

(Process 2)

The compound obtained in Process 1 and 2-methoxybenzaldehyde were reacted and treated in the same manner as in the methods described in Process 3 of Reference Example 2 and Example 1 to obtain the title compound.

MS (ESI+): 387 (M+H).

The compounds of the following Examples were synthesized from the compound obtained in Process 3 of Reference Example 3 as a starting material by reacting and treating in the same manner as in the method described in Example 245 using the respective corresponding benzaldehyde derivatives.

TABLE 15

| Ex. No. | Stereo-chemistry | $R^1$ | X | B | $R^2$ | MS (ESI) (M+H)+ |
|---|---|---|---|---|---|---|
| 245 | (±)-cis | H | NH | 2-MeO-phenyl | H | 387 |
| 271 | (±)-cis | H | NH | 3,5-bis(CF3)-phenyl | H | 493 |
| 295 | (±)-cis | H | NH | 2-MeO-4-OCF3-phenyl | H | 471 |
| 320 | (±)-cis | H | NH | 2-MeO-4-Br-phenyl | H | 465, 467 |

Example 319

4-[cis-3-Benzhydryl-4-[[2-methoxy-5-(trifluoromethoxy)benzyl]amino]-1-piperidinyl]-4-oxobutanoic acid trifluoroacetate

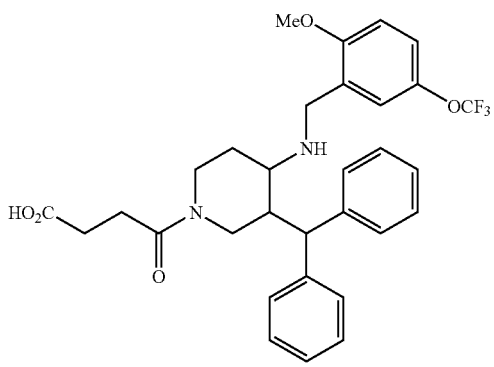

The compound (32.5 mg) obtained in Example 314 was reacted and treated in the same manner as in the method described in Example 151 to obtain the title compound.

Yield: 20.7 mg

HPLC analysis (Condition B): Purity 97% (Retention time: 1.61 minutes)

MS (ESI+): 571 (M+H)

Example 343 cis-3-[Bis(4-fluorophenyl)methyl]-4-[(3,5-dimethylbenzyl)amino]-N-ethyl-1-piperidinecarboxamide trifluoroacetate (Process 1)

To a solution of 4-amino-3-[bis(4-fluorophenyl)methyl]-1-piperidinecarboxylic acid tert-butyl ester (9.92 g) in THF (80 ml), 1-[[(benzyloxy)carbonyl]oxy]pyrrolidone-2,5-dione (6.75 g) was added, and the reaction mixture was stirred at room temperature for 14 hours. The reaction mixture was concentrated under reduced pressure, and then the residue was dissolved in ethyl acetate. The organic layer was washed with an aqueous 10% citric acid solution, an aqueous 5% sodium hydrogen carbonate solution and saturated brine, dried, and then the solvent was evaporated under reduced pressure. The obtained residue was isolated and purified by silica gel column chromatography (hexane:ethyl acetate=2:1) to obtain cis-4-[[(benzyloxy)carbonyl]amino]-3-[bis(4-fluorophenyl)methyl]-1-piperidinecarboxylic acid tert-butyl ester as colorless amorphous (9.30 g).

$^1$H-NMR (CDCl$_3$): δ 1.37 (9H, s), 1.68 (1H, br), 1.77 (1H, br), 2.50 (1H, br), 2.96 (1H, br), 3.74 (4H, m), 4.85 (1H, br), 4.95 (1H, d, J=11.4 Hz), 5.12 (1H, d, J=11.4 Hz), 6.87 (2H, t, J=8.6 Hz), 6.98 (2H, t, J=8.6 Hz), 7.09-7.39 (9H, m).

(Process 2)

To a solution of the compound (9.20 g) obtained in Process 1 in THF (40 ml), 4 N hydrogen chloride/ethyl acetate (15 ml) was added, and the reaction mixture was stirred at room temperature for 3 hours. The reaction mixture was concentrated under reduced pressure, and then the residue was crystallized from diethyl ether to obtain benzyl[cis-3-[bis($^4$-fluorophenyl)methyl]-piperidin-4-yl]carbamate hydrochloride as white powder (7.21 g).

MS (ESI+): 437 (M+H)

(Process 3)

To a solution of the compound (3.00 g) obtained in Process 2 and diisopropylethylamine (1.1 ml) in THF (40 ml), ethyl isocyanate (0.55 ml) was added, and the reaction mixture was stirred at room temperature for 12 hours. The reaction mixture was concentrated under reduced pressure, and then the residue was dissolved in ethyl acetate. The organic layer was washed with an aqueous 5% sodium hydrogen carbonate solution and saturated brine, dried, and then the solvent was evaporated under reduced pressure. The obtained residue was isolated and purified by amine-treated silica gel column chromatography (hexane:ethyl acetate=2:3) to obtain benzyl[cis-3-[bis(4-fluorophenyl)methyl]-1-[(ethylamino)carbonyl]piperidin-4-yl] carbamate as white powder (2.75 g).

MS (ESI+): 508 (M+H)

(Process 4)

To a solution of the compound (2.75 g) obtained in Process 3 in methanol (100 ml), 10% Pd—C (0.28 g) was added, and the reaction mixture was stirred at room temperature for 12 hours under hydrogen atmosphere of 1 atm. The catalyst was removed by filtration, and then the reaction solution was concentrated under reduced pressure. To the obtained residue, 4 N hydrogen chloride/ethyl acetate (5 ml) was added, and the mixture was crystallized from diethyl ether to obtain cis-4-[bis(4-fluorophenyl)methyl]-N-ethyl-1-piperidinecarboxamide hydrochloride as white powder (2.53 g).

MS (ESI+): 374 (M+H) Melting point: 184-186° C.

(Process 5)

To a solution of the compound (24.5 mg) obtained in Process 4 and 3,5-dimethylbenzaldehyde (16.1 mg) in dichloromethane (2.0 ml), NaBH(OAc)$_3$ (20.0 mg) was added, and the reaction mixture was stirred at room temperature for 12 hours. The solvent was evaporated under reduced pressure, and then the residue was poured into a mixed solution of ethyl acetate and water. The organic layer was washed with saturated brine, and dried, and the solvent was evaporated under reduced pressure, and then the residue was purified by preparative HPLC to obtain the title compound.

Yield: 14.0 mg

HPLC analysis (Condition B): Purity 100% (Retention time: 1.84 minutes)

MS (ESI+): 492 (M+H)

The compounds of the following Examples were synthesized from the compound obtained in Process 4 of Example 343 as a starting material by reacting and treating in the same manner as in the method described in Process 5 of Example 343 using the respective corresponding aldehyde derivatives.

TABLE 16
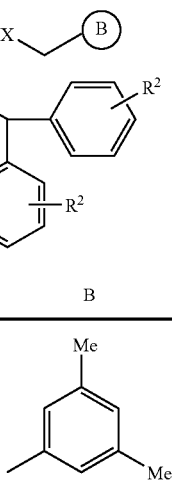
| Ex. No. | Stereochemistry | R¹ | X | B | R² | MS (ESI) (M + H)⁺ |
|---|---|---|---|---|---|---|
| 343 | (±)-cis | EtNHCO | NH | 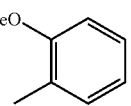 | 4-F | 492 |
| 344 | (±)-cis | EtNHCO | NH | 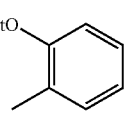 | 4-F | 494 |
| 345 | (±)-cis | EtNHCO | NH | 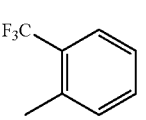 | 4-F | 508 |
| 346 | (±)-cis | EtNHCO | NH | 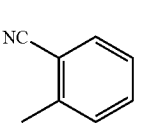 | 4-F | 532 |
| 347 | (±)-cis | EtNHCO | NH | 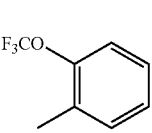 | 4-F | 489 |
| 348 | (±)-cis | EtNHCO | NH | 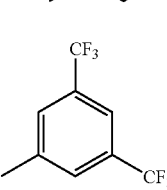 | 4-F | 548 |
| 349 | (±)-cis | EtNHCO | NH | 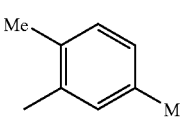 | 4-F | 600 |
| 350 | (±)-cis | EtNHCO | NH | 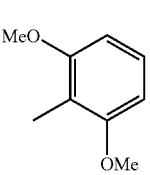 | 4-F | 492 |
| 351 | (±)-cis | EtNHCO | NH |  | 4-F | 524 |

TABLE 16-continued
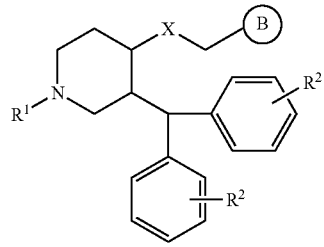
| Ex. No. | Stereochemistry | R¹ | X | B | R² | MS (ESI) (M + H)⁺ |
|---|---|---|---|---|---|---|
| 352 | (±)-cis | EtNHCO | NH | 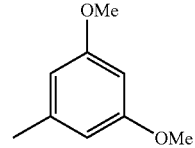 | 4-F | 524 |
| 353 | (±)-cis | EtNHCO | NH | 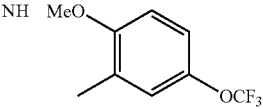 | 4-F | 554 |
| 354 | (±)-cis | EtNHCO | NH | 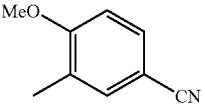 | 4-F | 578 |
| 355 | (±)-cis | EtNHCO | NH | 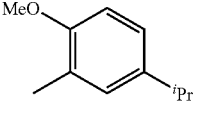 | 4-F | 519 |
| 356 | (±)-cis | EtNHCO | NH | 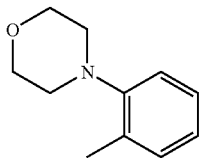 | 4-F | 536 |
| 357 | (±)-cis | EtNHCO | NH | 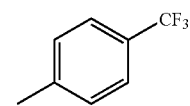 | 4-F | 549 |
| 358 | (±)-cis | EtNHCO | NH | 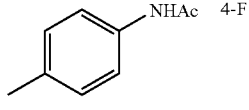 | 4-F | 532 |
| 359 | (±)-cis | EtNHCO | NH |  | 4-F | 521 |

TABLE 16-continued

| Ex. No. | Stereochemistry | R¹ | X | B | R² | MS (ESI) (M + H)⁺ |
|---|---|---|---|---|---|---|
| 360 | (±)-cis | EtNHCO | NH | 3,4-dichlorophenyl | 4-F | 532 |
| 361 | (±)-cis | EtNHCO | NH | 4-(SMe)phenyl | 4-F | 510 |
| 362 | (±)-cis | EtNHCO | NH | 2-furyl | 4-F | 454 |
| 363 | (±)-cis | EtNHCO | NH | 2-pyridyl | 4-F | 465 |
| 364 | (±)-cis | EtNHCO | NH | 2-naphthyl | 4-F | 514 |
| 365 | (±)-cis | EtNHCO | NH | 4-tBu-phenyl | 4-F | 520 |
| 366 | (±)-cis | EtNHCO | NH | 4-(CO₂Me)phenyl | 4-F | 522 |
| 367 | (±)-cis | EtNHCO | NH | 3-F-phenyl | 4-F | 482 |

TABLE 16-continued

| Ex. No. | Stereochemistry | R¹ | X | B | R² | MS (ESI) (M + H)⁺ |
|---|---|---|---|---|---|---|
| 368 | (±)-cis | EtNHCO | NH | 5-methyl-benzo[1,3]dioxole | 4-F | 508 |
| 369 | (±)-cis | EtNHCO | NH | 3,4,5-trimethoxyphenyl (with methyl) | 4-F | 554 |
| 370 | (±)-cis | EtNHCO | NH | 2-chlorophenyl (with methyl) | 4-F | 498 |
| 371 | (±)-cis | EtNHCO | NH | 2,5-dimethylthiophene | 4-F | 484 |
| 372 | (±)-cis | EtNHCO | NH | 2-methylthiophene | 4-F | 470 |
| 373 | (±)-cis | EtNHCO | NH | 3-methylpyridine | 4-F | 465 |

EXAMPLE 374 cis-3-[Bis(4-fluorophenyl)methyl]-1-[3-(diethylamino) propanoyl]-N-(3,5 -dimethylbenzyl)-4-dineamine trifluoroacetate (Process 1)

To a solution of the compound (3.00 g) obtained in Process 2 of Example 343, diisopropylethylamine (2.4 ml) and 3-diethylaminopropionic acid hydrochloride (1.38 g) in dichloromethane (40 ml), WSC.HCl (1.46 g) and HoBt.H₂O (1.03 g) were added, and the reaction mixture was stirred at room temperature for 24 hours. The reaction mixture was poured into water, and then the product was extracted with ethyl acetate. The organic layer was washed with an aqueous 5% sodium hydrogen carbonate solution and saturated brine, dried, and then the solvent was evaporated under reduced pressure. The obtained residue was isolated and purified by amine-treated silica gel column chromatography (hexane: ethyl acetate=1:3) to obtain benzyl[-cis-3-[bis(4-fluorphenyl)methyl]-1-[3-(diethylamino)propanoyl]piperidin-4-yl]carbamate as colorless amorphous (2.75 g).

MS (ESI+): 564 (M+H) (Process 2)

The compound (2.75 g) obtained in Process 1 was reacted and treated in the same manner as in the method described in Process 4 of Example 343 to obtain cis-3-[bis (4-fluorophenyl)methyl]-1-[3-(diethylamino)propanoyl]-4-piperidineamine hydrochloride as white powder (2.53 g).

MS (ESI+): 430 (M+H) Melting point: 183-185° C.

(Process 3)

The compound (28.0 mg) obtained in Process 2 and 3,5-dimethylbenzaldehyde (16.1 mg) were reacted and treated in the same manner as in the method described in Process 5 of Example 343 to obtain the title compound. Yield: 24.3 mg HPLC analysis (Condition B): Purity 99% (Retention time: 1.68 minutes)

MS (ESI+): 548 (M+H)

The compounds of the following Examples were synthesized from the compound obtained in Process 2 of Example 374 as a starting material by reacting and treating in the same manner as in the method described in Process 3 of Example 374 using the respective corresponding aldehyde derivatives.

TABLE 17

| Ex. No. | Stereochemistry | $R^1$ | X | B | $R^2$ | MS (ESI) $(M+H)^+$ |
|---|---|---|---|---|---|---|
| 374 | (±)-cis | 3,4-diOMe-phenyl | NH | 3,5-diMe-phenyl | 4-F | 548 |
| 375 | (±)-cis | Et₂N-CH₂CH₂-C(O)- | NH | 2-OMe-phenyl | 4-F | 550 |
| 376 | (±)-cis | Et₂N-CH₂CH₂-C(O)- | NH | 2-OEt-phenyl | 4-F | 564 |
| 377 | (±)-cis | Et₂N-CH₂CH₂-C(O)- | NH | 2-CF₃-phenyl | 4-F | 588 |
| 378 | (±)-cis | Et₂N-CH₂CH₂-C(O)- | NH | 3,5-di-CF₃-phenyl | 4-F | 656 |
| 379 | (±)-cis | Et₂N-CH₂CH₂-C(O)- | NH | 2,4-diMe-phenyl | 4-F | 548 |
| 380 | (±)-cis | Et₂N-CH₂CH₂-C(O)- | NH | 2,6-diOMe-phenyl | 4-F | 580 |
| 381 | (±)-cis | Et₂N-CH₂CH₂-C(O)- | NH | 3,4-diOMe-phenyl | 4-F | 580 |

TABLE 17-continued

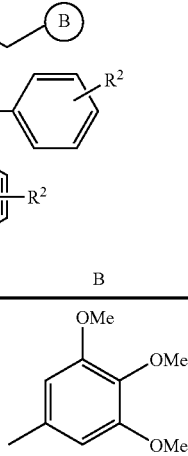

| Ex. No. | Stereochemistry | R$^1$ | X | B | R$^2$ | MS (ESI) (M + H)$^+$ |
|---|---|---|---|---|---|---|
| 382 | (±)-cis | Et$_2$N~~~C(O)~ | NH | 3,4,5-tri-OMe-phenyl | 4-F | 610 |
| 383 | (±)-cis | Et$_2$N~~~C(O)~ | NH | 4-MeO-3-Me, 4-OCF$_3$ phenyl | 4-F | 634 |
| 384 | (±)-cis | Et$_2$N~~~C(O)~ | NH | 4-MeO-3-Me-4-CN phenyl | 4-F | 575 |
| 385 | (±)-cis | Et$_2$N~~~C(O)~ | NH | 4-MeO-3-Me-4-iPr phenyl | 4-F | 592 |
| 386 | (±)-cis | Et$_2$N~~~C(O)~ | NH | 2-(morpholino)-phenyl | 4-F | 605 |
| 387 | (±)-cis | Et$_2$N~~~C(O)~ | NH | 4-OBn-phenyl | 4-F | 626 |
| 388 | (±)-cis | Et$_2$N~~~C(O)~ | NH | 4-CF$_3$-phenyl | 4-F | 588 |
| 389 | (±)-cis | Et$_2$N~~~C(O)~ | NH | 4-NHAc-phenyl | 4-F | 577 |
| 390 | (±)-cis | Et$_2$N~~~C(O)~ | NH | 3,4-diCl-phenyl | 4-F | 588 |
| 391 | (±)-cis | Et$_2$N~~~C(O)~ | NH | 4-SMe-phenyl | 4-F | 566 |

TABLE 17-continued

| Ex. No. | Stereochemistry | R¹ | X | B | R² | MS (ESI) (M + H)⁺ |
|---|---|---|---|---|---|---|
| 392 | (±)-cis | Et₂N~C(O)~ | NH | 2-furyl(Me) | 4-F | 510 |
| 393 | (±)-cis | Et₂N~C(O)~ | NH | 2-pyridyl(Me) | 4-F | 521 |
| 394 | (±)-cis | Et₂N~C(O)~ | NH | 4-tBu-phenyl(Me) | 4-F | 576 |
| 395 | (±)-cis | Et₂N~C(O)~ | NH | 4-CO₂Me-phenyl(Me) | 4-F | 578 |
| 396 | (±)-cis | Et₂N~C(O)~ | NH | 3-F-phenyl(Me) | 4-F | 538 |
| 397 | (±)-cis | Et₂N~C(O)~ | NH | methylenedioxyphenyl(Me) | 4-F | 564 |
| 398 | (±)-cis | Et₂N~C(O)~ | NH | 2,3,4-triOMe-phenyl(Me) | 4-F | 610 |
| 399 | (±)-cis | Et₂N~C(O)~ | NH | 2-Cl-phenyl(Me) | 4-F | 554 |
| 400 | (±)-cis | Et₂N~C(O)~ | NH | 2,5-diMe-thienyl | 4-F | 540 |
| 401 | (±)-cis | Et₂N~C(O)~ | NH | 2-thienyl(Me) | 4-F | 526 |

TABLE 17-continued

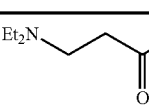

| Ex. No. | Stereochemistry | R¹ | X | B | R² | MS (ESI) (M + H)⁺ |
|---|---|---|---|---|---|---|
| 402 | (±)-cis | Et₂N~~~C(=O)~ | NH | 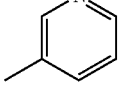 | 4-F | 521 |
| 403 | (±)-cis | Et₂N~~~C(=O)~ | NH | 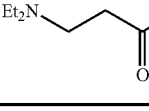 | 4-F | 521 |

Example 404 cis-3-Benzyl-4-[[3,5-bis(trifluoromethyl)benzyl]oxy]piperidine

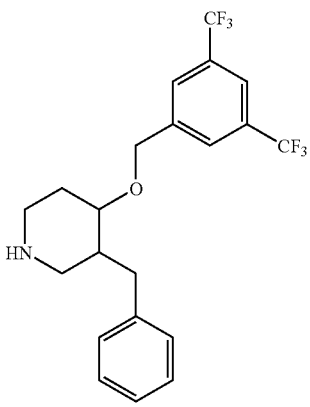

To a solution of the compound (4.15 g) obtained in Reference Example 55 in THF (10 ml), trifluoroacetic acid (25 ml) was added at 0° C., and the obtained mixture was stirred at room temperature for 2 hours. The reaction mixture was made basic with an aqueous 4 N sodium hydroxide solution, and then extracted with ethyl acetate. The extract was washed with an aqueous saturated sodium hydrogen carbonate solution and brine dried, and then the solvent was evaporated under reduced pressure to obtain the title compound as pale yellow oil 73 g, quantitative).

¹H-NMR (CDCl₃): δ 1.65-1.90 (1H, m), 1.95-2.40 (2H, m), 2.55-2.80 (2H, m), 2.80-3.20 (4H, m), 3.60 (1H, brs), 4.42 (1H, d, J=12.6 Hz), 4.69 (1H, d, J=12.6 Hz), 5.26 (1H, brs), 7.05-7.35 (5H, m), 7.82 (2H, s), 7.85 (1H, s).

MS (ESI+): 418 (M+H).

Example 405 cis-3-Benzyl-4-[[3,5-bis(trifluoromethyl)benzyl]oxy]-N-methyl-1-piperidinecarboxamide

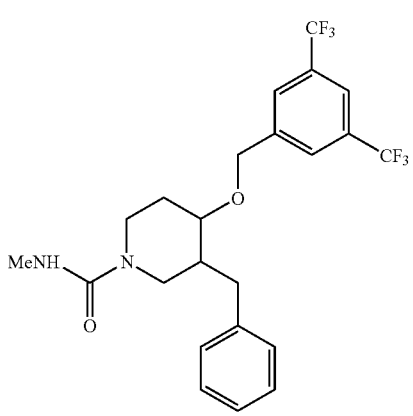

To a solution of the compound (0.39 g) obtained in Example 404 in THF (10 ml), methyl isocyanate (0.12 ml) was added, and the reaction mixture was stirred at room temperature for 17 hours. The solvent was evaporated under reduced pressure, and then the obtained residue was isolated and purified by silica gel column chromatography (ethyl acetate) to obtain the title compound as colorless crystals (0.27 g, 61%).

Melting point: 160-161° C. ¹H-NMR (CDCl₃): δ 1.5-1.7 (1H, m), 1.85-2.20 (2H, m), 2.57-2.82 (2H, m), 2.80 (3H, d, J=4.4 Hz), 3.14 (1H, dd, J=13.0, 9.8 Hz), 3.25-3.65 (4H, m), 4.33 (1H, q, J=4.4 Hz), 4.46 (1H, d, J=12.6 Hz), 4.70 (1H, d, J=12.6 Hz), 7.10-7.35 (5H, m), 7.83 (3H, s).

MS (ESI+): 475 (M+H)

Example 406 cis-1-Acetyl-3-benzyl-4-[[3,5-bis(trifluoromethyl)benzyl]oxy]piperidine

To a solution of the compound (0.40 g) obtained in Example 404 in THF (4 ml), acetyl chloride (0.075 ml) and Et$_3$N (0.147 ml) were added at room temperature, and the reaction mixture was stirred at the same temperature for 1 hour. The reaction mixture was concentrated under reduced pressure, and then the residue was dissolved in ethyl acetate. The organic layer was washed with 1 N hydrogen chloride and brine, dried, and then the solvent was evaporated under reduced pressure. The obtained residue was purified by preparative thin layer chromatography to obtain the title compound as pale yellow oil (0.275 g, 79%).

HPLC analysis (Condition B): Purity 96% (Retention time: 4.00 minutes)

MS (ESI+): 460 (M+H).

The compounds of the following Examples were synthesized from the compound obtained in Example 404 as a starting material by reacting and treating in the same manner as in the method described in Example 406 using the respective corresponding acid chloride or sulfonyl chloride derivatives.

Example 409 cis-N-[3-[3-Benzyl-4-[[3,5-bis(trifluoromethyl)benzyl]oxy]-1-piperidinyl]-3-oxopropyl]-N,N-diethylamine

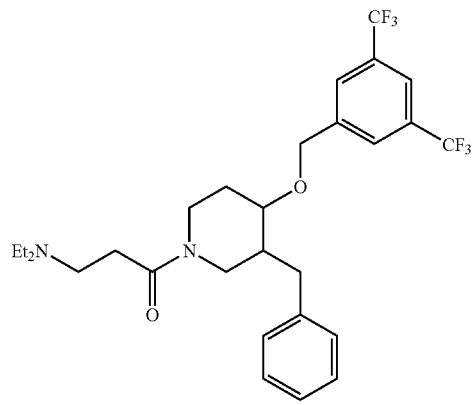

To a solution of the compound (0.15 g) obtained in Example 404, 3-diethylaminopropionic acid hydrochloride

TABLE 18

| Ex. No. | Stereochemistry | R$^1$ | X | B | R$^2$ | MS (ESI) (M + H)$^+$ |
|---|---|---|---|---|---|---|
| 406 | (±)-cis | Ac | O | 3,5-bis(CF$_3$)-phenyl | H | 460 |
| 407 | (±)-cis | MeSO$_2$ | O | 3,5-bis(CF$_3$)-phenyl | H | 496 |
| 408 | (±)-cis | PhC(O) | O | 3,5-bis(CF$_3$)-phenyl | H | 522 |

(0.078 mg), Et$_3$N (0.150 ml) and HoBt.H$_2$O (0.083 mg) in DMF (2 ml), WSC.HCl (0.138 mg) was added, and the reaction mixture was stirred at room temperature for 12 hours. The reaction mixture was concentrated under reduced pressure, and then the residue was dissolved in ethyl acetate. The organic layer was washed with an aqueous saturated sodium bicarbonate solution and brine, dried, and then the solvent was evaporated under reduced pressure. The obtained residue was purified by preparative thin layer chromatography to obtain the title compound as pale yellow oil (0.100 g, 51%).

HPLC analysis (Condition B): Purity 97% (Retention time: 3.31 minutes)

MS (ESI+): 545 (M+H).

Example 410

Ethyl 2-[[[3-benzyl-4-[[3,5-bis(trifluoromethyl)benzyl]oxy]-1-piperidinyl]carbonyl]amino]benzoate The compound (0.15 g) obtained in Example 404 and ethyl 2-isocyanatobenzoate (0.076 mg) were reacted and treated in the same manner as in the method described in Example 6 excluding Et$_3$N to obtain the title compound as pale yellow oil (0.139 g, 64%).

HPLC analysis (Condition B): Purity 97% (Retention time: 4.74 minutes)

MS (ESI+): 609 (M+H)

The compounds of the following Examples were synthesized by reacting and treating in the same manner as in the method described in Example 410 using the respective corresponding isocyanate derivatives.

Example 412

(−)-cis-4-[[3,5-Bis(trifluoromethyl)benzyl]oxy]-N-methyl-3-phenyl-1-piperidinecarboxamide

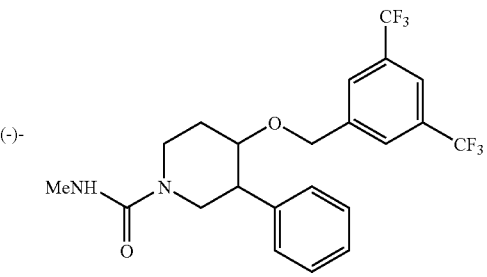

The compound (4.22 g) obtained in Example 6 was optically resolved with chiral HPLC, and the fractions were concentrated under reduced pressure to obtain the title compound (1.34 g) as white powder.

Chiral HPLC Condition

Column: CHIRALCEL OJ 50 mm ID×500 mm L

Solvent: hexane/ethanol=97/3

Flow rate: 70 ml/min

Temperature: 30° C.

Detection method: UV 220 nm

[α]$_D^{25}$ −121.4° (c 1.0, MeOH)

MS (ESI+): 461 (M+H)

TABLE 19

| Ex. No. | Stereochemistry | R$^1$ | X | B | R$^2$ | MS (ESI) (M + H)$^+$ |
|---|---|---|---|---|---|---|
| 410 | (±)-cis | EtO$_2$C-C$_6$H$_4$-NH-C(O)- | O | 3,5-(CF$_3$)$_2$-C$_6$H$_3$ | H | 609 |
| 411 | (±)-cis | EtO$_2$C-CH$_2$-NH-C(O)- | O | 3,5-(CF$_3$)$_2$-C$_6$H$_3$ | H | 547 |

Example 413

(+)-cis-4-[[3,5-Bis(trifluoromethyl)benzyl]oxy]-N-methyl-3-phenyl-1-piperidinecarboxamide

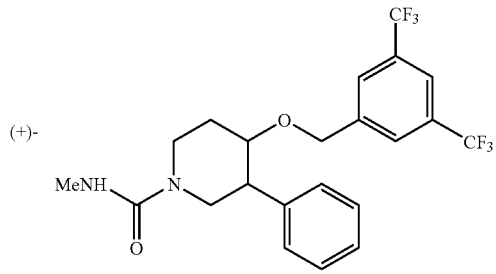

The compound (4.22 g) obtained in Example 6 was optically resolved with chiral HPLC, and the fractions were concentrated under reduced pressure to obtain the title compound (1.34 g) as white powder.
Chiral HPLC Condition
Column: CHIRALCEL OD 50 mm ID×500 mm L
Solvent: hexane/2-propanol=8/2
Flow rate: 70 ml/min
Temperature: 30° C.
Detection method: UV 220 nm
$[\alpha]_D^{25}$+120.7° (c 1.0, MeOH)
MS (ESI+): 461 (M+H)

Example 414

(−)-trans-4-[[3,5-Bis(trifluoromethyl)benzyl]oxy]-N-methyl-3-phenyl-1-piperidinecarboxamide

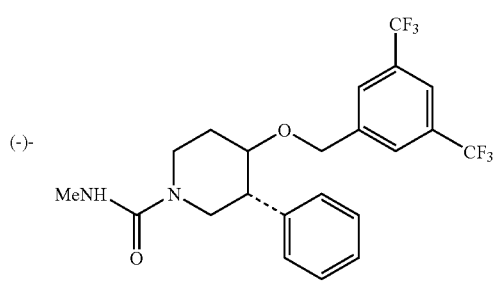

(Process 1)
A crude product (7.7 g, (±)-trans-form:(±)-cis-form=1:10) obtained in Process 3 of Reference Example 1 was reacted and treated in the same manner as in the methods described in Example 1 and Example 6 to obtain 4-[[3,5-bis(trifluoromethyl)benzyl]oxy]-N-methyl-3-phenyl-1-piperidinecarboxamide in a mixture (4.2 g) of (±)-trans-form:(±)-cis-form=1:10.
(Process 2)
The compound (4.22 g) obtained in Process 1 was optically resolved with chiral HPLC, and the fractions were concentrated under reduced pressure to obtain the title compound (0.18 g) as white powder.
Chiral HPLC Condition
Column: CHIRALCEL OD 50 mm ID×500 mm L
Solvent: hexane/2-propanol=9/1
Flow rate: 70 ml/min
Temperature: 30° C.
Detection method: UV 220 nm
$[\alpha]_D^{25}$−34.3° (c 1.0, MeOH)
MS (ESI+): 461 (M+H)

Example 415

(+)-trans-4-[[3,5-Bis(trifluoromethyl)benzyl]oxy]-N-methyl-3-phenyl-1-piperidinecarboxamide

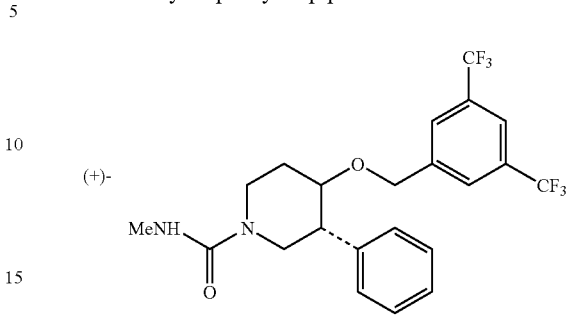

The compound (4.22 g) obtained in Process 1 of Example 414 was optically resolved with chiral HPLC, and the fractions were concentrated under reduced pressure to obtain the title compound (0.19 g) as white powder.
Chiral HPLC Condition
Column: CHIRALPAK AD 50 mm ID×500 mm L
Solvent: hexane/2-propanol=92/8
Flow rate: 70 ml/min
Temperature: 30° C.
Detection method: UV 220 nm
$[\alpha]_D^{25}$+33.0+ (c 1.0, MeOH)
MS (ESI+): 461 (M+H)

Example 416 cis-4-[[3,5-Bis(trifluoromethyl)benzyl]oxy]-N-methyl-3-phenyl-1-piperidinecarbothioamide

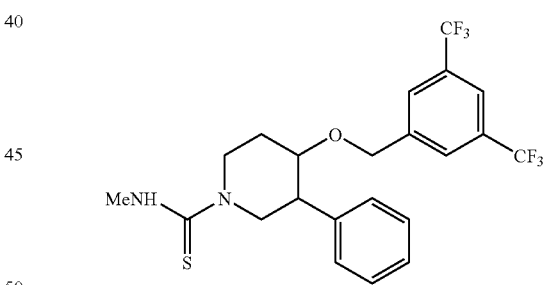

To a solution of the compound (0.20 g) obtained in Example 1 and Et$_3$N (0.16 ml) in acetonitrile (10 ml), methyl isothiocyanate (0.083 g) was added, and the reaction mixture was stirred at room temperature for 14 hours. The reaction mixture was poured into water, and then the product was extracted with ethyl acetate. The organic layer was washed with an aqueous 10% citric acid solution and saturated brine, dried, and then the solvent was evaporated under reduced pressure. The obtained residue was isolated and purified by silica gel column chromatography (ethyl acetate:hexane=1:1) to obtain the title compound as colorless oil (0.22 g, 99%).
HPLC analysis (Condition B): Purity 99% (Retention time: 3.92 minutes)
MS (ESI+): 477 (M+H)

Example 417 cis-4-[[3,5-Bis(trifluoromethyl)benzyl]oxy]-1-ethyl-3-phenylpiperidine oxalate

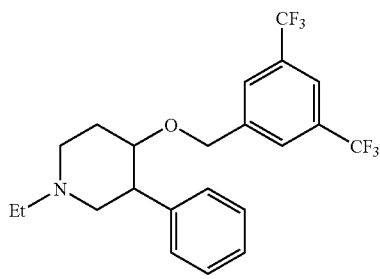

To a solution of the compound (0.88 g) obtained in Example 2 in THF (10 ml), 1 M borane and THF complex (10 ml) was added at 0° C., and the reaction mixture was stirred at 80° C. for 2 hours. The reaction mixture was cooled, and then methanol (2 ml) was added thereto, and concentrated under reduced pressure. To the obtained residue, 6 N hydrogen chloride (6 ml) and methanol (6 ml) were added, and the reaction mixture was stirred at 100° C. for 2 hours. The reaction mixture was cooled, and then made basic with an aqueous 12 N sodium hydroxide solution. The mixture was concentrated under reduced pressure, and then the product was extracted with ethyl acetate. The organic layer was washed with saturated brine, dried, and then the solvent was evaporated under reduced pressure. The obtained residue was isolated and purified by silica gel column chromatography (acetone:methanol=20:1), and treated with 1 equivalent of oxalic acid to obtain the title compound as colorless crystals (0.52 g, 61%).

HPLC analysis (Condition B): Purity 99% (Retention time: 2.91 minutes)

MS (ESI+): 432 (M+H)

Example 418 cis-4-[[3,5-Bis(trifluoromethyl)benzyl]oxy]-3-phenyl-1-propionylpiperidine

To a solution of the compound (132 mg) obtained in Example 1, propionic acid (32 mg) and Et$_3$N (0.083 ml) in DMF (5 ml), WSC.HCl (0.15 g) and HoBt.H$_2$O (0.092 g) were added, and the reaction mixture was stirred at room temperature for 24 hours. The reaction mixture was poured into water, and then the product was extracted with ethyl acetate. The organic layer was washed with an aqueous saturated sodium hydrogen carbonate solution and saturated brine, dried, and then the solvent was evaporated under reduced pressure. The obtained residue was purified by preparative HPLC to obtain the title compound as colorless amorphous.

Yield: 75 mg

MS (ESI+): 460 (M+H)

The compounds of the following Examples were synthesized from the compound obtained in Examples 1, 23, 487, 509, 515, 519, 521, 524, 527, 534, 537, 539, 541, 543, 545, 547, 549, 553, 566, 609, 663, 691, 696, 701, 703, 708, 711, 714, 720, 732, 733, 734, 744, 794, 795 or 796 as a starting material by reacting and treating in the same manner as in the method described in Example 418 using the respective corresponding carboxylic acid derivatives.

TABLE 20

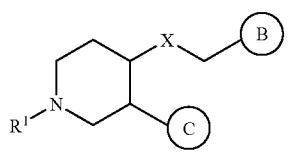

| Ex. No. | Stereo-chemistry | R$^1$ | X | B | C | MS (ESI) (M + H)$^+$ |
|---|---|---|---|---|---|---|
| 418 | (±)-cis | EtCO | O | 3,5-bis(CF$_3$)phenyl | phenyl | 460 |
| 419 | (±)-cis | 2-pyridyl-C(O)- | O | 3,5-bis(CF$_3$)phenyl | phenyl | 509 |
| 420 | (±)-cis | MeOCH$_2$CO | O | 3,5-bis(CF$_3$)phenyl | phenyl | 476 |

TABLE 20-continued

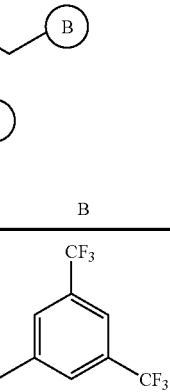

| Ex. No. | Stereo-chemistry | R[1] | X | B | C | MS (ESI) (M + H)[+] |
|---|---|---|---|---|---|---|
| 422 | (±)-cis | tBuCO | O | 3,5-bis(CF$_3$)phenyl | phenyl | 489 |
| 423 | (±)-cis | 2-pyridyl-CH$_2$-CO- | O | 3,5-bis(CF$_3$)phenyl | phenyl | 523 |
| 424 | (±)-cis | 1H-imidazol-4-yl-CH$_2$-CO- | O | 3,5-bis(CF$_3$)phenyl | phenyl | 512 |
| 425 | (±)-cis | PhCH=CH-CO- | O | 3,5-bis(CF$_3$)phenyl | phenyl | 534 |
| 426 | (±)-cis | 1H-tetrazol-1-yl-CH$_2$-CO- | O | 3,5-bis(CF$_3$)phenyl | phenyl | 514 |
| 428 | (±)-cis | pyrazin-2-yl-CO- | O | 3,5-bis(CF$_3$)phenyl | phenyl | 510 |
| 429 | (±)-cis | thien-2-yl-CO- | O | 3,5-bis(CF$_3$)phenyl | phenyl | 514 |
| 430 | (±)-cis | Et$_2$N-CH$_2$CH$_2$-CO- | O | 3,5-bis(CF$_3$)phenyl | phenyl | 531 |

TABLE 20-continued

| Ex. No. | Stereo-chemistry | R[1] | X | B | C | MS (ESI) (M + H)+ |
|---|---|---|---|---|---|---|
| 431 | (±)-cis | MeO₂C-CH₂CH₂-C(=O)- | O | 3,5-bis(CF₃)phenyl | phenyl | 518 |
| 432 | (±)-cis | thiophen-3-yl-C(=O)- | O | 3,5-bis(CF₃)phenyl | phenyl | 514 |
| 433 | (±)-cis | 1H-benzimidazol-5-yl-C(=O)- | O | 3,5-bis(CF₃)phenyl | phenyl | 548 |
| 434 | (±)-cis | 4-(Me₂N)phenyl-C(=O)- | O | 3,5-bis(CF₃)phenyl | phenyl | 551 |
| 435 | (±)-cis | pyridin-3-yl-CH₂CH₂-C(=O)- | O | 3,5-bis(CF₃)phenyl | phenyl | 537 |
| 436 | (±)-cis | pyridin-3-yl-C(=O)- | O | 3,5-bis(CF₃)phenyl | phenyl | 509 |
| 437 | (±)-cis | pyridin-4-yl-C(=O)- | O | 3,5-bis(CF₃)phenyl | phenyl | 509 |
| 438 | (±)-cis | pyridin-2-yl-C(=O)- | O | 3,5-bis(CF₃)phenyl | phenyl | 509 |

TABLE 20-continued

| Ex. No. | Stereo-chemistry | R¹ | X | B | C | MS (ESI) (M + H)⁺ |
|---|---|---|---|---|---|---|
| 439 | (±)-cis | 3-pyridyl-CH₂-C(O)- | O | 3,5-bis(CF₃)phenyl | phenyl | 523 |
| 442 | (±)-cis | ⁿPrCO | O | 3,5-bis(CF₃)phenyl | phenyl | 474 |
| 443 | (±)-cis | ⁱPrCO | O | 3,5-bis(CF₃)phenyl | phenyl | 474 |
| 444 | (±)-cis | ᵗBuCO | O | 3,5-bis(CF₃)phenyl | phenyl | 488 |
| 453 | (±)-cis | (N-Ac-pyrrolidin-2-yl)C(O)- | O | 3,5-bis(CF₃)phenyl | phenyl | 543 |
| 454 | (±)-cis | (N-Ac-pyrrolidin-2-yl)C(O)- | O | 3,5-bis(CF₃)phenyl | phenyl | 543 |
| 456 | (±)-cis | Et₂N-CH₂-CH₂-C(O)- | O | 3,5-bis(CF₃)phenyl | phenyl | 531 |
| 457 | (±)-cis | (pyrazin-2-yl)C(O)- | O | 3,5-bis(CF₃)phenyl | phenyl | 510 |

TABLE 20-continued

| Ex. No. | Stereo-chemistry | R¹ | X | B | C | MS (ESI) (M + H)⁺ |
|---|---|---|---|---|---|---|
| 458 | (±)-cis | 3-pyridyl-CH₂CH₂-C(O)-CH₃ | O | 3,5-bis(CF₃)phenyl | phenyl | 537 |
| 460 | (±)-cis | 4-(CF₃)benzoyl-N-piperidinyl-4-acetyl | O | 3,5-bis(CF₃)phenyl | phenyl | 687 |
| 465 | (±)-cis | N-Ac-prolyl-N-piperidinyl-4-acetyl | O | 3,5-bis(CF₃)phenyl | phenyl | 654 |
| 467 | (±)-cis | Me-C(O)-N-piperidinyl-4-acetyl | O | 3,5-bis(CF₃)phenyl | phenyl | 571 |
| 468 | (±)-cis | iPr-C(O)-N-piperidinyl-4-acetyl | O | 3,5-bis(CF₃)phenyl | phenyl | 585 |
| 470 | (±)-cis | MeO-CH₂-C(O)-N-piperidinyl-4-acetyl | O | 3,5-bis(CF₃)phenyl | phenyl | 587 |
| 471 | (±)-cis | Me₂N-CH₂-C(O)-N-piperidinyl-4-acetyl | O | 3,5-bis(CF₃)phenyl | phenyl | 600 |

TABLE 20-continued

| Ex. No. | Stereo-chemistry | R¹ | X | B | C | MS (ESI) (M + H)⁺ |
|---|---|---|---|---|---|---|
| 472 | (±)-cis | F₃C-CH₂-C(O)-N-piperidine-4-C(O)-CH₃ | O | 3,5-bis(CF₃)phenyl | phenyl | 625 |
| 473 | (±)-cis | AcHN-CH(CH₂Ph)-C(O)-CH₃ | O | 3,5-bis(CF₃)phenyl | phenyl | 593 |
| 474 | (±)-cis | HO-(NAc-pyrrolidinyl)-C(O)-CH₃ | O | 3,5-bis(CF₃)phenyl | phenyl | 559 |
| 475 | (±)-cis | AcHN-C₆H₄-C(O)-CH₃ | O | 3,5-bis(CF₃)phenyl | phenyl | 565 |
| 476 | (±)-cis | Ac-N-piperidine-4-C(O)-CH₃ | O | 3,5-bis(CF₃)phenyl | o-tolyl (Me) | 571 |
| 477 | (±)-cis | BnO-(NH-pyrrolidinyl)-C(O)-CH₃ | O | 3,5-bis(CF₃)phenyl | phenyl | 607 |
| 479 | (±)-cis | HF₂C-C(O)-N-piperidine-4-C(O)-CH₃ | O | 3,5-bis(CF₃)phenyl | phenyl | 593 |

TABLE 20-continued

| Ex. No. | Stereo-chemistry | R¹ | X | B | C | MS (ESI) (M + H)⁺ |
|---|---|---|---|---|---|---|
| 481 | (±)-cis | 1-hydroxycyclopropyl carbonyl methyl | O | 3,5-bis(CF₃)phenyl | phenyl | 488 |
| 483 | (±)-cis | 3-AcHN-phenyl acetyl | O | 3,5-bis(CF₃)phenyl | phenyl | 565 |
| 484 | (±)-cis | 5-oxopyrrolidin-2-yl carbonyl methyl | O | 3,5-bis(CF₃)phenyl | phenyl | 515 |
| 485 | (±)-cis | 2-AcHN-phenyl acetyl | O | 3,5-bis(CF₃)phenyl | phenyl | 565 |
| 488 | (±)-cis | 5-oxoprolyl-(4-acetyl)piperidinyl | O | 3,5-bis(CF₃)phenyl | phenyl | 626 |
| 489 | (±)-cis | 1-Ac-piperidin-3-yl carbonyl methyl | O | 3,5-bis(CF₃)phenyl | phenyl | 557 |
| 490 | (±)-cis | 1-hydroxycyclopropyl-carbonyl-(4-acetyl)piperidinyl | O | 3,5-bis(CF₃)phenyl | phenyl | 599 |

TABLE 20-continued

| Ex. No. | Stereo-chemistry | R¹ | X | B | C | MS (ESI) (M + H)⁺ |
|---|---|---|---|---|---|---|
| 496 | (±)-cis | cyclopropyl-C(O)-N-piperidinyl-C(O)- | O | 3,5-bis(CF₃)phenyl | phenyl | 583 |
| 497 | (±)-cis | AcHN-CH(CONH₂)-C(O)- | O | 3,5-bis(CF₃)phenyl | phenyl | 560 |
| 499 | (±)-cis | 5-MeO-oxazol-2-yl-C(O)- | O | 3,5-bis(CF₃)phenyl | phenyl | 529 |
| 502 | (±)-cis | AcN-piperidin-4-yl-C(O)-N-piperidin-4-yl-C(O)- | O | 3,5-bis(CF₃)phenyl | phenyl | 668 |
| 507 | (±)-cis | AcHN-CH₂-C(O)- | O | 3,5-bis(CF₃)phenyl | phenyl | 503 |
| 514 | (±)-cis | Et₂N-CH₂CH₂-C(O)- | O | 3,5-bis(CF₃)phenyl | 3,4-dichlorophenyl | 599 |
| 517 | (±)-cis | AcN-piperidin-4-yl-C(O)- | O | 3,5-bis(CF₃)phenyl | 3,4-dichlorophenyl | 625 |

TABLE 20-continued

| Ex. No. | Stereo-chemistry | R¹ | X | B | C | MS (ESI) (M + H)⁺ |
|---|---|---|---|---|---|---|
| 522 | (±)-cis | AcN-piperidine-C(O)- | O | 3,5-(CF₃)₂-phenyl | 4-Me-phenyl | 571 |
| 525 | (±)-cis | AcN-piperidine-C(O)- | O | 3,5-(CF₃)₂-phenyl | 3-F-phenyl | 575 |
| 528 | (±)-cis | AcN-piperidine-C(O)- | O | 3,5-(CF₃)₂-phenyl | 4-F-phenyl | 575 |
| 529 | (±)-cis | NAc-pyrrolidine-C(O)- | O | 3,5-(CF₃)₂-phenyl | 4-F-phenyl | 561 |
| 533 | (±)-cis | MeO-CH₂-C(O)-N-piperazine-N-CH₂-C(O)- | O | 3,5-(CF₃)₂-phenyl | 4-F-phenyl | 620 |
| 535 | (±)-cis | AcN-piperidine-C(O)- | O | 3,5-(CF₃)₂-phenyl | 2-Me-4-F-phenyl | 589 |
| 538 | (±)-cis | AcN-piperidine-C(O)- | O | 3,5-(CF₃)₂-phenyl | pyridin-2-yl | 558 |
| 540 | (±)-cis | AcN-piperidine-C(O)- | O | 4-MeO-2-OCF₃-phenyl | phenyl | 535 |

TABLE 20-continued

| Ex. No. | Stereo-chemistry | R¹ | X | B | C | MS (ESI) (M + H)⁺ |
|---|---|---|---|---|---|---|
| 542 | (±)-cis | AcN-piperidine-C(O)- | O | 2,4-diCl-phenyl | phenyl | 489 |
| 544 | (±)-cis | AcN-piperidine-C(O)- | O | 2,4-diMe-phenyl | phenyl | 449 |
| 546 | (±)-cis | AcN-piperidine-C(O)- | O | 4-CF₃-2-F-phenyl | phenyl | 507 |
| 548 | (±)-cis | AcN-piperidine-C(O)- | O | 3-F-5-CF₃-phenyl | phenyl | 507 |
| 550 | (±)-cis | AcN-piperidine-C(O)- | O | 3-NO₂-5-CF₃-phenyl | phenyl | 534 |
| 551 | (±)-cis | AcN-piperidine-C(O)- | O | 2,4-diCF₃-phenyl | phenyl | 557 |
| 552 | (±)-cis | AcN-piperidine-C(O)- | O | 3-Me-5-CF₃-phenyl | phenyl | 503 |
| 554 | (±)-cis | AcN-piperidine-C(O)- | O | 3-Br-5-CF₃-phenyl | phenyl | 567, 569 |

TABLE 20-continued
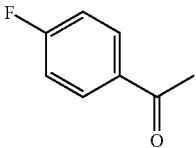
| Ex. No. | Stereo-chemistry | R¹ | X | B | C | MS (ESI) (M + H)⁺ |
|---|---|---|---|---|---|---|
| 558 | (±)-cis | 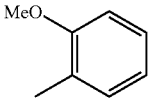 | NH | 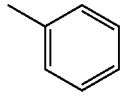 | 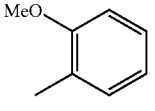 | 419 |
| 559 | (±)-cis | Ac | NH | 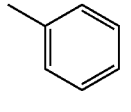 | 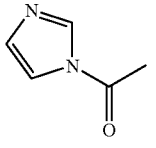 | 339 |
| 563 | (±)-cis | 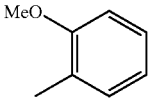 | NH | 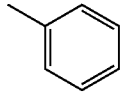 | 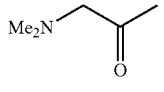 | 391 |
| 571 | (±)-cis | 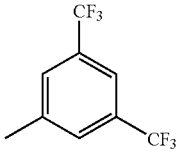 | NH | 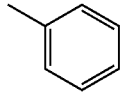 | 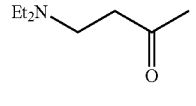 | 488 |
| 572 | (±)-cis | 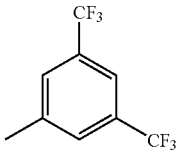 | NH | 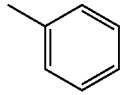 | 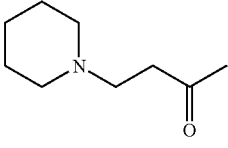 | 530 |
| 573 | (±)-cis | 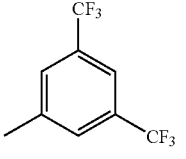 | NH | 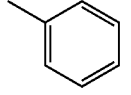 | 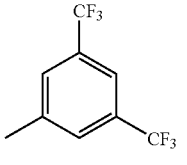 | 542 |
| 574 | (±)-cis | Ac | NH | 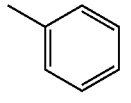 | 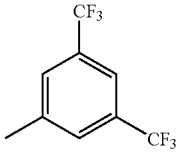 | 445 |
| 575 | (±)-cis | EtCO | NH | 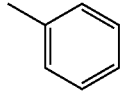 |  | 459 |

TABLE 20-continued

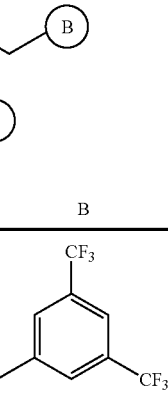

| Ex. No. | Stereo-chemistry | R[1] | X | B | C | MS (ESI) (M + H)+ |
|---|---|---|---|---|---|---|
| 576 | (±)-cis | MeOCH$_2$CO | NH | 3,5-bis(CF$_3$)C$_6$H$_3$ | C$_6$H$_5$ | 475 |
| 578 | (±)-cis | $^t$BuCO | NH | 3,5-bis(CF$_3$)C$_6$H$_3$ | C$_6$H$_5$ | 488 |
| 579 | (±)-cis | 2-pyridyl-CH$_2$-CO | NH | 3,5-bis(CF$_3$)C$_6$H$_3$ | C$_6$H$_5$ | 522 |
| 580 | (±)-cis | imidazol-4-yl-CH$_2$-CO | NH | 3,5-bis(CF$_3$)C$_6$H$_3$ | C$_6$H$_5$ | 511 |
| 581 | (±)-cis | PhCH=CH-CO | NH | 3,5-bis(CF$_3$)C$_6$H$_3$ | C$_6$H$_5$ | 533 |
| 582 | (±)-cis | tetrazol-1-yl-CH$_2$-CO | NH | 3,5-bis(CF$_3$)C$_6$H$_3$ | C$_6$H$_5$ | 513 |
| 584 | (±)-cis | pyrazin-2-yl-CO | NH | 3,5-bis(CF$_3$)C$_6$H$_3$ | C$_6$H$_5$ | 509 |
| 585 | (±)-cis | thien-2-yl-CO | NH | 3,5-bis(CF$_3$)C$_6$H$_3$ | C$_6$H$_5$ | 513 |

TABLE 20-continued

| Ex. No. | Stereo-chemistry | R¹ | X | B | C | MS (ESI) (M + H)⁺ |
|---|---|---|---|---|---|---|
| 586 | (±)-cis | Et₂N-CH₂CH₂-C(O)-CH₃ | NH | 3,5-bis(CF₃)phenyl | phenyl | 530 |
| 587 | (±)-cis | MeO₂C-CH₂CH₂-C(O)-CH₃ | NH | 3,5-bis(CF₃)phenyl | phenyl | 517 |
| 588 | (±)-cis | 3-thienyl-C(O)-CH₃ | NH | 3,5-bis(CF₃)phenyl | phenyl | 513 |
| 589 | (±)-cis | benzimidazol-5-yl-C(O)-CH₃ | NH | 3,5-bis(CF₃)phenyl | phenyl | 547 |
| 590 | (±)-cis | 4-(Me₂N)phenyl-C(O)-CH₃ | NH | 3,5-bis(CF₃)phenyl | phenyl | 550 |
| 591 | (±)-cis | 3-pyridyl-CH₂CH₂-C(O)-CH₃ | NH | 3,5-bis(CF₃)phenyl | phenyl | 536 |
| 592 | (±)-cis | 3-pyridyl-C(O)-CH₃ | NH | 3,5-bis(CF₃)phenyl | phenyl | 508 |
| 593 | (±)-cis | 4-pyridyl-C(O)-CH₃ | NH | 3,5-bis(CF₃)phenyl | phenyl | 508 |

TABLE 20-continued
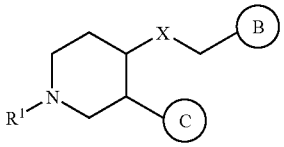
| Ex. No. | Stereo-chemistry | R¹ | X | B | C | MS (ESI) (M + H)⁺ |
|---|---|---|---|---|---|---|
| 594 | (±)-cis | 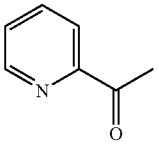 | NH | 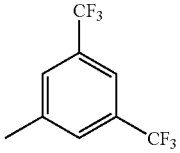 | 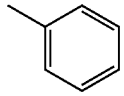 | 508 |
| 595 | (±)-cis | 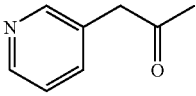 | NH | 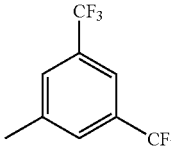 | 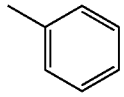 | 522 |
| 598 | (±)-cis | $^n$PrCO | NH | 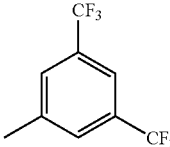 | 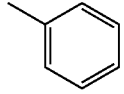 | 473 |
| 599 | (±)-cis | $^i$PrCO | NH | 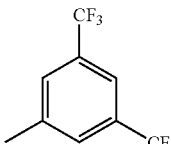 | 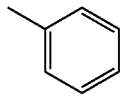 | 473 |
| 600 | (±)-cis | $^t$BuCO | NH | 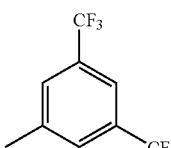 | 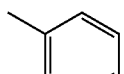 | 487 |
| 601 | (±)-cis | 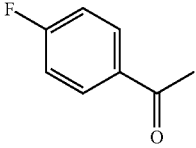 | NH | 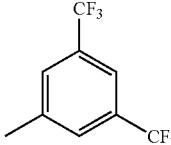 | 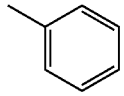 | 525 |
| 602 | (±)-cis | 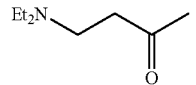 | NH | 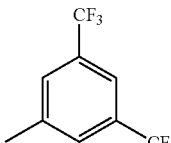 | 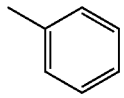 | 530 |
| 603 | (±)-cis | 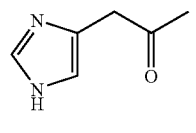 | NH | 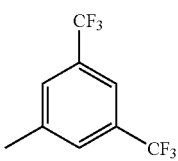 | 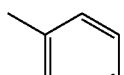 | 511 |

TABLE 20-continued

| Ex. No. | Stereo-chemistry | R¹ | X | B | C | MS (ESI) (M + H)⁺ |
|---|---|---|---|---|---|---|
| 604 | (±)-cis | pyrazinyl-C(O)CH₂- | NH | 3,5-bis(CF₃)phenyl | phenyl | 509 |
| 605 | (±)-cis | 1-Ac-piperidin-4-yl-C(O)CH₂- | NH | 3,5-bis(CF₃)phenyl | phenyl | 556 |
| 614 | (±)-cis | Ac | NH | 2-MeO-5-OCF₃-phenyl (with Me) | phenyl | 423 |
| 615 | (±)-cis | EtCO | NH | 2-MeO-5-OCF₃-phenyl (with Me) | phenyl | 437 |
| 616 | (±)-cis | MeOCH₂CO | NH | 2-MeO-5-OCF₃-phenyl (with Me) | phenyl | 453 |
| 618 | (±)-cis | ᵗBuCO | NH | 2-MeO-5-OCF₃-phenyl (with Me) | phenyl | 466 |
| 619 | (±)-cis | pyridin-2-yl-CH₂C(O)- | NH | 2-MeO-5-OCF₃-phenyl (with Me) | phenyl | 500 |
| 620 | (±)-cis | 1H-imidazol-4-yl-CH₂C(O)- | NH | 2-MeO-5-OCF₃-phenyl (with Me) | phenyl | 489 |
| 621 | (±)-cis | PhCH=CHC(O)CH₂- | NH | 2-MeO-5-OCF₃-phenyl (with Me) | phenyl | 511 |
| 622 | (±)-cis | tetrazol-1-yl-CH₂C(O)- | NH | 2-MeO-5-OCF₃-phenyl (with Me) | phenyl | 491 |

TABLE 20-continued
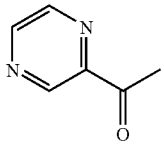
| Ex. No. | Stereo-chemistry | R¹ | X | B | C | MS (ESI) (M + H)⁺ |
|---|---|---|---|---|---|---|
| 624 | (±)-cis | 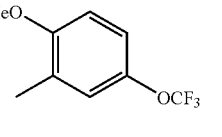 | NH | 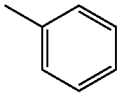 | 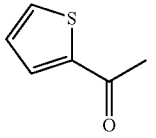 | 487 |
| 625 | (±)-cis | 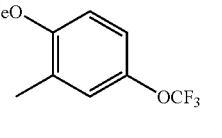 | NH | 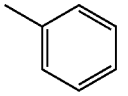 | 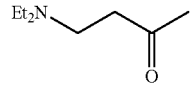 | 491 |
| 626 | (±)-cis | 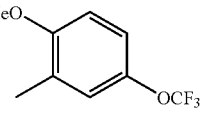 | NH | 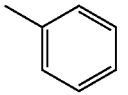 | 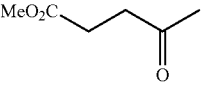 | 508 |
| 627 | (±)-cis | 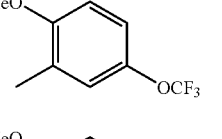 | NH | 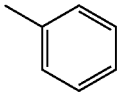 | 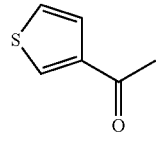 | 495 |
| 628 | (±)-cis | 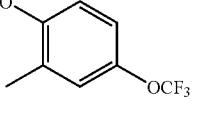 | NH | 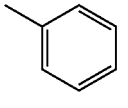 | 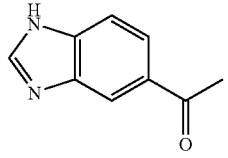 | 491 |
| 629 | (±)-cis | 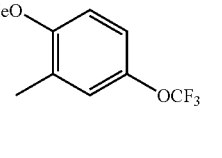 | NH | 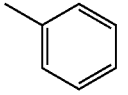 | 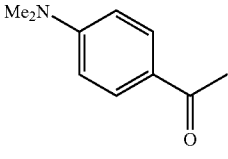 | 525 |
| 630 | (±)-cis | 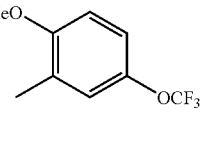 | NH | 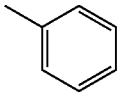 | 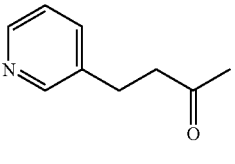 | 528 |
| 631 | (±)-cis | 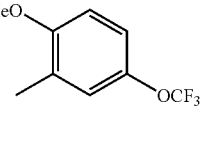 | NH | 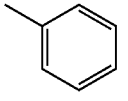 | 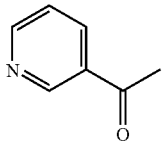 | 514 |
| 632 | (±)-cis | 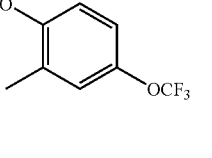 | NH | 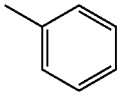 | | 486 |

TABLE 20-continued

| Ex. No. | Stereo-chemistry | R¹ | X | B | C | MS (ESI) (M + H)⁺ |
|---|---|---|---|---|---|---|
| 633 | (±)-cis | 4-pyridyl-C(O)CH₂- | NH | 2-Me-4-OCF₃-5-MeO-phenyl | phenyl | 486 |
| 634 | (±)-cis | 2-pyridyl-C(O)CH₂- | NH | 2-Me-4-OCF₃-5-MeO-phenyl | phenyl | 486 |
| 635 | (±)-cis | 3-pyridyl-CH₂-C(O)CH₂- | NH | 2-Me-4-OCF₃-5-MeO-phenyl | phenyl | 500 |
| 638 | (±)-cis | ⁿPrCO | NH | 2-Me-4-OCF₃-5-MeO-phenyl | phenyl | 451 |
| 639 | (±)-cis | ⁱPrCO | NH | 2-Me-4-OCF₃-5-MeO-phenyl | phenyl | 451 |
| 640 | (±)-cis | ᵗBuCO | NH | 2-Me-4-OCF₃-5-MeO-phenyl | phenyl | 465 |
| 641 | (±)-cis | pyrazin-2-yl-C(O)CH₂- | NH | 2-Me-4-OCF₃-5-MeO-phenyl | phenyl | 487 |
| 642 | (±)-cis | thien-2-yl-C(O)CH₂- | NH | 2-Me-4-OCF₃-5-MeO-phenyl | phenyl | 491 |
| 643 | (±)-cis | Et₂N-CH₂CH₂-C(O)CH₂- | NH | 2-Me-4-OCF₃-5-MeO-phenyl | phenyl | 508 |
| 644 | (±)-cis | EtCO | NH | 2-Me-4-OCF₃-5-MeO-phenyl | phenyl | 437 |

TABLE 20-continued
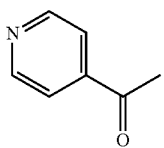
| Ex. No. | Stereo-chemistry | R¹ | X | B | C | MS (ESI) (M + H)⁺ |
|---|---|---|---|---|---|---|
| 646 | (±)-cis | 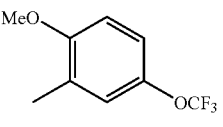 | NH | 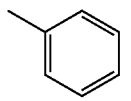 | 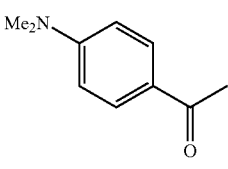 | 486 |
| 647 | (±)-cis | 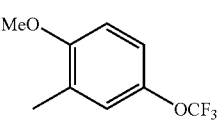 | NH | 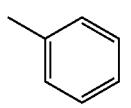 | 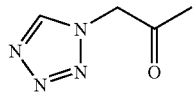 | 528 |
| 648 | (±)-cis | 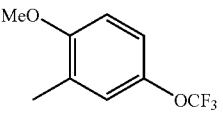 | NH | 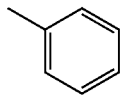 | 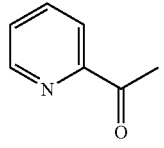 | 491 |
| 649 | (±)-cis | 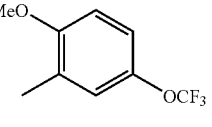 | NH | 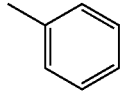 | 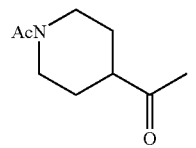 | 486 |
| 651 | (±)-cis | 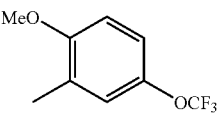 | NH | 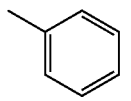 | 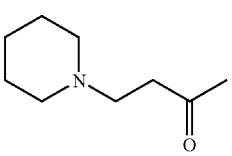 | 534 |
| 653 | (±)-cis | 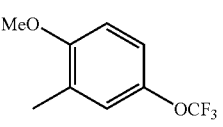 | NH | 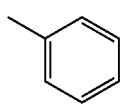 | 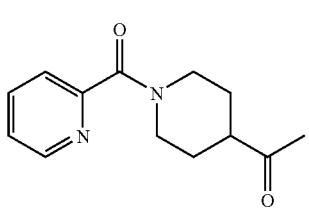 | 520 |
| 658 | (±)-cis | 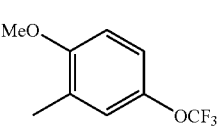 | NH | 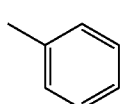 | 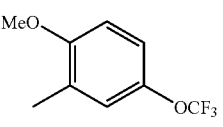 | 597 |
| 666 | (±)-cis | EtCO | NH | 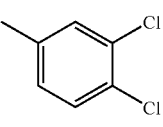 |  | 505 |

TABLE 20-continued

| Ex. No. | Stereo-chemistry | R¹ | X | B | C | MS (ESI) (M + H)⁺ |
|---|---|---|---|---|---|---|
| 694 | (±)-cis | MeOCH₂CO | NH | 2,3-dihydrobenzofuran, 7-Me, 5-iPr | phenyl | 423 |
| 695 | (±)-cis | AcN-piperidinyl-C(O)- | NH | 2,3-dihydrobenzofuran, 7-Me, 5-iPr | phenyl | 504 |
| 699 | (±)-cis | MeOCH₂CO | NH | 2,3-dihydrobenzofuran, 7-Me, 5-OCF₃ | phenyl | 465 |
| 700 | (±)-cis | AcN-piperidinyl-C(O)- | NH | 2,3-dihydrobenzofuran, 7-Me, 5-OCF₃ | phenyl | 546 |
| 705 | (±)-cis | MeOCH₂CO | NH | 4-MeO, 3-Me, 4-iPr phenyl | phenyl | 411 |
| 706 | (±)-cis | AcN-piperidinyl-C(O)- | NH | 4-MeO, 3-Me, 4-iPr phenyl | phenyl | 492 |
| 710 | (±)-cis | AcN-piperidinyl-C(O)- | NH | 4-MeO-3-Me-phenyl-[1,3,4-oxadiazol-2-yl]-5-CF₃ | phenyl | 586 |
| 713 | (±)-cis | AcN-piperidinyl-C(O)- | NH | 4-MeO-3-Me-phenyl-[thiazol-2-yl]-4-Me | phenyl | 547 |

TABLE 20-continued

| Ex. No. | Stereo-chemistry | R¹ | X | B | C | MS (ESI) (M + H)⁺ |
|---|---|---|---|---|---|---|
| 716 | (±)-cis | MeOCH2CO | NH | MeO-phenyl-Me with pyrazole-CF3 | phenyl | 503 |
| 717 | (±)-cis | AcN-piperidine-C(O)- | NH | MeO-phenyl-Me with pyrazole-CF3 | phenyl | 584 |
| 723 | (±)-cis | MeOCH₂CO | NH | methyl-dihydrobenzofuran with tetrazole-CF3 | phenyl | 517 |
| 736 | (±)-cis | F₃C-CH2-C(O)-CH3 | NH | MeO-phenyl-Me with tetrazole-CF3 | phenyl | 543 |
| 737 | (±)-cis | AcN-piperidine(3)-C(O)- | NH | MeO-phenyl-Me with tetrazole-CF3 | phenyl | 586 |
| 738 | (±)-cis | N(Ac)-piperidine(2)-C(O)- | NH | MeO-phenyl-Me with tetrazole-CF3 | phenyl | 586 |
| 739 | (±)-cis | 4H-pyran-4-one-2-C(O)- | NH | MeO-phenyl-Me with tetrazole-CF3 | phenyl | 555 |

TABLE 20-continued

| Ex. No. | Stereo-chemistry | R¹ | X | B | C | MS (ESI) (M + H)⁺ |
|---|---|---|---|---|---|---|
| 740 | (±)-cis | EtOCH₂CO | NH | MeO-phenyl(Me)-tetrazole-CF₃ | phenyl | 519 |
| 741 | (±)-cis | furan-2-yl-C(O)- | NH | MeO-phenyl(Me)-tetrazole-CF₃ | phenyl | 527 |
| 742 | (±)-cis | tetrahydrofuran-2-yl-C(O)- | NH | MeO-phenyl(Me)-tetrazole-CF₃ | phenyl | 531 |
| 743 | (±)-cis | 1-(3,3,3-trifluoropropanoyl)piperidin-4-yl-C(O)- | NH | MeO-phenyl(Me)-tetrazole-CF₃ | phenyl | 654 |
| 745 | (±)-cis | 1-acetylazetidin-3-yl-C(O)- | NH | MeO-phenyl(Me)-tetrazole-CF₃ | phenyl | 558 |
| 751 | (±)-cis | MeOCH₂CH₂OCH₂C(O)- | NH | MeO-phenyl(Me)-tetrazole-CF₃ | phenyl | 549 |
| 752 | (±)-cis | EtOCH₂CH₂C(O)- | NH | MeO-phenyl(Me)-tetrazole-CF₃ | phenyl | 533 |

TABLE 20-continued

| Ex. No. | Stereo-chemistry | R¹ | X | B | C | MS (ESI) (M + H)⁺ |
|---|---|---|---|---|---|---|
| 753 | (±)-cis | AcHN-CH₂-C(=O)- | NH | 4-MeO-3-Me-phenyl-tetrazole-CF₃ | phenyl | 532 |
| 756 | (±)-cis | thiadiazol-4-yl-C(=O)- | NH | 4-MeO-3-Me-phenyl-tetrazole-CF₃ | phenyl | 545 |
| 757 | (±)-cis | tetrazol-1-yl-CH₂-C(=O)- | NH | 4-MeO-3-Me-phenyl-tetrazole-CF₃ | phenyl | 543 |
| 758 | (±)-cis | 1-Me-imidazol-5-yl-C(=O)- | NH | 4-MeO-3-Me-phenyl-tetrazole-CF₃ | phenyl | 541 |
| 760 | (±)-cis | HOCH₂CO | NH | 4-MeO-3-Me-phenyl-tetrazole-CF₃ | phenyl | 491 |
| 761 | (±)-cis | AcNH-CH₂CH₂-C(=O)- | NH | 4-MeO-3-Me-phenyl-tetrazole-CF₃ | phenyl | 546 |
| 762 | (±)-cis | Ac | NH | 4-MeO-3-Me-phenyl-tetrazole-CF₃ | phenyl | 475 |
| 763 | (±)-cis | MeO₂S-CH₂-C(=O)- | NH | 4-MeO-3-Me-phenyl-tetrazole-CF₃ | phenyl | 553 |

TABLE 20-continued

| Ex. No. | Stereo-chemistry | R¹ | X | B | C | MS (ESI) (M + H)⁺ |
|---|---|---|---|---|---|---|
| 764 | (±)-cis | succinimidyl-CH₂-C(O)-Me | NH | MeO-phenyl-Me with tetrazole-CF₃ | phenyl | 572 |
| 765 | (±)-cis | 2-oxopyrrolidinyl-CH₂-C(O)-Me | NH | MeO-phenyl-Me with tetrazole-CF₃ | phenyl | 558 |
| 767 | (±)-cis | HO-C(Me)₂-C(O)- | NH | MeO-phenyl-Me with tetrazole-CF₃ | phenyl | 519 |
| 768 | (±)-cis | MeO₂C-CH₂CH₂-C(O)- | NH | MeO-phenyl-Me with tetrazole-CF₃ | phenyl | 547 |
| 769 | (±)-cis | 5-oxopyrrolidin-2-yl-C(O)- | NH | MeO-phenyl-Me with tetrazole-CF₃ | phenyl | 544 |
| 770 | (±)-cis | Me-C(O)-CH₂CH₂-C(O)- | NH | MeO-phenyl-Me with tetrazole-CF₃ | phenyl | 531 |
| 771 | (±)-cis | 1-hydroxycyclopropyl-C(O)- | NH | MeO-phenyl-Me with tetrazole-CF₃ | phenyl | 517 |

TABLE 20-continued

| Ex. No. | Stereo-chemistry | R¹ | X | B | C | MS (ESI) (M + H)⁺ |
|---|---|---|---|---|---|---|
| 773 | (±)-cis | AcN-piperidine-NHAc | NH | MeO-Ph(Me)-tetrazole-CF₃ | Ph | 601 |
| 774 | (±)-cis | HO-CH(Me)-C(=O)- | NH | MeO-Ph(Me)-tetrazole-CF₃ | Ph | 505 |
| 775 | (±)-cis | thiazolidine-2,4-dione-CH₂-C(=O)- | NH | MeO-Ph(Me)-tetrazole-CF₃ | Ph | 590 |
| 776 | (±)-cis | oxazolidin-2-one-CH₂-C(=O)- | NH | MeO-Ph(Me)-tetrazole-CF₃ | Ph | 560 |
| 777 | (±)-cis | imidazolidin-2-one-CH₂-C(=O)- | NH | MeO-Ph(Me)-tetrazole-CF₃ | Ph | 559 |
| 778 | (±)-cis | 1-Me-hydantoin-CH₂-C(=O)- | NH | MeO-Ph(Me)-tetrazole-CF₃ | Ph | 587 |
| 779 | (±)-cis | hydantoin-CH₂-C(=O)- | NH | MeO-Ph(Me)-tetrazole-CF₃ | Ph | 573 |
| 780 | (±)-cis | piperidin-2-one-CH₂-C(=O)- | NH | MeO-Ph(Me)-tetrazole-CF₃ | Ph | 572 |

TABLE 20-continued
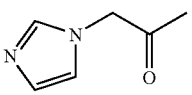
| Ex. No. | Stereo-chemistry | R¹ | X | B | C | MS (ESI) (M + H)⁺ |
|---|---|---|---|---|---|---|
| 781 | (±)-cis | 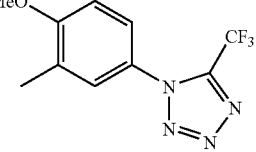 | NH | 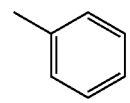 | 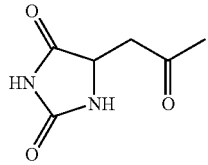 | 541 |
| 782 | (±)-cis | 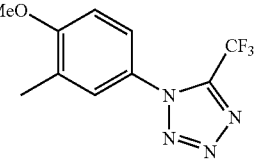 | NH | 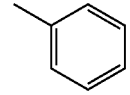 | 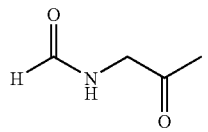 | 573 |
| 783 | (±)-cis | 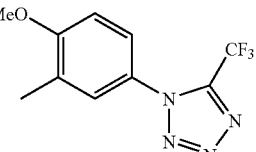 | NH | 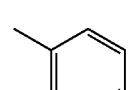 | 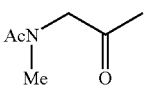 | 518 |
| 784 | (±)-cis | 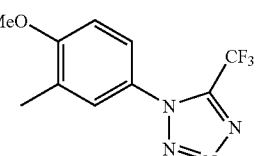 | NH | 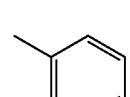 | 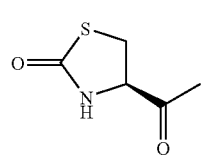 | 546 |
| 788 | (±)-cis | 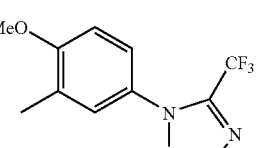 | NH | 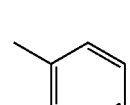 | 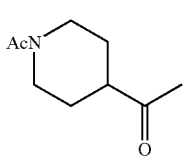 | 562 |
| 790 | (±)-cis | 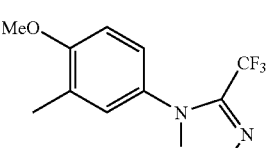 | NH | 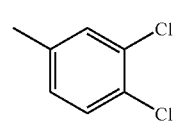 | 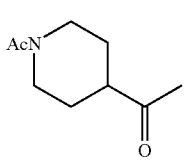 | 654 |
| 792 | (±)-cis | 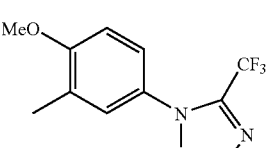 | NH | 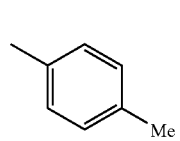 |  | 600 |

TABLE 20-continued

| Ex. No. | Stereo-chemistry | R¹ | X | B | C | MS (ESI) (M + H)⁺ |
|---|---|---|---|---|---|---|
| 797 | (±)-cis | 5-oxopyrrolidin-2-yl acetyl | NH | 4-MeO-3-Me-phenyl-1-(5-CF₃-tetrazol-1-yl) | phenyl | 544 |
| 798 | (±)-cis | 5-oxopyrrolidin-2-yl acetyl (enantiomer) | NH | 4-MeO-3-Me-phenyl-1-(5-CF₃-tetrazol-1-yl) | phenyl | 544 |
| 802 | (±)-cis | pyrazol-1-yl-acetonyl | NH | 4-MeO-3-Me-phenyl-1-(5-CF₃-tetrazol-1-yl) | phenyl | 541 |
| 803 | (±)-cis | 1,2,4-triazol-1-yl-acetonyl | NH | 4-MeO-3-Me-phenyl-1-(5-CF₃-tetrazol-1-yl) | phenyl | 542 |
| 804 | (±)-cis | (5,5-dimethyl-2,4-dioxooxazolidin-3-yl)acetonyl | NH | 4-MeO-3-Me-phenyl-1-(5-CF₃-tetrazol-1-yl) | phenyl | 602 |
| 805 | (±)-cis | (2,6-dioxopiperidin-1-yl)acetonyl | NH | 4-MeO-3-Me-phenyl-1-(5-CF₃-tetrazol-1-yl) | phenyl | 586 |
| 806 | (±)-cis | (2,4-dioxopyrimidin-3-yl)acetonyl | NH | 4-MeO-3-Me-phenyl-1-(5-CF₃-tetrazol-1-yl) | phenyl | 585 |

TABLE 20-continued

| Ex. No. | Stereo-chemistry | R¹ | X | B | C | MS (ESI) (M + H)⁺ |
|---|---|---|---|---|---|---|
| 807 | (±)-cis | 3-oxo-2,4-dihydro-1,2,4-triazol-5-yl-CH₂-C(O)- | NH | 4-MeO-3-Me-phenyl-N(tetrazole-CF₃) | phenyl | 558 |
| 808 | (±)-cis | NC-CH₂-C(O)- | NH | 4-MeO-3-Me-phenyl-N(tetrazole-CF₃) | phenyl | 500 |

Example 421 cis-2-[4-[[3,5-Bis(trifluoromethyl)benzyl]oxy]-3-phenyl-1-piperidinyl]-2-oxoethylamine trifluoroacetate To a solution of the compound (35 mg) obtained in Example 1, Boc-glycine (15 mg) and Et₃N (22 μl) in DMF (2.0 ml), WSC.HCl (17 mg) and HoBt.H₂O (13 mg) were added, and the reaction mixture was stirred at room temperature for 24 hours. The reaction mixture was poured into water, and then the product was extracted with ethyl acetate. The organic layer was washed with an aqueous saturated sodium hydrogen carbonate solution and saturated brine, and dried, and the solvent was evaporated under reduced pressure, and then the residue was purified by preparative HPLC. To the obtained product, trifluoroacetic acid (1 ml) was added and the reaction mixture was stirred for 1 hour, and then the solvent was evaporated to obtain the title compound.

Yield: 19 mg

MS (ESI+): 461 (M+H)

The compounds of the following Examples were synthesized by reacting and treating in the same manner as in the method described in Example 421 from the compounds obtained in Examples 1, 509, 527, 566, 609 or 701 as a starting material, using respective corresponding amino acid derivatives protected with Boc group.

TABLE 21

| Ex. No. | Stereochemistry | R¹ | X | B | C | MS (ESI) (M + H)⁺ |
|---|---|---|---|---|---|---|
| 421 | (±)-cis | H₂N-CH₂-C(O)- | O | 3,5-bis(CF₃)-phenyl | phenyl | 461 |
| 427 | (±)-cis | H₂N-(CH₂)₃-C(O)- | O | 3,5-bis(CF₃)-phenyl | phenyl | 489 |

TABLE 21-continued

[Structure: piperidine ring with N-R¹, 4-position connected to X-CH₂-B, 3-position connected to C]

| Ex. No. | Stereochemistry | R¹ | X | B | C | MS (ESI) (M + H)⁺ |
|---|---|---|---|---|---|---|
| 441 | (±)-cis | 4-acetyl-piperidine (HN-piperidine-C(O)-) | O | 3,5-bis(CF₃)phenyl | phenyl | 515 |
| 455 | (±)-cis | H₂N-C(Me)₂-C(O)- | O | 3,5-bis(CF₃)phenyl | phenyl | 489 |
| 486 | (±)-cis | 4-amino-1-methyl-2-acetyl-pyrrole | O | 3,5-bis(CF₃)phenyl | phenyl | 526 |
| 487 | (±)-cis | 3-acetyl-piperidine | O | 3,5-bis(CF₃)phenyl | phenyl | 515 |
| 493 | (±)-cis | 3-acetyl-azetidine | O | 3,5-bis(CF₃)phenyl | phenyl | 487 |
| 494 | (±)-cis | 4-piperidinyl-CH₂-C(O)- | O | 3,5-bis(CF₃)phenyl | phenyl | 529 |
| 515 | (±)-cis | 4-acetyl-piperidine | O | 3,5-bis(CF₃)phenyl | 3,4-dichlorophenyl | 583 |
| 531 | (±)-cis | piperazinyl-CH₂-C(O)- | O | 3,5-bis(CF₃)phenyl | 4-fluorophenyl | 548 |

TABLE 21-continued

| Ex. No. | Stereochemistry | R¹ | X | B | C | MS (ESI) (M + H)⁺ |
|---|---|---|---|---|---|---|
| 577 | (±)-cis | H₂N-CH₂-C(=O)- | NH | 3,5-bis(CF₃)phenyl | phenyl | 460 |
| 583 | (±)-cis | H₂N-(CH₂)₂-C(=O)- | NH | 3,5-bis(CF₃)phenyl | phenyl | 488 |
| 617 | (±)-cis | H₂N-CH₂-C(=O)- | NH | 4-MeO-3-Me-6-OCF₃-phenyl | phenyl | 438 |
| 623 | (±)-cis | H₂N-(CH₂)₂-C(=O)- | NH | 4-MeO-3-Me-6-OCF₃-phenyl | phenyl | 466 |
| 645 | (±)-cis | H₂N-C(Me)₂-C(=O)- | NH | 4-MeO-3-Me-6-OCF₃-phenyl | phenyl | 466 |
| 732 | (±)-cis | piperidin-4-yl-C(=O)- | NH | MeO, Me, 5-CF₃-tetrazol-1-yl phenyl | phenyl | 544 |
| 733 | (±)-cis | piperidin-3-yl-C(=O)- | NH | MeO, Me, 5-CF₃-tetrazol-1-yl phenyl | phenyl | 544 |
| 734 | (±)-cis | piperidin-2-yl-C(=O)- | NH | MeO, Me, 5-CF₃-tetrazol-1-yl phenyl | phenyl | 544 |

TABLE 21-continued

| Ex. No. | Stereochemistry | R¹ | X | B | C | MS (ESI) (M + H)⁺ |
|---|---|---|---|---|---|---|
| 744 | (±)-cis | 3-acetyl-azetidinyl (HN-azetidine-C(O)Me) | NH | 4-methoxy-2-methylphenyl with 5-(trifluoromethyl)tetrazol-1-yl | phenyl | 516 |

Example 440

Ethyl [[[cis-4-[[3,5-bis(trifluoromethyl)benzyl]oxy]-3-phenyl-1-piperidinyl]carbonyl]amino]acetate To a solution of the compound (35 mg) obtained in Example 1 and Et₃N (22 μl) in THF (2.0 ml), ethyl isocyanatoacetate (11 mg) was added at 0° C., and the reaction mixture was stirred at room temperature for 3 hours. To the reaction mixture, an aqueous saturated sodium hydrogen carbonate solution was added, and then the product was extracted with ethyl acetate. The organic layer was washed with saturated brine, dried, and then the solvent was evaporated under reduced pressure, and the residue was purified by preparative HPLC to obtain the title compound.

Yield: 17 mg
MS (ESI+): 533 (M+H)

The compounds of the following Examples were synthesized from the compound obtained in Examples 1, 23, 24, 509, 519, 521, 524, 527, 534, 566, 609, 663, 701, 708, 711, 714, 718, 720, 724, 726, 794, 795 or 796 as a starting material by reacting and treating in the same manner as in the method described in Example 440 using the respective corresponding isocyanate derivatives.

TABLE 22

| Ex. No. | Stereochemistry | R¹ | X | B | C | MS (ESI) (M + H)⁺ |
|---|---|---|---|---|---|---|
| 440 | (±)-cis | EtO₂C-CH₂-NH-C(O)- | O | 3,5-bis(trifluoromethyl)phenyl | phenyl | 533 |
| 469 | (±)-cis | MeNH-C(O)-N(piperidin-1-yl)-4-acetyl | O | 3,5-bis(trifluoromethyl)phenyl | phenyl | 572 |
| 513 | (±)-cis | MeNHCO | O | 3,5-bis(trifluoromethyl)phenyl | 3,4-dichlorophenyl | 529 |

TABLE 22-continued

| Ex. No. | Stereo-chemistry | R¹ | X | B | C | MS (ESI) (M + H)⁺ |
|---|---|---|---|---|---|---|
| 520 | (±)-cis | MeNHCO | O | 3,5-(CF₃)₂-C₆H₃ | 2-Me-C₆H₄ | 475 |
| 523 | (±)-cis | MeNHCO | O | 3,5-(CF₃)₂-C₆H₃ | 4-Me-C₆H₄ | 475 |
| 526 | (±)-cis | MeNHCO | O | 3,5-(CF₃)₂-C₆H₃ | 3-F-C₆H₄ | 479 |
| 530 | (±)-cis | MeNHCO | O | 3,5-(CF₃)₂-C₆H₃ | 4-F-C₆H₄ | 479 |
| 536 | (±)-cis | MeNHCO | O | 3,5-(CF₃)₂-C₆H₃ | 2-Me-4-F-C₆H₃ | 493 |
| 560 | (±)-cis | EtNHCO | NH | 2-MeO-C₆H₄ | C₆H₅ | 368 |
| 561 | (±)-cis | MeNHCO | NH | 2-MeO-C₆H₄ | C₆H₅ | 354 |
| 562 | (±)-trans | MeNHCO | NH | 2-MeO-C₆H₄ | C₆H₅ | 354 |
| 568 | (±)-cis | EtNHCO | NH | 3,5-(CF₃)₂-C₆H₃ | C₆H₅ | 474 |

TABLE 22-continued

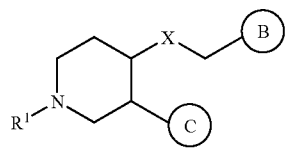

| Ex. No. | Stereo-chemistry | R¹ | X | B | C | MS (ESI) (M + H)⁺ |
|---|---|---|---|---|---|---|
| 569 | (±)-cis | MeNHCO | NH | 3,5-bis(CF₃)phenyl | phenyl | 460 |
| 570 | (±)-trans | MeNHCO | NH | 3,5-bis(CF₃)phenyl | phenyl | 460 |
| 596 | (±)-cis | EtO₂CCH₂NHCO | NH | 3,5-bis(CF₃)phenyl | phenyl | 532 |
| 597 | (±)-cis | PhNHCO | NH | 3,5-bis(CF₃)phenyl | phenyl | 522 |
| 610 | (±)-cis | EtNHCO | NH | 2-MeO-5-OCF₃-4-Me-phenyl | phenyl | 452 |
| 611 | (±)-cis | MeNHCO | NH | 2-MeO-5-OCF₃-4-Me-phenyl | phenyl | 438 |
| 636 | (±)-cis | EtO₂CCH₂NHCO | NH | 2-MeO-5-OCF₃-4-Me-phenyl | phenyl | 510 |
| 637 | (±)-cis | PhNHCO | NH | 2-MeO-5-OCF₃-4-Me-phenyl | phenyl | 500 |
| 650 | (±)-cis | CyNHCO | NH | 2-MeO-5-OCF₃-4-Me-phenyl | phenyl | 506 |

TABLE 22-continued

[Structure: piperidine core with R¹-N, 4-position linked via X-CH2 to ring B, 3-position linked to ring C]

| Ex. No. | Stereo-chemistry | R¹ | X | B | C | MS (ESI) (M + H)⁺ |
|---|---|---|---|---|---|---|
| 664 | (±)-cis | EtNHCO | NH | 4-MeO-3-Me-phenyl-OCF₃ | 3,4-dichlorophenyl | 520 |
| 665 | (±)-cis | ⁱPrNHCO | NH | 4-MeO-3-Me-phenyl-OCF₃ | 3,4-dichlorophenyl | 534 |
| 667 | (±)-cis | MeNHCO | NH | 4-MeO-3-Me-phenyl-OCF₃ | 3,4-dichlorophenyl | 506 |
| 709 | (±)-cis | EtNHCO | NH | 4-MeO-3-Me-phenyl-(5-CF₃-1,3,4-oxadiazol-2-yl) | phenyl | 504 |
| 712 | (±)-cis | EtNHCO | NH | 4-MeO-3-Me-phenyl-(4-Me-thiazol-2-yl) | phenyl | 465 |
| 715 | (±)-cis | EtNHCO | NH | 4-MeO-3-Me-phenyl-(5-CF₃-pyrazol-1-yl) | phenyl | 502 |
| 719 | (±)-cis | EtNHCO | NH | 4-MeO-3-Me-phenyl-(1,2,3-triazol-1-yl) | phenyl | 435 |
| 722 | (±)-cis | MeNHCO | NH | 7-Me-2,3-dihydrobenzofuran-5-yl-(5-CF₃-tetrazol-1-yl) | phenyl | 502 |

TABLE 22-continued
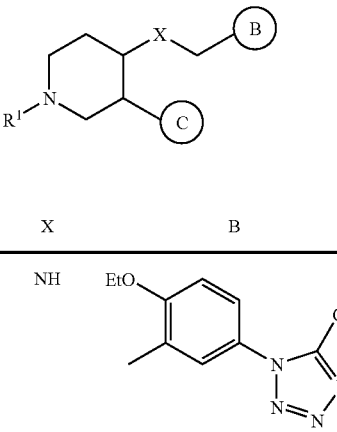
| Ex. No. | Stereo-chemistry | R¹ | X | B | C | MS (ESI) (M + H)⁺ |
|---|---|---|---|---|---|---|
| 725 | (±)-cis | EtNHCO | NH | 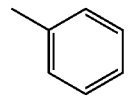 | 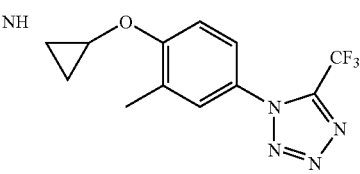 | 518 |
| 727 | (±)-cis | EtNHCO | NH | 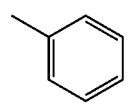 | 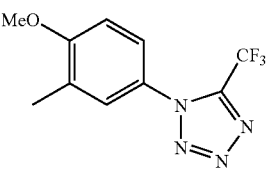 | 530 |
| 729 | (±)-cis | ⁱPrNHCO | NH | 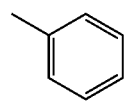 | 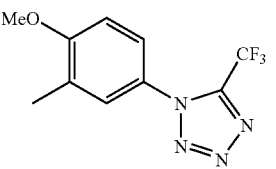 | 518 |
| 730 | (±)-cis | ᵗBuNHCO | NH | 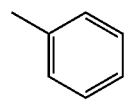 | 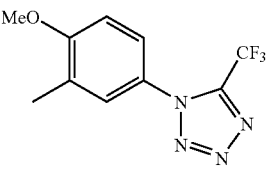 | 532 |
| 789 | (±)-cis | EtNHCO | NH | 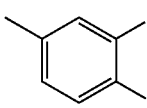 | 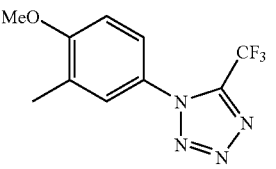 | 572 |
| 791 | (±)-cis | EtNHCO | NH | 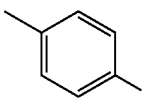 | 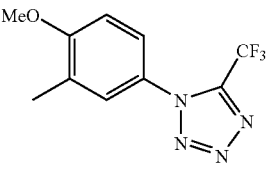 | 518 |
| 793 | (±)-cis | EtNHCO | NH | 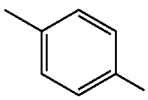 |  | 522 |

Example 445 cis-4-[[3,5-Bis(trifluoromethyl)benzyl]oxy]-3-phenyl-1-[(1-methyl-4-piperidinyl)carbonyl]piperidine To an aqueous solution of the compound (210 mg) obtained in Example 441 and Et₃N (38 mg) in 35% formalin (1.2 ml), formic acid (1.2 ml) was added, and the reaction mixture was stirred at 80° C. for 1 hour. The reaction mixture was concentrated under reduced pressure, and then to the residue, ethyl acetate was added. The reaction mixture was made basic with an aqueous sodium hydroxide solution, and then the organic layer was washed with saturated brine, dried, and then the solvent was evaporated under reduced pressure. The obtained residue was purified by preparative HPLC to obtain the title compound.

Yield: 173 mg

MS (ESI+): 529 (M+H)

The compounds of the following Examples were synthesized from the compound obtained in Example 515 as a starting material by reacting and treating in the same manner as in the method described in Example 445.

TABLE 23

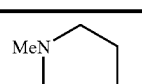

| Ex. No. | Stereochemistry | R¹ | X | B | C | MS (ESI) (M + H)⁺ |
|---|---|---|---|---|---|---|
| 445 | (±)-cis | 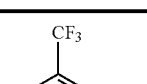 | O | 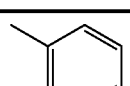 | 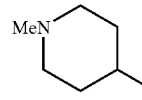 | 529 |
| 516 | (±)-cis | 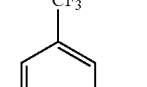 | O | 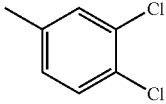 | | 597 |

Example 446 cis-4-[[3,5-Bis(trifluoromethyl)benzyl]oxy]-3-phenyl-1-(1-piperidinylcarbonyl)piperidine To a solution of the compound (100 mg) obtained in Example 1 and Et₃N (70 mg). in DMF (5.0 ml), piperidine-1-carbonyl chloride (44 mg) was added, and the reaction mixture was stirred at room temperature for 2 hours. The reaction mixture was poured into water, and then the product was extracted with ethyl acetate. The organic layer was washed with an aqueous 3% potassium hydrogensulfate solution and saturated brine, dried, and then the solvent was evaporated under reduced pressure. The obtained residue was isolated and purified by silica gel column chromatography (ethyl acetate) to obtain the title compound as pale yellow oil (0.11 g).

MS (ESI+): 515 (M+H)

The compounds of the following Examples were synthesized from the compounds obtained in Examples 1, 441, 493, 509, 527, 566, 609, 701 and 732 as starting materials by reacting and treating in the same manner as in the method described in Example 446 using the respective corresponding halides (carbamoyl chloride, sulfonyl chloride, acid chloride, alkyl halide, aryl halide, acid anhydride derivatives, etc).

TABLE 24
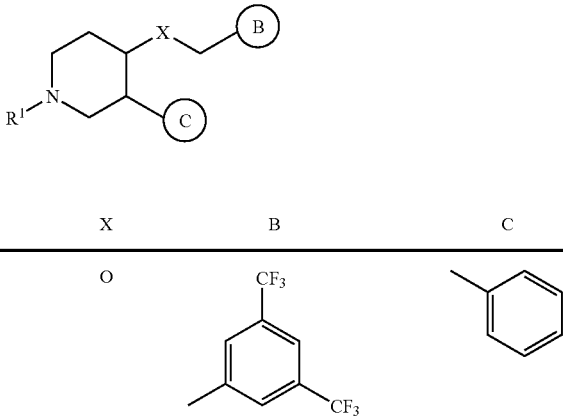
| Ex. No. | Stereo-chemistry | R¹ | X | B | C | MS (ESI) (M + H)⁺ |
|---|---|---|---|---|---|---|
| 446 | (±)-cis | 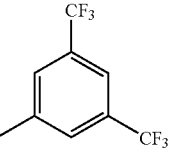 | O | 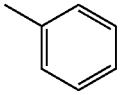 | 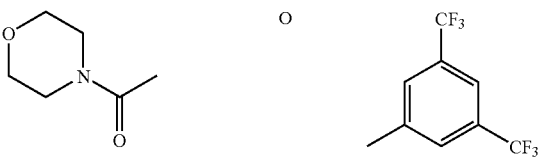 | 515 |
| 447 | (±)-cis | 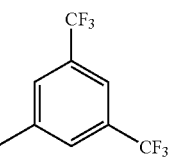 | O | 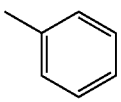 | 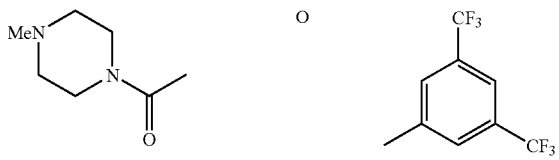 | 517 |
| 448 | (±)-cis | 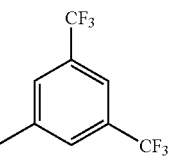 | O | 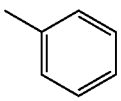 | 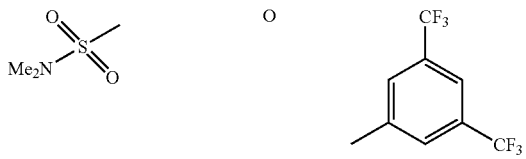 | 530 |
| 449 | (±)-cis | 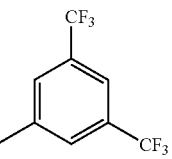 | O | 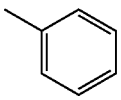 | 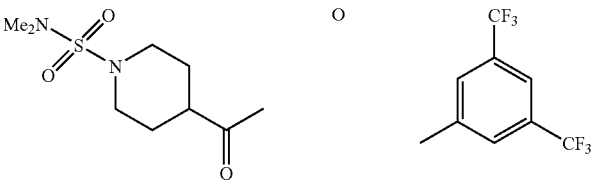 | 511 |
| 450 | (±)-cis | 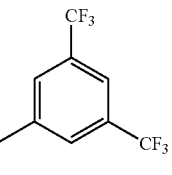 | O | 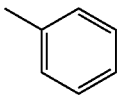 | 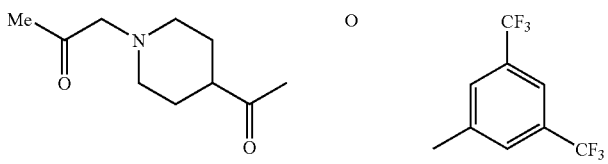 | 622 |
| 452 | (±)-cis | 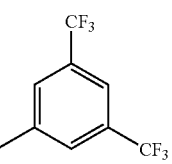 | O | 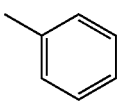 | 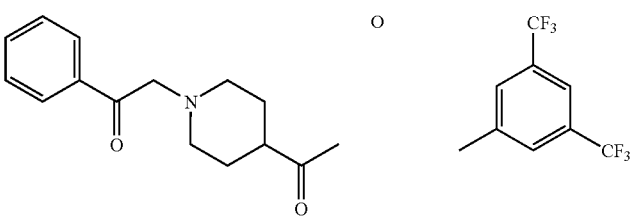 | 571 |
| 459 | (±)-cis | 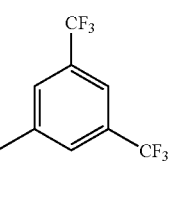 | O | 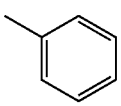 | | 633 |

TABLE 24-continued

| Ex. No. | Stereo-chemistry | R¹ | X | B | C | MS (ESI) (M + H)⁺ |
|---|---|---|---|---|---|---|
| 461 | (±)-cis | benzoyl-piperidine-4-yl-C(O)- | O | 3,5-bis(CF₃)phenyl | phenyl | 619 |
| 462 | (±)-cis | phenylacetyl-piperidine-4-yl-C(O)- | O | 3,5-bis(CF₃)phenyl | phenyl | 633 |
| 464 | (±)-cis | N-benzyl-piperidine-4-yl-C(O)- | O | 3,5-bis(CF₃)phenyl | phenyl | 605 |
| 466 | (±)-cis | N-iPr-piperidine-4-yl-C(O)- | O | 3,5-bis(CF₃)phenyl | phenyl | 557 |
| 478 | (±)-cis | trifluoroacetyl-piperidine-4-yl-C(O)- | O | 3,5-bis(CF₃)phenyl | phenyl | 611 |
| 480 | (±)-cis | 2-oxo-imidazolidin-1-yl-C(O)- | O | 3,5-bis(CF₃)phenyl | phenyl | 516 |
| 482 | (±)-cis | methanesulfonyl-piperidine-4-yl-C(O)- | O | 3,5-bis(CF₃)phenyl | phenyl | 593 |

TABLE 24-continued

| Ex. No. | Stereo-chemistry | R¹ | X | B | C | MS (ESI) (M + H)+ |
|---|---|---|---|---|---|---|
| 491 | (±)-cis | Me-NH-C(O)-CH(Me)-C(O)-Me | O | 3,5-bis(CF₃)phenyl | phenyl | 517 |
| 492 | (±)-cis | 3-(4-acetylpiperidin-1-yl)-tetrahydrofuran-2-one | O | 3,5-bis(CF₃)phenyl | phenyl | 599 |
| 495 | (±)-cis | 1-acetyl-3-acetylazetidine | O | 3,5-bis(CF₃)phenyl | phenyl | 529 |
| 498 | (±)-cis | 1-acetyl-4-(2-oxopropyl)piperidine | O | 3,5-bis(CF₃)phenyl | phenyl | 571 |
| 500 | (±)-cis | 5-[(4-acetylpiperidin-1-yl)methyl]-2,4-dihydro-3H-1,2,4-triazol-3-one | O | 3,5-bis(CF₃)phenyl | phenyl | 612 |
| 501 | (±)-cis | Et-C(O)-CH₂-N(4-acetylpiperidin-1-yl) | O | 3,5-bis(CF₃)phenyl | phenyl | 585 |
| 654 | (±)-cis | 4-methylpiperazin-1-yl acetyl | NH | 2-methyl-4-OCF₃-5-OMe-phenyl | phenyl | 507 |
| 508 | (±)-cis | MeO-C(O)-CH₂-N(4-acetylpiperidin-1-yl) | O | 3,5-bis(CF₃)phenyl | phenyl | 624 |

TABLE 24-continued

| Ex. No. | Stereo-chemistry | R¹ | X | B | C | MS (ESI) (M + H)⁺ |
|---|---|---|---|---|---|---|
| 510 | (±)-cis | 4-acetylmorpholine | O | 3,5-bis(CF₃)phenyl | 3,4-diCl-phenyl | 585 |
| 511 | (±)-cis | 4-acetyl-1-methylpiperazine | O | 3,5-bis(CF₃)phenyl | 3,4-diCl-phenyl | 598 |
| 532 | (±)-cis | 1-acetyl-4-(2-oxopropyl)piperazine | O | 3,5-bis(CF₃)phenyl | 4-F-phenyl | 590 |
| 606 | (±)-cis | Et | NH | 3,5-bis(CF₃)phenyl | phenyl | 409 |
| 607 | (±)-cis | MeSO₂ | NH | 3,5-bis(CF₃)phenyl | phenyl | 459 |
| 608 | (±)-cis | MeOCO | NH | 3,5-bis(CF₃)phenyl | phenyl | 439 |
| 652 | (±)-cis | 5-ethyl-2,4-dihydro-3H-1,2,4-triazol-3-one | NH | 2-methyl-4-OCF₃-5-OMe-phenyl | phenyl | 478 |
| 655 | (±)-cis | 4-acetylmorpholine | NH | 2-methyl-4-OCF₃-5-OMe-phenyl | phenyl | 494 |

TABLE 24-continued
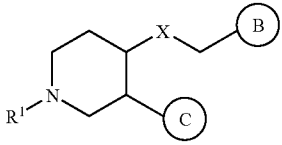
| Ex. No. | Stereo-chemistry | R¹ | X | B | C | MS (ESI) (M + H)⁺ |
|---|---|---|---|---|---|---|
| 656 | (±)-cis | 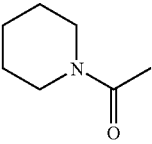 | NH | 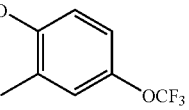 | 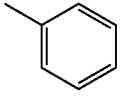 | 492 |
| 731 | (±)-cis | Me₂NCO | NH | 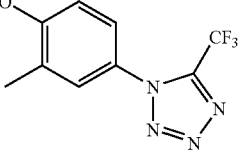 | 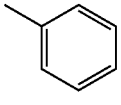 | 504 |
| 748 | (±)-cis | Et | NH | 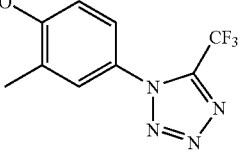 | 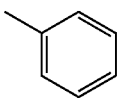 | 461 |
| 749 | (±)-cis | MeSO₂ | NH | 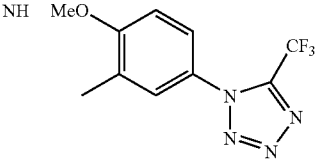 | 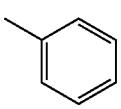 | 511 |
| 750 | (±)-cis | MeOCO | NH | 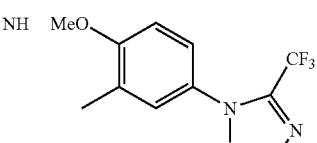 | 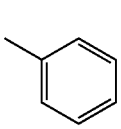 | 491 |
| 754 | (±)-cis | 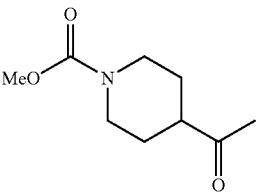 | NH | 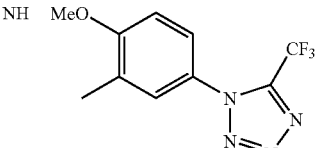 | 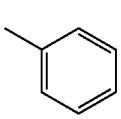 | 602 |

TABLE 24-continued

| Ex. No. | Stereo-chemistry | R¹ | X | B | C | MS (ESI) (M + H)⁺ |
|---|---|---|---|---|---|---|
| 755 | (±)-cis | Me-S(=O)₂-N-piperidinyl-C(=O)- | NH | MeO-, Me-phenyl-tetrazole-CF₃ | phenyl | 622 |
| 759 | (±)-cis | morpholine-N-C(=O)- | NH | MeO-, Me-phenyl-tetrazole-CF₃ | phenyl | 546 |
| 766 | (±)-cis | Ac-N-piperazine-N-C(=O)- | NH | MeO-, Me-phenyl-tetrazole-CF₃ | phenyl | 587 |

Example 451 cis-4-[[3,5-Bis(trifluoromethyl)benzyl]oxy]-1-[[1-[(1-methyl-1H-imidazol-2-yl)methyl]-4-piperidinyl]carbonyl]-3-phenylpiperidine hydrochloride

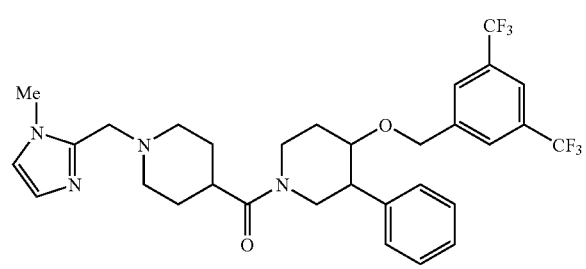

To a solution of the compound (100 mg) obtained in Process 2 of Example 69 and 1-methyl-1H-imidazole-2-carbaldehyde (80 mg) in DMF (1 ml)/THF (5 ml), acetic acid (110 mg) and NaBH(OAc)₃ (154 mg) were added, and the reaction mixture was stirred at room temperature for 13 hours. To the reaction solution, an aqueous saturated sodium bicarbonate solution was added, and the product was extracted with ethyl acetate. The organic layer was washed with saturated brine, dried, and then the solvent was evaporated under reduced pressure. The obtained residue was isolated and purified by silica gel column chromatography (chloroform:methanol=20:1), and treated with 4 N hydrogen chloride/ethyl acetate to obtain the title compound (80 mg) as colorless powder.

MS (ESI+): 609 (M+H)

Example 463

1-Acetyl-4-[[cis-4-[[3,5-bis(trifluoromethyl)benzyl]oxy]-3-phenyl-1-piperidinyl]carbonyl]piperazine To a solution of the compound (100 mg) obtained in Example 1 in DMF (5 ml), the compound (70 mg) obtained in Reference Example 24 and potassium carbonate (94 mg) were added, and the reaction mixture was stirred at 120° C. for 3 hours. To the reaction solution, water was added, and the product was extracted with ethyl acetate. The organic layer was washed with an aqueous 3% potassium hydrogensulfate solution, an aqueous saturated sodium bicarbonate solution and saturated brine, dried, and then the solvent was evaporated under reduced pressure. The obtained residue was isolated and purified by silica gel column chromatography (chloroform:methanol=100:1) to obtain the title compound (70 mg) as pale yellow oil.

MS (ESI+): 558 (M+H)

The compounds of the following Examples were synthesized from the compounds obtained in Examples 1, 609 or 701 starting materials by reacting and treating in the same manner as in the method described in Example 463 using the compounds obtained in Reference Examples 25 to 27 (the obtained product was treated with hydrochloric acid in Example 772).

TABLE 25

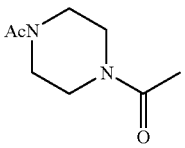

| Ex. No. | Stereochemistry | R¹ | X | B | C | MS (ESI) (M + H)⁺ |
|---|---|---|---|---|---|---|
| 463 | (±)-cis | 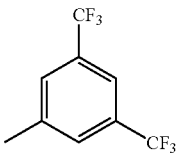 | O | 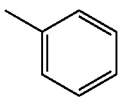 | 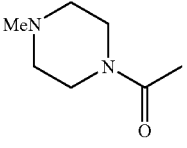 | 558 |
| 654 | (±)-cis | 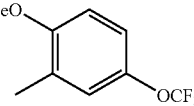 | NH | 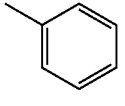 | 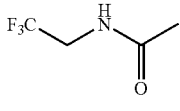 | 507 |
| 659 | (±)-cis | 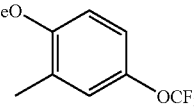 | NH | 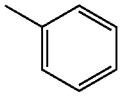 | 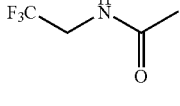 | 506 |
| 735 | (±)-cis | 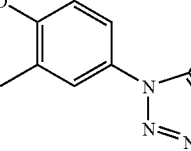 | NH | 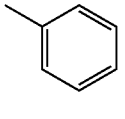 | 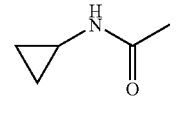 | 558 |
| 746 | (±)-cis | 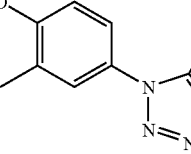 | NH | 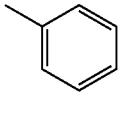 | 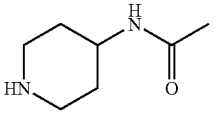 | 516 |
| 772 | (±)-cis | 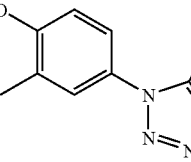 | NH | 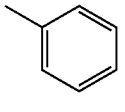 |  | 559 |

Example 509 cis-4-[[3,5-Bis(trifluoromethyl)benzyl]oxy]-3-(3,4-dichlorophenyl)piperidine hydrochloride To a solution of the compound (1.70 g) obtained in Reference Example 8 in THF (5 ml), trifluoroacetic acid (7 ml) was added at 0° C., and the reaction mixture was stirred at room temperature for 30 minutes. The reaction mixture was concentrated under reduced pressure, and then the residue was dissolved in ethyl acetate. The organic layer was washed with an aqueous saturated sodium hydrogen carbonate solution and brine, dried, and then the solvent was evaporated under reduced pressure. The obtained residue was treated with a 4 N hydrogen chloride/ethyl acetate solution (0.8 ml) to obtain the title compound as colorless crystals (1.20 g).

MS (ESI+): 472 (M+H)

The compounds of the following Examples were synthesized by reacting and treating in the same manner as in the method described in Example 509 using the compounds obtained in Reference Examples 9 to 23 and 35 to 54.

TABLE 26
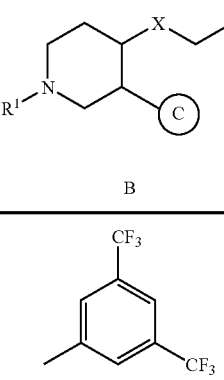
| Ex. No. | Stereochemistry | R¹ | X | B | C | MS (ESI) (M + H)⁺ |
|---|---|---|---|---|---|---|
| 509 | (±)-cis | H | O | 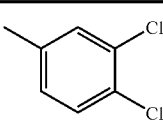 | 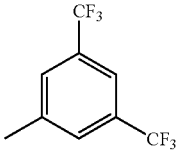 | 472 |
| 519 | (±)-cis | H | O | 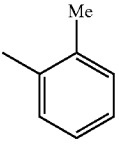 | 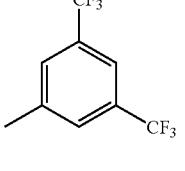 | 418 |
| 521 | (±)-cis | H | O | 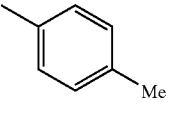 | 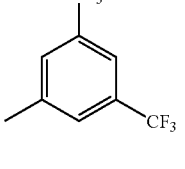 | 418 |
| 524 | (±)-cis | H | O | 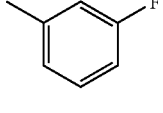 | 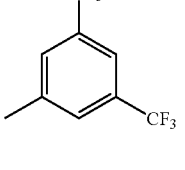 | 422 |
| 527 | (±)-cis | H | O | 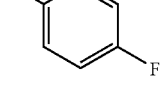 | 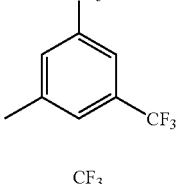 | 422 |
| 534 | (±)-cis | H | O | 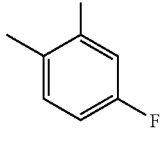 | 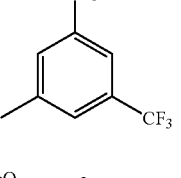 | 436 |
| 537 | (±)-cis | H | O | 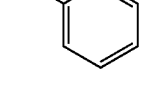 | 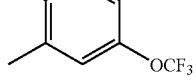 | 405 |
| 539 | (±)-cis | H | O | 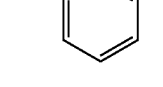 | | 382 |

TABLE 26-continued
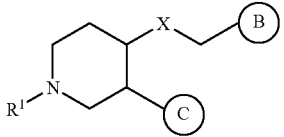
| Ex. No. | Stereochemistry | R¹ | X | B | C | MS (ESI) (M + H)⁺ |
|---|---|---|---|---|---|---|
| 541 | (±)-cis | H | O | 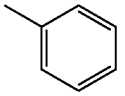 | 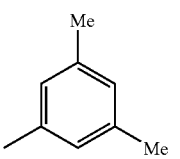 | 336 |
| 543 | (±)-cis | H | O | 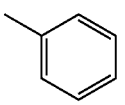 | 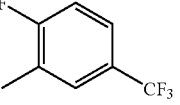 | 296 |
| 545 | (±)-cis | H | O | 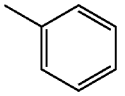 | 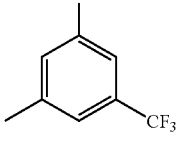 | 354 |
| 547 | (±)-cis | H | O | 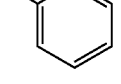 | 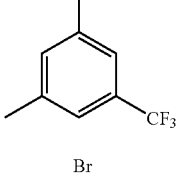 | 354 |
| 549 | (±)-cis | H | O | 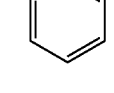 | 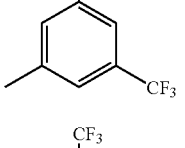 | 381 |
| 553 | (±)-cis | H | O | 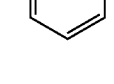 | 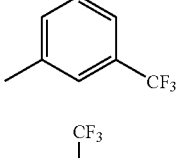 | 414, 416 |
| 566 | (±)-cis | H | NH | 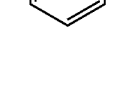 | 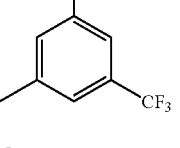 | 403 |
| 567 | (±)-trans | H | NH | 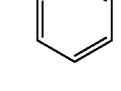 | 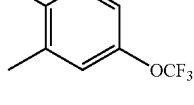 | 403 |
| 609 | (±)-cis | H | NH | 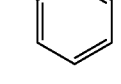 | | 381 |

TABLE 26-continued

| Ex. No. | Stereochemistry | R¹ | X | B | C | MS (ESI) (M + H)⁺ |
|---|---|---|---|---|---|---|
| 663 | (±)-cis | H | NH | MeO-phenyl(Me)(OCF₃) | 3,4-dichlorophenyl | 449 |
| 690 | (±)-cis | H | NH | 7-methyl-5-CF₃-2,3-dihydrobenzofuran | phenyl | 377 |
| 691 | (±)-cis | H | NH | 7-methyl-5-iPr-2,3-dihydrobenzofuran | phenyl | 351 |
| 692 | (±)-trans | H | NH | 7-methyl-5-iPr-2,3-dihydrobenzofuran | phenyl | 351 |
| 696 | (±)-cis | H | NH | 7-methyl-5-OCF₃-2,3-dihydrobenzofuran | phenyl | 393 |
| 697 | (±)-trans | H | NH | 7-methyl-5-OCF₃-2,3-dihydrobenzofuran | phenyl | 393 |
| 701 | (±)-cis | H | NH | MeO-phenyl(Me)-(5-CF₃-tetrazol-1-yl) | phenyl | 433 |
| 702 | (±)-trans | H | NH | MeO-phenyl(Me)-(5-CF₃-tetrazol-1-yl) | phenyl | 433 |

TABLE 26-continued

| Ex. No. | Stereochemistry | R¹ | X | B | C | MS (ESI) (M + H)⁺ |
|---|---|---|---|---|---|---|
| 703 | (±)-cis | H | NH | MeO-, Me, iPr phenyl | phenyl | 339 |
| 704 | (±)-trans | H | NH | MeO-, Me, iPr phenyl | phenyl | 339 |
| 708 | (±)-cis | H | NH | MeO-, Me-phenyl-1,3,4-oxadiazole-CF₃ | phenyl | 433 |
| 711 | (±)-cis | H | NH | MeO-, Me-phenyl-thiazole-Me | phenyl | 394 |
| 714 | (±)-cis | H | NH | MeO-, Me-phenyl-pyrazole-CF₃ | phenyl | 431 |
| 718 | (±)-cis | H | NH | MeO-, Me-phenyl-triazole | phenyl | 364 |
| 720 | (±)-cis | H | NH | Me-dihydrobenzofuran-tetrazole-CF₃ | phenyl | 445 |
| 721 | (±)-trans | H | NH | Me-dihydrobenzofuran-tetrazole-CF₃ | phenyl | 445 |

TABLE 26-continued

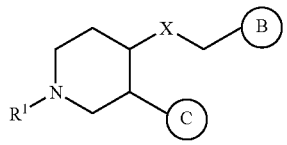

| Ex. No. | Stereochemistry | R¹ | X | B | C | MS (ESI) (M + H)+ |
|---|---|---|---|---|---|---|
| 724 | (±)-cis | H | NH | EtO-phenyl(Me)-tetrazole-CF₃ | phenyl | 447 |
| 726 | (±)-cis | H | NH | cyclopropyl-O-phenyl(Me)-tetrazole-CF₃ | phenyl | 459 |
| 794 | (±)-cis | H | NH | MeO-phenyl(Me)-tetrazole-CF₃ | 3,4-diCl-phenyl | 575 |
| 795 | (±)-cis | H | NH | MeO-phenyl(Me)-tetrazole-CF₃ | 4-Me-phenyl | 447 |
| 796 | (±)-cis | H | NH | MeO-phenyl(Me)-tetrazole-CF₃ | 4-F-phenyl | 451 |
| 799 | (±)-cis | H | O | 2-CF₃,4-CF₃,Me-phenyl | phenyl | 404 |
| 800 | (±)-cis | H | O | 3-Me,5-CF₃-phenyl | phenyl | 350 |
| 801 | (±)-cis | H | O | 3-NO₂,5-CF₃-phenyl | phenyl | 381 |

Example 503

1-Acetyl-4-[2-[cis-4-[[3,5-bis(trifluoromethyl)benzyl]oxy]-3-phenyl-1-piperidinyl]-2-oxoethyl]piperazine hydrochloride

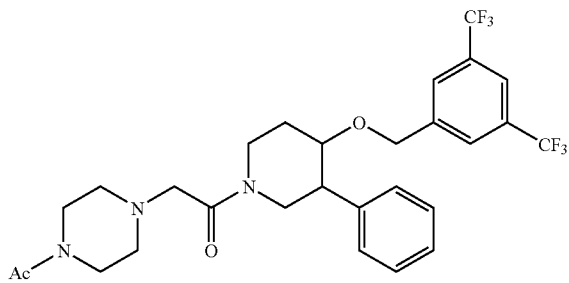

To a solution of the compound (175 mg) obtained in Example 1 and diisopropylethylamine (113 mg) in DMF (5 ml), chloroacetyl chloride (50 mg) was added at room temperature, and the reaction mixture was stirred for 1 hour. To the reaction solution, diisopropylethylamine (113 mg), sodium iodide (180 mg) and 1-acetylpiperazine (102 mg) were added and the reaction mixture was further stirred for 5 hours. To the reaction solution, water was added, and the product was extracted with ethyl acetate. The organic layer was washed with water and saturated brine, dried, and then the solvent was evaporated under reduced pressure. The obtained residue was treated with 4 N hydrogen chloride/ethyl acetate to obtain the title compound (150 mg) as colorless powder.

MS (ESI+): 572 (M+H)

Example 504

1-Acetyl-4-[[cis-4-[[3,5-bis(trifluoromethyl)benzyl]oxy]-3-phenyl-1-piperidinyl]acetyl]piperazine hydrochloride

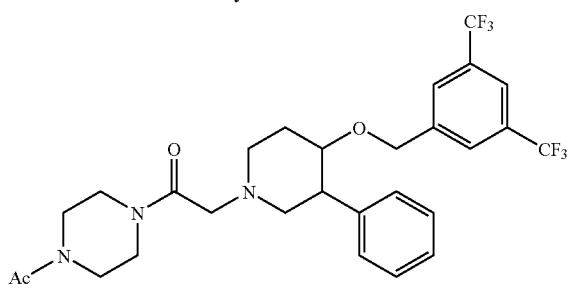

To a solution of 1-acetylpiperazine (38 mg) and diisopropylethylamine (45 mg) in DMF (5 ml), chloroacetyl chloride (34 mg) was added at room temperature, and the reaction mixture was stirred for 30 minutes. To the reaction solution, diisopropyethylamine (90 mg), sodium iodide (103 mg) and the compound (100 mg) obtained in Example 1 were added and the reaction mixture was further stirred for 4 hours. To the reaction solution, water was added, and the product was extracted with ethyl acetate. The organic layer was washed with water and saturated brine, dried, and then the solvent was evaporated under reduced pressure. The obtained residue was treated with 4 N hydrogen chloride/ethyl acetate to obtain the title compound (96 mg) as pale brown powder.

MS (ESI+): 572 (M+H).

Example 505

1-[1-[2-[cis-4-[[3,5-Bis(trifluoromethyl)benzyl]oxy]-3-phenyl-1-piperidinyl]-2-oxoethyl]-1H-imidazol-4-yl]-1-propanone

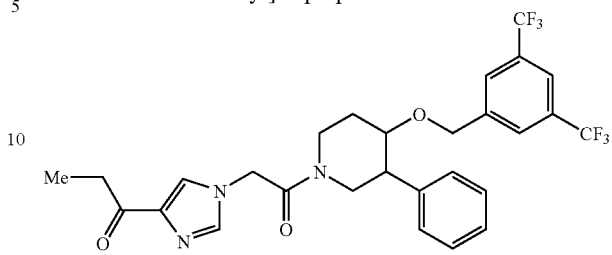

The compound obtained in Example 1 and (1H-imidazol-4-yl)-1-propanone were reacted and treated in the same manner as in the method described in Example 503 to obtain the title compound.

MS (ESI+): 568 (M+H).

Example 506

4-[[cis-4-[[3,5-Bis(trifluoromethyl)benzyl]oxy]-3-phenyl-1-piperidinyl]carbonyl]-1-piperidine carbaldehyde

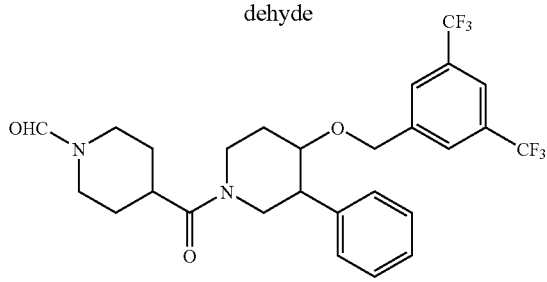

To a solution of the compound (102 mg) obtained in Process 2 of Example 69 in acetonitrile (8 ml), ammonium formate (876 mg) was added, and the reaction mixture was stirred for 60 hours under boiling reflux conditions. To the reaction solution, saturated brine was added, and the product was extracted with ethyl acetate. The organic layer was dried, and then the solvent was evaporated under reduced pressure. The obtained residue was isolated and purified by silica gel column chromatography (chloroform:methanol=10:1) to obtain the title compound (44 mg) as colorless amorphous.

MS (ESI+): 543 (M+H).

Example 512 cis-4-[[3,5-Bis(trifluoromethyl)benzyl]oxy]-3-(3,4-dichlorophenyl)-1-phenylpiperidine To a solution of the compound (200 mg) obtained in Example 509, bromobenzene (0.054 ml), tris(dibenzylideneacetone)dipalladium(0) (11 mg) and sodium tert-butoxide (94 mg) in toluene (5.0 ml), (±)-2,2'-bis(diphenylphosphino)-1,1'-binaphthyl((±)-BINAP) (7.3 mg) was added, and the reaction mixture was stirred at 85° C. for 17 hours under argon atmosphere. The reaction mixture was poured into water, and then the product was extracted with ethyl acetate. The organic layer was washed with saturated brine, dried, and then the solvent was evaporated under reduced pressure. The obtained residue was isolated and purified by silica gel column chromatography (ethyl acetate hexane=1:10→1:4) to obtain the title compound as colorless oil (120 mg, 55%).

MS (ESI+): 548 (M+H)

The compounds of the following Examples were synthesized from the compound of Examples 515 or 609 as a starting material by reacting and treating in the same manner as in the method described in Example 512 using the respective corresponding halides.

TABLE 27

[Structure: piperidine with R¹ on N, X-CH₂-B substituent at 4-position, C substituent at 3-position]

| Ex. No. | Stereochemistry | R¹ | X | B | C | MS (ESI) (M + H)⁺ |
|---|---|---|---|---|---|---|
| 512 | (±)-cis | Ph | O | 3,5-bis(trifluoromethyl)phenyl | 3,4-dichlorophenyl | 548 |
| 518 | (±)-cis | 1-(pyrimidin-2-yl)-4-acetylpiperidin-4-yl | O | 3,5-bis(trifluoromethyl)phenyl | 3,4-dichlorophenyl | 661 |
| 662 | (±)-cis | Ph | NH | 4-methoxy-3-methyl-... (MeO, OCF₃ substituted phenyl) | phenyl | 457 |

Example 555 cis-1-[(1-Acetyl-4-piperidinyl)carbonyl]-3-phenyl-4-[[5-(trifluoromethyl)-1,1'-biphenyl-3-yl]methoxy]piperidine To a solution of the compound (250 mg) obtained in Example 554 in toluene (4 ml)/ethanol (2 ml), dihydroxyphenylborane (107-mg), tetrakis(triphenylphosphine) palladium (0) (25 mg), sodium carbonate (186 mg) and water (2 ml) were added, and the reaction mixture was stirred at 100° C. for 4 hours. To the reaction solution, water was added, and the product was extracted with dichloromethane. The organic layer was dried, and then the solvent was evaporated under reduced pressure. The obtained residue was isolated and purified by silica gel column chromatography (chloroform:methanol=10:1) to obtain the title compound (111 mg) as colorless amorphous.

MS (ESI+): 565 (M+H)

The compounds of the following Examples were synthesized from the compound of Examples 554 or 564 as a starting material by reacting and treating in the same manner as in the method described in Example 555 using the respective corresponding boronic acid derivatives.

TABLE 28

[Structure: piperidine with R¹ on N, X-CH₂-B substituent at 4-position, C substituent at 3-position]

| Ex. No. | Stereochemistry | R¹ | X | B | C | MS (ESI) (M + H)⁺ |
|---|---|---|---|---|---|---|
| 555 | (±)-cis | 1-acetyl-4-piperidinylcarbonyl | O | 3-methyl-5-phenyl-(trifluoromethyl)phenyl | phenyl | 565 |

TABLE 28-continued
| Ex. No. | Stereochemistry | R¹ | X | B | C | MS (ESI) (M + H)⁺ |
|---|---|---|---|---|---|---|
| 556 | (±)-cis | 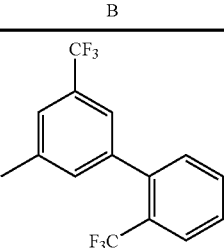 | O | 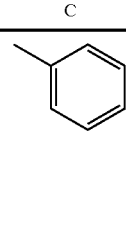 | 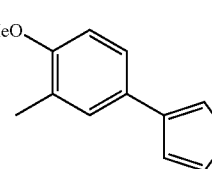 | 633 |
| 669 | (±)-cis | EtNHCO | NH | 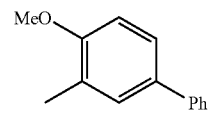 | 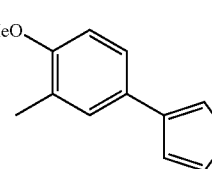 | 434 |
| 671 | (±)-cis | EtNHCO | NH | 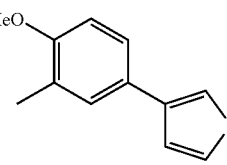 | 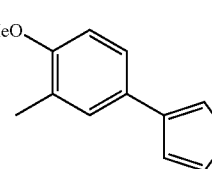 | 444 |
| 672 | (±)-cis | EtNHCO | NH | 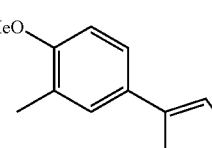 | 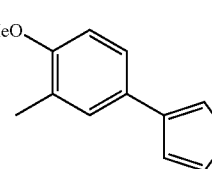 | 450 |
| 676 | (±)-cis | MeNHCO | NH | 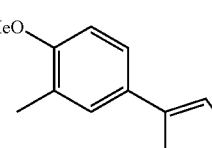 | 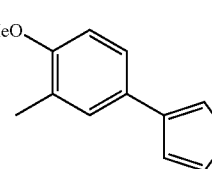 | 430 |
| 683 | (±)-cis | EtNHCO | NH | 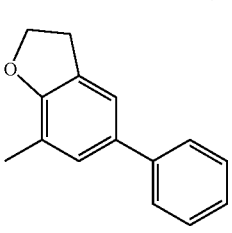 | 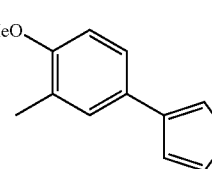 | 456 |
| 686 | (±)-cis | EtNHCO | NH | 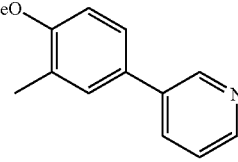 | 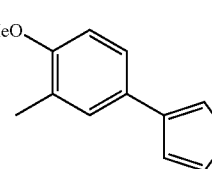 | 445 |
| 687 | (±)-cis | EtNHCO | NH | 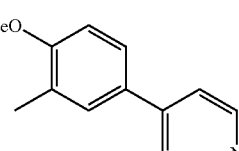 | 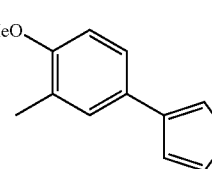 | 445 |

Example 557

N-[3-[[[cis-1-[(1-Acetyl-4-piperidinyl)carbonyl)]-3-phenyl-4-piperidinyl]oxy]methyl]-5-(trifluoromethyl)phenyl]-N(2,2,2-trifluoroethyl)amine

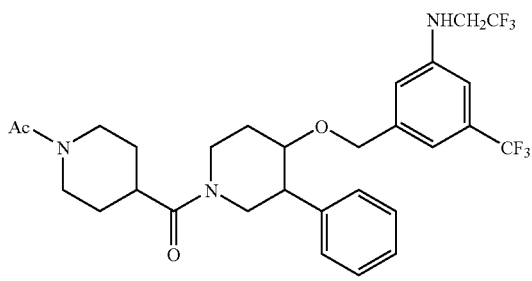

The compound (150 mg) obtained in Example 554, (±)-BINAP (12 mg), sodium tert-butoxide (39 mg), tris(dibenzylideneacetone)dipalladium(0) (8 mg), 2,2,2-trifluoroethylamine (40 mg) and toluene (15 ml) were mixed under argon atmosphere, and stirred at 100° C. for 2 hours (under argon atmosphere). To the reaction solution, water was added, and the product was extracted with ethyl acetate. The organic layer was washed with saturated brine, dried, and then the solvent was evaporated under reduced pressure. The obtained residue was isolated and purified by preparative HPLC to obtain the title compound (22 mg) as colorless amorphous.

MS (ESI+): 586 (M+H).

Example 564 cis-4-[(5-Bromo-2-methoxybenzyl)amino]-N-ethyl-3-phenyl-1-piperidinecarboxamide (Process 1)

To a solution of the compound (5.0 g) obtained in Process 4 of Reference Example 1 and $Et_3N$ (4.8 g) in acetonitrile (100 ml), ethyl isocyanate (5.3 g) was added, and the reaction mixture was stirred at room temperature for 6 hours. The reaction mixture was poured into water, and then the product was extracted with ethyl acetate. The organic layer was washed with an aqueous 10% citric acid solution and saturated brine, dried, and then the solvent was evaporated under reduced pressure. The obtained residue was isolated and purified by silica gel column chromatography (ethyl acetate:hexane:methanol=40:10:1) to obtain N-ethyl-4-oxo-3-phenylpiperidine-1-carboxamide as colorless oil (6.2 g).

(Process 2)

The compound (6.5 g) obtained in Process 1 was reacted and treated in the same manner as in the method described in Process 1 and Process 2 of Reference Example 2 to obtain 4-amino-N-ethyl-3-phenylpiperidine-1-carboxamide as pale yellow powder (3.3 g).

(Process 3)

The compound (0.31 g) obtained in Process 2 and 5-bromo-2-methoxybenzaldehyde (0.27 g) were reacted and treated in the same manner as in the method described in Process 3 of Reference Example 2 to obtain the title compound as colorless crystals (0.18 g).

MS (ESI+): 446, 448 (M+H).

The compounds of the following Examples were synthesized from the compound obtained in Process 4 of Reference Example 1 as a starting material by reacting and treating in the same manner as in the method described in Example 564 using methyl isocyanate or ethyl isocyanate and the respective corresponding benzaldehyde derivatives.

TABLE 29

| Ex. No. | Stereochemistry | R¹ | X | B | C | MS (ESI) (M + H)⁺ |
|---|---|---|---|---|---|---|
| 564 | (±)-cis | EtNHCO | NH | MeO-phenyl-Br (with methyl) | phenyl | 446, 448 |
| 565 | (±)-cis | MeNHCO | NH | MeO-phenyl-Br (with methyl) | phenyl | 432, 434 |
| 668 | (±)-cis | EtNHCO | NH | MeO-phenyl-OMe (with methyl) | phenyl | 398 |

TABLE 29-continued
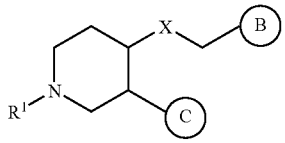
| Ex. No. | Stereochemistry | R¹ | X | B | C | MS (ESI) (M + H)⁺ |
|---|---|---|---|---|---|---|
| 670 | (±)-cis | EtNHCO | NH |  | 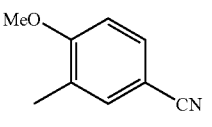 | 339 |
| 673 | (±)-cis | MeNHCO | NH |  | 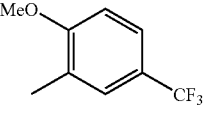 | 379 |
| 674 | (±)-cis | MeNHCO | NH |  | 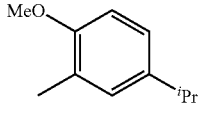 | 422 |
| 675 | (±)-cis | MeNHCO | NH |  | 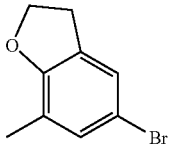 | 396 |
| 677 | (±)-cis | EtNHCO | NH |  | 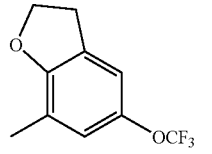 | 459 |
| 678 | (±)-cis | EtNHCO | NH |  | 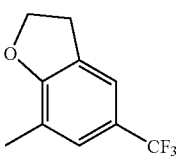 | 464 |
| 679 | (±)-cis | EtNHCO | NH |  | 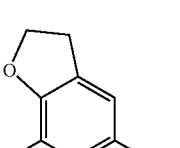 | 448 |
| 680 | (±)-cis | EtNHCO | NH |  | 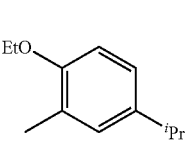 | 394 |
| 681 | (±)-cis | EtNHCO | NH |  | | 424 |

TABLE 29-continued

| Ex. No. | Stereochemistry | R¹ | X | B | C | MS (ESI) (M + H)⁺ |
|---|---|---|---|---|---|---|
| 682 | (±)-cis | EtNHCO | NH | 7-methyl-5-iPr-2,3-dihydrobenzofuran | phenyl | 422 |
| 684 | (±)-cis | EtNHCO | NH | 4-MeO-3-methyl-iPr-phenyl | phenyl | 410 |
| 685 | (±)-trans | EtNHCO | NH | 4-MeO-3-methyl-OCF₃-phenyl | phenyl | 452 |
| 688 | (±)-cis | EtNHCO | NH | 3-MeO-4-methyl-phenyl with 5-CF₃-tetrazol-1-yl | phenyl | 504 |
| 689 | (±)-cis | EtNHCO | NH | 2-MeO-1-methylnaphthyl | phenyl | 418 |
| 693 | (±)-cis | MeNHCO | NH | 7-methyl-5-iPr-2,3-dihydrobenzofuran | phenyl | 408 |
| 698 | (±)-cis | MeNHCO | NH | 7-methyl-5-OCF₃-2,3-dihydrobenzofuran | phenyl | 450 |
| 707 | (±)-cis | EtNHCO | NH | 4-MeO-3-methylphenyl with 5-(SMe)-1,3,4-oxadiazol-2-yl | phenyl | 482 |

TABLE 29-continued

| Ex. No. | Stereochemistry | R¹ | X | B | C | MS (ESI) (M + H)⁺ |
|---|---|---|---|---|---|---|
| 728 | (±)-cis | EtNHCO | NH | MeO-phenyl-oxadiazole-Me | phenyl | 450 |

Example 612

(−)-cis-N-Ethyl-4-[[2-methoxy-5-(trifluoromethoxy)benzyl]amino]-3-phenyl-1-piperidinecarboxamide

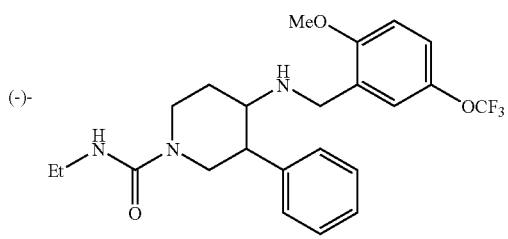

The compound (1.70 g) obtained in Example 610 was optically resolved with chiral HPLC, and the fractions were concentrated under reduced pressure to obtain the title compound (0.68 g) as white powder.

Chiral HPLC Condition
Column: CHIRALPAK AS 50 mm ID×500 mm L
Solvent: hexane/2-propanol=9/1
Flow rate: 70 ml/min→80 ml/min
Temperature: 25° C.
Detection method: UV 220 nm
[α]$_D^{25}$−96.1° (c 1.0, MeOH).
MS (ESI+): 452 (M+H).

Example 613

(+)-cis-N-Ethyl-4-[[2-methoxy-5-(trifluoromethoxy)benzyl]amino]-3-phenyl-1-piperidinecarboxamide

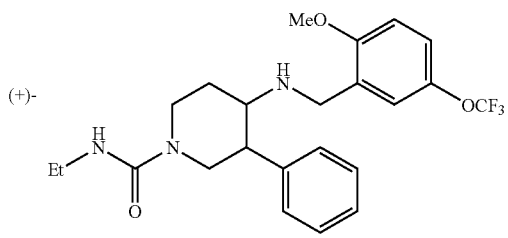

The compound (1.70 g) obtained in Example 610 was optically resolved with chiral HPLC, and the fractions were concentrated under reduced pressure to obtain the title compound (0.64 g) as white powder.

Chiral HPLC Condition
Column: CHIRALPAK AS 50 mm ID×500 mm L
Solvent: hexane/2-propanol=9/1
Flow rate: 70 ml/min→80 ml/min
Temperature: 25° C.
Detection method: UV 220 nm
[α]$_D^{25}$+97.0° (c 1.0, MeOH).
MS (ESI+): 452 (M+H).

Example 657 cis-4-[[2-Methoxy-5-(trifluoromethoxy)benzyl]amino]-3-phenyl-1-piperidinecarboxamide hydrochloride

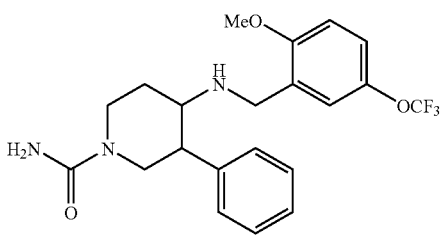

To a solution of the compound (0.23 g) obtained in Example 609, 4-dimethylaminopyridine (0.010 g) and Et₃N (0.10 g) in THF (3 ml), triphosgene (0.15 g) was added at 0° C., and the reaction mixture was stirred at 0° C. for 30 minutes. To the reaction mixture, 28% ammonia water (5 ml) was added, and the reaction mixture was stirred at room temperature for 4 hours. The reaction mixture was poured into water, and then the product was extracted with ethyl acetate. The organic layer was washed with an aqueous 10% citric acid solution and saturated brine, dried, and then the solvent was evaporated under reduced pressure. The obtained residue was isolated and purified by preparative HPLC, and the product was treated with 4 N hydrogen chloride/ethyl acetate to obtain the title compound (0.049 mg) as colorless amorphous.

MS (ESI+): 424 (M+H).

Example 660 cis-N-[2-Methoxy-5-(trifluoromethoxy)benzyl]-1-(3-methyl-1,2,4-thiazol-5-yl)3-phenyl-4-piperidineamine To a solution of the compound (0.45 g) obtained in Example 609 in THF (6 ml), Et$_3$N (0.20 g) was added, and the resulting precipitates was removed by filtration, and the filtrate was concentrated under reduced pressure. The obtained residue was dissolved in ethanol (6 ml), 5-chloro-3-methyl-1,2,4-thiazole (0.27 g) was added thereto, and the reaction mixture was stirred at room temperature for 14 hours. The reaction mixture was concentrated under reduced pressure, and then the obtained residue was isolated and purified by preparative HPLC to obtain the title compound (87 mg) as colorless amorphous.

MS (ESI+): 479 (M+H)

The compounds of the following Examples were synthesized from the compound of Examples 609 or 701 as a starting material by reacting and treating in the same manner as in the method described in Example 660 using the respective corresponding halides.

The compound (200 mg) obtained in Example 701 was reacted and treated in the same manner as in the method described in Example 503 to obtain the title compound (96 mg) as colorless amorphous.

MS (ESI+): 601 (M+H).

Example 786 cis-1-Acetyl-N-[2-methoxy-5-[5-(trifluoromethyl)-1H-tetrazol-1-yl]benzyl]-3-phenyl-4-piperidineamine To a solution of the compound (0.20 g) obtained in Example 701 in DMF (5 ml), trimethylsilyl chloride (0.13 g) and imidazole (0.082 g) were added, and the reaction mixture was stirred at 110° C. for 1 hour. The reaction mixture was poured into an aqueous saturated sodium hydrogen carbonate

TABLE 30

| Ex. No. | Stereochemistry | R$^1$ | X | B | C | MS (ESI) (M + H)$^+$ |
|---|---|---|---|---|---|---|
| 660 | (±)-cis | 3-methyl-1,2,4-thiadiazol-5-yl | NH | 2-MeO, 5-OCF$_3$-phenyl (with methyl) | phenyl | 479 |
| 661 | (±)-cis | thiazol-2-yl | NH | 2-MeO, 5-OCF$_3$-phenyl (with methyl) | phenyl | 464 |
| 747 | (±)-cis | 3-methyl-1,2,4-thiadiazol-5-yl | NH | 2-MeO-phenyl with 5-(5-CF$_3$-tetrazol-1-yl) | phenyl | 531 |

Example 785 cis-1-[2-(4-Acetyl-1-piperazinyl)-2-oxoethyl]-N-[2-methoxy-5-[5-(trifluoromethyl)-1H-tetrazol-1-yl]benzyl]-3-phenyl-4-piperidineamine

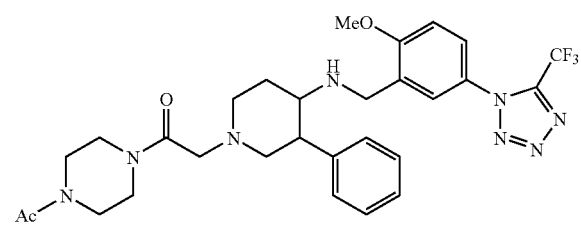

solution, and then the product was extracted with ethyl acetate. The organic layer was washed with saturated brine, dried, and then the solvent was evaporated under reduced pressure. The obtained residue was isolated and purified by silica gel column chromatography (ethyl acetate:hexane=2:1) to obtain the title compound as pale yellow amorphous(0.090 g).

MS (ESI+): 479 (M+H).

The compounds of the following Examples were synthesized from the compound of Example 732 as a starting material by reacting and treating in the same manner as in the method described in Example 786.

TABLE 31

[Structure: piperidine with R¹ on N, X-CH2-B at 4-position, C at 3-position]

| Ex. No. | Stereochemistry | R¹ | X | B | C | MS (ESI) (M + H)⁺ |
|---|---|---|---|---|---|---|
| 786 | (±)-cis | HCO | NH | MeO-phenyl(Me)-tetrazole-CF₃ | methylphenyl | 461 |
| 787 | (±)-cis | formyl-piperidinyl-acetyl | NH | MeO-phenyl(Me)-tetrazole-CF₃ | methylphenyl | 572 |

Preparative Example 1

| | |
|---|---|
| (1) Compound of Example 1 | 10 mg |
| (2) Lactose | 60 mg |
| (3) Corn starch | 35 mg |
| (4) Hydroxypropylmethylcellulose | 3 mg |
| (5) Magnesium stearate | 2 mg |

A mixture of 10 mg of the compound obtained in Example 1, 60 mg of lactose and 35 mg of corn starch was granulated using 0.03 ml of an aqueous solution of 10 wt % hydroxypropylmethylcellulose (3 mg as hydroxypropylmethylcellulose), and then dried at 40° C. and sieved. The obtained granules were mixed with 2 mg of magnesium stearate and compressed. The obtained uncoated tablets were sugar-coated with an aqueous suspension of sucrose, titanium dioxide, talc and gum Arabic. The thus-coated tablets were glazed with bees wax to obtain finally-coated tablets.

Preparative Example 2

| | |
|---|---|
| (1) Compound of Example 1 | 10 mg |
| (2) Lactose | 70 mg |
| (3) Corn starch | 50 mg |
| (4) Soluble starch | 7 mg |
| (5) Magnesium stearate | 3 mg |

10 mg of the compound obtained in Example 1 and 3 mg of magnesium stearate were granulated with 0.07 ml (7 mg as soluble starch) of an aqueous soluble starch solution, dried, and mixed with 70 mg of lactose and 50 mg of corn starch. The mixture was compressed to obtain tablets.

Reference Preparative Example 1

| | |
|---|---|
| (1) Rofecoxib | 5.0 mg |
| (2) Table salt | 20.0 mg |
| (3) Distilled water | to 2 ml of total volume |

5.0 mg of rofecoxib and 20.0 mg of table salt were dissolved in distilled water, and water was added to make 2.0 ml of total volume. The solution was filtered, and filled into 2 ml of ampoule under sterile condition. The ampoule was sterilized, and then sealed to obtain a solution for injection.

Reference Preparative Example 2

| | |
|---|---|
| (1) Rofecoxib | 50 mg |
| (2) Lactose | 34 mg |
| (3) Corn starch | 10.6 mg |
| (4) Corn starch (paste) | 5 mg |
| (5) Magnesium stearate | 0.4 mg |
| (6) Calcium carboxymethylcellulose | 20 mg |
| total | 120 mg |

The above-mentioned (1) to (6) were mixed according to a conventional method and were tableted by a tablet machine to obtain tablets.

Preparative Example 3

The formulation prepared in Preparative Example 1 or 2, and the formulation prepared in Reference Preparative Example 1 or 2 were combined.

Experimental Example 1

Radioligand receptor binding inhibitory activity (Binding inhibitory activity using receptor from human lymphoblast cells (IM-9))

The method of M. A. Cascieri et al., "Molecular Pharmacology 42, p. 458 (1992)" was modified and used. The receptor was prepared from human lymphoblast cells (IM-9). IM-9 cells (2×10⁵ cells/ml) were inoculated and incubated for 3 days (one liter), which was then subjected to centrifuge for 5 minutes at 500×G to obtain cell pellets. The obtained pellets were washed once with phosphate buffer (Flow Laboratories, CAT. No. 28-103-05), which were then crushed using Polytron homogenizer ("Kinematika", Germany) in 30 ml of 50 mM Tris-HCl buffer (pH 7.4) containing 120 mM sodium chloride, 5 mM potassium chloride, 2 μg/ml chymostatin, 40 μg/ml bacitracin, 5 μg/ml phosphoramidon, 0.5 mM phenylmethylsulfonyl fluoride, 1 mM ethylenediamine tetra-acetic acid, which was subjected to centrifuge at 40,000×G for 20 minutes. The residue was twice washed with 30 ml of the above-mentioned buffer, which was then preserved frozen (−80° C.) as a specimen of the receptor.

The specimen was suspended in a reaction buffer (50 mM Tri-HCl buffer (pH 7.4), 0.02% bovine serum albumin, 1 mM phenylmethylsulfonyl fluoride, 2 μg/ml chymostatin, 40 μg/ml bacitracin and 3 mM manganese chloride) to have protein in the concentration of 0.5 mg/ml of protein and 100 μl portion of the suspension was used in the reaction. After addition of the sample and $^{125}$I-BHSP (0.46 KBq), the reaction was allowed to proceed in 0.2 ml of reaction buffer at 25° C. for 30 minutes. The amount of nonspecific binding was determined by adding substance P at a final concentration of $2 \times 10^{-6}$ M.

After the reaction, using a cell harvester (290 PHD, Cambridge Technology, Inc, U.S.A.), rapid filtration was carried out through a glass filter (GF/B, Whatman, U.S.A.) to stop the reaction. After washing three times with 250 μl of 50 mM Tris-HCl buffer (pH 7.4) containing 0.02% bovine serum albumin, the radioactivity remaining on the filter was determined with a gamma counter. Before use, the filter was immersed in 0.1% polyethyleneimine for 24 hours and air-dried.

The antagonistic activity of each compound obtained in Examples was determined in terms of the concentration necessary to cause 50% inhibition ($IC_{50}$ value) under the above-described conditions, and the results were shown in Table 32.

TABLE 32

| Example No. | IC$_{50}$ Value (nM) |
|---|---|
| 70 | 0.150 |
| 72 | 0.032 |
| 75 | 0.025 |
| 78 | 0.060 |
| 81 | 0.058 |
| 84 | 0.051 |
| 88 | 0.060 |
| 413 | 0.230 |
| 613 | 0.070 |
| 722 | 0.110 |
| 753 | 0.073 |
| 755 | 0.096 |
| 757 | 0.067 |
| 760 | 0.085 |
| 761 | 0.054 |
| 762 | 0.049 |
| 763 | 0.080 |
| 764 | 0.042 |

Radioligand means substance P labeled with [$^{125}$I].

From Table 32, it is understood that the compounds of the present invention have an excellent substance P receptor antagonistic effect.

INDUSTRIAL APPLICABILITY

Compound (I), a salt thereof or a prodrug of the present invention has high antagonistic action for a tachykinin receptor, particularly antagonistic action for Substance P receptor, and has low toxicity, thus being safe as a medicament. Therefore, Compound (I), a salt thereof or a prodrug of the present invention is useful as a medicament, for example, a tachykinin receptor antagonist, an agent for ameliorating abnormal micturition, etc.

The invention claimed is:

1. A compound represented by the formula:

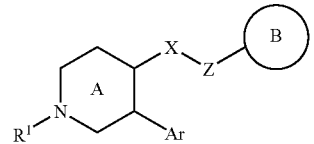

(I)

wherein

Ar is a phenyl group optionally having 1 to 4 substituents selected from
(A) a halogen atom,
(B) a C$_{1-6}$ alkyl group, and
(C) a 5- or 6-membered aromatic heterocyclic group having 1 to 4 hetero atoms of one or two kinds selected from a nitrogen atom, an oxygen atom and a sulfur atom in addition to carbon atoms, R$^1$ is an acyl group represented by the formula: —(C=O)—Ra, wherein Ra is
(A) a hydrogen atom, or
(B)
(a) a C$_{1-6}$ alkyl group, or
(b) a 5- or 6-membered aromatic or 4- to 6-membered non-aromatic heterocyclic group having 1 to 4 hetero atoms of one or two kinds selected from a nitrogen atom, an oxygen atom and a sulfur atom in addition to carbon atoms, each of which optionally has 1 or 2 substituents selected from
(i) a halogen atom,
(ii) a C$_{1-6}$ alkyl group optionally substituted with a 5- or 6-membered aromatic or non-aromatic heterocyclic group having 1 to 4 hetero atoms of one or two kinds selected from a nitrogen atom, an oxygen atom and a sulfur atom in addition to carbon atoms, a C$_{1-6}$ alkanoyl group, or a C$_{6-14}$ aryl-carbonyl group,
(iii) a C$_{1-6}$ alkoxy group,
(iv) an amino group,
(v) a mono- or di-C$_{1-6}$ alkylamino group,
(vi) a C$_{1-6}$ alkanoylamino group,
(vii) a N—C$_{1-6}$ alkyl-N'—C$_{1-6}$ alkanoylamino group,
(viii) a C$_{1-6}$ alkoxy-carbonyl group,
(ix) a C$_{1-6}$ alkanoyl group optionally substituted with C$_{1-6}$ alkoxy, mono- or di-C$_{1-6}$ alkylamino, halogeno C$_{1-6}$ alkyl or a halogen atom,
(x) a C$_{6-14}$ aryl-carbonyl group,
(xi) a C$_{7-19}$ aralkyl-carbonyl group,
(xii) a C$_{3-6}$ cycloalkyl-carbonyl group,
(xiii) a 5- or 6-membered aromatic or non-aromatic heterocyclic-carbonyl group having 1 to 4 hetero atoms of one or two kinds selected from a nitrogen atom, an oxygen atom and a sulfur atom in addition to carbon atoms,
(xiv) a hydroxy group,
(xv) a C$_{7-19}$ aralkyloxy group,
(xvi) a C$_{3-6}$ cycloalkyloxy group,
(xvii) a C$_{1-6}$ alkoxy-C$_{1-6}$ alkoxy group, (xviii) a carbamoyl group,
(xix) a mono- or di-$C_{1-6}$ alkylcarbamoyl group,
(xx) a $C_{1-6}$ alkylsulfonyl group,
(xxi) a mono- or di-$C_{1-6}$ alkylaminosulfonyl group,
(xxii) a formyl group,
(xxiii) a formylamino group,
(xxiv) an oxo group, and
(xxv) a 5- or 6-membered aromatic or non-aromatic heterocyclic group having 1 to 4 hetero atoms of one or two kinds selected from a nitrogen atom, an oxygen atom and a sulfur atom in addition to carbon atoms, which optionally has 1 or 2 substituents selected from $C_{1-6}$ alkanoyl and $C_{1-6}$ alkoxy-$C_{1-6}$ alkanoyl, X is an imino group,
Z is a methylene group,
Ring A is a piperidine ring, and
Ring B is a phenyl group substituted with a $C_{1-6}$ alkoxy group and a tetrazolyl group substituted with a halogenated $C_{1-6}$ alkyl group,
or a salt thereof.

2. The compound according to claim 1, wherein $R^1$ is —(C=O)—Rb wherein Rb is a $C_{1-6}$ alkyl group optionally having a substituent selected from (i) hydroxy, (ii) $C_{1-6}$ alkoxy, (iii) $C_{1-6}$ alkanoyl, (iv) $C_{1-6}$ alkylsulfonyl, (v) amino, (vi) mono- or di-$C_{1-6}$ alkylamino, (vii) $C_{1-6}$ alkanoylamino or (viii) a 5- or 6-membered aromatic heterocyclic group having 1 to 4 hetero atoms of one or two kinds selected from a nitrogen atom, an oxygen atom and a sulfur atom in addition to carbon atoms, which is optionally substituted with 1 or 2 oxo groups.

3. cis-1-(methoxyacetyl)-N-[2-methoxy-5-[5-(trifluoromethyl)-1H-tetrazol-1-yl]benzyl]-3-phenyl-4-piperidineamine, cis-1-[(1-acetyl-4-piperidinyl)carbonyl]-N-[2-methoxy-5-[5-(trifluoromethyl)-1H-tetrazol-1-yl]benzyl]-3-phenyl-4-piperidineamine, cis-N-[2-[4-[[2-methoxy-5-[5-(trifluoromethyl)-1H-tetrazol-1-yl]benzyl]amino]-3-phenyl-1-piperidinyl]-2-oxoethyl]acetamide, cis-N-[2-methoxy-5-[5-(trifluoromethyl)-1H-tetrazol-1-yl]benzyl]-1-[[1-(methylsulfonyl)-4-piperidinyl]carbonyl]-3-phenyl-4-piperidineamine, cis-N-[2-methoxy-5-[5-(trifluoromethyl)-1H-tetrazol-1-yl]benzyl]-3-phenyl-1-(1H-tetrazol-1-ylacetyl)-4-piperidineamine, cis-2-[4-[[2-methoxy-5-[5-(trifluoromethyl)-1H-tetrazol-1-yl]benzyl]amino]-3-phenyl-1-piperidinyl ]-2-oxoethanol, cis-N-[3-[4-[[2-methoxy-5-[5-(trifluoromethyl)-1H-tetrazol-1-yl]benzyl]amino]-3-phenyl-1-piperidinyl]-3-oxopropyl]acetamide, cis-1-acetyl-N-[2-methoxy-5-[5-(trifluoromethyl)-1H-tetrazol-1-yl]benzyl]-3-phenyl-4-piperidineamine, cis-N-[2-methoxy-5[5-(trifluoromethyl)-1H-tetrazol-1-yl]benzyl]-1-[(methylsulfonyl) acetyl]-3-phenyl-4-piperidineamine, or cis-1-[2-[4-[[2-methoxy-5-[5-(trifluoromethyl)-1H-tetrazol-1-yl]benzyl]amino]-3-phenyl-1-piperidinyl]-2-oxoethyl]-2,5-pyrrolidinedione, or a salt thereof.

4. A pharmaceutical composition comprising a therapeutically effective amount of a compound according to claim 1, and a pharmaceutically acceptable carrier.

5. A pharmaceutical composition comprising a compound according to claim 1, and a pharmaceutically acceptable carrier, which comprises a tachykinin receptor antagonistic effective amount of a compound according to claim 1.

6. A pharmaceutical composition comprising a compound according to claim 1, and a pharmaceutically acceptable carrier, which comprises a therapeutically effective amount of a compound according to claim 1 for treating urinary frequency and/or urinary incontinence.

7. A method of preparing a compound of claim 1, which comprises subjecting a compound represented by the formula:

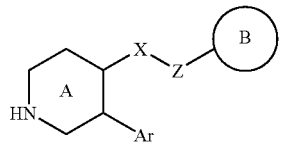

(Ia)

wherein each symbol has the same meaning as defined in claim 1, or a salt thereof to a reaction with a compound represented by the formula:

$R^{1a}$—OH wherein $R^{1a}$ is an acyl group represented by the formula: —(C=O)—Ra wherein Ra is as defined in claim 1, a salt thereof or a reactive derivative thereof, and optionally, to deacylation or dealkylation.

* * * * *